(12) United States Patent
Karsenty et al.

(10) Patent No.: US 8,883,739 B2
(45) Date of Patent: Nov. 11, 2014

(54) OSTEOCALCIN AS A TREATMENT FOR MALE REPRODUCTIVE DISORDERS

(75) Inventors: Gerard Karsenty, New York, NY (US); Patricia F. Ducy, New York, NY (US)

(73) Assignee: The Trustees of Columbia University in the City of New York, New York, NY (US)

( * ) Notice: Subject to any disclaimer, the term of this patent is extended or adjusted under 35 U.S.C. 154(b) by 0 days.

(21) Appl. No.: 13/574,196

(22) PCT Filed: Jan. 19, 2011

(86) PCT No.: PCT/US2011/021634
§ 371 (c)(1),
(2), (4) Date: Oct. 15, 2012

(87) PCT Pub. No.: WO2011/090971
PCT Pub. Date: Jul. 28, 2011

(65) Prior Publication Data
US 2013/0028902 A1    Jan. 31, 2013

Related U.S. Application Data

(60) Provisional application No. 61/296,415, filed on Jan. 19, 2010, provisional application No. 61/296,339, filed on Jan. 19, 2010.

(51) Int. Cl.
*A61K 38/16*    (2006.01)
*A61K 38/17*    (2006.01)
*A61K 38/22*    (2006.01)
*A61K 38/39*    (2006.01)

(52) U.S. Cl.
CPC ..................................... *A61K 38/39* (2013.01)
USPC .......................................... 514/21.3; 514/9.8

(58) Field of Classification Search
None
See application file for complete search history.

(56) References Cited

U.S. PATENT DOCUMENTS

| | | | |
|---|---|---|---|
| 4,059,589 | A | 11/1977 | Scherberich et al. |
| 4,250,088 | A | 2/1981 | Yang |
| 4,405,712 | A | 9/1983 | Vande Woude et al. |
| 4,426,330 | A | 1/1984 | Sears |
| 4,448,764 | A | 5/1984 | Smith et al. |
| 4,469,863 | A | 9/1984 | Ts'o et al. |
| 4,489,159 | A | 12/1984 | Markussen |

(Continued)

FOREIGN PATENT DOCUMENTS

| | | |
|---|---|---|
| CA | 2 045 869 A1 | 12/1991 |
| EP | 0 232 262 | 2/1987 |

(Continued)

OTHER PUBLICATIONS

Andrology, at http://www.springer.com/medicine/urology/book/978-3-540-78354-1, accessed Nov. 25, 2013.*

(Continued)

*Primary Examiner* — Elizabeth C Kemmerer
(74) *Attorney, Agent, or Firm* — Kenyon & Kenyon LLP

(57) ABSTRACT

Methods and compositions for treating, preventing, or diagnosing disorders related to reproduction in male mammals, preferably humans, are provided. The methods generally involve modulation of the OST-PTP signaling pathway or the PTP-IB signaling pathway involving gamma-carboxylase and osteocalcin. Disorders amenable to treatment by the methods include, but are not limited to, male infertility, low sperm count, impaired sperm motility, impaired sperm viability, low testosterone levels, reduced libido, erectile dysfunction, underdevelopment of testes, and excess apoptosis in testes.

10 Claims, 24 Drawing Sheets

(56) References Cited

U.S. PATENT DOCUMENTS

| | | | |
|---|---|---|---|
| 4,522,811 | A | 6/1985 | Eppstein et al. |
| 4,534,894 | A | 8/1985 | Cerami et al. |
| 4,534,899 | A | 8/1985 | Sears |
| 4,631,211 | A | 12/1986 | Houghten |
| 4,650,764 | A | 3/1987 | Temin et al. |
| 4,801,742 | A | 1/1989 | Quirk et al. |
| 4,946,778 | A | 8/1990 | Ladner et al. |
| 5,013,556 | A | 5/1991 | Woodle et al. |
| 5,034,506 | A | 7/1991 | Summerton et al. |
| 5,108,921 | A | 4/1992 | Low et al. |
| 5,213,804 | A | 5/1993 | Martin et al. |
| 5,216,141 | A | 6/1993 | Benner |
| 5,227,170 | A | 7/1993 | Sullivan |
| 5,235,033 | A | 8/1993 | Summerton et al. |
| 5,264,221 | A | 11/1993 | Tagawa et al. |
| 5,354,844 | A | 10/1994 | Beug et al. |
| 5,356,633 | A | 10/1994 | Woodle et al. |
| 5,386,023 | A | 1/1995 | Sanghvi et al. |
| 5,395,619 | A | 3/1995 | Zalipsky et al. |
| 5,416,016 | A | 5/1995 | Low et al. |
| 5,417,978 | A | 5/1995 | Tari et al. |
| 5,459,127 | A | 10/1995 | Felgner et al. |
| 5,462,854 | A | 10/1995 | Coassin et al. |
| 5,469,854 | A | 11/1995 | Unger |
| 5,512,295 | A | 4/1996 | Kornberg et al. |
| 5,521,291 | A | 5/1996 | Curiel et al. |
| 5,527,528 | A | 6/1996 | Allen et al. |
| 5,534,259 | A | 7/1996 | Zalipsky et al. |
| 5,543,152 | A | 8/1996 | Webb et al. |
| 5,543,158 | A | 8/1996 | Gref et al. |
| 5,547,932 | A | 8/1996 | Curiel et al. |
| 5,556,948 | A | 9/1996 | Tagawa et al. |
| 5,580,575 | A | 12/1996 | Unger et al. |
| 5,583,020 | A | 12/1996 | Sullivan |
| 5,591,721 | A | 1/1997 | Agrawal et al. |
| 5,595,756 | A | 1/1997 | Bally et al. |
| 5,602,240 | A | 2/1997 | De Mesmaeler et al. |
| 5,637,684 | A | 6/1997 | Cook et al. |
| 5,644,048 | A | 7/1997 | Yau |
| 5,681,707 | A | 10/1997 | Hosoda et al. |
| 5,733,761 | A | 3/1998 | Treco et al. |
| 5,830,682 | A | 11/1998 | Moore |
| 6,270,985 | B1 | 8/2001 | Gottschalk et al. |
| 6,303,326 | B1 | 10/2001 | Felton et al. |
| 6,350,902 | B2 | 2/2002 | Hill et al. |
| 6,452,035 | B2 | 9/2002 | Dupont et al. |
| 6,511,958 | B1 | 1/2003 | Atkinson et al. |
| 6,514,514 | B1 | 2/2003 | Atkinson et al. |
| 6,560,471 | B1 | 5/2003 | Heller et al. |
| 6,828,151 | B2 | 12/2004 | Borchers et al. |
| 6,899,871 | B2 | 5/2005 | Kasahara et al. |
| 2003/0158302 | A1 | 8/2003 | Chaput |
| 2003/0199615 | A1 | 10/2003 | Chaput |
| 2004/0023390 | A1 | 2/2004 | Davidson |
| 2004/0082018 | A1 | 4/2004 | Ekema |
| 2004/0157864 | A1 | 8/2004 | Wu |
| 2006/0052327 | A1 | 3/2006 | Liu |
| 2006/0063699 | A1 | 3/2006 | Larsen |
| 2006/0257492 | A1 | 11/2006 | Wen |
| 2006/0292670 | A1 | 12/2006 | Ting et al. |
| 2007/0059731 | A1 | 3/2007 | Kerppola |
| 2007/0099831 | A1 | 5/2007 | Morley |

FOREIGN PATENT DOCUMENTS

| | | |
|---|---|---|
| EP | 0 464 533 A1 | 6/1991 |
| WO | 87/01130 A1 | 2/1987 |
| WO | 94/12650 A2 | 6/1994 |
| WO | 95/31560 A1 | 11/1995 |
| WO | 96/29411 A1 | 9/1996 |
| WO | 99/15650 A1 | 4/1999 |
| WO | 00/49162 A2 | 8/2000 |
| WO | 2008-033518 A2 | 3/2008 |
| WO | 2008/033518 A2 | 3/2008 |

OTHER PUBLICATIONS

Berkner, K.L. et al., "The physiology of vitamin K nutriture and vitamin K-dependent protein function in atherosclerosis", J of Thrombosis and Haemostasis (2004), vol. 2, pp. 2118-2132.

Comhaire, F.H. et al., "Mechanisms and effects of male genital tract infection on sperm quality and fertilizing potential: the andrologist's viewpoint", Human Reproduction Update (1999), vol. 5:5, pp. 393-398.

Mauro, L. J. et al., "Identification of a hormonally regulated protein tyrosine phosphatase associated with bone and testicular differentiation", J. of Biological Chemistry (1994), vol. 269:48, pp. 306959-30667.

Mesmaeker, A.D. et al., "Comparison of Rigid and Flexible Backbones in Antisense Oligonucleotides", Bioorganic & Medicinal Chem. Ltrs. (1994), vol. 4:3, pp. 395-398.

Pi, M. et al., "GPRC6A Mediates the Non-Genomic Effects of Steroids" J. Biol. Chem. (2010), vol. 285:51, pp. 39953-39964.

Houghten, R. et al., "General Method for the Rapid Solid-Phase Synthesis of Large Numbers of Peptides: Specificity of Antigen-Antibody Interaction at the Level of Individual Amino Acids", Proc. Natl. Acad. Sci. USA (1985) vol. 82, pp. 5131-5135.

Hunter, M. et al., "The Functional Activity of Adult Mouse Leydig Cells in Monolayer Culture", Mol. Cell. Endocrinology (1982), vol. 25, pp. 35-47.

Huse, W. et al., "Generation of a Large Combinatorial Library of the Immunoglobulin Repertoire in Phage Lambda", Science (1989), vol. 246, pp. 1275-1281.

Jamin, S. et al., "Genetic Studies of the AMH/MIS Signaling Pathway for Mullerian Duct Regression", Mol. Cell. Endocrinology (2003), vol. 211, pp. 15-19.

Johanson, K. et al., "Binding Interactions of Human Interleukin 5 with Its Receptor a Subunit", J. Biol. Chem. (1995), vol. 270:16, pp. 9459-9471.

Johnston, J. et al, "Minimum Requirements for Efficient Transduction of Dividing and Non-dividing Cells by Feline Immunodeficiency Virus Vectors", J. Virology (1999), vol. 73:6, pp. 4991-5000.

Johnston, J. et al., "Productive Infection of Human Peripheral Blood Mononuclear Cells by Feline Immunodeficiency Virus: Implications for Vector Development", J. Virology (1999), vol. 73:3, pp. 2491-2498.

Kaplitt, M. et al., "Long-Term Gene Expression and Phenotypic Correction Using Adeno-Associated Virus Vectors in the Mammalian Brain", Nature Genetics (1994), vol. 8, pp. 148-154.

Karlin, S. et al., "Applications and Statistics for Multiple High-Scoring Segments in Molecular Sequences", Proc. Natl. Acad. Sci. USA (1993), vol. 90, pp. 5873-5877.

Kiedrowski, G. et al., "Parabolic Growth of a Self-Replicating Hexadeoxynucleotide Bearing a 3'-5'- Phosphoamidate Linkage", Angew Chem. Intl. Ed. English (1991), vol. 30:4, pp. 423-426.

Kim, V. et al., "Minimal Requirement for a Lentivirus Vector Based on Human Immunodeficiency Virus Type 1", J. Virology (1998), vol. 72:1, pp. 811-816.

Krogsgaard-Larsen, P. et al., "Design and Application of Prodrugs" A Textbook of Drug Design and Development, Ed., Harwood Academic (1991) Chapter 5, pp. 113-191.

Laface, D. et al., "Gene Transfer into Hematopoietic Progenitor Cells Mediated by an Adeno-Associated Virus Vector", J. Virology (1988), vol. 162, pp. 483-486.

Lebkowski, J. et al., "Adeno-Associated Virus: a Vector System for Efficient Introduction and Integration of DNA into a Variety of Mammalian Cell Types", Mol. Cell. Biol. (1988) vol. 8:10, pp. 3988-3996.

Lee, K. et al., "Identification of a Developmentally Regulated Protein Tyrosine Phosphatase in Embryonic Stem Cells that is a Marker of Pluripotential Epiblast and Early Mesoderm", Mech. Dev. (1996) vol. 59, pp. 153-164.

Lee, A. et al., "Measurement of Osteocalcin", Ann. Clin. Biochem. (2000), vol. 37, pp. 432-446.

Lee, N. K. et al., "Endocrine Regulation of Energy Metabolism by the Skeleton", Cell (2007), vol. 130, pp. 456-469.

Letsinger, R. et al., "Phosphoramidate Analogs of Oligonucleotides", J. Organic Chemistry (1970), vol. 35:11, pp. 3800-3803.

(56) References Cited

OTHER PUBLICATIONS

Letsinger, R. et al., "Effects of Pendant Groups at Phosphorus on Binding Properties of d-ApA Analogues", Nucl. Acids Res. (1986) vol. 14:8, pp. 3487-3499.
Letsinger, R. et al., "Cationic Oligonucleotides" J. Am. Chem. Soc. (1988) vol. 110, pp. 4470-4471.
Jung, P. et al., "Hybridization of Alternating Cationic/Anionic Oligonucleotides to RNA Segments", Nucleoside & Nucleotide (1994), vol. 13 (6 &7), pp. 1597-1605.
Luo, F. et al., "Adeno-Associated Virus 2-Mediated Transfer and Functional Expression of a Gene Encoding the Human Granulocyte-Macrophage Colony-Stimulating Factor", Blood: The Journal of the American Society of Hematology, (1994), Abstract #1196, pp. 303a.
Maddry, J. et al., "Synthesis of Nonionic Oligonucleotide Analogues", Chapter 3, pp. pp. 40-51, in SC Symposium Series 580, Carbohydrate Modifications in Antisense Research (1994), Eds. Yogesh S. Sanghvi and P. Dan Cook.
Mag, M. et al., "Synthesis and Selective Cleavage of an Oligodeoxynucleotide Containing a Bridged Internucleotide 5'-Phosphorothioate Linkage", Nucleic Acids Res. (1991), vol. 19:7, pp. 1437-1441.
Mather, J. "Establishment and Characterization of Two Distinct Mouse Testicular Epithelial Cell Lines", Biol. Reprod. (1980), vol. 23, pp. 243-252.
McLaughlin, S. et al., "Adeno-Associated Virus General Transduction Vectors: Analysis of Proviral Structure", J. Virology (1988), vol. 62:6, pp. 1963-1973.
Meier, C. et al., "Peptide Nucleic Acids (PNAs)—Unusual Properties of Nonionic Oligonucleotide Analogues" Chem. Int. Ed. Engl. (1992) vol. 31, 1008-1009.
Mesmaeker, A.D. et al., "Novel Backbone Replacements for Oligonucleotides", Chapter 2, pp. 24-37 in ASC Symposium Series 580, Carbohydrate Modifications in Antisense Research (1994), Eds. Yogesh S. Sanghvi and P. Dan Cook.
Morgan, R. "Human Gene Therapy", BioPharm, (1993), vol. 6:1, pp. 32-35.
Mulligan, R. "The Basic Science of Gene Therapy", Science (1993), vol. 260, pp. 926-932.
Naldini, L. et al., "In vivo Gene Delivery and Stable Transduction of Non-dividing Cells by a Lentiviral Vector", Science (1996), vol. 272, pp. 263-267.
Needleman, S. et al., "A General Method Applicable to the Search for Similarities in the Amino Acid Sequence of Two Proteins", J. Mol. Biol. (1970), vol. 48, pp. 444-453.
Nelson, L. et al.,"Estrogen Production and Action", J. Am. Acad. Dermatol. (2001), vol. 45:3, pp. S116-S124.
Ohi, S. et al., "Construction and Replication of an Adeno-Associated Virus Expression Vector that Contains Human B-Globin cDNA", Gene (1990), vol. 89, pp. 279-282.
Pauwels, R. et al., "Biological Activity of New 2-5A Analogues", Chemica Scripta (1986), vol. 26, pp. 141-145.
Pi, M. et al, "GPRC6A Null Mice Exhibit Osteopenia, Feminization and Metabolic Syndrome", PLoS One (2008), vol. 3:12-e3858, pp. 1-10.
Pi, M. et al., "Identification of a Novel Extracellular Cation-Sensing G-Protein-Coupled Receptor", J. Biol. Chem. (2005), vol. 280:48, pp. 40201-40209.
Poeschla, E. et al., "Development of HIV Vectors for Anti-HIV Gene Therapy", Proc. Natl. Acad. Sci. USA (1996), vol. 93, pp. 11395-11399.
Poeschla, E. et al., "Efficient Transduction of Non-Dividing Human Cells by Feline Immunodeficiency Virus Lentiviral Vectors", Nat. Med. (1998), vol. 4:3, pp. 354-357.
Poser, J. et al., "Isolation and Sequence of the Vitamin K-Dependent Protein from Human Bone", J. Biol. Chem. (1980), vol. 255:18, pp. 8685-8691.
Poser, J. et al., "A Method for Decarboxylation of γ-Carboxyglutamic Acid in Proteins", J. Biol. Chem. (1979), vol. 254:2, pp. 431-436.

Powlin, S. et al., "Ex Vivo and in Vitro Testis and Ovary Explants: Utility for Identifying Steroid Biosynthesis Inhibitors and Comparison to a Tier I Screening Battery", Toxicol. Sci. (1998), vol. 46, pp. 61-74.
Price, P., "Gla-Containing Proteins of Bone", Connect. Tissue Res. (1989), vol. 21, pp. 51-57 (discussion 57-60).
Qin, J. et al., "Essential Roles of COUP-TFII in Leydig Cell Differentiation and Male Fertility", PLoS One (2008), vol. 3:9:e3285, pp. 1-11.
Rattan, S. et al., "Protein Synthesis, Posttranslational Modifications, and Aging", Ann. New York Acad. Sci. (1992) vol. 663, pp. 48-62.
Rawls, R. "Optimistic about Antisense: Promising Clinical Results and Chemical Strategies for Further Improvements Delight Antisense Drug Researchers", Chemical & Engineering News (1997), pp. 35-39.
Russell, D. et al., "Foamy Virus Vectors", J. Virology (1996), vol. 70:1, pp. 217-222.
Samulski, R. et al., "Helper-Free Stocks of Recombinant Adeno-Associated Viruses: Normal Integration Does Not Require Viral Gene Expression", J. Virology (1989), vol. 63:9, pp. 3822-3828.
Sawai, H. et al, "Synthesis and Properties of Oligoadenylic Acids Containing 2'-5' Phosphoramide Linkage", Chemistry Letters (1984), pp. 805-808.
Schumacher, T. et al, "Identification of D-Peptide Ligands through Mirror-Image Phage Display", Science (1996), vol. 271, pp. 1854-1857.
Schumacher, M. et al., "Rapid Isolation of Mouse Leydig Cells by Centrifugation in Percoll Density Gradients with Complete Retention of Morphological and Biochemical Integrity", FEBS Lett. (1978), vol. 91:2, pp. 333-338.
Seifter, S. et al., "Analysis for Protein Modifications and Non-Protein Co-Factors", Methods in Enzymol. (1990), vol. 182, pp. 626-646.
Sheng, Y. et al., "Gonadotropin-Regulated Testicular RNA Helicase (GRTH/Ddx25) Is a Transport Protein Involved in Gene-Specific mRNA Export and Protein Translation During Spermatogenesis", J. Biol. Chem. (2006), vol. 281:46, pp. 35048-35056.
Shelling, A. et al., "Targeted Integration of Transfected and Infected Adeno-Associated Virus Vectors Containing the Neomycin Resistance Gene", Gene Therapy (1994), vol. 1:3, pp. 165-169.
Simon, R. et al., "Peptoids: A Modular Approach to Drug Discovery", Proc. Natl. Acad. Sci. (1992), vol. 89, pp. 9367-9371.
Simpson, E. et al., "The Role of Local Estrogen Biosynthesis in Males and Females", Trends Endocrinol. Metab. (2000), vol. 11:5, pp. 184-188.
Simpson E, "Sources of Estrogen and Their Importance", J. Steroid Biochem. Mol.Biol. (2003), vol. 86, pp. 225-230.
Sinha, A. (Hikim), et al., "Hormonal and Genetic Control of Germ Cell Apoptosis in the Testis", Reviews of Reprod. (1999), vol. 4, pp. 38-47.
Springer, M. et al, "High-Efficiency Retroviral Infection of Primary Myoblasts", Somatic Cell Mol. Genetics (1997), vol. 23:3, pp. 203-209.
Sprinzl, M. et al., "Enzymatic Incorporation of ATP and CTP Analogues into the 3' End of tRNA", Eur. J. Biochem. (1977), vol. 81, pp. 579-589.
Srinivasakumar, N. et al., "The Effect of Viral Regulatory Protein Expression on Gene Delivery by Human Immunodeficiency Virus Type 1 Vectors Produced in Stable Packaging Cell Lines", J. of Virology (1997), vol. 71:8, pp. 5841-5848.
Suarez, S. et al., "Initiation of Hyperactivated Flagellar Bending in Mouse Sperm within the Female Reproductive Tract", Biol. of Reprod. (1987), vol. 36, pp. 1191-1198.
Suarez, S., "Control of Hyperactivation in Sperm", Human Reprod. Update (2008), vol. 14:6, pp. 647-657.
Svoboda, P. et al., "Selective Reduction of Dormant Maternal mRNAs in Mouse Oocytes by RNA Interference", Development (2000), vol. 127:19, pp. 4147-4156.
Taylor, A. et al., "Multiple Osteocalcin Fragments in Human Urine and Serum as Detected by a Midmolecule Osteocalcin Radioimmunoassay", J. Clin. Endocrin. Metab. (1990), vol. 70:2, pp. 467-472.
Timmons, L. et al., "Specific Interference by Ingested dsRNA", Nature (1998), vol. 395,:6705 p. 854.

(56) References Cited

OTHER PUBLICATIONS

Tratschin, J et al., "A Human Parvovirus, Adeno-Associated Virus, as a Eucaryotic Vector: Transient Expression and Encapsidation of the Procaryotic Gene for Chloramphenicol Acetyltransferase", Mol. Cell. Biol., (1984), vol. 4:10, pp. 2072-2081.
Tsai-Morris et al., "Polymorphism of the GRTH/DDX25 Gene in Normal and Infertile Japanese Men: a Missense Mutation Associated with Loss of GRTH Phosphorylation", Mol. Human Reprod. (2007) vol. 13:12, pp. 887-892.
Wang, G. et al., "Effects of Insulin-Like Growth Factor I on Steroidogenic Enzyme Expression Levels in Mouse Leydig Cells", Endocrinology (2003), vol. 144:11, pp. 5058-5064.
Walters, K. et al., "Female Mice Haploinsufficient for an Inactivated Androgen Receptor (AR) Exhibit Age-Dependent Defects That Resemble the AR Null Phenotype of Dysfunctional Late Follicle Development, Ovulation, and Fertility", Endocrinology (2007), vol. 148:8, pp. 3674-3684.
Walsh, C. et al., "Regulated High Level Expression of a Human γ-Globin Gene Introduced into Erythroid Cells by an Adeno-Associated Virus Vector", Proc. Natl. Acad. Sci. USA (1992), vol. 89, pp. 7257-7261.
Wei, J. et al., "Expression of the Human Glucocerebrosidase and Arylsulfatase A Genes in Murine and Patient Primary Fibroblasts Transduced by an Adeno-Associated Virus Vector", Gene Therapy (1994), vol. 1:4, pp. 261-268.
Wellendorph, P. et al., "Molecular Cloning, Expression, and Sequence Analysis of GPRC6A, a Novel Family C G-Protein-Coupled Receptor", Gene (2004), vol. 335, pp. 37-46.
Wianny, F. et al., "Specific Interference with Gene Function by Double-Stranded RNA in Early Mouse Development", Nature Cell Biology (2000), vol. 2:2, pp. 70-75.
Wold, F., "Posttranslational Covalent Modification of Proteins: Perspectives and Prospectives", in Posttranslational Covalent Modification of Proteins, edited by B. C. Johnson, Ed., Academic Press, New York 1-12 (1983).
Wu, M. et al., "Packaging Cell Lines for Simian Foamy Virus Type 1 Vectors", J. of Virology (1999), vol. 73:5, pp. 4498-4501.
Yoder, M. et al., "In Vivo Gene Transfer in Murine Hematopoietic Reconstituting Stem Cells Mediated by the Adeno-Associated Virus 2-Based Vectors", Blood, (1993) vol. 82:10, Supplemental 1, Abstract No. 1373, p. 347a.
Zhang, X. et al., "Genome-Wide Analysis of cAMP-Response Element Binding Protein Occupancy, Phosphorylation, and Target Gene Activation in Human Tissues", Proc. Natl. Acad. Sci. U S A. (2005), vol. 102:12, pp. 4459-4464.
Zhao, Q. et al., "Cellular Distribution of Phosphorothioate Oligonucleotide Following Intravenous Administration in Mice", Antisense Nucleic Acid Drug Dev. (1998), vol. 8:6, pp. 451-458.
Zhou, S. et al., Adeno-Associated Virus 2-Mediated Gene Transfer in Murine Hematopoietic Progenitor Cells, Exp. Hematol. (1993), vol. 21:7, pp. 928-933.
Zhou, S. et al., Adeno-Associated Virus 2-Mediated High Efficiency Gene Transfer into Immature and Mature Subsets of Hematopoietic Progenitor Cells in Human Umbilical Cord Blood, J. Exp. Med. (1994), vol. 179, pp. 1867-1875.
Zufferey, R. et al., "Multiply Attenuated Lentiviral Vector Achieves Efficient Gene Delivery in Vivo", Nat. Biotechnol. (1997) vol. 15:9, pp. 871-875.
Muzyczka, N. "Use of Adeno-Associated Virus as a General Transduction Vector for Mammalian Cells", Curr. Topics in Micro. and Immo. (1992), vol. 158, pp. 97-129.
Adelman, J. et al., "In Vitro Deletional Mutagenesis for Bacterial Production of the 20,000-Dalton Form of Human Pituitary Growth Hormone", DNA (1983), vol. 2:3, pp. 183-193.
Agrawal, S. et al., "Pharmacokinetics of Oligonucleotides", CIBA Found. Symp. (1997), vol. 209, pp. 60-78.
Agrawal, S. et al., "Antisense Therapeutics" Current Opinion in Chemical Biology, (1998), vol. 2 pp. 519-528.
Anderson, K. et al., "Inhibition of Human Cytomegalovirus Immediate-Early Gene Expression by an Antisense Oligonucleotide Complementary to Immediate-Early RNA", Antimicrobiol. Agents Chemotherapy (1996), vol. 40:9, pp. 2004-2011.
Ausubel, et al., "Hybridization Analysis of a DNA Blot with a Radiolabeled DNA Probe" eds., Current Protocols in Molecular Biology (1989), vol. I, Green Publishing Associates, Inc., and John Wiley & sons, Inc., New York, at pp. 2.10.2-2.10.3.
Basura, G. et al., "Ontogeny of Serotonin and Serotonin 2A Receptors in Rat Auditory Cortex", Hearing Research (2008), vol. 244, pp. 45-50.
Baulcombe, D., "RNA as a Target and an Initiator of Post-Transcriptional Gene Silencing in Trangenic Plants", Plant Mol. Biol. (1996), vol. 32, pp. 79-88.
Beaucage, S. et al., "The Functionalization of Oligonucleotides Via Phosphoramidite Derivatives" Tetrahedron (1993) vol. 49:10, pp. 1925-1963.
Bennett, D. et al., "Kinetic Characterization of the Interaction of Biotinylated Human Interleukin 5 with an Fc Chimera of its Receptor a Subunit and Development of an ELISA Screening Assay using Real-Time Interaction Biosensor Analysis", J. Mol. Recog. (1995), vol. 8, pp. 52-58.
Bentley, M., et al., "Reductive Amination Using Poly(ethylene Glycol) Acetaldehyde Hydrate Generated in Situ: Applications to Chitosan and Lysozyme", J. Pharm. Sci. (1998), vol. 87:11, pp. 1446-1449.
Bolli, M. et al., "α-Bicyclo-DNA: Synthesis, Characterization, and Pairing Properties of x-DNA-Analogues With Restricted Conformational Flexibility in the Sugar-Phosphate Backbone", Chapter 7, pp. 100-116, in ASC Symposium Series 580, Carbohydrate Modifications in Antisense Research (1994), Eds. Yogesh S. Sanghui and P. Dan Cook.
Bowie, J., et al., "Deciphering the Message in Protein Sequences: Tolerance to Amino Acid Substitutions", Science (1990), vol. 247, pp. 1306-1310.
Brill, W.K-D. et al., "Synthesis of Oligodeoxynucleoside Phosphorodithioates Via Thioamidites" J. Am. Chem. Soc. (1989), vol. 111, pp. 2321-2322.
Brinkworth, M. et al., "Identification of Male Germ Cells Undergoing Apoptosis in Adult Rats", J. Reprod. Fertil. (1995) vol. 105, pp. 25-33.
Brody, E. et al., "The Use of Aptamers in Large Arrays for Molecular Diagnostics", Mol. Diagn. (1999), vol. 4:4, pp. 381-388.
Bundgaard, H., "(C) Means to Enhance Penetration (1) Prodrugs as a Means to Improve the Delivery of Peptide Drugs" Advanced Drug Delivery Review (1992), vol. 8, pp. 1-38.
Cammas, F. et al., "The Mouse Adrenocorticotropin Receptor Gene: Cloning and Characterization of Its Promoter and Evidence for a Role for the Orphan Nuclear Receptor Steroidogenic Factor 1" Mol. Endocrinol. (1997), vol. 11:7, pp. 867-876.
Carlsson, C. et al., "Screening for Genetic Mutations" Nature (1996), vol. 380, pp. 207.
Charbonneau, H. et al., "Human Placenta Protein-Tyrosine-Phosphatase: Amino Acid Sequence and Relationship to a Family of Receptor-Like Proteins" Proc. Natl. Acad. Sci. USA (1989), vol. 86, pp. 5252-5256.
Cho, C. et al., "An Unnatural Biopolymer" Science 1993, vol. 261, pp. 1303-1305.
Christiansen, B. et al. "Pharmacological Characterization of Mouse GPRC6A, and L-α-Amino-Acid Receptor Modulated by Divalent Cations" Br. J. Pharmacol. (2007), vol. 150, pp. 798-807.
Crystal, R. et al. "Transfer of Genes to Humans: Early Lessons and Obstacles to Success" Science (1995), vol. 270, pp. 404-410.
Dacquin, R. et al., "Knock-in of Nuclear Localised Beta-Galactosidase Reveals That the Tyrosine Phosphatase Ptprv Is Specifically Expressed in Cells of the Bone Collar", Dev. Dyn. (2004) vol. 229, pp. 826-834.
Dacquin, R., et al, " Mouse α1(I)-Collagen Promoter Is the Best Known Promoter to Drive Efficient Cre Recombinase Expression in Osteoblast", DEV DYN (2002), vol. 224, pp. 245-251.
Dakhova, O. et al., "Dickkopf-Like 1 Regulates Postpubertal Spermatocyte Apoptosis and Testosterone Production" Endocrinology (2009), vol. 150, pp. 404-412.

(56) References Cited

OTHER PUBLICATIONS

Dempcy, R. et al., "Synthesis of a Thymidyl Pentamer of Deoxyribonucleic Guanidine and Binding Studies With DNA Homopolynucleotides", Proc. Natl. Acad. Sci. USA (1995), vol. 92, pp. 6097-6101.
Ducy, P. et al., "Increased Bone Formation in Osteocalcin-Deficient Mice" Nature (1996) vol. 382, pp. 448-452.
Ducy, P. et al., "The Osteoblast: A Sophisticated Fibroblast under Central Surveillance" Science (2000) vol. 289, pp. 1501-1504.
Dufau, M. et al., "Gonadotropin-Regulated Testicular Helicase (GRTH/DDX25): an Essential Regulator of Spermatogenesis" Trends Endocrinol. Metab. (2007) vol. 18:8, pp. 314-320.
Egholm, J. et al., "Peptide Nucleic Acids (PNA). Oligonucleotide Analogues with an Achiral Peptide Backbone" J. Am. Chem. Soc. (1992), vol. 114, pp. 1895-1897.
Egholm, M et al., "PNA Hybridizes to Complimentary Oligonucleotides Obeying the Watson-Crick Hydrogen-Bonding Rules" Nature (1993), vol. 365, pp. 566-568.
Elbashir, S. et al., "Duplexes of 21-Nucleotide RNAs Mediate RNA Interference in Cultured Mammalian Cells" Nature (2001) vol. 411, pp. 494-498.
Ferron, M. et al., "Osteocalcin Differentially Regulates Beta Cell and Adipocyte Gene Expression and Affects the Development of Metabolic Diseases in Wild-Type Mice" Proc. Natl. Acad. Sci. USA (2008) vol. 105:13, pp. 5266-5270.
Ferron, M. et al., "An ELISA-Based Method to Quantity Osteocalcin Carboxylation in Mice" Biochem. Biophys. Res. Comm. (2010), vol. 397, pp. 691-696.
Flotte, T. et al., "Stable in Vivo Expression of the Cystic Fibrosis Transmembrane Conductance Regulator with an Adeno-Associated Virus Vector" Proc. Natl. Acad. Sci. USA (1993) vol. 90, pp. 10613-10617.
Flotte, T. et al., "Gene Expression from Adeno-Associated Virus Vectors in Airway Epithelial Cells" Am. J. Respir. Cell Mol. Biol. (1992) vol. 7, pp. 349-356.
Friedmann, T. "Progress Toward Human Gene Therapy" Science, (1989) vol. 244, pp. 1275-1281.
Gao, X. et al., "Unusual Conformation of a 3'-Thioformacetal Linkage in a DNA Duplex" J. Biomol NMR (1994) vol. 4, pp. 17-34.
Garnero, P. et al., "Characterization of Immunoreative Forms of Human Osteocalcin Generated in Vivo and in Vitro" J. Bone Miner. Res. (1994) vol. 9:2, pp. 255-264.
Lorenz-Depiereux, B. et al, "*Homo sapiens* G Protein-coupled receptor, family C, group 6, member A (GPRC6A) mRNA, complete cds", GenBank Accession No. AF502962 (2002).
Goodman, S. et al., "Recombinant Adeno-Associated Virus-Mediated Gene Transfer into Hematopoietic Progenitor Cells" Blood (1994) vol. 84:5, pp. 1492-1500.
Goldstein, B. "Regulation of Insulin Receptor Signaling by Protein-Tyrosine Dephosphorylation" Receptor (1993), vol. 3, pp. 1-15.
Gutti, R. et al., "Gonadotropin-Regulated Testicular Helicase (DDX25), an Essential Regulator of Spermatogenesis, Prevents Testicular Germ Cell Apoptosis" J. Biol. Chem. (2008) vol. 283:25, pp. 17055-17064.
Hakkinen, L. et al., "An Improved Method for Culture of Epidermal Keratinocytes from Newborn Mouse Skin" Methods in Cell Science (2002) vol. 23, pp. 189-196.
Harada, S. et al., "Control of Osteoblast Function and Regulation of Bone Mass" Nature (2003), vol. 423, pp. 349-355.
Hauschka, P. et al., "Osteocalcin and Matrix Gla Protein: Vitamin K-Dependent Proteins in Bone" Physiol. Reviews (1989) vol. 69:3, pp. 990-1047.
Henriksen, K. et al., "Testosterone Inhibits and Induces Apoptosis in Rat Seminiferous Tubules in a Stage-Specific Manner: In Situ Quantification in Squash Preparations after Administration of Ethane Dimethane Sulfonate" Endocrinology (1995), vol. 136:8, pp. 3285-3291.
Herdewijin, P. et al., "Hexopyranosyl-Like Oligonucleotides", Chapter 6, pp. 80-98 in ASC Symposium Series 580, Carbohydrate Modifications in Antisense Research (1994), Eds. Yogesh S. Sanghvi and P. Dan Cook.
Hermonat, P. et al., "Use of Adeno-Associated Virus as a Mammalian DNA Cloning Vector: Transduction of Neomycin Resistance into Mammalian Tissue Culture Cells" Proc. Natl. Acad. Sci. USA. (1984), vol. 81, pp. 6466-6470.
Hinoi, E. et al., "The Sympathetic Tone Mediates Leptin's Inhibition of Insulin Secretion by Modulating Osteocalcin Bioactivity" J. Cell Biol. (2008) vol. 183:7, pp. 1235-1242.

\* cited by examiner

FIGURE 23

```
   1 aotgagcaaa tgagataqaa acatggcatc cttaattata ctaattacct gctttgtgat
  61 tattcttgct acttcacagc cttgccagac cctgatgac tttgtggctg ccacttctcc
 121 gggacatatc ataattggag gtttgtttgc tattcatgaa aaaatgttgt cctcagaaga
 181 ctctcccaga cgaccacaaa tccaggagtg tgttggcttt gaaatatcag ttttcttca
 241 aactcttgct atgatccata gcattgagat gatcaacaat tcaccactct tatctggagt
 301 caaactgggg tatgaaatct atgacacttg tacagaagtc acagtggcaa tggcagccac
 361 tctgaggttt cttttcaaat tcactgctc cagagaaact gtggagttta agtgtgacta
 421 ttccagctac atgccaagag ttaaggctgt natagyttct gggtacttag aaataactat
 481 ggctgtctcc aggatgttga atttacagct catgccacag gtgggttatg aatcaactgc
 541 agaaatcctg agtgacaaaa ttcgcttct ttcattttta cggactgtgc ccagtgactt
 601 ccatcaaatt aaagcaatgg ctcacctgat tcagaaatct ggttggaact ggattggcat
 661 cataaccaca gatgatgact atggacgatt ggctttaac actttataa ttcaggctga
 721 agcaaataac gtgtgctag ccttcaaaga ggttcttca gacttttctt cagataataac
 781 cattgaagtc agaatcaatc ggacactgaa gaaaatcatt ttagaagccc aggttaatgt
 841 cattgtggta tctctgaggc aattccatgc ttttgatctc ttcaataag ccattgaaat
 901 gaatataaat aagatgtgga ttgctagtga taatggtca actgccacca agattaccac
 961 cattcctact gttaaaaga ttggcaaagt tgtagggttt gcctttagaa gaggaatat
1021 atctctttc cattcctta ttcaaatct gcacttgctt cccagtgaca gtcacaact
1081 cttacatgaa tatgccatgc atttatctgc ctgcgcatat gtcaaggaca ctgatttgag
1141 tcaatgcata ttcaatcatt ctcaaggac tttggcctac aaggctaaca aggctataga
1201 aaggaactta gtcatgagaa atgacttcct ctgggactat gctgagcagg gactcattca
1261 tagtattcag cttgcagtgt ttgcccttgg ttatgccatt cgggatctgt gtcaagctcg
1321 tgactgtcag aaccccaacg ccctccacc atggagttaa cttggtgtgc taaaaaatgt
1381 gacattcact gatggatgga attcatttca tttgatgct cacgggatt taaatactgg
1441 atatgatgtt gtgctctgaa aggagatcaa tggacacatg actgtcacta agatggcaga
1501 atatgaccta cagaatgatg tcttcatcat cccagatcag gaaacaaaaa atgagttcag
1561 gaatcttaag caaattcaat ctaaatgctc caaggaatgc agtcctgggc aaatgaagaa
1621 aactacaaga agtcaacaca tctgttgcta tgaatgtcag aactgtcctg aaaatcatta
1691 cactaatcag acagatatgc ctcactgcct tttatgcaac aacaaaacct actgggccca
1741 tgttaggagc actatgtgct ttgaaaagga agtggaatat ctcaactgga atgactcctt
1801 ggccatccta ctcctgatttc tctcctact gggaatcata tttgttctgg tgttggcat
1861 aatatttaca agaaacctga acaacctgt tgtgaaatca tcggggggat taagagtctg
1921 ctatgtgatc ctttctctgt attcctcaa ttttgcagc acgagctttt tcattggaga
1981 accacaagac ttcacatgta aaacaggca gacaatgttt ggagtgagct ttactcttg
2041 catctcctgc atttgacga gtctctgaa aattttgcta gcttcagct ttgatccaa
2101 attacagaaa tttctgaagt gcttctatag acgatcctt attatcttca cttgcacggg
2161 catccaggtt gtcattgca cactctgct aatcttgca gcactactg tagaggtgaa
2221 tgtctccttg cccagagtca tcatcctgga gtgtgaggag ggatccatac ttgcatttgg
2281 caccatgctg ggctacattt tcatcttggc cttcattttgc cttcatattttg cttccaagg
2341 caaatattgag aattacaatg aagccaaatt cattacattc ggcatgctca tttacttcat
2401 agcttggata acattcatca ttatctatgc taccacattt ggcaaatatg tactagtgt
2461 ggagattatt gtcatattaa tatctaacta tggaatcctg tatgcacat tcatcccaa
2521 atgctatgtt attatttgta agcaagagat tacacaaaag tctgccttta tcaagatgat
2581 ctacagttat tcttcccata gtgtgagcag catgccccg agtcctgctt cactggactc
2641 catgagcggc aatgccacaa tgaccaatcc cagtctagt ggcagtctg aacctgcca
2701 gaaaagcaaa gatcttcagg cacaagcatt tgcatacata tgcagggaaa atgccacaag
2761 tgtatctaaa actttgctc gaaaaagaat gtcaagtata tgaataagcc ttaggagatg
2821 ccacattcca gaataaaatg ttttcagggt ccttgcatct
```

SEQ ID NO: 30

FIGURE 24

/translation="MAFLIILITCFVIILATSQPCQTPDDFVAATSPGHIIIGGLFAI
HEKMLSSEDSPRRPQIQECVGFEISVFLQTLAMIHSIEMINNSTLLSGVKLGYEIYDT
CTEVTVAMAATLRFLSKFNCSRETVEFKCDYSSYMPRVKAVIGSGYSEITMAVSRMLN
LQLMPQVGYESTAEILSDKIRFPSFLRTVPSDFHQIKAMAHLIQKSGNNWIGIITTDD
DYGRLALNTFIIQAEANNVCIAFKEVLPAFLSDNTIEVRINRTLNKIILEAQVNVIVV
FLRQFHVFDLFNKAIEMNINKMWNIASDNWSTATKITTIPNVKKIGNVVGFAFRRGNIS
SFHSFLQNLHLLPSDSHKLLHEYANHLSACAYVKDTDLSQCIFNHSQRTLAYKANKAI
ERNFVMRNDFLNDYAEPGLIHSIQLAVFALGYAIRDLQQARDCQNPNAFQPWELLGVL
KNVIFIDGWNSFHFDAHGDLNTGYDVVLNKEINGHMTVTKMAEYDLQNDVFIIPDQET
KNEFRNLKQIQSKCSKECSPGQMKKTIRSQHICCYECQNCPENHYTMQTDMPHCLLCN
NKTHWAPVRSTMCFEKEVEYLNWNDSLAILLLILSLLGIIFVLVVGIIFTRMLNIPVV
KSSGGLRVCYVILLCHFLNFASTSFFIGEPQDFTCKTRQTMFGVSFTLCISCILTKSL
KILLAFSFDPKLQKFLKCLYRPILIIFICTGIQVVICTLWLIFAAPTVEVNVSLPRVI
ILECEESSILAFSTMLGYIAILAFICFIFAFNGNYENYNEARFITFRKLIYFIAWITF
IPIYAITFGKYVPAVEIIVILISNYGILYCTFIPKCYVIICKQEINTKSAFLKMIYSY
SSHSVSSIALSFASLDSNSGNVTMTNPSSSGKSATWQKSKDLQRQAFAHICRENATSV
SKTLPRKRMSSI"

SEQ ID NO: 31

OSTEOCALCIN AS A TREATMENT FOR MALE REPRODUCTIVE DISORDERS

CROSS-REFERENCE TO RELATED APPLICATIONS

This application is a 371 of International Patent Application No. PCT/US2011/021634, filed Jan. 19, 2011, which claims priority to U.S. Provisional Patent Application Ser. No. 61/296,339, filed Jan. 19, 2010 and U.S. Provisional Patent Application Ser. No. 61/296,415, filed Jan. 19, 2010. The contents of these applications are hereby incorporated by reference in their entireties.

This invention was made with Government support under Grant No. PHS 398/2590 (Rev. September 4, Reissued April 2006). The Government has certain rights in the invention.

FIELD OF THE INVENTION

The present invention is directed to methods and compositions for treating, preventing, and diagnosing disorders related to reproduction in male mammals. Such disorders include, but are not limited to, male infertility, low sperm count, impaired sperm motility, impaired sperm viability, low testosterone levels, reduced libido, erectile dysfunction, underdevelopment of testes, and excess apoptosis in testes. The present invention also provides methods of contraception for use in male mammals.

BACKGROUND OF THE INVENTION

Osteocalcin, one of the very few osteoblast-specific proteins, has several features of a hormone. For instance, it is synthesized as a pre-pro-molecule and is secreted in the general circulation (Hauschka et al., 1989, Physiol. Review 69:990-1047; Price, 1989, Connect. Tissue Res. 21:51-57 (discussion 57-60)). Because of their exquisite cell-specific expression, the osteocalcin genes have been intensively studied to identify osteoblast-specific transcription factors and to define the molecular bases of bone physiology (Ducy et al., 2000, Science 289:1501-1504; Harada & Rodan, 2003, Nature 423:349-355).

Osteocalcin is the most abundant non-collagenous protein found associated with the mineralized bone matrix and it is currently being used as a biological marker for clinical assessment of bone turnover. Osteocalcin is a small (46-50 residue) bone specific protein that contains 3 gamma-carboxylated glutamic acid residues in its primary structure. The name osteocalcin (osteo, Greek for bone; calc, Latin for lime salts; in, protein) derives from the protein's ability to bind $Ca^{2+}$ and its abundance in bone. Osteocalcin undergoes a peculiar post-translational modification whereby glutamic acid residues are carboxylated to form gamma-carboxyglutamic acid (Gla) residues; hence osteocalcin's other name, bone Gla protein (Hauschka et al., 1989, Physiol. Review 69:990-1047).

Mature human osteocalcin contains 49 amino acids with a predicted molecular mass of 5,800 kDa (Poser et al., 1980, J. Biol. Chem. 255:8685-8691). Osteocalcin is synthesized primarily by osteoblasts and ondontoblasts and comprises 15 to 20% of the non-collagenous protein of bone. Poser et al., 1980, J. Biol. Chem. 255:8685-8691 showed that mature osteocalcin contains three carboxyglutamic acid residues which are formed by post-translational vitamin K-dependent modification of glutamic acid residues. The carboxylated Gla residues are at positions 17, 21 and 24 of human mature osteocalcin. Some human osteocalcin has been shown to contain only 2 Gla residues (Poser & Price, 1979, J. Biol. Chem. 254:431-436).

Osteocalcin has several features of a hormone. Ducy et al., 1996, Nature 382:448-452 demonstrated that mineralized bone from aging osteocalcin-deficient mice was two times thicker than that of wild-type. It was shown that the absence of osteocalcin led to an increase in bone formation without impairing bone resorption and did not affect mineralization. Multiple immunoreactive forms of human osteocalcin have been discovered in circulation (Garnero et al., 1994, J. Bone Miner. Res. 9:255-264) and also in urine (Taylor et al., 1990, J. Clin. Endocrin. Metab. 70:467-472). Fragments of human osteocalcin can be produced either during osteoclastic degradation of bone matrix or as the result of the catabolic breakdown of the circulating protein after synthesis by osteoblasts.

OST-PTP is the protein encoded by the Esp gene. The Esp gene was originally named for embryonic stem (ES) cell phosphatase and it has also been called the Ptprv gene in mice. (Lee et al, 1996, Mech. Dev. 59:153-164). Because of its bone and testicular localization, the gene product of Esp is often referred to as osteoblast testicular protein tyrosine phosphatase (OST-PTP). OST-PTP is a large, 1711 amino-acid long protein that includes three distinct domains. OST-PTP has a 1068 amino-acid long extracellular domain containing multiple fibronectin type III repeats.

Esp expression is restricted to ES cells, the gonads and the skeleton. In the gonads, Esp is specifically expressed in Sertoli cells of the testis and coelomic epithelial cells of the ovaries. During development, Esp is initially expressed in the apical ectodermal ridge of the limbs. Later during embryonic development and after birth, its expression becomes restricted to pre-osteoblasts and osteoblasts (i.e., Runx2-positive cells) of the perichondrium and periosteum.

Protein tyrosine phosphatase-1B (PTP-1B) is an ~50 kd intracellular protein present in abundant amounts in various human tissues (Charbonneau et al., 1989, Proc. Natl. Acad. Sci. USA 86:5252-5256; Goldstein, 1993, Receptor 3:1-15).

GPRC6A is an orphan receptor that belongs to the C family of GPCRs (Wellendorph and Brauner-Osborne, 2004, Gene 335:37-46) and has been proposed to be a receptor for amino acids or for calcium in the presence of osteocalcin as a cofactor, and for androgens (Pi et al., 2008, PLoS One. 3:e3858; Pi et al., 2005, J. Biol. Chem. 280:40201-40209; Pi et al., 2010, J. Biol. Chem. 285:39953-39964).

SUMMARY OF THE INVENTION

The present invention provides methods of treating disorders related to reproduction in male mammals comprising administering to a male mammal in need of treatment for a disorder related to reproduction a pharmaceutical composition comprising a therapeutically effective amount of undercarboxylated/uncarboxylated osteocalcin and a pharmaceutically acceptable carrier or excipient. In certain embodiments, the osteocalcin is human osteocalcin. In certain embodiments, the disorder is male infertility, low sperm count, impaired sperm motility, impaired sperm viability, low testosterone levels, reduced libido, erectile dysfunction, underdevelopment of testes, or excess apoptosis in testes.

The present invention also provides methods of treating disorders related to reproduction in male mammals comprising administering to a male mammal in need of treatment for a disorder related to reproduction a pharmaceutical composition comprising an agent that modulates the OST-PTP signaling pathway or the PTP-1B signaling pathway, wherein the agent reduces OST-PTP phosphorylase expression or activity or reduces PTP-1B phosphorylase expression or activity, reduces gamma-carboxylase expression or activity, or increases the level of undercarboxylated/uncarboxylated osteocalcin, wherein the pharmaceutical composition comprises the agent in an amount that produces an effect in a male mammal selected from the group consisting of increasing fertility, raising sperm count, increasing sperm motility, increasing sperm viability, increasing serum testosterone levels, increasing libido, ameliorating erectile dysfunction, reducing underdevelopment of testes, and reducing excess apoptosis in testes.

In certain embodiments, the male mammal is a human.

In certain embodiments, the agent is undercarboxylated/uncarboxylated osteocalcin. In certain embodiments, the agent is human undercarboxylated/uncarboxylated osteocalcin.

In certain embodiments, the agent inhibits the expression or activity of OST-PTP, inhibits the expression or activity of PTP-1B, inhibits the expression or activity of gamma-carboxylase, inhibits phosphorylation of gamma-carboxylase, inhibits carboxylation of osteocalcin, or decarboxylates osteocalcin. In certain embodiments, the agent is selected from the group consisting of a small molecule, an antibody, or a nucleic acid.

In certain embodiments where the agent is undercarboxylated/uncarboxylated osteocalcin, at least one of the glutamic acids in the undercarboxylated/uncarboxylated osteocalcin at the positions corresponding to positions 17, 21 and 24 of mature human osteocalcin is not carboxylated. In certain embodiments, all three of the glutamic acids in the undercarboxylated/uncarboxylated osteocalcin at the positions corresponding to positions 17, 21 and 24 of mature human osteocalcin are not carboxylated.

In certain embodiments, the undercarboxylated/uncarboxylated osteocalcin is a preparation of undercarboxylated/uncarboxylated osteocalcin in which more than about 20% of the total Glu residues at the positions corresponding to positions 17, 21 and 24 of mature human osteocalcin in the preparation are not carboxylated. In certain embodiments, the undercarboxylated/uncarboxylated osteocalcin shares at least 80% amino acid sequence identity with mature human osteocalcin when the undercarboxylated/uncarboxylated osteocalcin and mature human osteocalcin are aligned for maximum sequence homology. In certain embodiments, the undercarboxylated/uncarboxylated osteocalcin shares about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, or about 98% amino acid sequence identity with mature human osteocalcin when the undercarboxylated/uncarboxylated osteocalcin and mature human osteocalcin are aligned for maximum sequence homology. In certain embodiments, the undercarboxylated/uncarboxylated osteocalcin differs at 1, 2, 3, 4, 5, 6, 7, 8, 9, or 10 amino acid residues from mature human osteocalcin.

In certain embodiments, at least one of the glutamic acids in the undercarboxylated/uncarboxylated osteocalcin at the positions corresponding to positions 17, 21 and 24 of mature human osteocalcin is not carboxylated. In certain embodiments, all three of the glutamic acids in the undercarboxylated/uncarboxylated osteocalcin at the positions corresponding to positions 17, 21 and 24 of mature human osteocalcin are not carboxylated. In certain embodiments, the present invention provides methods of administering undercarboxylated/uncarboxylated osteocalcin to a mammal to increase fertility, raise sperm count, increase sperm motility, increase sperm viability, increase serum testosterone levels, increase libido, or ameliorate erectile dysfunction.

In certain embodiments, the undercarboxylated/uncarboxylated osteocalcin is a polypeptide selected from the group consisting of:
(a) a fragment comprising mature human osteocalcin missing the last 10 amino acids from the C-terminal end;
(b) a fragment comprising mature human osteocalcin missing the first 10 amino acids from the N-terminal end;
(c) a fragment comprising amino acids 62-90 of SEQ ID NO:2;
(d) a fragment comprising amino acids 1-36 of mature human osteocalcin; and
(e) variants of the above.

In certain embodiments, the pharmaceutical composition comprises a small molecule selected from the group consisting of warfarin, vitamin K inhibitors, and biologically active fragments or variants thereof. In a preferred embodiment, the small molecule is warfarin. In another preferred embodiment, the agent is a small molecule that increases the activity or expression of osteocalcin.

In certain embodiments, the pharmaceutical composition comprises an antibody or antibody fragment that binds to and inhibits the activity of OST-PTP, PTP-1B, or gamma-carboxylase. Preferably, the antibody or antibody fragment is a monoclonal antibody. In certain embodiments, the antibody or antibody fragment binds to the extracellular domain of OST-PTP or PTP-1B. In preferred embodiments, the OST-PTP is human OST-PTP or the PTP-1B is human PTP-1B. In certain embodiments, the OST-PTP is the mouse OST-PTP of SEQ ID NO:11 or an OST-PTP having an amino acid sequence that is substantially homologous or identical to SEQ ID NO:11. In certain embodiments, the OST-PTP is an OST-PTP having an amino acid sequence that is at least 70% homologous or identical to SEQ ID NO:11. In certain embodiments, the PTP-1B is human PTP-1B of SEQ ID NO:17 or a PTP-1B having an amino acid sequence that is substantially homologous or identical to SEQ ID NO:17. In certain embodiments, the PTP-1B is a PTP-1B having an amino acid sequence that is at least 70%, at least 80%, at least 90%, at least 95%, or at least 98% homologous or identical to SEQ ID NO:17.

In certain embodiments, the pharmaceutical composition comprises a nucleic acid that inhibits the expression or activity of OST-PTP, PTP-1B, or gamma-carboxylase. In certain embodiments, the nucleic acid is an antisense oligonucleotide or a small interfering RNA (siRNA). In certain embodiments, the nucleic acid is an isolated nucleic acid that is selected from the group consisting of an antisense DNA, antisense RNA, and siRNA, which nucleic acid is sufficiently complementary to SEQ ID NO:10 or a sequence that is substantially homologous or identical to SEQ ID NO:10 to permit specific hybridization to SEQ ID NO:10 or a sequence that is substantially homologous or identical to SEQ ID NO:10, and wherein the hybridization prevents or reduces expression of OST-PTP in osteoblasts. In certain embodiments, the nucleic acid is an isolated nucleic acid that is selected from the group consisting of an antisense DNA, antisense RNA, and siRNA, which nucleic acid is sufficiently complementary to SEQ ID NO:16 or a sequence that is substantially homologous or identical to SEQ ID NO:16 to permit specific hybridization to SEQ ID NO:16 or a sequence that is substantially homologous or identical to SEQ ID NO:16, and wherein the hybridization prevents or reduces expression of PTP-1B in osteoblasts.

In certain embodiments, the pharmaceutical composition comprises about 0.5 mg to about 5 g, about 1 mg to about 1 g, about 5 mg to about 750 mg, about 10 mg to about 500 mg, about 20 mg to about 250 mg, or about 25 mg to about 200 mg, of the agent. In certain embodiments, the pharmaceutical composition comprises an agent that is formulated into a controlled release preparation. In certain embodiments, the pharmaceutical composition comprises an agent that is chemically modified to prolong its half life in the human body.

In certain embodiments, the pharmaceutical composition for treating a disorder related to reproduction in male mammals comprises an undercarboxylated/uncarboxylated osteocalcin polypeptide comprising an amino acid sequence (SEQ ID NO: 13)
YLYQWLGAPVPYPDPLX$_1$PRRX$_2$VCX$_3$LNPDCDELADHIGFQEAYRRFY
GPV wherein $X_1$, $X_2$ and $X_3$ are each independently selected from an amino acid or amino acid analog, with the proviso that if $X_1$, $X_2$ and $X_3$ are each glutamic acid, then $X_1$ is not carboxylated, or less than 50 percent of $X_2$ is carboxylated, and/or less than 50 percent of $X_3$ is carboxylated, or said osteocalcin polypeptide comprises an amino acid sequence that is different from SEQ. ID. NO:13 at 1 to 7 positions other than $X_1$, $X_2$ and $X_3$; and/or wherein said amino acid sequence can include one or more amide backbone substitutions.

In certain embodiments, the osteocalcin polypeptide of SEQ. ID. NO:13 is a fusion protein. In certain embodiments, the arginine at position 43 of SEQ. ID. NO:13 is replaced with an amino acid or amino acid analog that reduces susceptibility of the osteocalcin polypeptide to proteolytic degradation. In certain embodiments, the arginine at position 44 of SEQ. ID. NO:13 is replaced with β-dimethyl-arginine. In certain embodiments, the osteocalcin polypeptide is a retroenantiomer of uncarboxylated human osteocalcin (1-49).

The present invention also provides a method of treating a disorder related to reproduction in male mammals by modulating the OST-PTP signaling pathway or the PTP-1B signaling pathway, the method comprising administering an agent that reduces OST-PTP phosphorylase activity or reduces PTP-1B phosphorylase activity, reduces gamma-carboxylase activity, or increases undercarboxylated/uncarboxylated osteocalcin, wherein the agent is administered in an amount that produces an effect in a male mammal selected from the group consisting of increasing fertility, raising sperm count, increasing sperm motility, increasing sperm viability, increasing serum testosterone levels, increasing libido, ameliorating erectile dysfunction, reducing underdevelopment of testes, and reducing excess apoptosis in testes.

The present invention also provides a method of diagnosing a patient as having or being at risk of developing a disorder related to reproduction in male mammals comprising (i) determining the ratio of undercarboxylated/uncarboxylated osteocalcin to total osteocalcin in a biological sample from the patient; and (ii) comparing the ratio to a standard ratio; wherein, if the patient ratio is lower than the standard ratio, the patient is diagnosed as having or being at risk of developing a disorder related to reproduction in male mammals. In certain embodiments, the method comprises the further step of administering a therapeutic agent as described herein to the patient diagnosed as having or being at risk of developing a disorder related to reproduction in male mammals.

In certain embodiments, the patient has or is at risk for a disorder related to reproduction in male mammals selected from the group consisting of male infertility, low sperm count, impaired sperm motility, impaired sperm viability, low testosterone levels, reduced libido, erectile dysfunction, underdevelopment of testes, and excess apoptosis in testes.

In certain embodiments, the biological sample is blood.

In certain embodiments of the diagnostic method described above, the standard ratio is 5%-10%, 10%-15%, 15%-20%, 20%-25%, 25%-30%, 30%-35%, or 35%-40%.

The present invention provides a use of an agent that reduces OST-PTP phosphorylase activity, reduces PTP-1B phosphorylase activity, reduces gamma-carboxylase activity, and/or increases undercarboxylated/uncarboxylated osteocalcin as a medicament for treating or preventing a disorder related to reproduction in male mammals.

In certain embodiments, the agent inhibits phosphorylation of gamma-carboxylase. In certain embodiments, the agent increases the level of undercarboxylated/uncarboxylated osteocalcin. In certain embodiments, the agent increases the ratio of undercarboxylated/uncarboxylated osteocalcin compared to carboxylated osteocalcin. In certain embodiments, the agent inhibits carboxylation of osteocalcin. In certain embodiments, the agent decarboxylates osteocalcin.

In certain embodiments of the use described above, the agent is undercarboxylated/uncarboxylated osteocalcin. In certain embodiments of the use described above, the undercarboxylated/uncarboxylated osteocalcin increases fertility, raises sperm count, increases sperm motility, increases sperm viability, increases serum testosterone levels, increases libido, ameliorates erectile dysfunction, reduces underdevelopment of testes, or reduces excess apoptosis in testes. In certain embodiments, at least one of the glutamic acids in the undercarboxylated/uncarboxylated osteocalcin at the positions corresponding to positions 17, 21 and 24 of mature human osteocalcin is not carboxylated. In certain embodiments, all three of the glutamic acids in the undercarboxylated/uncarboxylated osteocalcin at the positions corresponding to positions 17, 21 and 24 of mature human osteocalcin are not carboxylated. In certain embodiments, the undercarboxylated/uncarboxylated osteocalcin is a preparation of undercarboxylated/uncarboxylated osteocalcin in which more than about 20% of the total Glu residues at the positions corresponding to positions 17, 21 and 24 of mature human osteocalcin in the preparation are not carboxylated. In certain embodiments, the undercarboxylated/uncarboxylated osteocalcin shares about 75%, about 76%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, or about 98% amino acid sequence identity with mature human osteocalcin when the undercarboxylated/uncarboxylated osteocalcin and mature human osteocalcin are aligned for maximum sequence homology. In certain embodiments, the undercarboxylated/uncarboxylated osteocalcin differs at 1, 2, 3, 4, 5, 6, 7, 8, 9, or 10 amino acid residues from mature human osteocalcin.

In certain embodiments of the use described above, the agent is selected from the group consisting of a small molecule, an antibody, or a nucleic acid.

In certain embodiments of the use described above, the agent is a small molecule that inhibits the expression or activity of OST-PTP, PTP-1B, or gamma-carboxylase. In certain embodiments, the agent is a small molecule selected from the group consisting of warfarin, vitamin K inhibitors, and biologically active fragments or variants thereof. In a preferred embodiment, the small molecule is warfarin. In another preferred embodiment, the agent is a small molecule that increases the activity or expression of osteocalcin.

The present invention provides the use of an undercarboxylated osteocalcin polypeptide, or mimetic thereof, for the manufacture of a medicament for treatment of a disorder related to reproduction in male mammals. In certain embodiments, the disorder is selected from the group consisting of male infertility, low sperm count, impaired sperm motility, impaired sperm viability, low testosterone levels, reduced libido, erectile dysfunction, underdevelopment of testes, and excess apoptosis in testes.

The present invention also provides the use of an agent that reduces OST-PTP phosphorylase activity, reduces PTP-1B phosphorylase activity, reduces gamma-carboxylase activity, and/or increases undercarboxylated/uncarboxylated osteocalcin for the manufacture of a medicament for treatment of a disorder related to reproduction in male mammals. In certain embodiments, the disorder is selected from the group consisting of male infertility, low sperm count, impaired sperm motility, impaired sperm viability, low testosterone levels, reduced libido, erectile dysfunction, underdevelopment of testes, and excess apoptosis in testes.

The present invention provides methods of contraception for use in male mammals. comprising administering to a male mammal in need of contraception a pharmaceutical composition comprising a therapeutically effective amount of an antagonist of undercarboxylated/uncarboxylated osteocalcin and a pharmaceutically acceptable carrier or excipient. In certain embodiments, the antagonist is an antagonist of human undercarboxylated/uncarboxylated osteocalcin.

BRIEF DESCRIPTION OF THE FIGURES

FIG. 23. Nucleotide sequence encoding human GPRC6A from GenBank accession no. AF502962.

FIG. 24. Amino acid sequence of human GPRC6A from GenBank accession no. AF502962.

DETAILED DESCRIPTION OF THE INVENTION

Figure 1:
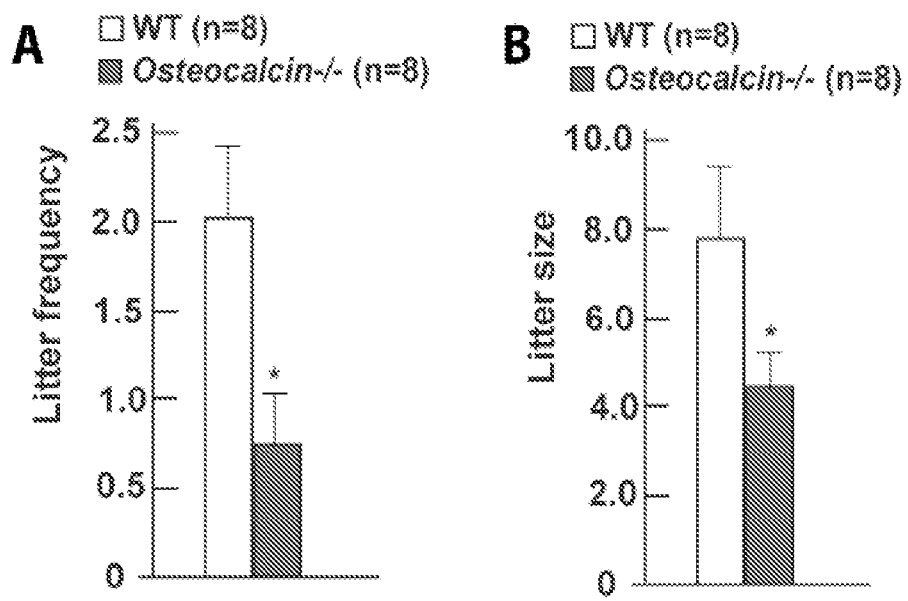
FIG. 1. Comparison between the average litter frequency (A) and size (B) generated by Osteocalcin−/− and wild type (WT) male mice crossed with WT females (breedings were tested from 6 weeks to 4 months of age).

The present invention is based in part on the discovery of a previously unknown biochemical pathway linking osteocalcin and reproductive biology in male mammals by which increased activity of osteocalcin leads to increased activity of enzymes involved in the synthesis of testosterone. This in turn leads to beneficial effects on male reproduction.

The present invention is also based in part on the observation that Osteocalcin-deficient male mice have significantly smaller testes than their wild type (WT) littermates. These mutant mice are also subfertile and display low sperm counts. Histological and molecular studies revealed that in the absence of osteocalcin the entire spermatogenic process seems to be affected because of an increase in apoptosis. Circulating levels of testosterone are also quite low in Osteocalcin-deficient mice. These observations indicate that osteocalcin is a critical regulator of male fertility in these mice.

In view of the observations described above, certain aspects of the invention are directed to the therapeutic use of undercarboxylated/uncarboxylated osteocalcin, as well as fragments and variants thereof, to treat or prevent disorders related to reproduction in male mammals.

Preventing a disorder related to reproduction in male mammals means actively intervening as described herein prior to overt onset of the disorder to prevent or minimize the extent of the disorder or slow its course of development.

Treating a disorder related to reproduction in male mammals means actively intervening after onset of the disorder to slow down, ameliorate symptoms of, minimize the extent of, or reverse the disorder in a patient who is known or suspected of having the disorder.

The present invention also provides methods of increasing testosterone levels, particularly serum testosterone levels, in male mammals by administering the therapeutic agents described herein to male mammals known to be in need of treatment to increase testosterone levels. In some embodiments of the methods of the present invention, the therapeutic agent increases serum testosterone levels by about 10%-25%, 20%-35%, 30%-50%, 50%-500%, 70%-400%, 100%-300%, or 100%-500% compared to pre-treatment serum testosterone levels.

A "patient" is a mammal, preferably a human, but can also be a companion animal such as dogs or cats, or farm animals such as horses, cattle, pigs, or sheep.

A patient in need of treatment or prevention for a disorder related to reproduction in male mammals includes a patient known or suspected of having or being at risk of developing a disorder related to reproduction in male mammals. Such a patient in need of treatment could be, e.g., a male mammal known to have low testosterone levels. Patients in need of treatment or prevention by the methods of the present invention include patients who are known to be in need of therapy to increase serum testosterone levels in order to treat or prevent a disorder related to reproduction in male mammals. In some embodiments, such patients might include male mammals who have been identified as having a serum testosterone level that is about 25%, about 50%, or about 75% lower than the serum testosterone level in normal subjects.

A patient in need of treatment or prevention for a disorder related to reproduction in male mammals by the methods of the present invention does not include a patient being administered the therapeutic agents described herein where the patient is being administered the therapeutic agents described herein only for a purpose other than to treat or prevent a disorder related to reproduction in male mammals. Thus, e.g., a patient in need of treatment or prevention for a disorder related to reproduction in male mammals by the methods of the present invention does not include a patient being treated with osteocalcin only for the purpose of treating a bone mass disease or a metabolic disorder such as diabetes. A patient in need of treatment or prevention for a disorder related to reproduction in male mammals by the methods of the present invention also does not include a patient being treated with osteocalcin that is not undercarboxylated/uncarboxylated osteocalcin.

In certain embodiments, the methods of the present invention comprise the step of identifying a patient in need of therapy for a disorder related to reproduction in male mammals. Thus, the present invention provides a method comprising:

(a) identifying a patient in need of therapy for a disorder related to reproduction in male mammals;

(b) administering to the patient a therapeutically effective amount of undercarboxylated/uncarboxylated osteocalcin or an agent that modulates the OST-PTP signaling pathway or the PTP-1B signaling pathway, wherein the agent reduces OST-PTP phosphorylase expression or activity, reduces PTP-1B phosphorylase expression or activity, or reduces gamma-carboxylase expression or activity.

The present invention is also based on the observation that gamma-carboxylase carboxylates osteocalcin, thereby producing carboxylated osteocalcin. This provides the opportunity to modulate the degree of carboxylation of the osteocalcin used in the methods of the present invention by modulating the activity of gamma-carboxylase. In particular, this provides the opportunity to lower the degree of carboxylation of the osteocalcin used in the methods of the present invention, thus providing undercarboxylated/uncarboxylated osteocalcin for use in the methods of the present invention. Therefore, certain aspects of the invention are directed to the therapeutic use of agents that inhibit the activity of gamma-carboxylase to treat or prevent a disorder related to reproduction in male mammals.

The present invention is further based on the observation that OST-PTP activates gamma-carboxylase through dephosphorylation. As indicated above, activation of gamma-carboxylase leads to carboxylation of osteocalcin. This provides the opportunity to indirectly modulate the degree of carboxylation of the osteocalcin used in the methods of the present invention by modulating the activity of OST-PTP (which will then modulate the activity of gamma-carboxylase). Therefore certain aspects of the invention are directed to the therapeutic use of agents that inhibit the activity of OST-PTP to treat or prevent a disorder related to reproduction in male mammals.

The present invention is further based on the observation that, in humans, PTP-1B activates gamma-carboxylase through dephosphorylation. As indicated above, activation of gamma-carboxylase leads to carboxylation of osteocalcin. This provides the opportunity to indirectly modulate the degree of carboxylation of the osteocalcin used in the methods of the present invention by modulating the activity of PTP-1B in male humans (which will then modulate the activity of gamma-carboxylase). Therefore certain aspects of the invention are directed to the therapeutic use in male humans of agents that inhibit the activity of PTP-1B to treat or prevent a disorder related to reproduction in male humans.

Other aspects of the invention are directed to diagnostic methods based on detection of the level of undercarboxylated/uncarboxylated osteocalcin in a patient, which level is associated with disorders related to reproduction in male mammals.

In one aspect, the method of diagnosing a disorder related to reproduction in male mammals in a patient comprises (i) determining a patient level of undercarboxylated/uncarboxylated osteocalcin in a biological sample taken from the patient (ii) comparing the patient level of undercarboxylated/uncarboxylated osteocalcin and a control level of undercarboxylated/uncarboxylated osteocalcin, and (iii) if the patient level is significantly lower than the control level, then diagnosing the patient as having, or being at risk for, the disorder related to reproduction in male mammals.

Other aspects of the invention are directed to diagnostic methods based on detection of decreased ratios of undercarboxylated/uncarboxylated vs carboxylated osteocalcin. Such ratios may be associated with disorders related to reproduction in male mammals. In one aspect, the method of diagnosing a disorder related to reproduction in male mammals in a patient comprises (i) determining a patient ratio of undercarboxylated/uncarboxylated vs. carboxylated osteocalcin in a biological sample taken from the patient (ii) comparing the patient ratio of undercarboxylated/uncarboxylated vs carboxylated osteocalcin and a control ratio of undercarboxylated/uncarboxylated vs carboxylated osteocalcin, and (iii) if the patient ratio is significantly lower than the control ratio, then the patient is diagnosed has having, or being at risk for, the disorder related to reproduction in male mammals.

Pharmaceutical Compositions for Use in the Methods of the Invention

The present invention provides pharmaceutical compositions for use in the treatment of a disorder related to reproduction in male mammals comprising an agent for modulating the OST-PTP signaling pathway or for modulating the PTP-1B signaling pathway, which pathways involve gamma-carboxylase and osteocalcin. In particular embodiments, the agent inhibits OST-PTP phosphorylase activity, inhibits PTP-1B phosphorylase activity reduces gamma-carboxylase activity, and/or increases undercarboxylated/uncarboxylated osteocalcin. In particular embodiments, the agent decarboxylates osteocalcin. The agent may be selected from the group consisting of small molecules, polypeptides, antibodies, and nucleic acids. The pharmaceutical compositions of the invention provide an amount of the agent effective to treat or prevent a disorder related to reproduction in male mammals. In certain embodiments, the pharmaceutical composition provides an amount of the agent effective to treat or prevent male infertility, low sperm count, impaired sperm motility, impaired sperm viability, low testosterone levels, reduced libido, erectile dysfunction, underdevelopment of testes, or excess apoptosis in testes.

In certain embodiments, the pharmaceutical compositions for use in the methods of the invention may function to increase serum undercarboxylated/uncarboxylated osteocalcin serum levels.

In particular embodiments of the invention, therapeutic agents that may be administered in the methods of the present invention include undercarboxylated osteocalcin; uncarboxylated osteocalcin; or inhibitors that reduce the expression or activity of gamma-carboxylase, PTP-1B, or OST-PTP (e.g., antibodies, small molecules, antisense nucleic acids or siRNA). The pharmaceutical agents may also include agents that decarboxylate osteocalcin.

The therapeutic agents are generally administered in an amount sufficient to treat or prevent male infertility, low sperm count, impaired sperm motility, impaired sperm viability, low testosterone levels, reduced libido, erectile dysfunction, underdevelopment of testes, or excess apoptosis in testes.

Biologically active fragments or variants of the therapeutic agents are also within the scope of the present invention. By "biologically active" is meant capable of modulating the OST-PTP signaling pathway or the PTP-1B signaling pathway involving gamma-carboxylase and osteocalcin. "Biologically active" may also mean reducing the expression of OST-PTP or its ability to dephosphorylate gamma-carboxylase and reducing the expression of gamma-carboxylase or its ability to carboxylate osteocalcin, or decarboxylating carboxylated osteocalcin thereby leading to increased levels of undercarboxylated/uncarboxylated osteocalcin.

"Biologically active" also means reducing the expression of PTP-1B or its ability to dephosphorylate gamma-carboxylase and reducing the expression of gamma-carboxylase or its ability to carboxylate osteocalcin, or decarboxylating carboxylated osteocalcin thereby leading to increased levels of undercarboxylated/uncarboxylated osteocalcin.

"Biologically active" also refers to fragments or variants of osteocalcin that retain the ability of undercarboxylated/uncarboxylated osteocalcin to treat or prevent a disorder related to reproduction in male mammals.

"Biologically active" also means capable of producing at least one effect in a male mammal selected from the group consisting of increasing fertility, raising sperm count, increasing sperm motility, increasing sperm viability, increasing serum testosterone levels, increasing libido, ameliorating erectile dysfunction, reducing underdevelopment of testes, and reducing excess apoptosis in testes.

Pharmaceutical Compositions Comprising Undercarboxylated/Uncarboxylated Osteocalcin In a specific embodiment of the invention, pharmaceutical compositions comprising undercarboxylated/uncarboxylated osteocalcin are provided for use in treating or preventing a disorder related to reproduction in a male mammal.

"Undercarboxylated osteocalcin" means osteocalcin in which one or more of the Glu residues at positions Glu17, Glu21 and Glu24 of the amino acid sequence of the mature human osteocalcin having 49 amino acids, or at the positions corresponding to Glu17, Glu21 and Glu24 in other forms of osteocalcin, are not carboxylated. Undercarboxylated osteocalcin includes "uncarboxylated osteocalcin," i.e., osteocalcin in which all three of the glutamic acid residues at positions 17, 21, and 24 are not carboxylated. Preparations of osteocalcin are considered to be "undercarboxylated osteocalcin" if more than about 10% of the total Glu residues at positions Glu17, Glu21 and Glu24 (taken together) in mature osteocalcin (or the corresponding Glu residues in other forms) of the preparation are not carboxylated. In particular preparations of undercarboxylated osteocalcin, more than about 20%, more than about 30%, more than about 40%, more than about 50%, more than about 60%, more than about 70%, more than about 80%, more than about 90%, more than about 95%, or more than about 99% of the total Glu residues at positions Glu17, Glu21 and Glu24 in mature osteocalcin (or the corresponding Glu residues in other forms) of the preparation are not carboxylated. In particularly preferred embodiments, essentially all of the Glu residues at positions Glu17, Glu21 and Glu24 in mature osteocalcin (or the corresponding Glu residues in other forms) of the preparation are not carboxylated.

"Undercarboxylated/uncarboxylated osteocalcin" is used herein to refer collectively to undercarboxylated and uncarboxylated osteocalcin.

Human osteocalcin cDNA (SEQ ID NO:1) encodes a mature osteocalcin protein represented by the last 49 amino acids of SEQ ID NO:2 (i.e., positions 52-100) with a predicted molecular mass of 5,800 kDa (Poser et al., 1980, J. Biol. Chem. 255:8685-8691). SEQ ID NO:2 is the pre-prosequence of human osteocalcin encoded by SEQ ID NO:1 and mature human osteocalcin (SEQ ID NO:12) is the processed product of SEQ ID NO:2. In this application, the amino acid positions of mature human osteocalcin are referred to. It will be understood that the amino acid positions of mature human osteocalcin correspond to those of SEQ ID NO:2 as follows: position 1 of mature human osteocalcin corresponds to position 52 of SEQ ID NO:2; position 2 of mature human osteocalcin corresponds to position 53 of SEQ ID NO:2, etc. In particular, positions 17, 21, and 24 of mature human osteocalcin correspond to positions 68, 72, and 75, respectively, of SEQ ID NO:2.

When positions in two amino acid sequences correspond, it is meant that the two positions align with each other when the two amino acid sequences are aligned with one another to provide maximum homology between them. This same concept of correspondence also applies to nucleic acids.

For example, in the two amino acid sequences AGLYSTVLMGRPS and GLVSTVLMGN, positions 2-11 of the first sequence correspond to positions 1-10 of the second sequence, respectively. Thus, position 2 of the first sequence corresponds to position 1 of the second sequence; position 4 of the first sequence corresponds to position 3 of the second sequence; etc. It should be noted that a position in one sequence may correspond to a position in another sequence, even if the positions in the two sequence are not occupied by the same amino acid.

"Osteocalcin" includes the mature protein and further includes biologically active fragments derived from full-length osteocalcin (SEQ ID NO:2) or the mature protein, including various domains, as well as variants as described herein.

In one embodiment of the present invention, the pharmaceutical compositions for use in the methods of the invention comprise a mammalian uncarboxylated osteocalcin. In a preferred embodiment of the invention, the compositions for use in the methods of the invention comprise human uncarboxylated osteocalcin having the amino acid sequence of SEQ ID NO:2, or portions thereof, and encoded for by the nucleic acid of SEQ ID NO:1, or portions thereof. In some embodiments, the compositions for use in the methods of the invention may comprise one or more of the human osteocalcin fragments described herein.

In a preferred embodiment of the invention, the compositions for use in the methods of the invention comprise human uncarboxylated osteocalcin having the amino acid sequence of SEQ ID NO:12.

In a specific embodiment, the present invention provides pharmaceutical compositions comprising human undercarboxylated osteocalcin which does not contain a carboxylated glutamic acid at one or more of positions corresponding to positions 17, 21 and 24 of mature human osteocalcin. A preferred form of osteocalcin for use in the methods of the present invention is mature human osteocalcin wherein at least one of the glutamic acid residues at positions 17, 21, and 24 is not carboxylated. In certain embodiments, the glutamic acid residue at position 17 is not carboxylated. Preferably, all three of the glutamic acid residues at positions 17, 21, and 24 are not carboxylated. The amino acid sequence of mature human osteocalcin is shown in SEQ. ID. NO:12.

The primary sequence of osteocalcin is highly conserved among species and it is one of the ten most abundant proteins in the human body, suggesting that its function is preserved throughout evolution. Conserved features include 3 Gla residues at positions 17, 21, and 24 and a disulfide bridge between Cys23 and Cys29. In addition, most species contain a hydroxyproline at position 9. The N-terminus of osteocalcin shows highest sequence variation in comparison to other parts of the molecule. The high degree of conservation of human and mouse osteocalcin underscores the relevance of the mouse as an animal model for the human, in both healthy and diseased states, and validates the therapeutic and diagnostic use of osteocalcin to treat or prevent disorders related to reproduction in male humans based on the experimental data derived from the mouse model disclosed herein.

The present invention also includes the use of polypeptide fragments of osteocalcin. Fragments can be derived from the full-length, naturally occurring amino acid sequence of osteocalcin (e.g., SEQ. ID. NO:2). Fragments may also be derived from mature osteocalcin (e.g., SEQ. ID. NO:12). The invention also encompasses fragments of the variants of osteocalcin described herein. A fragment can comprise an amino acid sequence of any length that is biologically active.

Preferred fragments of osteocalcin include fragments containing Glu17, Glu21 and Glu24 of the mature protein. Also preferred are fragments of the mature protein missing the last 10 amino acids from the C-terminal end of the mature protein. Also preferred are fragments missing the first 10 amino acids from the N-terminal end of the mature protein. Also preferred is a fragment of the mature protein missing both the last 10 amino acids from the C-terminal end and the first 10 amino acids from the N-terminal end. Such a fragment comprises amino acids 62-90 of SEQ ID NO:2.

Other preferred fragments of osteocalcin for the pharmaceutical compositions of the invention described herein include polypeptides comprising, consisting of, or consisting essentially of, the following sequences of amino acids:

positions 1-19 of mature human osteocalcin
positions 20-43 of mature human osteocalcin
positions 20-49 of mature human osteocalcin
positions 1-43 of mature human osteocalcin
positions 1-42 of mature human osteocalcin
positions 1-41 of mature human osteocalcin
positions 1-40 of mature human osteocalcin
positions 1-39 of mature human osteocalcin
positions 1-38 of mature human osteocalcin
positions 1-37 of mature human osteocalcin
positions 1-36 of mature human osteocalcin
positions 1-35 of mature human osteocalcin
positions 1-34 of mature human osteocalcin
positions 1-33 of mature human osteocalcin
positions 1-32 of mature human osteocalcin
positions 1-31 of mature human osteocalcin
positions 1-30 of mature human osteocalcin
positions 1-29 of mature human osteocalcin
positions 2-49 of mature human osteocalcin
positions 2-45 of mature human osteocalcin
positions 2-40 of mature human osteocalcin
positions 2-35 of mature human osteocalcin
positions 2-30 of mature human osteocalcin
positions 2-25 of mature human osteocalcin
positions 2-20 of mature human osteocalcin
positions 4-49 of mature human osteocalcin
positions 4-45 of mature human osteocalcin
positions 4-40 of mature human osteocalcin
positions 4-35 of mature human osteocalcin
positions 4-30 of mature human osteocalcin
positions 4-25 of mature human osteocalcin
positions 4-20 of mature human osteocalcin
positions 8-49 of mature human osteocalcin
positions 8-45 of mature human osteocalcin
positions 8-40 of mature human osteocalcin
positions 8-35 of mature human osteocalcin
positions 8-30 of mature human osteocalcin
positions 8-25 of mature human osteocalcin
positions 8-20 of mature human osteocalcin
positions 10-49 of mature human osteocalcin
positions 10-45 of mature human osteocalcin
positions 10-40 of mature human osteocalcin
positions 10-35 of mature human osteocalcin
positions 10-30 of mature human osteocalcin
positions 10-25 of mature human osteocalcin
positions 10-20 of mature human osteocalcin
positions 6-34 of mature human osteocalcin
positions 6-35 of mature human osteocalcin
positions 6-36 of mature human osteocalcin
positions 6-37 of mature human osteocalcin
positions 6-38 of mature human osteocalcin
positions 7-34 of mature human osteocalcin
positions 7-35 of mature human osteocalcin
positions 7-36 of mature human osteocalcin
positions 7-37 of mature human osteocalcin
positions 7-38 of mature human osteocalcin
positions 7-30 of mature human osteocalcin
positions 7-25 of mature human osteocalcin
positions 7-23 of mature human osteocalcin
positions 7-21 of mature human osteocalcin
positions 7-19 of mature human osteocalcin
positions 7-17 of mature human osteocalcin
positions 8-30 of mature human osteocalcin
positions 8-25 of mature human osteocalcin
positions 8-23 of mature human osteocalcin
positions 8-21 of mature human osteocalcin
positions 8-19 of mature human osteocalcin
positions 8-17 of mature human osteocalcin
positions 9-30 of mature human osteocalcin
positions 9-25 of mature human osteocalcin
positions 9-23 of mature human osteocalcin
positions 9-21 of mature human osteocalcin
positions 9-19 of mature human osteocalcin
positions 9-17 of mature human osteocalcin Especially preferred is a fragment comprising positions 1-36 of mature human osteocalcin. Another preferred fragment is a fragment comprising positions 20-49 of mature human osteocalcin. Other fragments can be designed to contain Pro13 to Tyr76 or Pro 13 to Asn26 of mature human osteocalcin. Additionally, fragments containing the cysteine residues at positions 23 and 29 of mature human osteocalcin, and capable of forming a disulfide bond between those two cysteines, are useful.

Fragments can be discrete (not fused to other amino acids or polypeptides) or can be within a larger polypeptide. Further, several fragments can be comprised within a single larger polypeptide. In one embodiment, a fragment designed for expression in a host can have heterologous pre- and pro-polypeptide regions fused to the amino terminus of the osteocalcin fragment and/or an additional region fused to the carboxyl terminus of the fragment.

Also provided for use in the compositions and methods of the present invention are variants of osteocalcin and the osteocalcin fragments described above. "Variants" refers to osteocalcin peptides that contain modifications in their amino acid sequences such as one or more amino acid substitutions, additions, deletions and/or insertions but that are still biologically active. In some instances, the antigenic and/or immunogenic properties of the variants are not substantially altered, relative to the corresponding peptide from which the variant was derived. Such modifications may be readily introduced using standard mutagenesis techniques, such as oligonucleotide directed site-specific mutagenesis as taught, for example, by Adelman et al., 1983, DNA 2:183, or by chemical synthesis. Variants and fragments are not mutually exclusive terms. Fragments also include peptides that may contain one or more amino acid substitutions, additions, deletions and/or insertions such that the fragments are still biologically active.

One particular type of variant that is within the scope of the present invention is a variant in which one of more of the positions corresponding to positions 17, 21 and 24 of mature human osteocalcin is occupied by an amino acid that is not glutamic acid. In some embodiments, the amino acid that is not glutamic acid is also not aspartic acid. Such variants are versions of undercarboxylated osteocalcin because at least one of the three positions corresponding to positions 17, 21 and 24 of mature human osteocalcin is not carboxylated glutamic acid, since at least one of those positions is not occupied by glutamic acid.

In particular embodiments, the present invention provides osteocalcin variants comprising the amino acid sequence YLYQWLGAPV PYPDPLX$_1$PRR X$_2$VCX$_3$LNPDCD ELADHIGFQE AYRRFYGPV (SEQ. ID. NO:13) wherein X$_1$, X$_2$ and X$_3$ are each independently selected from an amino acid or amino acid analog, with the proviso that if X$_1$, $X_2$ and $X_3$ are each glutamic acid, then $X_1$ is not carboxylated, or less than 50 percent of $X_2$ is carboxylated, and/or less than 50 percent of $X_3$ is carboxylated.

In certain embodiments, the osteocalcin variants comprise an amino acid sequence that is different from SEQ. ID. NO:13 at 1 to 7 positions other than $X_1$, $X_2$ and $X_3$.

In other embodiments, the osteocalcin variants comprise an amino acid sequence that includes one or more amide backbone substitutions.

Fully functional variants typically contain only conservative variation or variation in non-critical residues or in non-critical regions. Functional variants can also contain substitutions of similar amino acids, which results in no change, or an insignificant change, in function. Alternatively, such substitutions may positively or negatively affect function to some degree. The activity of such functional osteocalcin variants can be determined using assays such as those described herein.

Variants can be naturally-occurring or can be made by recombinant means, or chemical synthesis, to provide useful and novel characteristics for undercarboxylated/uncarboxylated osteocalcin. For example, the variant osteocalcin polypeptides may have reduced immunogenicity, increased serum half-life, increased bioavailability and/or increased potency. In particular embodiments, serum half-life is increased by substituting one or more of the native Arg residues at positions 19, 20, 43, and 44 of mature osteocalcin with another amino acid or an amino acid analog, e.g., β-dimethyl-arginine. Such substitutions can be combined with the other changes in the native amino acid sequence of osteocalcin described herein.

Provided for use in the pharmaceutical compositions and methods of the present invention are variants that are also derivatives of the osteocalcin and osteocalcin fragments described above. Derivatization is a technique used in chemistry which transforms a chemical compound into a product of similar chemical structure, called derivative. Generally, a specific functional group of the compound participates in the derivatization reaction and transforms the compound to a derivate of different reactivity, solubility, boiling point, melting point, aggregate state, functional activity, or chemical composition. Resulting new chemical properties can be used for quantification or separation of the derivatized compound or can be used to optimize the derivatized compound as a therapeutic agent. The well-known techniques for derivatization can be applied to the above-described osteocalcin and osteocalcin fragments. Thus, derivatives of the osteocalcin and osteocalcin fragments described above will contain amino acids that have been chemically modified in some way so that they differ from the natural amino acids.

Provided also are osteocalcin mimetics. "Mimetic" refers to a synthetic chemical compound that has substantially the same structural and functional characteristics of a naturally or non-naturally occurring osteocalcin polypeptide, and includes, for instance, polypeptide- and polynucleotide-like polymers having modified backbones, side chains, and/or bases. Peptide mimetics are commonly used in the pharmaceutical industry as non-peptide drugs with properties analogous to those of the template peptide. Generally, mimetics are structurally similar (i.e., have the same shape) to a paradigm polypeptide that has a biological or pharmacological activity, but one or more polypeptide linkages are replaced. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity.

By way of examples that can be adapted to osteocalcin by those skilled in the art: Cho et al., 1993, Science 261:1303-1305 discloses an "unnatural biopolymer" consisting of chiral aminocarbonate monomers substituted with a variety of side chains, synthesis of a library of such polymers, and screening for binding affinity to a monoclonal antibody. Simon et al., 1992, Proc. Natl. Acad. Sci. 89:9367-9371 discloses a polymer consisting of N-substituted glycines ("peptoids") with diverse side chains. Schumacher et al, 1996, Science 271:1854-1857 discloses D-peptide ligands identified by screening phage libraries of L-peptides against proteins synthesized with D-amino acids and then synthesizing a selected L-peptide using D-amino acids. Brody et al., 1999, Mol. Diagn. 4:381-8 describes generation and screening of hundreds to thousands of aptamers.

A particular type of osteocalcin variant within the scope of the invention is an osteocalcin mimetic in which one or more backbone amides is replaced by a different chemical structure or in which one or more amino acids are replaced by an amino acid analog. In a particular embodiment, the osteocalcin mimetic is a retroenantiomer of uncarboxylated human osteocalcin.

Osteocalcin, as well as its fragments and variants, is optionally produced by chemical synthesis or recombinant methods and may be produced as a modified osteocalcin molecule (i.e., osteocalcin fragments or variants) as described herein. Osteocalcin polypeptides can be produced by any conventional means (Houghten, 1985, Proc. Natl. Acad. Sci. USA 82:5131-5135). Simultaneous multiple peptide synthesis is described in U.S. Pat. No. 4,631,211 and can also be used. When produced recombinantly, osteocalcin may be produced as a fusion protein, e.g., a GST-osteocalcin fusion protein.

Undercarboxylated/uncarboxylated osteocalcin molecules that can be used in the methods of the invention include proteins substantially homologous to human osteocalcin, including proteins derived from another organism, i.e., an ortholog of human osteocalcin. One particular ortholog is mouse osteocalcin. Mouse osteocalcin gene 1 cDNA is SEQ ID NO:3; mouse osteocalcin gene 2 cDNA is SEQ ID NO:4; the amino acid sequence of mouse osteocalcin gene 1 and gene 2 is SEQ ID NO:5.

As used herein, two proteins are substantially homologous when their amino acid sequences are at least about 70-75% homologous. Typically the degree of homology is at least about 80-85%, and most typically at least about 90-95%, 97%, 98% or 99% or more. "Homology" between two amino acid sequences or nucleic acid sequences can be determined by using the algorithms disclosed herein. These algorithms can also be used to determine percent identity between two amino acid sequences or nucleic acid sequences.

In a specific embodiment of the invention, the undercarboxylated/uncarboxylated osteocalcin is an osteocalcin molecule sharing at least 80% homology with the human osteocalcin of SEQ ID:2 or a portion of SEQ ID:2 that is at least 8 amino acids long. In another embodiment, the undercarboxylated/uncarboxylated osteocalcin is an osteocalcin molecule sharing at least 80%, at least 90%, at least 95%, or at least 97% amino acid sequence identity with the human osteocalcin of SEQ ID:2 or a portion of SEQ ID:2 that is at least 8 amino acids long. Homologous sequences include those sequences that are substantially identical. In preferred embodiments, the homology or identity is over the entire length of mature human osteocalcin.

To determine the percent homology or percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). Preferably, the length of a reference sequence aligned for comparison purposes is at least 30%, preferably at least 40%, more preferably at least 50%, even more preferably at least 60%, and even more preferably at least 70%, 80%, or 90% or more of the length of the sequence that the reference sequence is compared to. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position. The percent identity between the two sequences is a function of the number of identical positions shared by the sequences, taking into account the number of gaps, and the length of each gap, which need to be introduced for optimal alignment of the two sequences.

The invention also encompasses polypeptides having a lower degree of identity but which have sufficient similarity so as to perform one or more of the same functions performed by undercarboxylated/uncarboxylated osteocalcin. Similarity is determined by considering conserved amino acid substitutions. Such substitutions are those that substitute a given amino acid in a polypeptide by another amino acid of like characteristics. Conservative substitutions are likely to be phenotypically silent. Guidance concerning which amino acid changes are likely to be phenotypically silent may be found in Bowie et al., 1990, Science 247:1306-1310.

Examples of conservative substitutions are the replacements, one for another, among the hydrophobic amino acids Ala, Val, Leu, and Ile; interchange of the hydroxyl residues Ser and Thr; exchange of the acidic residues Asp and Glu; substitution between the amide residues Asn and Gln; exchange of the basic residues Lys, His and Arg; replacements among the aromatic residues Phe, Trp and Tyr; exchange of the polar residues Gln and Asn; and exchange of the small residues Ala, Ser, Thr, Met, and Gly.

The comparison of sequences and determination of percent identity and homology between two osteocalcin polypeptides can be accomplished using a mathematical algorithm. See, for example, Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H G., eds., Humana Press, New Jersey, 1994; Sequence Analysis in Molecular Biology, van Heinje, G., Academic Press, 1987; and Sequence Analysis Primer, Gribskov, M. and Devereux, J., eds., M Stockton Press, New York, 1991. A non-limiting example of such a mathematical algorithm is described in Karlin et al., 1993, Proc. Natl. Acad. Sci. USA 90:5873-5877.

The percent identity or homology between two osteocalcin amino acid sequences may be determined using the Needleman et al., 1970, J. Mol. Biol. 48:444-453 algorithm.

A substantially homologous osteocalcin, according to the present invention, may also be a polypeptide encoded by a nucleic acid sequence capable of hybridizing to the human osteocalcin nucleic acid sequence under highly stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel et al., eds., 1989, Current Protocols in Molecular Biology, Vol. I, Green Publishing Associates, Inc., and John Wiley & sons, Inc., New York, at p. 2.10.3) and encoding a functionally equivalent gene product; or under less stringent conditions, such as moderately stringent conditions, e.g., washing in 0.2×SSC/0.1% SDS at 42° C. (Ausubel et al., 1989 supra), yet which still encodes a biologically active undercarboxylated/uncarboxylated osteocalcin.

A substantially homologous osteocalcin according to the present invention may also be a polypeptide encoded by a nucleic acid sequence capable of hybridizing to a sequence having at least 70-75%, typically at least about 80-85%, and most typically at least about 90-95%, 97%, 98% or 99% identity to the human osteocalcin nucleic acid sequence, under stringent conditions, e.g., hybridization to filter-bound DNA in 0.5 M $NaHPO_4$, 7% sodium dodecyl sulfate (SDS), 1 mM EDTA at 65° C., and washing in 0.1×SSC/0.1% SDS at 68° C. (Ausubel F. M. et al., eds., 1989, Current Protocols in Molecular Biology, Vol. I, Green Publishing Associates, Inc., and John Wiley & sons, Inc., New York, at p. 2.10.3) and encoding a functionally equivalent gene product; or under less stringent conditions, such as moderately stringent conditions, e.g., washing in 0.2×SSC/0.1% SDS at 42° C. (Ausubel et al., 1989 supra), yet which still encodes a biologically active undercarboxylated/uncarboxylated osteocalcin.

It will be understood that a biologically active fragment or variant of human osteocalcin may contain a different number of amino acids than native human osteocalcin. Accordingly, the position number of the amino acid residues corresponding to positions 17, 21 and 24 of mature human osteocalcin may differ in the fragment or variant. One skilled in the art would easily recognize such corresponding positions from a comparison of the amino acid sequence of the fragment or variant with the amino acid sequence of mature human osteocalcin.

Peptides corresponding to fusion proteins in which full length osteocalcin, mature osteocalcin, or an osteocalcin fragment or variant is fused to an unrelated protein or polypeptide are also within the scope of the invention and can be designed on the basis of the osteocalcin nucleotide and amino acid sequences disclosed herein. Such fusion proteins include fusions to an enzyme, fluorescent protein, or luminescent protein which provides a marker function. In a preferred embodiment of the invention, the fusion protein comprises fusion to a polypeptide capable of targeting the osteocalcin to a particular target cell or location in the body. For example, osteocalcin polypeptide sequences may be fused to a ligand molecule capable of targeting the fusion protein to a cell expressing the receptor for said ligand. In a particular embodiment, osteocalcin polypeptide sequences may be fused to a ligand capable of targeting the fusion protein to cells of the testes, e.g., Leydig cells.

Osteocalcin can also be made as part of a chimeric protein for drug screening or use in making recombinant protein. These chimeric proteins comprise an osteocalcin peptide sequence linked to a heterologous peptide having an amino acid sequence not substantially homologous to the osteocalcin. The heterologous peptide can be fused to the N-terminus or C-terminus of osteocalcin or can be internally located. In one embodiment, the fusion protein does not affect osteocalcin function. For example, the fusion protein can be a GST-fusion protein in which the osteocalcin sequences are fused to the N- or C-terminus of the GST sequences. Other types of fusion proteins include, but are not limited to, enzymatic fusion proteins, for example beta-galactosidase fusions, yeast two-hybrid GAL-4 fusions, poly-His fusions and Ig fusions. Such fusion proteins, particularly poly-His fusions, can facilitate the purification of recombinant osteocalcin. In certain host cells (e.g., mammalian host cells), expression and/or secretion of a protein can be increased by using a heterologous signal sequence. Therefore, the fusion protein may contain a heterologous signal sequence at its N-terminus.

Those skilled in art would understand how to adapt well-known techniques for use with osteocalcin. For example, EP 0 464 533 discloses fusion proteins comprising various portions of immunoglobulin constant regions (Fc regions). The Fc region is useful in therapy and diagnosis and thus results, for example, in improved pharmacokinetic properties (see, e.g., EP 0 232 262). In drug discovery, for example, human proteins have been fused with Fc regions for the purpose of high-throughput screening assays to identify antagonists (Bennett et al., 1995, J. Mol. Recog. 8:52-58 and Johanson et al., 1995, J. Biol. Chem. 270:9459-9471). Thus, various embodiments of this invention also utilize soluble fusion proteins containing an osteocalcin polypeptide and various portions of the constant regions of heavy or light chains of immunoglobulins of various subclasses (e.g., IgG, IgM, IgA, IgE, IgB). Preferred as immunoglobulin is the constant part of the heavy chain of human IgG, particularly IgG1, where fusion takes place at the hinge region. For some uses, it is desirable to remove the Fc region after the fusion protein has been used for its intended purpose. In a particular embodiment, the Fc part can be removed in a simple way by a cleavage sequence, which is also incorporated and can be cleaved, e.g., with factor Xa.

A chimeric or fusion protein can be produced by standard recombinant DNA techniques. For example, DNA fragments coding for the different protein sequences can be ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al., 1992, Current Protocols in Molecular Biology). Moreover, many expression vectors are commercially available that already encode a fusion moiety (e.g., a GST protein). An osteocalcin-encoding nucleic acid can be cloned into such an expression vector such that the fusion moiety is linked in-frame to osteocalcin.

Chimeric osteocalcin proteins can be produced in which one or more functional sites are derived from a different isoform, or from another osteocalcin molecule from another species. Sites also could be derived from osteocalcin-related proteins that occur in the mammalian genome but which have not yet been discovered or characterized.

Polypeptides often contain amino acids other than the 20 amino acids commonly referred to as the 20 naturally-occurring amino acids. Further, many amino acids, including the terminal amino acids, may be modified by natural processes, such as processing and other post-translational modifications, or by chemical modification techniques well known in the art.

Accordingly, the osteocalcin polypeptides useful in the methods of the present invention also encompass derivatives which contain a substituted non-naturally occurring amino acid residue that is not one encoded by the genetic code, in which a substituent group is included, in which the mature polypeptide is fused with another compound, such as a compound to increase the half-life of the polypeptide (for example, polyethylene glycol), or in which the additional amino acids are fused to the osteocalcin polypeptide, such as a leader or secretory sequence or a sequence for purification of the osteocalcin polypeptide or a pro-protein sequence.

Undercarboxylated/uncarboxylated osteocalcin can be modified according to known methods in medicinal chemistry to increase its stability, half-life, uptake or efficacy. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent crosslinks, formation of cystine, formation of pyroglutamate, formylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

In a specific embodiment of the invention, modifications may be made to the osteocalcin to reduce susceptibility to proteolysis at residue Arg43 as a means for increasing serum half life. Such modifications include, for example, the use of retroenantio isomers, D-amino acids, or other amino acid analogs.

Acylation of the N-terminal amino group can be accomplished using a hydrophilic compound, such as hydroorotic acid or the like, or by reaction with a suitable isocyanate, such as methylisocyanate or isopropylisocyanate, to create a urea moiety at the N-terminus. Other agents can also be N-terminally linked that will increase the duration of action of the osteocalcin derivative.

Reductive amination is the process by which ammonia is condensed with aldehydes or ketones to form imines which are subsequently reduced to amines. Reductive amination is a useful method for conjugating undercarboxylated/uncarboxylated osteocalcin and its fragments or variants to polyethylene glycol (PEG). Covalent linkage of PEG to undercarboxylated/uncarboxylated osteocalcin and its fragments and variants may result in conjugates with increased water solubility, altered bioavailability, pharmacokinetics, immunogenic properties, and biological activities. See, e.g., Bentley et al., 1998, J. Pharm. Sci. 87:1446-1449.

Several particularly common modifications that may be applied to undercarboxylated/uncarboxylated osteocalcin and its fragments and variants such as glycosylation, lipid attachment, sulfation, hydroxylation and ADP-ribosylation are described in most basic texts, such as Proteins-Structure and Molecular Properties, 2nd ed., T. E. Creighton, W.H. Freeman and Company, New York (1993). Many detailed reviews are available on this subject, such as by Wold, F., Posttranslational Covalent Modification of Proteins, B. C. Johnson, Ed., Academic Press, New York 1-12 (1983); Seifter et al., 1990, Meth. Enzymol. 182:626-646 and Rattan et al., 1992, Ann. New York Acad. Sci. 663:48-62.

As is also well known, polypeptides are not always entirely linear. For instance, polypeptides may be branched as a result of ubiquitination, and they may be circular, with or without branching, generally as a result of post-translation events, including natural processing events and events brought about by human manipulation which do not occur naturally. Circular, branched and branched circular polypeptides may be synthesized by non-translational natural processes and by synthetic methods. Well-known techniques for preparing such non-linear polypeptides may be adapted by those skilled in the art to produce non-linear osteocalcin polypeptides.

Modifications can occur anywhere in the undercarboxylated/uncarboxylated osteocalcin and its fragments and variants, including the peptide backbone, the amino acid side-chains and the amino or carboxyl termini. Blockage of the amino or carboxyl group in a polypeptide, or both, by a covalent modification, is common in naturally-occurring and synthetic polypeptides and may be applied to the undercarboxylated/uncarboxylated osteocalcin or its fragments and variants used in the present invention. For instance, the amino terminal residue of polypeptides made in E. coli, prior to proteolytic processing, almost invariably will be N-formylmethionine. Thus, the use of undercarboxylated/uncarboxylated osteocalcin and its fragments and variants with N-formylmethionine as the amino terminal residue are within the scope of the present invention.

A brief description of various protein modifications that come within the scope of this invention are set forth in the table below:

TABLE 1

| Protein Modification | Description |
| --- | --- |
| Acetylation | Acetylation of N-terminus or ε-lysines. Introducing an acetyl group into a protein, specifically, the substitution of an acetyl group for an active hydrogen atom. A reaction involving the replacement of the hydrogen atom of a hydroxyl group with an acetyl group ($CH_3CO$) yields a specific ester, the acetate. Acetic anhydride is commonly used as an acetylating agent, which reacts with free hydroxyl groups. Acylation may facilitate addition of other functional groups. A common reaction is acylation of e.g., conserved lysine residues with a biotin appendage. |
| ADP-ribosylation | Covalently linking proteins or other compounds via an arginine-specific reaction. |
| Alkylation | Alkylation is the transfer of an alkyl group from one molecule to another. The alkyl group may be transferred as an alkyl carbocation, a free radical or a carbanion (or their equivalents). Alkylation is accomplished by using certain functional groups such as alkyl electrophiles, alkyl nucleophiles or sometimes alkyl radicals or carbene acceptors. A common example is methylation (usually at a lysine or arginine residue). |
| Amidation | Reductive animation of the N-terminus. Methods for amidation of insulin are described in U.S. Pat. No. 4,489,159. |
| Carbamylation | Nigen et al. describes a method of carbamylating hemoglobin. |
| Citrullination | Citrullination involves the addition of citrulline amino acids to the arginine residues of a protein, which is catalyzed by peptidylarginine deaminase enzymes (PADs). This generally converts a positively charged arginine into a neutral citrulline residue, which may affect the hydrophobicity of the protein (and can lead to unfolding). |
| Condensation of amines with aspartate or glutamate | Such reactions, may be used, e.g., to attach a peptide to other proteins labels. |
| Covalent attachment of flavin | Flavin mononucleotide (FAD) may be covalently attached to serine and/or threonine residues. May be used, e.g., as a light-activated tag. |
| Covalent attachment of heme moiety | A heme moiety is generally a prosthetic group that consists of an iron atom contained in the center of a large heterocyclic organic ring, which is referred to as a porphyrin. The heme moiety may be used, e.g., as a tag for the peptide. |
| Attachment of a nucleotide or nucleotide derivative | May be used as a tag or as a basis for further derivatising a peptide. |
| Cross-linking | Cross-linking is a method of covalently joining two proteins. Cross-linkers contain reactive ends to specific functional groups (primary amines, sulfhydryls, etc.) on proteins or other molecules. Several chemical groups may be targets for reactions in proteins and peptides. For example, Ethylene glycol bis[succinimidylsuccinate, Bis[2-(succinimidooxycarbonyloxy)ethyl]sulfone, and Bis[sulfosuccinimidyl] suberate link amines to amines. |
| Cyclization | For example, cyclization of amino acids to create optimized delivery forms that are resistant to, e.g., aminopeptidases (e.g., formation of pyroglutamate, a cyclized form of glutamic acid). |
| Disulfide bond formation | Disulfide bonds in proteins are formed by thiol-disulfide exchange reactions, particularly between cysteine residues (e.g., formation of cystine). |
| Demethylation | See, e.g., U.S. Pat. No. 4,250,088 (Process for demethylating lignin). |
| Formylation | The addition of a formyl group to, e.g., the N-terminus of a protein. See, e.g., U.S. Pat. Nos. 4,059,589, 4,801,742, and 6,350,902. |
| Glycylation | The covalent linkage of one to more than 40 glycine residues to the tubulin C-terminal tail. |
| Glycosylation | Glycosylation may be used to add saccharides (or polysaccharides) to the hydroxy oxygen atoms of serine and threonine side chains (which is also known as O-linked Glycosylation). Glycosylation may also be used to add |

TABLE 1-continued

| Protein Modification | Description |
|---|---|
| | saccharides (or polysaccharides) to the amide nitrogen of asparagine side chains (which is also known as N-linked Glycosylation), e.g., via oligosaccharyl transferase. |
| GPI anchor formation | The addition of glycosylphosphatidylinositol to the C-terminus of a protein. GPI anchor formation involves the addition of a hydrophobic phosphatidylinositol group-linked through a carbohydrate containing linker (e.g., glucosamine and mannose linked to phosphoryl ethanolamine residue)-to the C-terminal amino acid of a protein. |
| Hydroxylation | Chemical process that introduces one or more hydroxyl groups (—OH) into a protein (or radical). Hydroxylation reactions are typically catalyzed by hydroxylases. Proline is the principal residue to be hydroxylated in proteins, which occurs at the $C^\gamma$ atom, forming hydroxyproline (Hyp). In some cases, proline may be hydroxylated at its $C^\beta$ atom. Lysine may also be hydroxylated on its $C^\delta$ atom, forming hydroxylysine (Hyl). These three reactions are catalyzed by large, multi-subunit enzymes known as prolyl 4-hydroxylase, prolyl 3-hydroxylase and lysyl 5-hydroxylase, respectively. These reactions require iron (as well as molecular oxygen and α-ketoglutarate) to carry out the oxidation, and use ascorbic acid to return the iron to its reduced state. |
| Iodination | See, e.g., U.S. Pat. No. 6,303,326 for a disclosure of an enzyme that is capable of iodinating proteins. U.S. Pat. No. 4,448,764 discloses, e.g., a reagent that may be used to iodinate proteins. |
| ISGylation | Covalently linking a peptide to the ISG15 (Interferon-Stimulated Gene 15) protein, for, e.g., modulating immune response. |
| Methylation | Reductive methylation of protein amino acids with formaldehyde and sodium cyanoborohydride has been shown to provide up to 25% yield of N-cyanomethyl (—CH$_2$CN) product. The addition of metal ions, such as Ni$^{2+}$, which complex with free cyanide ions, improves reductive methylation yields by suppressing by-product formation. The N-cyanomethyl group itself, produced in good yield when cyanide ion replaces cyanoborohydride, may have some value as a reversible modifier of amino groups in proteins. (Gidley et al.) Methylation may occur at the arginine and lysine residues of a protein, as well as the N- and C-terminus thereof. |
| Myristoylation | Myristoylation involves the covalent attachment of a myristoyl group (a derivative of myristic acid), via an amide bond, to the alpha-amino group of an N-terminal glycine residue. This addition is catalyzed by the N-myristoyltransferase enzyme. |
| Oxidation | Oxidation of cysteines.<br>Oxidation of N-terminal Serine or Threonine residues (followed by hydrazine or aminooxy condensations).<br>Oxidation of glycosylations (followed by hydrazine or aminooxy condensations). |
| Palmitoylation | Palmitoylation is the attachment of fatty acids, such as palmitic acid, to cysteine residues of proteins. Palmitoylation increases the hydrophobicity of a protein. |
| (Poly)glutamylation | Polyglutamylation occurs at the glutamate residues of a protein. Specifically, the gamma-carboxy group of a glutamate will form a peptide-like bond with the amino group of a free glutamate whose alpha-carboxy group may be extended into a polyglutamate chain. The glutamylation reaction is catalyzed by a glutamylase enzyme (or removed by a deglutamylase enzyme). Polyglutamylation has been carried out at the C-terminus of proteins to add up to about six glutamate residues. Using such a reaction, Tubulin and other proteins can be covalently linked to glutamic acid residues. |
| Phosphopantetheinylation | The addition of a 4'-phosphopantetheinyl group. |
| Phosphorylation | A process for phosphorylation of a protein or peptide by contacting a protein or peptide with phosphoric acid in the presence of a non-aqueous apolar organic solvent and contacting the resultant solution with a dehydrating agent is disclosed e.g., in U.S. Pat. No. 4,534,894. Insulin products are described to be amenable to this process. See, e.g., U.S. Pat. No. 4,534,894. Typically, phosphorylation occurs at the serine, threonine, and tyrosine residues of a protein. |

TABLE 1-continued

| Protein Modification | Description |
|---|---|
| Prenylation | Prenylation (or isoprenylation or lipidation) is the addition of hydrophobic molecules to a protein. Protein prenylation involves the transfer of either a farnesyl (linear grouping of three isoprene units) or a geranyl-geranyl moiety to C-terminal cysteine(s) of the target protein. |
| Proteolytic Processing | Processing, e.g., cleavage of a protein at a peptide bond. |
| Selenoylation | The exchange of, e.g., a sulfur atom in the peptide for selenium, using a selenium donor, such as selenophosphate. |
| Sulfation | Processes for sulfating hydroxyl moieties, particularly tertiary amines, are described in, e.g., U.S. Pat. No. 6,452,035. A process for sulphation of a protein or peptide by contacting the protein or peptide with sulphuric acid in the presence of a non-aqueous apolar organic solvent and contacting the resultant solution with a dehydrating agent is disclosed. Insulin products are described to be amenable to this process. See, e.g., U.S. Pat. No. 4,534,894. |
| SUMOylation | Covalently linking a peptide a SUMO (small ubiquitin-related Modifier) protein, for, e.g., stabilizing the peptide. |
| Transglutamination | Covalently linking other protein(s) or chemical groups (e.g., PEG) via a bridge at glutamine residues |
| tRNA-mediated addition of amino acids (e.g., arginylation) | For example, the site-specific modification (insertion) of an amino acid analog into a peptide. |
| Ubiquitination | The small peptide ubiquitin is covalently linked to, e.g., lysine residues of a protein. The ubiquitin-proteasome system can be used to carryout such reaction. See, e.g., U.S. 2007-0059731. |

The present invention also encompasses the use of prodrugs of undercarboxylated/uncarboxylated osteocalcin or derivative or variant thereof that can be produced by esterifying the carboxylic acid functions of the undercarboxylated/uncarboxylated osteocalcin or derivative or variant thereof with a lower alcohol, e.g., methanol, ethanol, propanol, isopropanol, butanol, etc. The use of prodrugs of the undercarboxylated/uncarboxylated osteocalcin or derivative or variant thereof that are not esters is also contemplated. For example, pharmaceutically acceptable carbonates, thiocarbonates, N-acyl derivatives, N-acyloxyalkyl derivatives, quaternary derivatives of tertiary amines, N-Mannich bases, Schiff bases, amino acid conjugates, phosphate esters, metal salts and sulfonate esters of the undercarboxylated/uncarboxylated osteocalcin or derivative or variant thereof are also contemplated. In some embodiments, the prodrugs will contain a biohydrolyzable moiety (e.g., a biohydrolyzable amide, biohydrolyzable carbamate, biohydrolyzable carbonate, biohydrolyzable ester, biohydrolyzable phosphate, or biohydrolyzable ureide analog). Guidance for the preparation of prodrugs of the undercarboxylated/uncarboxylated osteocalcin or derivative or variant thereof disclosed herein can be found in publications such as *Design of Prodrugs*, Bundgaard, A. Ed., Elsevier, 1985; *Design and Application of Prodrugs, A Textbook of Drug Design and Development*, Krosgaard-Larsen and H. Bundgaard, Ed., 1991, Chapter 5, pages 113-191; and Bundgaard, H., Advanced Drug Delivery Review, 1992, 8, pages 1-38.

To practice the methods of the present invention, it may be desirable to recombinantly express osteocalcin, e.g., by recombinantly expressing a cDNA sequence encoding osteocalcin. The cDNA sequence and deduced amino acid sequence of human osteocalcin is represented in SEQ ID NO:1 and SEQ ID NO:2. Osteocalcin nucleotide sequences may be isolated using a variety of different methods known to those skilled in the art. For example, a cDNA library constructed using RNA from a tissue known to express osteocalcin can be screened using a labeled osteocalcin probe. Alternatively, a genomic library may be screened to derive nucleic acid molecules encoding osteocalcin. Further, osteocalcin nucleic acid sequences may be derived by performing a polymerase chain reaction (PCR) using two oligonucleotide primers designed on the basis of known osteocalcin nucleotide sequences. The template for the reaction may be cDNA obtained by reverse transcription of mRNA prepared from cell lines or tissue known to express osteocalcin.

While the osteocalcin polypeptides and peptides can be chemically synthesized (e.g., see Creighton, 1983, Proteins: Structures and Molecular Principles, W.H. Freeman & Co., N.Y.), large polypeptides derived from osteocalcin and the full length osteocalcin itself may be advantageously produced by recombinant DNA technology using techniques well known in the art for expressing a nucleic acid. Such methods can be used to construct expression vectors containing the osteocalcin nucleotide sequences and appropriate transcriptional and translational control signals. These methods include, for example, in vitro recombinant DNA techniques, synthetic techniques, and in vivo genetic recombination. See, for example, the techniques described in Ausubel et al., 1989, supra.

A variety of host-expression vector systems may be utilized to express the osteocalcin nucleotide sequences. In a preferred embodiment, the osteocalcin peptide or polypeptide is secreted and may be recovered from the culture media.

Appropriate expression systems can be chosen to ensure that the correct modification, processing and subcellular localization of the osteocalcin protein occurs. To this end, bacterial host cells are useful for expression of osteocalcin, as such cells are unable to carboxylate osteocalcin.

The isolated osteocalcin can be purified from cells that naturally express it, e.g., osteoblasts, or purified from cells that naturally express osteocalcin but have been recombinantly modified to overproduce osteocalcin, or purified from cells that that do not naturally express osteocalcin but have been recombinantly modified to express osteocalcin. In a particular embodiment, a recombinant cell has been manipulated to activate expression of the endogenous osteocalcin gene. For example, International Patent Publications WO 99/15650 and WO 00/49162 describe a method of expressing endogenous genes termed random activation of gene expression (RAGE), which can be used to activate or increase expression of endogenous osteocalcin. The RAGE methodology involves non-homologous recombination of a regulatory sequence to activate expression of a downstream endogenous gene. Alternatively, International Patent Publications WO 94/12650, WO 95/31560, and WO 96/29411, as well as U.S. Pat. No. 5,733,761 and U.S. Pat. No. 6,270,985, describe a method of increasing expression of an endogenous gene that involves homologous recombination of a DNA construct that includes a targeting sequence, a regulatory sequence, an exon, and a splice-donor site. Upon homologous recombination, a downstream endogenous gene is expressed. The methods of expressing endogenous genes described in the foregoing patents are hereby expressly incorporated by reference.

In certain embodiments of methods of the present invention where the therapeutic agent is undercarboxylated/uncarboxylated osteocalcin or a derivative or variant thereof, the undercarboxylated/uncarboxylated osteocalcin or a derivative or variant thereof is administered to a patient in a dosage range of from about 0.5 µg/kg/day to about 100 mg/kg/day, from about 1 µg/kg/day to about 90 mg/kg/day, from about 5 µg/kg/day to about 85 mg/kg/day, from about 10 µg/kg/day to about 80 mg/kg/day, from about 20 µg/kg/day to about 75 mg/kg/day, from about 50 µg/kg/day to about 70 mg/kg/day, from about 150 µg/kg/day to about 65 mg/kg/day, from about 250 µg/kg/day to about 50 mg/kg/day, from about 500 µg/kg/day to about 50 mg/kg/day, from about 1 mg/kg/day to about 50 mg/kg/day, from about 5 mg/kg/day to about 40 mg/kg/day, from about 10 mg/kg/day to about 35 mg/kg/day, from about 15 mg/kg/day to about 30 mg/kg/day, from about 5 mg/kg/day to about 16 mg/kg/day, or from about 5 mg/kg/day to about 15 mg/kg/day.

In certain embodiments of methods of the present invention where the therapeutic agent is undercarboxylated/uncarboxylated osteocalcin or a derivative or variant thereof, the undercarboxylated/uncarboxylated osteocalcin or a derivative or variant thereof is administered to a patient in a dosage range of from about 0.5 µg/kg/day to about 100 µg/kg/day, from about 1 µg/kg/day to about 80 µg/kg/day, from about 3 µg/kg/day to about 50 µg/kg/day, or from about 3 µg/kg/day to about 30 µg/kg/day.

In certain embodiments of methods of the present invention where the therapeutic agent is undercarboxylated/uncarboxylated osteocalcin or a derivative or variant thereof, the undercarboxylated/uncarboxylated osteocalcin or a derivative or variant thereof is administered to a patient in a dosage range of from about 0.5 ng/kg/day to about 100 ng/kg/day, from about 1 ng/kg/day to about 80 ng/kg/day, from about 3 ng/kg/day to about 50 ng/kg/day, or from about 3 ng/kg/day to about 30 ng/kg/day.

Compositions Comprising Inhibitors of Gamma-Carboxylase, PTP-1B, and/or OST-PTP

In certain embodiments of the invention, the pharmaceutical compositions useful in the method of the invention comprise an inhibitor that reduces the expression or activity of gamma-carboxylase, PTP-1B, or OST-PTP. Preferably, the biological activity of gamma-carboxylase, PTP-1B, or OST-PTP is inhibited. The inhibitors may be antibodies (monoclonal or polyclonal) or fragments of antibodies, small molecules, polypeptides or proteins, or nucleic acids (e.g., antisense DNA or RNA, siRNA).

In certain embodiments, the inhibitors reduce the activity of OST-PTP having the amino acid sequence of SEQ ID NO:11. In other embodiments, the inhibitors reduce the activity of an OST-PTP having an amino acid sequence that is substantially homologous or substantially identical, as previously described, to the amino acid sequence of SEQ ID NO:11.

In certain embodiments, the inhibitors reduce the activity of human PTP-1B having the amino acid sequence of SEQ ID NO:17. In other embodiments, the inhibitors reduce the activity of a PTP-1B having an amino acid sequence that is substantially homologous or substantially identical, as previously described, to the amino acid sequence of SEQ ID NO:17.

In certain embodiments, the inhibitors reduce the activity of human gamma-carboxylase having the amino acid sequence of SEQ ID NO:7. In other embodiments, the inhibitors reduce the activity of a gamma-carboxylase having an amino acid sequence that is substantially homologous or identical to SEQ ID NO:7.

Small Molecule Inhibitors of OST-PTP, PTP-1B, and Gamma-Carboxylase

In certain embodiments, the agent is a small molecule. By "small molecule" is meant organic compounds of molecular weight of more than 100 and less than about 2,500 daltons, and preferably less than 500 daltons. Such small molecules inhibit the biological activity of OST-PTP, PTP-1B, or gamma-carboxylase.

The small molecule inhibitors may comprise agents that act as inhibitors of vitamin K. Warfarin and other vitamin K inhibitors, including Coumadin and other derivatives, may be administered to patients who would benefit from inhibition of gamma-carboxylase in order to treat or prevent a disorder related to reproduction in male mammals. In a specific embodiment of the invention, the small molecule warfarin may be used to inhibit the activity of gamma-carboxylase. Warfarin derivatives are exemplified by acenocoumarol, phenprocoumon and phenindione. Warfarin and other Coumadin derivatives block vitamin K-dependent gamma-carboxylation of osteocalcin, thus increasing the level of undercarboxylated/uncarboxylated osteocalcin.

Other inhibitors include thiol specific inhibitors of gamma-carboxylase. Cys and His residues of gamma-carboxylase are implicated in the carboxylase mechanism of gamma-carboxylase and it is observed that the enzyme is inhibited by thiol-specific inhibitors, such as N-ethylmaleimide (NEM) and mercurials such as p-hydroxymurcuribenzoate (pHMB). Additional non-limiting examples of these inhibitors include 5,5-dithiobis-(2-nitrobenzoic acid) (DTNB), 2-nitro-5-thiocyanobenzoic acid (NTCB), iodoacetamide (IA), N-phenylmaleimide (PheM), N-(1-pyrenyl) maleimide (PyrM), naphthalene-1,5-dimaleimide (NDM), N,N'-(1,2-phenylene) dimaleimide (oPDM), N,N'-1,4-phenylene dimaleimide (pPDM), N,N'-1,3-phenylene dimaleimide (mPDM), 1,1-(methylenedi-4,1-phenylene)bismaleimide (BM), 4-(N-maleimido)phenyltrimethylammonium (MPTM), N,N'-bis(3-maleimidopropionyl)-2-hydroxy-1,3-propanediamine (BMP), N-succinimidyl 3-(2-pyridyldithio)propionate, diethyl pyrocarbonate, p-chloromercuribenzene sulphonic acid and thiosulfinates. These inhibitors may also be provided as conjugate or derivative, such as with, e.g., BSA or aminodextran.

Antibody Inhibitors of OST-PTP, PTP-1B, and Gamma-Carboxylase

The present invention also provides compositions comprising an antibody or antibodies, as well as biologically active fragments or variants thereof, that are capable of binding to an epitope of OST-PTP, PTP-1B, or gamma-carboxylase polypeptides and inhibiting the activity of OST-PTP, PTP-1B, or gamma-carboxylase.

An antibody against OST-PTP that decreases its activity can be used therapeutically. In certain embodiments, the antibody against OST-PTP binds to the extracellular domain of OST-PTP.

In certain embodiments, the antibody against OST-PTP binds to an epitope in the mouse OST-PTP of SEQ ID NO:11 or an OST-PTP having an amino acid sequence that is substantially homologous or identical to SEQ ID NO:11. In other embodiments, the antibody against OST-PTP binds to an epitope in an OST-PTP having an amino acid sequence that is at least 70% homologous or identical to SEQ ID NO:11.

Human OST-PTP can be obtained by isolating the human ortholog of mouse OST-PTP (SEQ ID NO:10) or rat OST-PTP (SEQ ID NO:14) by methods known in the art. For example, one could prepare a cDNA library from human osteoblasts and identify human OST-PTP cDNA by hybridizing the cDNA clones from the library to a mouse probe. The mouse probe could be based on a portion of mouse OST-PTP (SEQ ID NO:10). Alternatively, PCR, using primers based on the mouse sequence, can be used to obtain the human OST-PTP gene.

An antibody against human PTP-1B that decreases its activity can be used therapeutically in the methods of the present invention. In certain embodiments, the antibody against human PTP-1B binds to the extracellular domain of human PTP-1B.

In certain embodiments, the antibody against human PTP-1B binds to an epitope in the human PTP-1B of SEQ ID NO:17 or an OST-PTP having an amino acid sequence that is substantially homologous or identical to SEQ ID NO:17. In other embodiments, the antibody against human PTP-1B binds to an epitope in a human PTP-1B having an amino acid sequence that is at least 70% homologous or identical to SEQ ID NO:17.

Gamma-carboxylase is an intracellular protein, so antibodies or fragments of antibodies against it are preferably used therapeutically when combined with technologies for delivering the antibodies, fragments or variants into the interior of target cells expressing gamma-carboxylase, e.g., osteoblasts. Antibodies or antibody fragments or variants against osteocalcin similarly can be used with technologies for delivering the antibodies or fragments into the interior of target cells and can also be used in diagnostics and drug screening assays.

In a particular embodiment, the present invention provides antibodies, fragments or variants of antibodies that recognize an epitope in OST-PTP that includes the amino acid at position 1316 of mouse OST-PTP or the corresponding position of human OST-PTP. In certain embodiments, these antibodies, fragments or variants of antibodies block or inhibit the ability of OST-PTP to activate gamma-carboxylase. In certain embodiments, use of these antibodies or fragments results in OST-PTP losing 50%, 60%, 70%, 80%, 90%, 95%, or essentially all of its ability to activate gamma-carboxylase.

The term "epitope" refers to an antigenic determinant on an antigen to which an antibody binds. Epitopes usually consist of chemically active surface groupings of molecules such as amino acids or sugar side chains, and typically have specific three-dimensional structural characteristics, as well as specific charge characteristics. Epitopes generally have at least five contiguous amino acids but some epitopes are formed by discontiguous amino acids that are brought together by the folding of the protein that contains them.

The terms "antibody" and "antibodies" include polyclonal antibodies, monoclonal antibodies, humanized or chimeric antibodies, single chain Fv antibody fragments, Fab fragments, and F(ab')$_2$ fragments. Polyclonal antibodies are heterogeneous populations of antibody molecules that are specific for a particular antigen, while monoclonal antibodies are homogeneous populations of antibodies to a particular epitope contained within an antigen. Monoclonal antibodies are particularly useful in the present invention.

Antibody fragments that have specific binding affinity for the polypeptide of interest (e.g., OST-PTP, PTP-1B, or gamma-carboxylase) can be generated by known techniques. Such antibody fragments include, but are not limited to, F(ab')$_2$ fragments that can be produced by pepsin digestion of an antibody molecule, and Fab fragments that can be generated by reducing the disulfide bridges of F(ab')$_2$ fragments. Alternatively, Fab expression libraries can be constructed. See, for example, Huse et al., 1989, Science 246:1275-1281. Single chain Fv antibody fragments are formed by linking the heavy and light chain fragments of the Fv region via an amino acid bridge (e.g., 15 to 18 amino acids), resulting in a single chain polypeptide. Single chain Fv antibody fragments can be produced through standard techniques, such as those disclosed in U.S. Pat. No. 4,946,778.

Once produced, antibodies or fragments thereof can be tested for recognition of the target polypeptide by standard immunoassay methods including, for example, enzyme-linked immunosorbent assay (ELISA) or radioimmunoassay assay (RIA). See, Short Protocols in Molecular Biology eds. Ausubel et al., Green Publishing Associates and John Wiley & Sons (1992).

The immunoassays, immunohistochemistry, RIA, IRMAs used herein are based on the generation of various antibodies, including those that specifically bind to osteocalcin, OST-PTP, PTP-1B, gamma-carboxylase, vitamin K, or their fragments or variants. Antibodies and methods of using antibodies to quantitate the amount of osteocalcin, in particular, in a sample are also described in U.S. Pat. No. 5,681,707. U.S. Pat. No. 5,681,707 discloses antibodies that bind to the N-terminal 20 amino acids, or the C-terminal 14 amino acids of osteocalcin. Anti-OST-PTP antibodies are commercially available.

In one embodiment, antibodies against OST-PTP, PTP-1B, or gamma-carboxylase that reduce its activity are useful in the treatment of a patient having a disorder related to reproduction in male mammals.

Nucleic Acid Inhibitors of OST-PTP, PTP-1B, and Gamma-Carboxylase

Other embodiments of the present invention are directed to the use of antisense nucleic acids or small interfering RNA (siRNA) to reduce or inhibit expression and hence the biological activity of osteocalcin, OST-PTP, PTP-1B, and/or gamma-carboxylase. cDNA sequences encoding osteocalcin, OST-PTP, PTP-1B, and/or gamma-carboxylase are set forth herein. Based on these sequences, antisense DNA or RNA that hybridize sufficiently to the respective gene or mRNA encoding osteocalcin, OST-PTP, PTP-1B, and/or gamma-carboxylase to turn off or reduce expression can be readily designed and engineered, using methods known in the art.

In a specific embodiment of the invention, antisense or siRNA molecules for use in the methods of the present invention include those that bind under stringent conditions to the human gamma-carboxylase nucleic acid sequence of SEQ ID NO:6. In yet another embodiment of the invention, the antisense or siRNA molecules are those that that bind under stringent conditions to the OST-PTP nucleic acid sequence of SEQ ID NO:10, or sequences that are substantially homologous to SEQ ID NO:10.

In a specific embodiment of the invention, antisense or siRNA molecules for use in the methods of the present invention include those that bind under stringent conditions to the human PTP-1B nucleic acid sequence of SEQ ID NO:16, or sequences that are substantially homologous to SEQ ID NO:16.

Antisense-RNA and anti-sense DNA have been used therapeutically in mammals to treat various diseases. See for example Agrawal & Zhao, 1998, Curr. Opin. Chemical Biol. 2: 519-528; Agrawal & Zhao, 1997, CIBA Found. Symp. 209:60-78; and Zhao et al., 1998, Antisense Nucleic Acid Drug Dev. 8:451-458; the entire contents of which are hereby incorporated by reference as if fully set forth herein. Antisense oligodeoxyribonucleotides (antisense-DNA), oligoribonucleotides (antisense-RNA), and other polymeric antisense compounds (e.g., oligonucleotides composed of naturally-occurring nucleobases, sugars and covalent internucleoside linkages and non-naturally-occurring portions which function similarly) can base pair with a gene or its transcript. Anderson et al., 1996, Antimicrobiol. Agents Chemother. 40:2004-2011 and U.S. Pat. No. 6,828,151 describe methods for making and using antisense nucleic acids and their formulation, the entire contents of which are hereby incorporated by reference as if fully set forth herein. The disclosures of the foregoing publications can adapted by those skilled in the art for use in the methods of the present invention.

Methods of making antisense nucleic acids are well known in the art. Further provided by the present invention are methods of modulating the expression of OST-PTP, PTP1B, and gamma-carboxylase genes and mRNA in cells or tissues by contacting the cells or tissues with one or more antisense compounds or compositions in order to treat or prevent a disorder related to reproduction in male mammals. As used herein, the term "target nucleic acid" encompasses DNA encoding osteocalcin, OST-PTP, PTP-1B, or gamma-carboxylase and RNA (including pre-mRNA and mRNA) transcribed from such DNA. The specific hybridization of a nucleic acid oligomeric compound with its target nucleic acid interferes with the normal function of the target nucleic acid. This modulation of function of a target nucleic acid by compounds which specifically hybridize to it is generally referred to as "antisense." The functions of DNA to be interfered with include replication and transcription. The functions of RNA to be interfered with include all vital functions such as, for example, translocation of the RNA to the site of protein translation, translation of protein from the RNA, and catalytic activity which may be engaged in or facilitated by the RNA. The overall effect of such interference with target nucleic acid function is modulation of the expression of the protein encoded by the DNA or RNA. In the context of the present invention, "modulation" means reducing or inhibiting in the expression of the gene or mRNA for osteocalcin, OST-PTP and/or gamma-carboxylase. DNA is the preferred antisense nucleic acid.

The targeting process includes determination of a site or sites within the target DNA or RNA encoding the osteocalcin, OST-PTP, PTP-1B, and/or gamma-carboxylase for the antisense interaction to occur such that the desired inhibitory effect is achieved. Within the context of the present invention, a preferred intragenic site is the region encompassing the translation initiation or termination codon of the open reading frame (ORF) of the mRNA for osteocalcin, OST-PTP, PTP-1B, or gamma-carboxylase, preferably human osteocalcin, OST-PTP, PTP-1B, or gamma-carboxylase. Since, as is known in the art, the translation initiation codon is typically 5'-AUG (in transcribed mRNA molecules; 5'-ATG in the corresponding DNA molecule), the translation initiation codon is also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine in eukaryotes. It is also known in the art that eukaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene. Routine experimentation will determine the optimal sequence of the antisense or siRNA.

It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively).

The terms "start codon region" and "translation initiation codon region" refer to a portion of such an mRNA or gene that encompasses from about 25 to about 50 contiguous nucleotides in either direction (i.e., 5' or 3') from a translation initiation codon. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon.

The open reading frame (ORF) or "coding region," which is known in the art to refer to the region between the translation initiation codon and the translation termination codon, is also a region which may be targeted effectively. Other target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene, and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene.

It is also known in the art that variants can be produced through the use of alternative signals to start or stop transcription and that pre-mRNAs and mRNAs can possess more that one start codon or stop codon. Variants that originate from a pre-mRNA or mRNA that use alternative start codons are known as "alternative start variants" of that pre-mRNA or mRNA. Those transcripts that use an alternative stop codon are known as "alternative stop variants" of that pre-mRNA or mRNA. One specific type of alternative stop variant is the "polyA variant" in which the multiple transcripts produced result from the alternative selection of one of the "polyA stop signals" by the transcription machinery, thereby producing transcripts that terminate at unique polyA sites.

Once one or more target sites have been identified, nucleic acids are chosen which are sufficiently complementary to the target, i.e., hybridize sufficiently well and with sufficient specificity, to give the desired effect of inhibiting gene expression and transcription or mRNA translation.

In the context of this invention, "hybridization" means hydrogen bonding, which may be Watson-Crick, Hoogsteen or reversed Hoogsteen hydrogen bonding, between complementary nucleoside or nucleotide bases. For example, adenine and thymine are complementary nucleobases which pair through the formation of hydrogen bonds. "Complementary," as used herein, refers to the capacity for precise pairing between two nucleotides. For example, if a nucleotide at a certain position of a nucleic acid is capable of hydrogen bonding with a nucleotide at the same position of a DNA or RNA molecule, then the nucleic acid and the DNA or RNA are considered to be complementary to each other at that position. The nucleic acid and the DNA or RNA are complementary to each other when a sufficient number of corresponding positions in each molecule are occupied by nucleotides which can hydrogen bond with each other. Thus, "specifically hybridizable" and "complementary" are terms which are used to indicate a sufficient degree of complementarity or precise pairing such that stable and specific binding occurs between the nucleic acid and the DNA or RNA target. It is understood in the art that the sequence of an antisense compound need not be 100% complementary to that of its target nucleic acid to be specifically hybridizable. An antisense compound is specifically hybridizable when binding of the compound to the target DNA or RNA molecule interferes with the normal function of the target DNA or RNA to cause a loss of function, and there is a sufficient degree of complementarity to avoid non-specific binding of the antisense compound to non-target sequences under conditions in which specific binding is desired, i.e., under physiological conditions in the case of in vivo assays or therapeutic treatment, and in the case of in vitro assays, under conditions in which the assays are performed.

Antisense nucleic acids have been employed as therapeutic moieties in the treatment of disease states in animals and man. Antisense nucleic acid drugs, including ribozymes, have been safely and effectively administered to humans in numerous clinical trials. It is thus established that nucleic acids can be useful therapeutic modalities that can be configured to be useful in treatment regimes for treatment of cells, tissues and animals, especially humans, for example to regulate expression of osteocalcin, OST-PTP, PTP-1B, and/or gamma-carboxylase.

Nucleic acids in the context of this invention includes "oligonucleotides," which refers to an oligomer or polymer of ribonucleic acid (RNA) or deoxyribonucleic acid (DNA) or mimetics thereof. This term includes oligonucleotides composed of naturally-occurring nucleobases, sugars and covalent internucleoside (backbone) linkages as well as oligonucleotides having non-naturally-occurring portions which function similarly. Such modified or substituted oligonucleotides are often preferred over native forms because of desirable properties such as, for example, enhanced cellular uptake, enhanced affinity for nucleic acid target and increased stability in the presence of nucleases.

While antisense nucleic acids are a preferred form of antisense compound, the present invention comprehends other oligomeric antisense compounds, including but not limited to oligonucleotide mimetics. The antisense compounds in accordance with this invention preferably comprise from about 8 to about 50 nucleobases (i.e., from about 8 to about 50 linked nucleosides). Particularly preferred antisense compounds are antisense nucleic acids comprising from about 12 to about 30 nucleobases. Antisense compounds include ribozymes, external guide sequence (EGS) nucleic acids (oligozymes), and other short catalytic RNAs or catalytic nucleic acids which hybridize to the target nucleic acid and modulate its expression.

The antisense compounds used in accordance with this invention may be conveniently and routinely made through the well-known technique of solid phase synthesis. Equipment for such synthesis is sold by several vendors including, for example, Applied Biosystems (Foster City, Calif.). Any other means for such synthesis known in the art may additionally or alternatively be employed. It is well known to use similar techniques to prepare nucleic acids such as the phosphorothioates and alkylated derivatives.

The antisense compounds of the present invention can be utilized for diagnostics, therapeutics, and prophylaxis and as research reagents and kits. For therapeutics, an animal, preferably a human, suspected of having a disease or disorder such male infertility, low sperm count, impaired sperm motility, impaired sperm viability, low testosterone levels, reduced libido, erectile dysfunction, underdevelopment of testes, or excess apoptosis in testes, which can be treated by modulating the expression of osteocalcin, gamma-carboxylase, PTP-1B, or OST-PTP, is treated by administering antisense compounds in accordance with this invention. The compounds useful in the methods of the invention can be formulated into pharmaceutical compositions by adding an effective amount of an antisense compound to a suitable pharmaceutically acceptable diluent or carrier. The antisense compounds and methods of the present invention are useful prophylactically, e.g., to prevent or delay the appearance of male infertility, low sperm count, impaired sperm motility, impaired sperm viability, low testosterone levels, reduced libido, erectile dysfunction, underdevelopment of testes, or excess apoptosis in testes. The antisense compounds and methods of the invention are also useful to retard the progression of male infertility, low sperm count, impaired sperm motility, impaired sperm viability, low testosterone levels, reduced libido, erectile dysfunction, underdevelopment of testes, or excess apoptosis in testes.

The present invention also encompasses the use of siRNA to treat or prevent a disorder related to reproduction in male mammals. U.S. Patent Application Publication No. 2004/0023390 (the entire contents of which are hereby incorporated by reference as if fully set forth herein) teaches that double-stranded RNA (dsRNA) can induce sequence-specific posttranscriptional gene silencing in many organisms by a process known as RNA interference (RNAi). However, in mammalian cells, dsRNA that is 30 base pairs or longer can induce sequence-nonspecific responses that trigger a shutdown of protein synthesis and even cell death through apoptosis. Recent work shows that RNA fragments are the sequence-specific mediators of RNAi (Elbashir et al., 2001, Nature 411:494-498). Interference of gene expression by these small interfering RNA (siRNA) is now recognized as a naturally occurring strategy for silencing genes in C. elegans, Drosophila, plants, and in mouse embryonic stem cells, oocytes and early embryos (Baulcombe, 1996, Plant Mol. Biol. 32:79-88; Timmons & Fire, 1998, Nature 395:854; Wianny and Zernicka-Goetz, 2000, Nat Cell Biol. 2:70-75; Svoboda et al., 2000, Development 127:4147-4156).

In mammalian cell culture, a siRNA-mediated reduction in gene expression has been accomplished by transfecting cells with synthetic RNA nucleic acids (Elbashir et al., 2001, Nature 411:494-498). U.S. Patent Application Publication No. 2004/0023390, the entire contents of which are hereby incorporated by reference as if fully set forth herein, provides exemplary methods using a viral vector containing an expression cassette containing a pol II promoter operably-linked to a nucleic acid sequence encoding a small interfering RNA molecule (siRNA) targeted against a gene of interest.

As used herein, RNAi is the process of RNA interference. A typical mRNA produces approximately 5,000 copies of a protein. RNAi is a process that interferes with or significantly reduces the number of protein copies made by an mRNA, preferably encoding osteocalcin, OST-PTP, PTP-1B, or gamma-carboxylase. For example, a double-stranded short interfering RNA (siRNA) molecule is engineered to complement and match the protein-encoding nucleotide sequence of the target mRNA to be interfered with. In certain embodiments of the present invention, following intracellular delivery, the siRNA molecule associates with an RNA-induced silencing complex (RISC) and binds the target mRNA (such as mRNA encoding osteocalcin, gamma-carboxylase, PTP-1B or OST-PTP) through a base-pairing interaction and degrades it. The RISC remains capable of degrading additional copies of the targeted mRNA. Other forms of RNA such as short hairpin RNA and longer RNA molecules can be used in the methods of the present invention. Longer molecules cause cell death, for example by instigating apoptosis and inducing an interferon response. Cell death was the major hurdle to achieving RNAi in mammals because dsRNAs longer than 30 nucleotides activated defense mechanisms that resulted in non-specific degradation of RNA transcripts and a general shutdown of the host cell. Using from about 20 to about 29 nucleotide siRNAs to mediate gene-specific suppression in mammalian cells has apparently overcome this obstacle. These siRNAs are long enough to cause gene suppression but not of a length that induces an interferon response. In a specific embodiment of the present invention, the targets for suppression are osteocalcin mRNA, OST-PTP mRNA, PTP-1B mRNA, or gamma-carboxylase mRNA. siRNA molecules useful in the methods of the present invention include those sequences that bind under stringent conditions to the human PTP-1B sequence of SEQ ID:16, the human gamma-carboxylase sequence of SEQ ID:6, or the mouse OST-PTP sequence of SEQ ID NO:10. siRNA molecules useful in the methods of the present invention also include those sequences that bind under stringent conditions to nucleic acids that are 80%, 85%, 90%, or 95% homologous to SEQ ID NO:16, SEQ ID NO:6 or SEQ ID NO:10.

Formulation and Administration of Pharmaceutical Compositions

The present invention encompasses the use of the polypeptides, nucleic acids, antibodies, small molecules and other therapeutic agents described herein formulated in pharmaceutical compositions to administer to a subject. The therapeutic agents (also referred to as "active compounds") can be incorporated into pharmaceutical compositions suitable for administration to a subject, e.g., a human. Such compositions typically comprise the polypeptides, nucleic acids, antibodies, small molecules and a pharmaceutically acceptable carrier. Preferably, such compositions are non-pyrogenic when administered to humans.

The pharmaceutical compositions of the invention are administered in an amount sufficient to modulate the OST-PTP signaling pathway or the PTP-1B signaling pathway involving gamma-carboxylase and osteocalcin.

As used herein the language "pharmaceutically acceptable carrier" is intended to include any and all solvents, binders, diluents, disintegrants, lubricants, dispersion media, coatings, antibacterial and antifungal agents, isotonic and absorption delaying agents, and the like, compatible with pharmaceutical administration. The use of such media and agents for pharmaceutically active substances is well known in the art. As long as any conventional media or agent is compatible with the active compound, such media can be used in the compositions of the invention. Supplementary active compounds or therapeutic agents can also be incorporated into the compositions. A pharmaceutical composition of the invention is formulated to be compatible with its intended route of administration. Examples of routes of administration include parenteral, e.g., intravenous, intradermal, intranasal, subcutaneous, oral, inhalation, transdermal (topical), transmucosal, and rectal administration.

The term "administer" is used in its broadest sense and includes any method of introducing the compositions of the present invention into a subject. This includes producing polypeptides or polynucleotides in vivo as by transcription or translation of polynucleotides that have been exogenously introduced into a subject. Thus, polypeptides or nucleic acids produced in the subject from the exogenous compositions are encompassed in the term "administer."

Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylene diamine tetra acetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where the therapeutic agents are water soluble) or dispersions and sterile powders for the extemporaneous preparation of sterile injectable solutions or dispersion. For intravenous administration, suitable carriers include physiological saline, bacteriostatic water, Cremophor EL® (BASF, Parsippany, N.J.) or phosphate buffered saline (PBS). In all cases, the composition must be sterile and should be fluid to the extent that easy syringability exists. It should be stable under the conditions of manufacture and storage and should be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., undercarboxylated/uncarboxylated osteocalcin protein or anti-OST-PTP antibody) in the required amount in an appropriate solvent with one or a combination of the ingredients enumerated above, as required, followed by filter sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yield a powder of the active ingredient plus any additional desired ingredient from a previously sterile-filtered solution thereof.

Oral compositions generally include an inert diluent or an edible carrier. They can be enclosed in gelatin capsules or compressed into tablets. Depending on the specific conditions being treated, pharmaceutical compositions of the present invention for treatment of disorders relating to reproduction in male mammals can be formulated and administered systemically or locally. Techniques for formulation and administration can be found in "Remington: The Science and Practice of Pharmacy" ($20^{th}$ edition, Gennaro (ed.) and Gennaro, Lippincott, Williams & Wilkins, 2000). For oral administration, the agent can be contained in enteric forms to survive the stomach or further coated or mixed to be released in a particular region of the GI tract by known methods. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, PRIMOGEL®, or corn starch; a lubricant such as magnesium stearate or STEROTES®; a glidant such as colloidal silicon dioxide; a sweetening agent such as sucrose or saccharin; or a flavoring agent such as peppermint, methyl salicylate, or orange flavoring.

For administration by inhalation, the compounds may be delivered in the form of an aerosol spray from pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

If appropriate, the compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to particular cells with, e.g., monoclonal antibodies) can also be used as pharmaceutically acceptable carriers. These can be prepared according to methods known to those skilled in the art, for example, as described in U.S. Pat. No. 4,522,811.

It is especially advantageous to formulate oral or parenteral compositions in unit dosage form for ease of administration and uniformity of dosage. "Unit dosage form" as used herein refers to physically discrete units suited as unitary dosages for the subject to be treated; each unit containing a predetermined quantity of active compound calculated to produce the desired therapeutic effect in association with the required pharmaceutical carrier. The specification for the unit dosage forms of the invention are dictated by and directly dependent on the unique characteristics of the active compound and the particular therapeutic effect to be achieved, and the limitations inherent in the art of compounding such an active compound for the treatment of individuals.

As previously noted, the agent may be administered continuously by pump or frequently during the day for extended periods of time. In certain embodiments, the agent may be administered at a rate of from about 0.3-100 ng/hour, preferably about 1-75 ng/hour, more preferably about 5-50 ng/hour, and even more preferably about 10-30 ng/hour. The agent may be administered at a rate of from about 0.1-100 µg/hr, preferably about 1-75 µg/hr, more preferably about 5-50 µg/hr, and even more preferably about 10-30 µg/hr. It will also be appreciated that the effective dosage of antibody, protein, or polypeptide used for treatment may increase or decrease over the course of a particular treatment. Changes in dosage may result and become apparent from monitoring the level of undercarboxylated/uncarboxylated osteocalcin in a biological sample, preferably blood or serum.

In an embodiment of the invention, the agent can be delivered by subcutaneous, long-term, automated drug delivery using an osmotic pump to infuse a desired dose of the agent for a desired time. Insulin pumps are widely available and are used by diabetics to automatically deliver insulin over extended periods of time. Such insulin pumps can be adapted to deliver the agent for use in the methods of the present invention. The delivery rate of the agent can be readily adjusted through a large range to accommodate changing requirements of an individual (e.g., basal rates and bolus doses). New pumps permit a periodic dosing manner, i.e., liquid is delivered in periodic discrete doses of a small fixed volume rather than in a continuous flow manner. The overall liquid delivery rate for the device is controlled and adjusted by controlling and adjusting the dosing period. The pump can be coupled with a continuous monitoring device and remote unit, such as a system described in U.S. Pat. No. 6,560,471, entitled "Analyte Monitoring Device and Methods of Use." In such an arrangement, the hand-held remote unit that controls the continuous blood monitoring device could wirelessly communicate with and control both the blood monitoring unit and the fluid delivery device delivering therapeutic agents for use in the methods of the present invention.

In some embodiments of the present invention, routine experimentation may be used to determine the appropriate dosage value for each patient by monitoring the effect of the therapeutic agent on serum testosterone levels, which can be frequently and easily monitored. The agent can be administered once or multiple times per day. Serum testosterone levels can be monitored before and during therapy to determine the appropriate amount of therapeutic agent to administer to raise serum testosterone levels or bring serum testosterone levels to normal and to maintain normal levels over extended periods of time. In a preferred embodiment, a patient is tested to determine if his serum testosterone levels are significantly lower than normal levels (about 25% below) before administering treatment with the therapeutic agent. The frequency of administration may vary from a single dose per day to multiple doses per day. Preferred routes of administration include oral, intravenous and intraperitoneal, but other forms of administration may be chosen as well.

A "therapeutically effective amount" of a protein or polypeptide, small molecule, antibody, or nucleic acid is an amount that achieves the desired therapeutic result. For example, if a therapeutic agent is administered to treat or prevent a disorder relating to reproduction in male mammals, a therapeutically effective amount is an amount that ameliorates one or more symptoms of the disorder, or produces at least one effect selected from the group consisting of increasing fertility, raising sperm count, increasing sperm motility, increasing sperm viability, increasing serum testosterone levels, increasing libido, ameliorating erectile dysfunction, reducing underdevelopment of testes, or reducing excess apoptosis in testes.

A therapeutically effective amount of protein or polypeptide, small molecule or nucleic acid for use in the present invention typically varies and can be an amount sufficient to achieve serum therapeutic agent levels typically of between about 1 nanogram per milliliter and about 10 micrograms per milliliter in the subject, or an amount sufficient to achieve serum therapeutic agent levels of between about 1 nanogram per milliliter and about 7 micrograms per milliliter in the subject. Other preferred serum therapeutic agent levels include about 0.1 nanogram per milliliter to about 3 micrograms per milliliter, about 0.5 nanograms per milliliter to about 1 microgram per milliliter, about 1 nanogram per milliliter to about 750 nanograms per milliliter, about 5 nanograms per milliliter to about 500 nanograms per milliliter, and about 5 nanograms per milliliter to about 100 nanograms per milliliter.

The amount of therapeutic agent disclosed herein to be administered to a patient in the methods of the present invention may range from about 5 mg/kg/day to about 500 mg/kg/day, from about 5 mg/kg/day to about 400 mg/kg/day, from about 5 mg/kg/day to about 300 mg/kg/day, from about 5 mg/kg/day to about 250 mg/kg/day, from about 5 mg/kg/day to about 200 mg/kg/day, from about 5 mg/kg/day to about 150 mg/kg/day, from about 5 mg/kg/day to about 100 mg/kg/day, from about 5 mg/kg/day to about 75 mg/kg/day, from about 5 mg/kg/day to about 50 mg/kg/day, from about 5 mg/kg/day to about 40 mg/kg/day, from about 5 mg/kg/day to about 35 mg/kg/day, from about 5 mg/kg/day to about 30 mg/kg/day, from about 5 mg/kg/day to about 25 mg/kg/day, from about 5 mg/kg/day to about 24 mg/kg/day, from about 5 mg/kg/day to about 23 mg/kg/day, from about 5 mg/kg/day to about 22 mg/kg/day, from about 5 mg/kg/day to about 21 mg/kg/day, from about 5 mg/kg/day to about 20 mg/kg/day, from about 5 mg/kg/day to about 19 mg/kg/day, from about 5 mg/kg/day to about 18 mg/kg/day, from about 5 mg/kg/day to about 17 mg/kg/day, from about 5 mg/kg/day to about 16 mg/kg/day, from about 5 mg/kg/day to about 15 mg/kg/day, from about 5 mg/kg/day to about 14 mg/kg/day, from about 5 mg/kg/day to about 13 mg/kg/day, from about 5 mg/kg/day to about 12 mg/kg/day, from about 5 mg/kg/day to about 11 mg/kg/day, or from about 5 mg/kg/day to about 10 mg/kg/day.

Other dose ranges that may be used include from about 10 mg/kg/day to about 500 mg/kg/day, from about 10 mg/kg/day to about 400 mg/kg/day, from about 10 mg/kg/day to about 300 mg/kg/day, from about 10 mg/kg/day to about 250 mg/kg/day, from about 10 mg/kg/day to about 200 mg/kg/day, from about 10 mg/kg/day to about 150 mg/kg/day, from about 10 mg/kg/day to about 100 mg/kg/day, from about 10 mg/kg/day to about 75 mg/kg/day, from about 10 mg/kg/day to about 50 mg/kg/day, from about 10 mg/kg/day to about 45 mg/kg/day, from about 10 mg/kg/day to about 40 mg/kg/day, from about 10 mg/kg/day to about 35 mg/kg/day, from about 10 mg/kg/day to about 34 mg/kg/day, from about 10 mg/kg/day to about 33 mg/kg/day, from about 10 mg/kg/day to about 32 mg/kg/day, from about 10 mg/kg/day to about 31 mg/kg/day, from about 10 mg/kg/day to about 30 mg/kg/day, from about 10 mg/kg/day to about 29 mg/kg/day, from about 10 mg/kg/day to about 28 mg/kg/day, from about 10 mg/kg/day to about 27 mg/kg/day, from about 10 mg/kg/day to about 26 mg/kg/day, from about 10 mg/kg/day to about 25 mg/kg/day, from about 10 mg/kg/day to about 24 mg/kg/day, from about 10 mg/kg/day to about 23 mg/kg/day, from about 10 mg/kg/day to about 22 mg/kg/day, from about 10 mg/kg/day to about 21 mg/kg/day, from about 10 mg/kg/day to about 20 mg/kg/day, from about 10 mg/kg/day to about 19 mg/kg/day, from about 10 mg/kg/day to about 18 mg/kg/day, from about 10 mg/kg/day to about 17 mg/kg/day, from about 10 mg/kg/day to about 16 mg/kg/day, or from about 10 mg/kg/day to about 15 mg/kg/day.

Other dose ranges that may be used include from about 15 mg/kg/day to about 500 mg/kg/day, from about 15 mg/kg/day to about 400 mg/kg/day, from about 15 mg/kg/day to about 300 mg/kg/day, from about 15 mg/kg/day to about 250 mg/kg/day, from about 15 mg/kg/day to about 200 mg/kg/day, from about 15 mg/kg/day to about 150 mg/kg/day, from about 15 mg/kg/day to about 100 mg/kg/day, from about 15 mg/kg/day to about 75 mg/kg/day, from about 15 mg/kg/day to about 50 mg/kg/day, from about 15 mg/kg/day to about 40 mg/kg/day, from about 15 mg/kg/day to about 30 mg/kg/day, from about 15 mg/kg/day to about 25 mg/kg/day, or from about 15 mg/kg/day to about 20 mg/kg/day.

Other dose ranges that may be used include from about 20 mg/kg/day to about 500 mg/kg/day, from about 20 mg/kg/day to about 400 mg/kg/day, from about 20 mg/kg/day to about 300 mg/kg/day, from about 20 mg/kg/day to about 250 mg/kg/day, from about 20 mg/kg/day to about 200 mg/kg/day, from about 20 mg/kg/day to about 150 mg/kg/day, from about 20 mg/kg/day to about 100 mg/kg/day, from about 20 mg/kg/day to about 75 mg/kg/day, from about 20 mg/kg/day to about 50 mg/kg/day, from about 20 mg/kg/day to about 40 mg/kg/day, from about 20 mg/kg/day to about 30 mg/kg/day, or from about 20 mg/kg/day to about 25 mg/kg/day.

Other dose ranges that may be used include from about 25 mg/kg/day to about 500 mg/kg/day, from about 25 mg/kg/day to about 400 mg/kg/day, from about 25 mg/kg/day to about 300 mg/kg/day, from about 25 mg/kg/day to about 250 mg/kg/day, from about 25 mg/kg/day to about 200 mg/kg/day, from about 25 mg/kg/day to about 150 mg/kg/day, from about 25 mg/kg/day to about 100 mg/kg/day, from about 25 mg/kg/day to about 75 mg/kg/day, from about 25 mg/kg/day to about 50 mg/kg/day, from about 25 mg/kg/day to about 40 mg/kg/day, or from about 25 mg/kg/day to about 30 mg/kg/day.

Other dose ranges that may be used include from about 30 mg/kg/day to about 500 mg/kg/day, from about 30 mg/kg/day to about 400 mg/kg/day, from about 30 mg/kg/day to about 300 mg/kg/day, from about 30 mg/kg/day to about 250 mg/kg/day, from about 30 mg/kg/day to about 200 mg/kg/day, from about 30 mg/kg/day to about 150 mg/kg/day, from about 30 mg/kg/day to about 100 mg/kg/day, from about 30 mg/kg/day to about 75 mg/kg/day, from about 30 mg/kg/day to about 50 mg/kg/day, or from about 30 mg/kg/day to about 40 mg/kg/day.

Other dose ranges that may be used include from about 40 mg/kg/day to about 500 mg/kg/day, from about 40 mg/kg/day to about 400 mg/kg/day, from about 40 mg/kg/day to about 300 mg/kg/day, from about 40 mg/kg/day to about 250 mg/kg/day, from about 40 mg/kg/day to about 200 mg/kg/day, from about 40 mg/kg/day to about 150 mg/kg/day, from about 40 mg/kg/day to about 100 mg/kg/day, from about 40 mg/kg/day to about 75 mg/kg/day, from about 40 mg/kg/day to about 60 mg/kg/day, or from about 40 mg/kg/day to about 50 mg/kg/day.

Other dose ranges that may be used include from about 50 mg/kg/day to about 500 mg/kg/day, from about 50 mg/kg/day to about 400 mg/kg/day, from about 50 mg/kg/day to about 300 mg/kg/day, from about 50 mg/kg/day to about 250 mg/kg/day, from about 50 mg/kg/day to about 200 mg/kg/day, from about 50 mg/kg/day to about 175 mg/kg/day, from about 50 mg/kg/day to about 150 mg/kg/day, from about 50 mg/kg/day to about 125 mg/kg/day, from about 50 mg/kg/day to about 100 mg/kg/day, from about 50 mg/kg/day to about 75 mg/kg/day, or from about 50 mg/kg/day to about 60 mg/kg/day.

Other dose ranges that may be used include from about 60 mg/kg/day to about 500 mg/kg/day, from about 60 mg/kg/day to about 400 mg/kg/day, from about 60 mg/kg/day to about 300 mg/kg/day, from about 60 mg/kg/day to about 250 mg/kg/day, from about 60 mg/kg/day to about 200 mg/kg/day, from about 60 mg/kg/day to about 175 mg/kg/day, from about 60 mg/kg/day to about 150 mg/kg/day, from about 60 mg/kg/day to about 125 mg/kg/day, from about 60 mg/kg/day to about 100 mg/kg/day, or from about 60 mg/kg/day to about 75 mg/kg/day.

Other dose ranges that may be used include from about 70 mg/kg/day to about 500 mg/kg/day, from about 70 mg/kg/day to about 400 mg/kg/day, from about 70 mg/kg/day to about 300 mg/kg/day, from about 70 mg/kg/day to about 250 mg/kg/day, from about 70 mg/kg/day to about 200 mg/kg/day, from about 70 mg/kg/day to about 175 mg/kg/day, from about 70 mg/kg/day to about 150 mg/kg/day, from about 70 mg/kg/day to about 125 mg/kg/day, or from about 70 mg/kg/day to about 100 mg/kg/day.

Other dose ranges that may be used include from about 80 mg/kg/day to about 500 mg/kg/day, from about 80 mg/kg/day to about 400 mg/kg/day, from about 80 mg/kg/day to about 300 mg/kg/day, from about 80 mg/kg/day to about 250 mg/kg/day, from about 80 mg/kg/day to about 200 mg/kg/day, from about 80 mg/kg/day to about 175 mg/kg/day, from about 80 mg/kg/day to about 150 mg/kg/day, from about 80 mg/kg/day to about 125 mg/kg/day, or from about 80 mg/kg/day to about 100 mg/kg/day.

Other dose ranges that may be used include from about 90 mg/kg/day to about 500 mg/kg/day, from about 90 mg/kg/day to about 400 mg/kg/day, from about 90 mg/kg/day to about 300 mg/kg/day, from about 90 mg/kg/day to about 250 mg/kg/day, from about 90 mg/kg/day to about 200 mg/kg/day, from about 90 mg/kg/day to about 175 mg/kg/day, from about 90 mg/kg/day to about 150 mg/kg/day, from about 90 mg/kg/day to about 125 mg/kg/day, or from about 90 mg/kg/day to about 100 mg/kg/day.

Other dose ranges that may be used include from about 100 mg/kg/day to about 500 mg/kg/day, from about 100 mg/kg/day to about 400 mg/kg/day, from about 100 mg/kg/day to about 300 mg/kg/day, from about 100 mg/kg/day to about 250 mg/kg/day, from about 100 mg/kg/day to about 200 mg/kg/day, from about 100 mg/kg/day to about 175 mg/kg/day, from about 100 mg/kg/day to about 150 mg/kg/day, or from about 100 mg/kg/day to about 125 mg/kg/day.

Other dosages that may be used include about 5 mg/kg/day, about 6 mg/kg/day, about 7 mg/kg/day, about 8 mg/kg/day, about 9 mg/kg/day, about 10 mg/kg/day, about 11 mg/kg/day, about 12 mg/kg/day, about 13 mg/kg/day, about 14 mg/kg/day, about 15 mg/kg/day, about 16 mg/kg/day, about 17 mg/kg/day, about 18 mg/kg/day, about 19 mg/kg/day, about 20 mg/kg/day, about 21 mg/kg/day, about 22 mg/kg/day, about 23 mg/kg/day, about 24 mg/kg/day, about 25 mg/kg/day, about 26 mg/kg/day, about 27 mg/kg/day, about 28 mg/kg/day, about 29 mg/kg/day, about 30 mg/kg/day, about 31 mg/kg/day, about 32 mg/kg/day, about 33 mg/kg/day, about 34 mg/kg/day, about 35 mg/kg/day, about 36 mg/kg/day, about 37 mg/kg/day, about 38 mg/kg/day, about 39 mg/kg/day, about 40 mg/kg/day, about 45 mg/kg/day, about 50 mg/kg/day, about 60 mg/kg/day, about 70 mg/kg/day, about 80 mg/kg/day, about 90 mg/kg/day, about 100 mg/kg/day, about 125 mg/kg/day, about 150 mg/kg/day, about 175 mg/kg/day, about 200 mg/kg/day, about 250 mg/kg/day, or about 350 mg/kg/day.

The skilled artisan will appreciate that certain factors may influence the dosage required to effectively treat a subject, including but not limited to the severity of the condition, previous treatments, the general health and/or age of the subject, and other disorders or diseases present.

Treatment of a subject with a therapeutically effective amount of a protein, polypeptide, nucleotide or antibody can include a single treatment or, preferably, can include a series of treatments.

In certain embodiments, treatment of a subject with undercarboxylated/uncarboxylated osteocalcin leads to undercarboxylated/uncarboxylated osteocalcin being about 10%, about 15%, about 20%, about 25%, about 30%, about 35%, about 40%, about 45%, or about 50% of the total osteocalcin in the blood of the patient.

It is understood that the appropriate dose of a small molecule agent depends upon a number of factors within the ken of the ordinarily skilled physician, veterinarian, or researcher. The dose(s) of the small molecule will vary, for example, depending upon the identity, size, and condition of the subject or sample being treated, further depending upon the route by which the composition is to be administered, and the effect which the practitioner desires the small molecule to have. It is furthermore understood that appropriate doses of a small molecule depend upon the potency of the small molecule with respect to the expression or activity to be modulated. When one or more of these small molecules is to be administered to an animal (e.g., a human) in order to modulate expression or activity of OST-PTP, PTP-1B, or gamma-carboxylase, a relatively low dose may be prescribed at first, with the dose subsequently increased until an appropriate response is obtained. In addition, it is understood that the specific dose level for any particular subject will depend upon a variety of factors including the activity of the specific compound employed, the age, body weight, general health, and diet of the subject, the time of administration, the route of administration, the rate of excretion, whether other drugs are being administered to the patient, and the degree of expression or activity to be modulated.

For prevention or treatment, a suitable subject can be an individual who is suspected of having, has been diagnosed as having, or is at risk of developing a disorder relating to reproduction in male mammals.

Suitable routes of administration of the pharmaceutical compositions useful in the methods of the present invention can include oral, intestinal, parenteral, transmucosal, transdermal, intramuscular, subcutaneous, transdermal, rectal, intramedullary, intrathecal, intravenous, intraventricular, intraatrial, intraaortal, intraarterial, or intraperitoneal administration. The pharmaceutical compositions useful in the methods of the present invention can be administered to the subject by a medical device, such as, but not limited to, catheters, balloons, implantable devices, biodegradable implants, prostheses, grafts, sutures, patches, shunts, or stents. In one preferred embodiment, the therapeutic agent (e.g., undercarboxylated/uncarboxylated osteocalcin) can be coated on a stent for localized administration to the target area. In this situation a slow release preparation of undercarboxylated/uncarboxylated osteocalcin, for example, is preferred.

The compounds of the invention may also be admixed, encapsulated, conjugated or otherwise associated with other molecules, molecule structures or mixtures of compounds, as for example, liposomes, receptor targeted molecules, oral, rectal, topical or other formulations, for assisting in uptake, distribution and/or absorption. Representative United States patents that teach the preparation of such uptake, distribution and/or absorption assisting formulations and that may be consulted by those skilled in the art for techniques useful for practicing the present invention include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

In yet another aspect of the invention, undercarboxylated/uncarboxylated osteocalcin is administered as a pharmaceutical composition with a pharmaceutically acceptable excipient. Exemplary pharmaceutical compositions for undercarboxylated/uncarboxylated osteocalcin include injections as solutions or injections as injectable self-setting or self-gelling mineral polymer hybrids. Undercarboxylated/uncarboxylated osteocalcin may be administered using a porous crystalline biomimetic bioactive composition of calcium phosphate. See U.S. Pat. Nos. 5,830,682; 6,514,514; and 6,511,958 and U.S. Patent Application Publications Nos. 2006/0063699; 2006/0052327; 2003/199615; 2003/0158302; 2004/0157864; 2006/0292670; 2007/0099831 and 2006/0257492, all of which are incorporated herein in their entirety by reference.

Methods of Treatment

The present invention provides methods for modulating the level of undercarboxylated/uncarboxylated osteocalcin in male mammals through modulating the OST-PTP signaling pathway or the PTP-1B signaling pathway for treating or preventing a variety of different disorders relating to reproduction in the male mammals. In particular, the methods are used to inhibit OST-PTP phosphorylase activity, inhibit PTP-1B phosphorylase activity, reduce gamma-carboxylase activity, and/or increase undercarboxylated/uncarboxylated osteocalcin. According to the invention, the methods provide an amount of an agent effective to treat or prevent a disorder associated with the OST-PTP signaling pathway or the PTP-1B signaling pathway. The agent may be selected from the group consisting of small molecules, antibodies and nucleic acids. Such disorders include, but are not limited to, male infertility, low sperm count, impaired sperm motility, impaired sperm viability, low testosterone levels, reduced libido, erectile dysfunction, underdevelopment of testes, and excess apoptosis in testes.

In certain embodiments, the methods comprise identifying a patient in need of treatment or prevention of male infertility, low sperm count, impaired sperm motility, impaired sperm viability, low testosterone levels, reduced libido, erectile dysfunction, underdevelopment of testes, or excess apoptosis in testes and then applying the methods disclosed herein to the patient.

In one embodiment of the invention, the method of treatment comprises administering to a patient in need thereof a therapeutically effective amount of undercarboxylated/uncarboxylated osteocalcin sufficient to raise the patient's blood level of undercarboxylated/uncarboxylated osteocalcin compared to the pretreatment patient level. Preferably, the patient is a male human. In another embodiment, the method of treatment comprises administering to a patient in need thereof a therapeutically effective amount of undercarboxylated/uncarboxylated osteocalcin sufficient to raise the ratio of undercarboxylated/uncarboxylated osteocalcin to total osteocalcin in the patient's blood compared to the pretreatment patient ratio.

In another aspect of the invention, a method is provided for treating or preventing a disorder relating to reproduction in a male mammal comprising administering to a male mammal in need thereof undercarboxylated/uncarboxylated osteocalcin in a therapeutically effective amount that produces at least one effect selected from the group consisting of increasing fertility, raising sperm count, increasing sperm motility, increasing sperm viability, increasing serum testosterone levels, increasing libido, ameliorating erectile dysfunction, reducing underdevelopment of testes, and reducing excess apoptosis in testes, compared to pretreatment levels. Preferably, the male mammal is a human.

In an embodiment of the invention, a method is provided for treating or preventing a disorder relating to reproduction in a male mammal comprising administering to a male mammal in need of such treatment or prevention a therapeutically effective amount of an agent that reduces OST-PTP expression or activity in osteoblasts, or reduces PTP-1B expression or activity in osteoblasts, sufficient to produce at least one effect selected from the group consisting of increasing fertility, raising sperm count, increasing sperm motility, increasing sperm viability, increasing serum testosterone levels, increasing libido, ameliorating erectile dysfunction, reducing underdevelopment of testes, and reducing excess apoptosis in testes, compared to pretreatment levels. Preferably, the patient is a human.

The present invention is directed to methods (i) for treating or preventing a disorder relating to reproduction in a male mammal comprising administering to a male mammal in need of such treatment or prevention in a therapeutically effective amount an agent that reduces gamma-carboxylase expression or activity in osteoblasts sufficient to produce at least one effect selected from the group consisting of increasing fertility, raising sperm count, increasing sperm motility, increasing sperm viability, increasing serum testosterone levels, increasing libido, ameliorating erectile dysfunction, reducing underdevelopment of testes, and reducing excess apoptosis in testes, compared to pretreatment levels comprising administering to the male mammal in need of such treatment or prevention in a therapeutically effective amount an agent that reduces gamma-carboxylase expression or activity in osteoblasts sufficient to increase fertility, raise sperm count, increase sperm motility, increase sperm viability, increase serum testosterone levels, increase libido, ameliorate erectile dysfunction, reduce underdevelopment of testes, or reduce excess apoptosis in testes. Preferably, the male mammal is a human. In an embodiment of the invention, the agent is an isolated nucleic acid that is selected from the group consisting of cDNA, antisense DNA, antisense RNA, and small interfering RNA, which nucleic acid is sufficiently complementary to the gene or mRNA encoding gamma-carboxylase to permit specific hybridization to the gene or mRNA, and wherein the hybridization prevents or reduces expression of gamma-carboxylase in osteoblasts. In another embodiment of the invention, the nucleic acid is conjugated to a phosphate group or other targeting ligand to facilitate uptake by osteoblasts.

In the methods described herein, it will be understood that "treating" a disease or disorder encompasses not only improving the disease or disorder or its symptoms but also retarding the progression of the disease or disorder or ameliorating the deleterious effects of the disease or disorder.

The present invention also encompasses the use of gene therapy for treatment of disorders relating to reproduction in male mammals. This can be accomplished by introducing a gene encoding osteocalcin or a biologically active fragment or variant thereof into a vector, and transfecting or infecting cells from a patient afflicted with the disorder or at a high risk of developing the disorder with the vector, according to various methods known in the art. The cells may be transfected or infected by ex vivo or by in vivo methods.

Methods of gene therapy known in the art can be adapted for use in the methods of the present invention. Adeno-associated virus (AAV) is one of the most promising vectors for gene therapy and may be used in the methods of the present invention. Conventional methods of gene transfer and gene therapy are described in, e.g., Gene Therapy: Principles and Applications, ed. T. Blackenstein, Springer Verlag, 1999; Gene Therapy Protocols (Methods in Molecular Medicine), ed. P. D. Robbins, Humana Press, 1997; and Retro-vectors for Human Gene Therapy, ed. C. P. Hodgson, Springer Verlag, 1996. AAV is an attractive vector system for human gene therapy because it is non-pathogenic for humans, it has a high frequency of integration, and it can infect non-dividing cells, thus making it useful for delivery of genes into mammalian cells both in tissue culture and in whole animals. See, e.g., Muzyczka, 1992, Curr. Top. Microbiol. Immunol., 158:97-129. Recent studies have demonstrated AAV to be a potentially useful vector for gene delivery. LaFace et al., 1998, Virology, 162:483-486; Zhou et al., 1993, Exp. Hematol. (NY), 21:928-933; Flotte et al., 1993, Proc. Natl. Acad. Sci. USA 90:10613-10617; and Walsh et al., 1994, Blood 84:1492-1500. Recombinant AAV vectors have been used successfully for in vitro and in vivo transduction of marker genes (Kaplitt et al., 1994, Nature Genetics, 8:148-154; Lebkowski et al., 1988, Mol. Cell. Biol. 8:3988-3996; Samulski et al., 1989, J. Virol., 63:3822-3828; Shelling & Smith, 1994, Gene Therapy 1:165-169; Yoder et al., 1994, Blood, 82:suppl. 1:347 A; Zhou et al., 1994, J. Exp. Med., 179:1867-1875; Hermonat & Muzyczka, 1984, Proc. Natl. Acad. Sci. USA., 81:6466-6470; Tratschin et al., 1984, Mol. Cell. Biol., 4:2072-2081; McLaughlin et al., 1988, J. Virol., 62:1963-1973) as well as genes involved in human diseases (Flotte et al., 1992, Am. J. Respir. Cell Mol. Biol. 7:349-356; Luo et al., 1994, Blood, 82:suppl. 1,303A; Ohi et al., 1990, Gene, 89:279-282; Walsh et al., 1992, Proc. Natl. Acad. Sci. USA 89:7257-7261; Wei et al., 1994, Gene Therapy, 1:261-268).

In certain other embodiments, the gene of interest (e.g., osteocalcin) can be transferred into a target cell using a retroviral vector. Retroviruses refer to viruses that belong to the Retroviridae family, and include oncoviruses, foamy viruses (Russell & Miller, 1996, J. Virol. 70:217-222; Wu et al., 1999, J. Virol. 73:4498-4501, and lentiviruses (for example, HIV-1 (Naldini et al., 1996, Science 272:263-267; Poeschla et al., 1996, Proc. Natl. Acad. Sci. USA 93:11395-11399; Srinivasakumar et al., 1997, J. Virol. 71:5841-5848; Zufferey et al., 1997, Nat. Biotechnol. 15:871-875; Kim et al., 1998, J. Virol. 72:811-816) and feline immunodeficiency virus (Johnston et al., 1999, J. Virol. 73:4991-5000; Johnston & Power, 1999, Virol. 73:2491-2498; Poeschla et al., 1998, Nat. Med. 4:354-357). The disclosures of these publications may be adapted for use in the methods of the present invention. Numerous gene therapy methods that take advantage of retroviral vectors for treating a wide variety of diseases are well-known in the art and can be adapted for use in the methods of the present invention (see, e.g., U.S. Pat. Nos. 4,405,712 and 4,650,764; Friedmann, 1989, Science, 244:1275-1281; Mulligan, 1993, Science, 260:926-932; Crystal, 1995, Science 270:404-410, and U.S. Pat. No. 6,899,871, each of which are incorporated herein by reference in their entirety). An increasing number of these methods are currently being applied in human clinical trials (Morgan, 1993, BioPharm, 6:32-35; see also The Development of Human Gene Therapy, Theodore Friedmann, Ed., Cold Spring Harbor Laboratory Press, Cold Spring Harbor, N.Y., 1999. ISBN 0-87969-528-5, which is incorporated herein by reference in its entirety).

Efficacy of the methods of treatment described herein can be monitored by determining whether the methods ameliorate any of the symptoms of the disease or disorder being treated. Alternatively, one can monitor the level of serum undercarboxylated/uncarboxylated osteocalcin (either in absolute terms or as a ratio of undercarboxylated/uncarboxylated osteocalcin/total osteocalcin), which levels should increase in response to therapy.

Methods of Male Contraception

The discovery of the previously unknown biochemical pathway linking osteocalcin and reproductive biology in male mammals provides methods of contraception for use in male mammals. In such methods, a male mammal in need of contraception is administered a pharmaceutical composition comprising a therapeutically effective amount of an agent that antagonizes the effect of undercarboxylated/uncarboxylated osteocalcin. In certain embodiments, the agent has the effect of lowering the serum level of undercarboxylated/uncarboxylated osteocalcin in the male mammal. In certain embodiments, the agent acts as an antagonist of undercarboxylated/ uncarboxylated osteocalcin.

In certain embodiments, the male mammal in need of contraception is a human.

In certain embodiments, the pharmaceutical compositions useful in the methods of contraception comprise an agent that increases the expression or activity of gamma-carboxylase, PTP-1B, or OST-PTP. This results in a greater amount of osteocalcin being present in the carboxylated state rather than the undercarboxylated/uncarboxylated state. The agents that increase the expression or activity of gamma-carboxylase, PTP-1B, or OST-PTP may be antibodies (monoclonal or polyclonal) or fragments of antibodies, small molecules, polypeptides or proteins, or nucleic acids (e.g., antisense DNA or RNA, siRNA).

In other embodiments, the pharmaceutical compositions useful in the methods of contraception comprise an agent that is a "negative mimetic" of undercarboxylated/uncarboxylated osteocalcin. A "negative mimetic" refers to a synthetic chemical compound that has substantially the same structural characteristics of naturally occurring undercarboxylated/uncarboxylated osteocalcin but antagonizes the biological effects of naturally occurring undercarboxylated/uncarboxylated osteocalcin. Such negative mimetics may include, for instance, polypeptide- and polynucleotide-like polymers having modified backbones, side chains, and/or bases.

Diagnostics

The present invention provides methods and compositions for diagnosing disorders related to reproduction in male mammals based on decreased levels of undercarboxylated/uncarboxylated osteocalcin. Such disorders include, but are not limited to, male infertility, low sperm count, impaired sperm motility, impaired sperm viability, low testosterone levels, reduced libido, erectile dysfunction, underdevelopment of testes, and excess apoptosis in testes.

In a specific embodiment of the invention, a method is provided for diagnosing a patient having or at risk of developing a disorder selected from the group consisting of male infertility, low sperm count, impaired sperm motility, impaired sperm viability, low testosterone levels, reduced libido, erectile dysfunction, underdevelopment of testes, and excess apoptosis in testes, comprising: (i) determining a patient level of undercarboxylated/uncarboxylated osteocalcin in a biological sample taken from the patient and a control level of undercarboxylated/uncarboxylated osteocalcin in a biological sample taken from a subject that does not have the disorder, (ii) comparing the patient and control levels, and (iii) diagnosing the patient as having or as being at risk of developing the disorder if the patient level is lower than the control level.

"Biological samples" include solid and fluid body samples. The biological samples of the present invention may include tissue, organs, cells, protein or membrane extracts of cells, blood or biological fluids such as blood, serum, ascites fluid or brain fluid (e.g., cerebrospinal fluid). Preferably, the biological sample is blood.

In another embodiment of the invention, a method is provided for diagnosing a patient having or at risk of developing a disorder selected from the group consisting of male infertility, low sperm count, impaired sperm motility, impaired sperm viability, low testosterone levels, reduced libido, erectile dysfunction, underdevelopment of testes, and excess apoptosis in testes, comprising: (i) determining a patient level of undercarboxylated/uncarboxylated osteocalcin in a biological sample taken from the patient; and (ii) comparing the patient level to a standard level; where, if the patient level is lower than the standard level, diagnosing the patient as having or at risk of developing the disorder. In instances where the method is practiced on male humans, the standard level can be a level of undercarboxylated/uncarboxylated osteocalcin that has been previously determined to be the normal range for men who are not at risk of developing the disorder. In preferred embodiments, the biological sample is blood, serum, plasma, cerebrospinal fluid, urine, a cell sample, or a tissue sample.

A "standard level" of undercarboxylated/uncarboxylated osteocalcin in male humans can include values of 0.1 ng/ml to 10 ng/ml, preferably 0.2 ng/ml to 7.5 ng/ml, more preferably 0.5 ng/ml to 5 ng/ml, and even more preferably 1 ng/ml to 5 ng/ml of undercarboxylated/uncarboxylated osteocalcin. A standard level of undercarboxylated/uncarboxylated osteocalcin in humans can also include about 0.1 ng/ml, about 0.5 ng/ml, about 1 ng/ml, about 2 ng/ml, about 3 ng/ml, about 4 ng/ml, about 5 ng/ml, about 6 ng/ml, about 7 ng/ml, or about 10 ng/ml of undercarboxylated/uncarboxylated osteocalcin.

In another embodiment of the invention, a method is provided for diagnosing a patient having or at risk of developing a disorder selected from the group consisting of male infertility, low sperm count, impaired sperm motility, impaired sperm viability, low testosterone levels, reduced libido, erectile dysfunction, underdevelopment of testes, and excess apoptosis in testes, comprising: (i) determining the ratio of undercarboxylated/uncarboxylated osteocalcin to total osteocalcin in a biological sample taken from the patient; and (ii) comparing the ratio to a standard ratio; where, if the patient ratio is lower than the standard ratio, diagnosing the patient as having or being at risk of developing the disorder. In certain embodiments, the standard ratio is 5%-10%, 10%-15%, 15%-20%, 20%-25%, 25%-30%, or 30%-35%. In certain embodiments, the standard ratio is about 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, or 35%. Preferably, the patient is a male human. In preferred embodiments, the biological sample is blood, serum, plasma, cerebrospinal fluid, urine, a cell sample, or a tissue sample.

Assays for detecting the levels of protein expression, e.g., osteocalcin expression, are well known to those of skill in the art. Such assays include, for example, antibody-based immunoassays. Methods for using antibodies as disclosed herein are particularly applicable to the cells, tissues and other biological samples from patient with disorders relating to reproduction in male mammals that differentially express osteocalcin, OST-PTP, PTP-1B, or gamma-carboxylase. The methods use antibodies that selectively bind to the protein of interest and its fragments or variants.

The amount of osteocalcin in a biological sample may be determined by an assay such as a radioimmunoassay, an immunoradiometric assay, and/or an enzyme immunoassay. A "radioimmunoassay" is a technique for detecting and measuring the concentration of an antigen using a labeled (e.g., radioactively labeled) form of the antigen. Examples of radioactive labels for antigens include $^{3}H$, $^{14}C$, and $^{125}I$. The concentration of antigen (e.g., osteocalcin) in a biological sample may be measured by having the antigen in the sample compete with a labeled (e.g., radioactively, fluorescently) antigen for binding to an antibody to the antigen. To ensure competitive binding between the labeled antigen and the unlabeled antigen, the labeled antigen is present in a concentration sufficient to saturate the binding sites of the antibody. The higher the concentration of antigen in the sample, the lower the concentration of labeled antigen that will bind to the antibody.

In a radioimmunoassay, to determine the concentration of labeled antigen bound to antibody, the antigen-antibody complex must be separated from the free antigen. One method for separating the antigen-antibody complex from the free antigen is by precipitating the antigen-antibody complex with an anti-isotype antiserum. Another method for separating the antigen-antibody complex from the free antigen is by precipitating the antigen-antibody complex with formalin-killed *S. aureus*. Yet another method for separating the antigen-antibody complex from the free antigen is by performing a "solid-phase radioimmunoassay" where the antibody is linked (e.g., covalently) to Sepharose® beads, polystyrene wells, polyvinylchloride wells, or microtiter wells. By comparing the concentration of labeled antigen bound to antibody to a standard curve based on samples having a known concentration of antigen, the concentration of antigen in the biological sample can be determined.

An "Immunoradiometric Assay" (IRMA) is an immunoassay in which the antibody reagent is radioactively labeled. An IRMA requires the production of a multivalent antigen conjugate, by techniques such as conjugation to a protein, e.g., rabbit serum albumin (RSA). The multivalent antigen conjugate must have at least 2 antigen residues per molecule and the antigen residues must be of sufficient distance apart to allow binding by at least two antibodies to the antigen. For example, in an IRMA the multivalent antigen conjugate can be attached to a solid surface such as a plastic sphere. Unlabeled "sample" antigen and antibody to antigen which is radioactively labeled are added to a test tube containing the multivalent antigen conjugate coated sphere. The antigen in the sample competes with the multivalent antigen conjugate for antigen antibody binding sites. After an appropriate incubation period, the unbound reactants are removed by washing and the amount of radioactivity on the solid phase is determined. The amount of bound radioactive antibody is inversely proportional to the concentration of antigen in the sample.

The most common enzyme immunoassay is the "Enzyme-Linked Immunosorbent Assay (ELISA)." The "Enzyme-Linked Immunosorbent Assay (ELISA)" is a technique for detecting and measuring the concentration of an antigen using a labeled (e.g., enzyme linked) form of the antibody. In a "sandwich ELISA," an antibody (e.g., to osteocalcin) is linked to a solid phase (e.g., a microtiter plate) and exposed to a biological sample containing antigen (e.g., osteocalcin). The solid phase is then washed to remove unbound antigen. A labeled (e.g., enzyme linked) antibody is then bound to the bound-antigen (if present) forming an antibody-antigen-antibody sandwich. Examples of enzymes that can be linked to the antibody include alkaline phosphatase, horseradish peroxidase, luciferase, urease, and β-galactosidase. The enzyme linked antibody reacts with a substrate to generate a colored reaction product that can be assayed.

In a "competitive ELISA," antibody is incubated with a sample containing antigen (e.g., osteocalcin). The antigen-antibody mixture is then contacted with an antigen-coated solid phase (e.g., a microtiter plate). The more antigen present in the sample, the less free antibody that will be available to bind to the solid phase. A labeled (e.g., enzyme linked) secondary antibody is then added to the solid phase to determine the amount of primary antibody bound to the solid phase.

In an "immunohistochemistry assay," a section of tissue is tested for specific proteins by exposing the tissue to antibodies that are specific for the protein that is being assayed. The antibodies are then visualized by any of a number of methods to determine the presence and amount of the protein present. Examples of methods used to visualize antibodies are, for example, through enzymes linked to the antibodies (e.g., luciferase, alkaline phosphatase, horseradish peroxidase, or β-galactosidase), or chemical methods (e.g., DAB/Substrate chromagen).

In addition to detecting levels of protein expression, the diagnostic assays of the invention may employ methods designed to detect the level of RNA expression. Levels of RNA expression may be determined using methods well known to those of skill in the art, including, for example, the use of northern blots, RT-PCR or in situ hybridizations.

Carboxylation of osteocalcin confers a greater affinity for hydroxyapatite. Total osteocalcin may be measured by immunoassay followed by incubation with hydroxyapatite and centrifugation. The supernatant, which contains osteocalcin that has not adsorbed to hydroxyapatite is then measured using the same immunoassay. The results of this procedure can be expressed either as absolute concentrations or as a ratio of undercarboxylated to carboxylated osteocalcin.

Another procedure uses monoclonal antibodies that distinguish the carboxylation state of all or some of the Glu/Gla residues of osteocalcin. For example, GluOC4-5 (TaKaRa catalog no. M171) reacts with human osteocalcin with glutamic acid residues (decarboxylated) at positions 21 and 24, and does not react with react with Gla-type osteocalcin.

For a review of osteocalcin measurement methods, see Lee et al., 2000, Ann. Clin. Biochem. 37:432-446.

Drug Screening and Assays

Cell-based and non-cell based methods of drug screening are provided to identify candidate agents that reduce OST-PTP, PTP-1B, or gamma-carboxylase activity or expression, and/or increase the level of undercarboxylated/uncarboxylated osteocalcin activity or expression. Such agents find use in treating or preventing disorders related to reproduction in male mammals. Such agents may also be used to treat disorders characterized by decreased testosterone production.

Non-cell based screening methods are provided to identify compounds that bind to OST-PTP, PTP-1B, gamma-carboxylase or osteocalcin and thereby modulate the activity of these proteins.

Such non-cell based methods include a method to identify, or assay for, an agent that binds to OST-PTP, the method comprising the steps of: (i) providing a mixture comprising OST-PTP or a fragment or variant thereof, (ii) contacting the mixture with a candidate agent, (iii) determining whether the candidate agent binds to the OST-PTP, wherein if the agent binds to the OST-PTP or a fragment or variant thereof (iv) determining whether the agent reduces the ability of OST-PTP to dephosphorylate gamma-carboxylase and (v) administering the agent to a patient in need of treatment for a disorder related to reproduction in male mammals. In certain embodiments, the mixture comprises membrane fragments comprising OST-PTP or a fragment or variant thereof.

A screening method is provided to identify or assay for an agent that binds to the phosphatase 1 domain of OST-PTP, the method comprising the steps of: (i) providing a mixture comprising the phosphatase 1 domain of OST-PTP or a fragment or variant thereof, (ii) contacting the mixture with an agent, (iii) determining whether the agent binds to the phosphatase 1 domain of OST-PTP, wherein if the agent binds to the phosphatase 1 domain of OST-PTP or a fragment or variant thereof (iv) determining whether the agent inhibits the phosphatase 1 domain of OST-PTP and, if the agent inhibits the phosphatase 1 domain of OST-PTP (v) administering the agent to a patient in need of treatment for a disorder related to reproduction in male mammals.

A screening method is provided to identify or assay for an agent that binds to PTP-1B, the method comprising the steps of: (i) providing a mixture comprising PTP-1B or a fragment or variant thereof, (ii) contacting the mixture with a candidate agent, (iii) determining whether the candidate agent binds to the PTP-1B, wherein if the agent binds to the PTP-1B or a fragment or variant thereof (iv) determining whether the agent reduces the ability of PTP-1B to dephosphorylate gamma-carboxylase and (v) administering the agent to a patient in need of treatment for a disorder related to reproduction in male mammals. In certain embodiments, the mixture comprises membrane fragments comprising PTP-1B or a fragment or variant thereof.

A screening method is provided to identify, or assay for, an agent that binds to gamma-carboxylase, the method comprising the steps of: (i) providing a mixture comprising the gamma-carboxylase or a fragment or variant thereof, (ii) contacting the mixture with an agent, (iii) determining whether the agent binds to the gamma-carboxylase, wherein if the agent binds to the gamma-carboxylase or a fragment or variant thereof (iv) administering the agent to a patient in need of treatment for a disorder related to reproduction in male mammals. The method may further comprise the step of determining whether the agent reduces gamma-carboxylase activity.

The binding of the agent to the target molecule in the above-described assays may be determined through the use of competitive binding assays. The competitor is a binding moiety known to bind to the target molecule. Under certain circumstances, there may be competitive binding as between the agent and the binding moiety, with the binding moiety displacing the agent or the agent displacing the binding moiety.

Either the agent or the competitor may be labeled. Either the agent, or the competitor is added first to the protein for a time sufficient to allow binding. Incubations may be performed at any temperature which facilitates optimal binding, typically between 4° C. and 40° C. Incubation periods may also be chosen for optimum binding, but may also optimized to facilitate rapid high throughput screening. Typically, between 0.1 and 1 hour will be sufficient. Excess agent and competitor are generally removed or washed away.

Using such assays, the competitor may be added first, followed by the agent. Displacement of the competitor is an indication that the agent is binding to the target molecule and thus is capable of binding to, and potentially modulating, the activity of the target molecule. In this embodiment, either component can be labeled. Thus, for example, if the competitor is labeled, the presence of label in the wash solution indicates displacement by the agent.

In another example, the agent is added first, with incubation and washing, followed by the competitor. The absence of binding by the competitor may indicate that the agent is bound to the target molecule with a higher affinity than the competitor. Thus, if the agent is labeled, the presence of the label on the target molecule, coupled with a lack of competitor binding, may indicate that the agent is capable of binding to the target molecule.

The method may comprise differential screening to identify agents that are capable of modulating the activity of the target molecule. In such an instance, the methods comprise combining the target molecule and a competitor in a first sample. A second sample comprises an agent, the target molecule, and a competitor. Addition of the agent is performed under conditions which allow the modulation of the activity of the target molecule. The binding of the competitor is determined for both samples, and a change, or difference in binding between the two samples indicates the presence of an agent capable of binding to the target molecule and potentially modulating its activity. That is, if the binding of the competitor is different in the second sample relative to the first sample, the agent is capable of binding to the target molecule.

Positive controls and negative controls may be used in the assays. Preferably, all control and test samples are performed in at least triplicate to obtain statistically significant results. Incubation of all samples is for a time sufficient for the binding of the agent to the target molecule. Following incubation, all samples are washed free of non-specifically bound material and the amount of bound, generally labeled agent determined. For example, where a radiolabel is employed, the samples may be counted in a scintillation counter to determine the amount of bound agent.

A variety of other reagents may be included in the screening assays. These include reagents like salts, neutral proteins, e.g. albumin, detergents, etc. which may be used to facilitate optimal protein-protein binding and/or reduce non-specific or background interactions. Also, reagents that otherwise improve the efficiency of the assay, such as protease inhibitors, nuclease inhibitors, anti-microbial agents, etc., may be used. The mixture of components may be added in any order that provides for the requisite binding.

Thus, in one example, the methods comprise combining a sample comprising OST-PTP, PTP-1B, or gamma-carboxylase and an agent, and evaluating the effect on OST-PTP, PTP-1B, or gamma-carboxylase enzyme activity. By enzyme activity, specifically OST-PTP, PTP-1B, or gamma-carboxylase enzyme activity, is meant one or more of the biological activities associated with the enzyme. For OST-PTP and PTP-1B, this activity is preferably the dephosphorylation of gamma-carboxylase; for gamma-carboxylase, it is the carboxylation of osteocalcin. The screening assays are designed to find agents that reduce OST-PTP, PTP-1B, or gamma-carboxylase activity, and/or increase levels of undercarboxylated/uncarboxylated osteocalcin.

Specifically, a screening method is provided to identify an agent that reduces OST-PTP activity, the method comprising the steps of: (a) providing a control mixture comprising OST-PTP or a fragment or variant thereof and a test mixture comprising OST-PTP or a fragment or variant thereof, (b) contacting the test mixture with an agent, (c) determining the level of activity of OST-PTP in the test mixture and in the control mixture, (d) identifying the agent as an agent that reduces OST-PTP activity if the level of OST-PTP activity in the test mixture is lower than the level of OST-PTP activity in the control mixture, and (e) administering the identified agent to a patient in need of treatment for a disorder related to reproduction in male mammals.

A screening method is provided to identify an agent that reduces PTP-1B activity, the method comprising the steps of: (a) providing a control mixture comprising PTP-1B or a fragment or variant thereof and a test mixture comprising PTP-1B or a fragment or variant thereof, (b) contacting the test mixture with an agent, (c) determining the level of activity of PTP-1B in the test mixture and in the control mixture, (d) identifying the agent as an agent that reduces PTP-1B activity if the level of PTP-1B activity in the test mixture is lower than the level of PTP-1B activity in the control mixture, and (e) administering the identified agent to a patient in need of treatment for a disorder related to reproduction in male mammals.

A screening method is provided to identify an agent that reduces gamma-carboxylase activity, the method comprising the steps of: (a) providing a control mixture comprising gamma-carboxylase or a fragment or variant thereof and a test mixture comprising gamma-carboxylase or a fragment or variant thereof, (b) contacting the test mixture with an agent, (c) determining the level of activity of gamma-carboxylase in the test mixture and in the control mixture, (d) identifying the agent as an agent that reduces gamma-carboxylase activity if the level of gamma-carboxylase activity in the test mixture is lower than the level of gamma-carboxylase activity in the control mixture, and (e) administering the identified agent to a patient in need of treatment for a disorder related to reproduction in male mammals.

The present invention also provides a screening method to identify an agent that decarboxylates osteocalcin, the method comprising the steps of: (a) providing a control mixture comprising carboxylated osteocalcin and a test mixture comprising carboxylated osteocalcin, (b) adding to the test mixture an agent, (c) determining the level of carboxylated osteocalcin in the test mixture and in the control mixture, (d) identifying the agent as an agent that decarboxylates osteocalcin if the level of carboxylated osteocalcin in the test mixture is lower than the level of carboxylated osteocalcin in the control mixture, and (e) administering the identified agent to a patient in need of treatment for a disorder related to reproduction in male mammals.

A cell-based method is provided for identifying an agent that increases osteocalcin gene expression, the method comprising steps: (a) determining a first expression level of osteocalcin in a cell, (b) determining a second expression level of osteocalcin after contact with a test agent; and (c) comparing the first expression level with the second expression level, wherein if the first expression level is lower than the second expression level the agent is identified as an agent that increases osteocalcin gene expression, and (e) administering the identified agent to a patient in need of treatment for a disorder related to reproduction in male mammals. The level of osteocalcin gene expression may be determined by measuring the amount of osteocalcin mRNA made or the amount of osteocalcin protein made. In certain embodiments, the cell is an osteoblast.

The present invention also provides screening methods to identify agents that activate GPRC6A and are suitable for use in the prevention and treatment of a reproductive disorder in male mammals. In certain embodiments, the method comprises:

(a) providing a cell that expresses GPRC6A;
(b) exposing the cell to a candidate substance; and
(c) determining if the candidate substance binds to and/or activates the GPRC6A expressed by the cell.

Optionally, the method also comprises: (d) determining if the candidate substance is suitable for use in the prevention and treatment of a reproductive disorder in male mammals.

In certain embodiments, step (a) comprises providing Leydig cells, testis explants, or cells that recombinantly express GPRC6A. In certain embodiments, the cells that recombinantly express GPRC6A are NIH 3T3 cells, HEK 293 cells, BHK cells, COS cells, CHO cells, *Xenopus* oocytes, or insect cells. In certain embodiments, the GPRC6A is human GPRC6A. In certain embodiments, the GPRC6A is encoded by the nucleotide sequence shown in SEQ ID NO: 30. In certain embodiments, the GPRC6A comprises the amino acid sequence shown in SEQ ID NO: 31.

In certain embodiments, the candidate substance is from a library of candidate substances. In certain embodiments, the entire library of substances is exposed to the cell. In certain embodiments, a portion of the library is exposed to the cell.

In certain embodiments, step (b) is carried out by growing the cell in tissue culture and adding the candidate substance to the medium in which the cell is growing or has been grown. Alternatively, the medium in which the cell is growing or has been grown may be removed and fresh medium containing the candidate substance may be added the tissue culture plate or well in which the cell is growing or has been grown.

In certain embodiments, step (c) comprises determining if the candidate substance competes with labeled uncarboxlated osteocalcin for binding to the GPRC6A. In certain embodiments, step (c) comprises labeling the candidate substance and determining if the labeled candidate substance binds to the GPRC6A expressed by the cell.

In certain embodiments, step (c) comprises determining if the candidate substance produces a physiological response in the cell selected from the group consisting of: an increase in the concentration of cAMP in the cell, an increase in testosterone synthesis in the cell, an increase in the expression of StAR in the cell, an increase in the expression of Cyp11a in the cell, an increase in the expression of Cyp17 in the cell, an increase in the expression of 3β-HSD in the cell, an increase in the expression of Grth in the cell, an increase in the expression of tACE in the cell, an increase in CREB phosphorylation in the cell, and a decrease in the amount cleaved Caspase 3 in the cell. The physiological response may also be a combination of any of the foregoing physiological responses. In certain embodiments, the physiological response is an increase in the concentration of cAMP in the cell together with a lack of an increase in tyrosine phosphorylation, ERK activation, and intracellular calcium accumulation. In embodiments where a physiological response is determined, it may be advantageous to use a cell that does not naturally express GPRC6A but that has been engineered to recombinantly expresses GPRC6A. In such cases, the cell prior to transformation to a state that recombinantly expresses GPRC6A can serve as a negative control. In such case, the candidate substance should evoke the physiological response in the cell that recombinantly expresses GPRC6A but not in the negative control cell.

In certain embodiments, step (c) comprises determining if the candidate substance affects the binding of a G protein to the GPRC6A. Here, too, it may be advantageous to use cells that recombinantly express GPRC6A and to use those same cells before transformation as negative controls. In certain embodiments, the cell is co-transfected with a construct encoding GPRC6A and a construct encoding a $G_\alpha$ protein. See, e.g., Christiansen et al., 2007, Br. J. Pharmacol. 150:798-807 and Pi et al., 2005, J. Biol. Chem. 280:40201-40209.

In certain embodiments, step (d) comprises administering the candidate substance to a male mammal and determining that the candidate substance produces an effect in the male mammal selected from the group consisting of increased fertility, raised sperm count, increased sperm motility, increased sperm viability, increased serum testosterone levels, increased libido, amelioration of erectile dysfunction, reduction of the underdevelopment of testes, and reduction of excess apoptosis in testes.

The present invention also provides screening methods to identify agents that activate GPRC6A and are suitable for use in the prevention and treatment of a reproductive disorder in male mammals where the methods comprise:

(a) providing cell membranes containing GPRC6A protein;
(b) exposing the cell membranes to a candidate substance;
(c) determining if the candidate substance binds to the GPRC6A in the cell membranes; and
(d) determining if the candidate substance is suitable for use in the prevention and treatment of a reproductive disorder in male mammals.

In certain embodiments, step (a) comprises providing cell membranes from Leydig cells, testis explants, or cells that recombinantly express GPRC6A. In certain embodiments, the cells that recombinantly express GPRC6A are NIH 3T3 cells, HEK 293 cells, BHK cells, COS cells, CHO cells, *Xenopus* oocytes, or insect cells. In certain embodiments, the GPRC6A is human GPRC6A. In certain embodiments, the GPRC6A is encoded by the nucleotide sequence shown in SEQ ID NO: 30. In certain embodiments, the GPRC6A comprises the amino acid sequence shown in SEQ ID NO: 31

In certain embodiments, the candidate substance is from a library of candidate substances. In certain embodiments, the entire library of substances is exposed to the cell membranes. In certain embodiments, a portion of the library is exposed to the cell membranes.

In certain embodiments, step (c) comprises determining if the candidate substance competes with labeled uncarboxlated osteocalcin for binding to the GPRC6A. In certain embodiments, step (c) comprises labeling the candidate substance and determining if the labeled candidate substance binds to the GPRC6A in the cell membranes.

In certain embodiments, step (d) comprises administering the candidate substance to a male mammal and determining that the candidate substance produces an effect in the male mammal selected from the group consisting of increased fertility, raised sperm count, increased sperm motility, increased sperm viability, increased serum testosterone levels, increased libido, amelioration of erectile dysfunction, reduction of the underdevelopment of testes, and reduction of excess apoptosis in testes.

In certain embodiments of the methods disclosed above, GPRC6A is the protein disclosed at GenBank accession no. AF502962. The nucleotide and amino acid sequences disclosed at GenBank accession no. AF502962 are shown in FIGS. 23 and 24 herein, respectively.

In certain embodiments of the methods disclosed above, GPRC6A is a protein homologous to the protein disclosed at GenBank accession no. AF502962. In certain embodiments of the methods disclosed above, GPRC6A is a protein having about 80-99%, about 85-97%, or about 90-95% amino acid sequence identity to the protein disclosed at GenBank accession no. AF502962.

In certain embodiments of the methods disclosed above, GPRC6A is the protein disclosed Wellendorph & Brauner-Osborne, 2004, Gene 335:37-46.

In certain embodiments of the present invention, the agents identified by the methods of screening against GPRC6A are administered to a male mammal in need of treatment for a disorder related to reproduction. Accordingly, the present invention includes a method of treating disorders related to reproduction in male mammals comprising administering to a male mammal in need of treatment for a disorder related to reproduction a pharmaceutical composition comprising a therapeutically effective amount of an agent that activates GPRC6A and a pharmaceutically acceptable carrier or excipient.

In certain embodiments, the an agent that activates GPRC6A is identified by a method comprising:
(a) providing a cell that expresses GPRC6A;
(b) exposing the cell to a candidate substance; and
(c) determining if the candidate substance binds to and/or activates the GPRC6A expressed by the cell.

Agents that activate GPCR6A include ornithine, lysine, and arginine (Christiansen et al., 2007, Br. J. Pharmacol. 150:798-807).

Gamma carboxylase catalyzes the posttranslational modification of specific glutamic acid residues within osteocalcin to form γ-carboxyglutamic acid residues. In an embodiment of the assays described herein, the level of gamma carboxylase activity or decarboxylase activity is determined by measuring the level of osteocalcin carboxylation.

Cells to be used in the screening or assaying methods described herein include cells that naturally express OST-PTP, the phosphatase 1 domain of OST-PTP, PTP-1B, gamma-carboxylase, or osteocalcin as well as cells that have been genetically engineered to express (or overexpress) OST-PTP, the phosphatase 1 domain of OST-PTP, PTP-1B gamma-carboxylase, or osteocalcin. Such cells include transformed osteoblasts that overexpress OST-PTP, the phosphatase 1 domain of OST-PTP, PTP-1B, or gamma-carboxylase.

A method is provided for identifying an agent useful for treating or preventing a disorder related to reproduction in male mammals comprising: (a) providing an animal that has a disorder related to reproduction in male mammals, (b) determining the amount of undercarboxylated/uncarboxylated osteocalcin in a pre-administration biological sample taken from the animal, (c) administering an agent to the animal, (d) determining the amount of undercarboxylated/uncarboxylated osteocalcin in a post-administration biological sample taken from the animal, and (e) identifying the agent as useful for treating or preventing the disorder related to reproduction in male mammals if the amount of undercarboxylated/uncarboxylated osteocalcin in the post-administration biological sample is higher than the amount of undercarboxylated/uncarboxylated osteocalcin in the pre-administration biological sample.

The term "agent" as used herein includes any molecule, e.g., protein, oligopeptide, small organic molecule, polysaccharide, polynucleotide, lipid, etc., or mixtures thereof. Some of the agents can be used therapeutically. An agent may be OST-PTP, PTP-1B, gamma-carboxylase, osteocalcin, or fragments thereof.

Generally, in the assays described herein, a plurality of assay mixtures is run in parallel with different agent concentrations to obtain a differential response to the various concentrations. Typically, one of these concentrations serves as a negative control, i.e., is at zero concentration or below the level of detection.

Agents for use in screening encompass numerous chemical classes, though typically they are organic molecules, preferably small organic compounds having a molecular weight of more than 100 and less than about 2,500 daltons, preferably less than about 500 daltons. Agents comprise functional groups necessary for structural interaction with proteins, particularly hydrogen bonding, and typically include at least an amine, carbonyl, hydroxyl or carboxyl group, preferably at least two of these functional chemical groups. The agents often comprise cyclical carbon or heterocyclic structures and/or aromatic or polyaromatic structures substituted with one or more of the above functional groups. Agents are also found among biomolecules including peptides, saccharides, fatty acids, steroids, purines, pyrimidines, derivatives, structural analogs or combinations thereof. Particularly preferred biomolecules are peptides.

Libraries of high-purity small organic ligands and peptides that have well-documented pharmacological activities are available from numerous sources for use in the assays herein. One example is an NCI diversity set which contains 1,866 drug-like compounds (small, intermediate hydrophobicity). Another is an Institute of Chemistry and Cell Biology (ICCB; maintained by Harvard Medical School) set of known bioactives (467 compounds) which includes many extended, flexible compounds. Some other examples of the ICCB libraries are: Chem Bridge DiverSet E (16,320 compounds); Bionet 1 (4,800 compounds); CEREP (4,800 compounds); Maybridge 1 (8,800 compounds); Maybridge 2 (704 compounds); Maybridge HitFinder (14,379 compounds); Peakdale 1 (2,816 compounds); Peakdale 2 (352 compounds); ChemDiv Combilab and International (28,864 compounds); Mixed Commercial Plate 1 (352 compounds); Mixed Commercial Plate 2 (320 compounds); Mixed Commercial Plate 3 (251 compounds); Mixed Commercial Plate 4 (331 compounds); ChemBridge Microformat (50,000 compounds); Commercial Diversity Set1 (5,056 compounds). Other NCI Collections are: Structural Diversity Set, version 2 (1,900 compounds); Mechanistic Diversity Set (879 compounds); Open Collection 1 (90,000 compounds); Open Collection 2 (10,240 compounds); Known Bioactives Collections: NINDS Custom Collection (1,040 compounds); ICCB Bioactives 1 (489 compounds); SpecPlus Collection (960 compounds); ICCB Discretes Collections. The following ICCB compounds were collected individually from chemists at the ICCB, Harvard, and other collaborating institutions: ICCB1 (190 compounds); ICCB2 (352 compounds); ICCB3 (352 compounds); ICCB4 (352 compounds). Natural Product Extracts:

NCI Marine Extracts (352 wells); Organic fractions—NCI Plant and Fungal Extracts (1,408 wells); Philippines Plant Extracts 1 (200 wells); ICCB-ICG Diversity Oriented Synthesis (DOS) Collections; DDS1 (DOS Diversity Set) (9600 wells). Compound libraries are also available from commercial suppliers, such as ActiMol, Albany Molecular, Bachem, Sigma-Aldrich, TimTec, and others.

Known and novel pharmacological agents identified in screens may be further subjected to directed or random chemical modifications, such as acylation, alkylation, esterification, or amidification to produce structural analogs.

When screening, designing, or modifying compounds, other factors to consider include the Lipinski rule-of-five (not more than 5 hydrogen bond donors (OH and NH groups); not more than 10 hydrogen bond acceptors (notably N and O); molecular weight under 500 g/mol; partition coefficient log P less than 5), and Veber criteria, which are recognized in the pharmaceutical art and relate to properties and structural features that make molecules more or less drug-like.

The agent may be a protein. By "protein" in this context is meant at least two covalently attached amino acids, and includes proteins, polypeptides, oligopeptides and peptides. The protein may be made up of naturally occurring amino acids and peptide bonds, or synthetic peptidomimetic structures. Thus "amino acid," or "peptide residue," as used herein means both naturally occurring and synthetic amino acids. For example, homo-phenylalanine, citrulline and norleucine are considered amino acids for the purposes of the invention. "Amino acids" also includes imino acid residues such as proline and hydroxyproline. The side chains may be in either the (R) or the (S) configuration. In the preferred embodiment, the amino acids are in the (S) or L-configuration. If non-naturally occurring side chains are used, non-amino acid substituents may be used, for example to prevent or retard in vivo degradations.

The agent may be a naturally occurring protein or fragment or variant of a naturally occurring protein. Thus, for example, cellular extracts containing proteins, or random or directed digests of proteinaceous cellular extracts, may be used. In this way, libraries of prokaryotic and eukaryotic proteins may be made for screening against one of the various proteins. Libraries of bacterial, fungal, viral, and mammalian proteins, with the latter being preferred, and human proteins being especially preferred, may be used.

Agents may be peptides of from about 5 to about 30 amino acids, with from about 5 to about 20 amino acids being preferred, and from about 7 to about 15 being particularly preferred. The peptides may be digests of naturally occurring proteins as is outlined above, random peptides, or "biased" random peptides. By "random" or grammatical equivalents herein is meant that each nucleic acid and peptide consists of essentially random nucleotides and amino acids, respectively. Since generally these random peptides (or nucleic acids, discussed below) are chemically synthesized, they may incorporate any nucleotide or amino acid at any position. The synthetic process can be designed to generate randomized proteins or nucleic acids, to allow the formation of all or most of the possible combinations over the length of the sequence, thus forming a library of randomized agent bioactive proteinaceous agents.

The library may be fully randomized, with no sequence preferences or constants at any position. Alternatively, the library may be biased. That is, some positions within the sequence are either held constant, or are selected from a limited number of possibilities. For example, the nucleotides or amino acid residues are randomized within a defined class, for example, of hydrophobic amino acids, hydrophilic residues, sterically biased (either small or large) residues, towards the creation of cysteines, for cross-linking, prolines for SH3 domains, serines, threonines, tyrosines or histidines for phosphorylation sites, etc., or to purines, etc.

The agent may be an isolated nucleic acid, preferably antisense, siRNA, or cDNA that binds to either the gene encoding the protein of interest, or its mRNA, to block gene expression or mRNA translation, respectively. By "nucleic acid" or "oligonucleotide" or grammatical equivalents herein means at least two nucleotides covalently linked together. Such nucleic acids will generally contain phosphodiester bonds, although in some cases, as outlined below, nucleic acid analogs are included that may have alternate backbones, comprising, for example, phosphoramide (Beaucage et al., 1993, Tetrahedron 49:1925 and references therein; Letsinger, 1970, J. Org. Chem. 35:3800; Sprinzl et al., 1977, Eur. J. Biochem. 81:579; Letsinger et al., 1986, Nucl. Acids Res. 14:3487; Sawai et al, 1984, Chem. Lett. 805; Letsinger et al., 1988, J. Am. Chem. Soc. 110:4470; and Pauwels et al., 1986, Chemica Scripta 26:141); phosphorothioate (Mag et al., 1991, Nucleic Acids Res. 19:1437; and U.S. Pat. No. 5,644,048), phosphorodithioate (Briu et al., 1989, J. Am. Chem. Soc. 111:2321); O-methylphosphoroamidite linkages (see Eckstein, Oligonucleotides and Analogues: A Practical Approach, Oxford University Press), and peptide nucleic acid backbones and linkages (see Egholm, 1992, J. Am. Chem. Soc. 114:1895; Meier et al., 1992, Chem. Int. Ed. Engl. 31:1008; Nielsen, 1993, Nature, 365:566; Carlsson et al., 1996, Nature 380: 207); all of which publications are incorporated by reference and may be consulted by those skilled in the art for guidance in designing nucleic acid agents for use in the methods described herein.

Other analog nucleic acids include those with positive backbones (Denpcy et al., 1995, Proc. Natl. Acad. Sci. USA 92:6097); non-ionic backbones (U.S. Pat. Nos. 5,386,023; 5,637,684; 5,602,240; 5,216,141; and 4,469,863; Kiedrowshi et al., 1991, Angew. Chem. Intl. Ed. English 30:423; Letsinger et al., 1988, J. Am. Chem. Soc. 110:4470; Letsinger et al., 1994, Nucleoside & Nucleoside 13:1597; Chapters 2 and 3, ASC Symposium Series 580, "Carbohydrate Modifications in Antisense Research," Ed. Y. S. Sanghui and P. Dan Cook; Mesmaeker et al., 1994, Bioorganic & Medicinal Chem. Lett. 4:395; Jeffs et al., 1994, J. Biomolecular NMR 34:17); and non-ribose backbones, including those described in U.S. Pat. Nos. 5,235,033 and 5,034,506, and Chapters 6 and 7, ASC Symposium Series 580, "Carbohydrate Modifications in antisense Research," Ed. Y. S. Sanghui and P. Dan Cook. Nucleic acids containing one or more carbocyclic sugars are also included within the definition of nucleic acids that may be used as agents as described herein. Several nucleic acid analogs are described in Rawls, C & E News Jun. 2, 1997 page 35. All of these references are hereby expressly incorporated by reference. These modifications of the ribose-phosphate backbone may be done to facilitate the addition of additional moieties such as labels, or to increase the stability and half-life of such molecules in physiological environments. In addition, mixtures of naturally occurring acids and analogs can be made. Alternatively, mixtures of different nucleic acid analogs, and mixtures of naturally occurring nucleic acids and analogs may be made. The nucleic acids may be single stranded or double stranded, or contain portions of both double stranded or single stranded sequence. The nucleic acid may be DNA, both genomic and cDNA, RNA or a hybrid, where the nucleic acid contains any combination of deoxyribo- and ribo-nucleotides, and any combination of bases, including uracil, adenine, thymine, cytosine, guanine, inosine, xanthine hypoxanthine, isocytosine, isoguanine, etc.

As described above generally for proteins, nucleic acid agents may be naturally occurring nucleic acids, random nucleic acids, or "biased" random nucleic acids. For example, digests of prokaryotic or eukaryotic genomes may be used as outlined above for proteins.

The agents may be obtained from combinatorial chemical libraries, a wide variety of which are available in the literature. By "combinatorial chemical library" herein is meant a collection of diverse chemical compounds generated in a defined or random manner, generally by chemical synthesis. Millions of chemical compounds can be synthesized through combinatorial mixing.

The determination of the binding of the agent to one of the various proteins such as OST-PTP, PTP-1B, or gamma-carboxylase may be done in a number of ways. In a preferred embodiment, the agent is labeled, and binding determined directly. For example, this may be done by attaching all or a portion of one of the various proteins to a solid support, adding a labeled agent (for example an agent comprising a radioactive or fluorescent label), washing off excess reagent, and determining whether the label is present on the solid support. Various blocking and washing steps may be utilized as is known in the art.

By "labeled" herein is meant that the agent is either directly or indirectly labeled with a label which provides a detectable signal, e.g. a radioisotope (such as $^{3}H$, $^{14}C$, $^{32}P$, $^{33}P$, $^{35}S$, or $^{125}I$), a fluorescent or chemiluminescent compound (such as fluorescein isothiocyanate, rhodamine, or luciferin), an enzyme (such as alkaline phosphatase, beta-galactosidase or horseradish peroxidase), antibodies, particles such as magnetic particles, or specific binding molecules, etc. Specific binding molecules include pairs, such as biotin and streptavidin, digoxin and antidigoxin, etc. For the specific binding members, the complementary member would normally be labeled with a molecule which provides for detection, in accordance with known procedures, as outlined above. The label can directly or indirectly provide a detectable signal. Only one of the components may be labeled. Alternatively, more than one component may be labeled with different labels.

Transgenic mice, including knock in and knock out mice, and isolated cells from them (especially osteoblasts) that over or under express the nucleic acids disclosed herein (e.g., cDNA for Esp, PTP-1B, osteocalcin, gamma-carboxylase) can be made using routine methods known in the art. In certain instances, nucleic acids are inserted into the genome of the host organism operably connected to and under the control of a promoter and regulatory elements (endogenous or heterogeneous) that will cause the organism to over express the nucleic acid gene or mRNA. One example of an exogenous/heterogeneous promoter included in the transfecting vector carrying the gene to be amplified is alpha 1(I) collagen. Many such promoters are known in the art.

Human osteoblasts can be transfected with vectors carrying the cDNA for human Esp, human PTP-1B, or human osteocalcin (or fragments or variants thereof) operably linked to known promoters and regulatory elements that cause the transfected human osteoblast to overexpress osteocalcin (or fragments or variants thereof).

Disclosed herein are transgenic mice and mouse cells, and transfected human cells overexpressing osteocalcin (or fragments or variants thereof), OST-PTP, PTP-1B, or gamma-carboxylase. Also disclosed herein are double mutant mice that have deletions of one or both alleles for osteocalcin, Esp, and gamma-carboxylase, and various combinations of double mutants.

Also disclosed herein are vectors carrying the cDNA or mRNA encoding the proteins for insertion into the genome of a target animal or cell. Such vectors can optionally include promoters and regulatory elements operably linked to the cDNA or mRNA. By "operably linked" is meant that promoters and regulatory elements are connected to the cDNA or mRNA in such a way as to permit expression of the cDNA or mRNA under the control of the promoters and regulatory elements.

Antisense and small interfering RNAs for use in reducing expression of OST-PTP, PTP-1B, and/or gamma-carboxylase, thereby treating or preventing a disorder related to reproduction in a male mammal can be made that specifically hybridize to the gene and/or mRNA encoding OST-PTP, PTP-1B, or gamma-carboxylase, respectively. The sequence for mouse (OST-PTP, Ptprv) cDNA is set forth in SEQ ID NO:10. The amino acid sequence for OST-PTP, Ptprv) protein is set forth in SEQ ID NO:11. This cDNA, or antisense and small interfering RNAs based on this cDNA, will hybridize with mRNA for OST-PTP and thereby interfere with its translation. Reducing OST-PTP expression will increase the level of undercarboxylated/uncarboxylated osteocalcin, thereby providing a therapeutic benefit with respect to disorders related to reproduction in male mammals. The sequence for human PTP-1B cDNA is set forth in SEQ ID NO:16. The amino acid sequence for human PTP-1B protein is set forth in SEQ ID NO:17. This cDNA, or antisense and small interfering RNAs based on this cDNA, will hybridize with mRNA for human PTP-1B and thereby interfere with its translation. Reducing human PTP-1B expression will increase the level of undercarboxylated/uncarboxylated osteocalcin, thereby providing a therapeutic benefit with respect to disorders related to reproduction in male mammals. The cDNA for mouse gamma-carboxylase is identified by SEQ ID NO:8, and its amino acid sequence is SEQ ID NO:9. This cDNA, or antisense and small interfering RNAs based on this cDNA, will hybridize with mRNA for gamma-carboxylase and thereby interfere with its translation and is a preferred embodiment. The cDNA for human gamma-carboxylase is identified by SEQ ID NO:6, and the amino acid sequence is SEQ ID NO:7. Human gamma-carboxylase cDNA can be used therapeutically to reduce gamma-carboxylase expression to treat or prevent a disorder related to reproduction in male humans.

The invention is illustrated herein by the following examples, which should not be construed as limiting. The contents of all references, pending patent applications and published patents, cited throughout this application are hereby expressly incorporated by reference. Those skilled in the art will understand that this invention may be embodied in many different forms and should not be construed as limited to the embodiments set forth herein. Rather, these embodiments are provided so that this disclosure will fully convey the invention to those skilled in the art. Many modifications and other embodiments of the invention will come to mind in one skilled in the art to which this invention pertains having the benefit of the teachings presented in the foregoing description. Although specific terms are employed, they are used as in the art unless otherwise indicated.

EXAMPLES

Example 1

Male Osteocalcin-Deficient Mice have Decreased Fertility

Male mice in which both alleles of osteocalcin were disrupted and non-functional (Osteocalcin−/− mice) that were crossed with wild-type (WT) littermates show impaired fertility. Whether the Osteocalcin-mutation was on the C57Bl/6J or on the 129sv/ev genetic background, very few litters were obtained over the course of 3 months. Moreover, the litters were of significantly smaller size than those obtained when crossing WT male mice with WT female mice. When 8 Osteocalcin−/− male mice were placed with 2 WT female mice each from 6 to 12 weeks of age, only 17 pups were obtained and the litter size was 4.25 pups per litter. In contrast, when 8 WT male mice were placed with 2 WT female mice each for the same period of time, 63 pups were obtained and the litter size was also significantly larger (7.93 pups per litter) (FIG. 1). Furthermore, it was observed that after 6 months of age, and unlike what is the case for WT mice, male Osteocalcin−/− mice were totally infertile. This reproduction phenotype was not observed in Osteocalcin+/− mice (mice having a single allele of osteocalcin disrupted).

Example 2

Male Mice have Abnormal Spermatogenesis in the Absence of Osteocalcin

Figure 2:
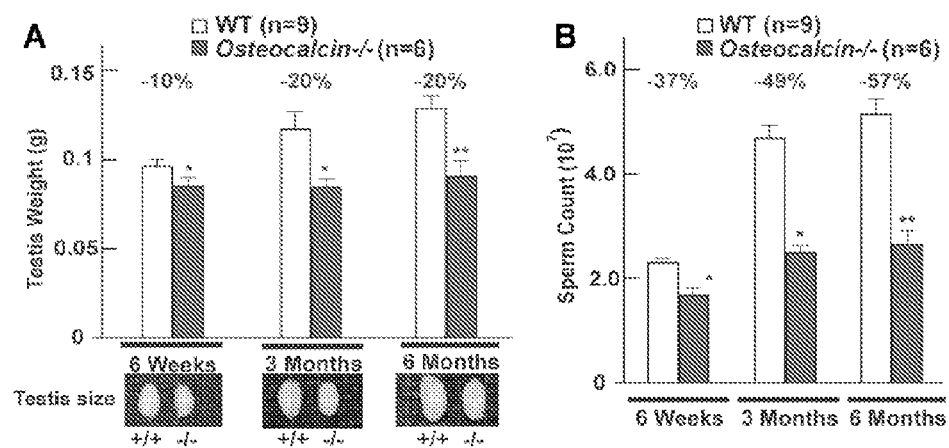
FIG. 2. Analysis of testicular weight (A), size (lower panel in A) and sperm count (B) of Osteocalcin−/− and wild-type (+/+) littermate mice at 6 weeks, 3 months, and 6 months of age.

Testis weight was measured at different ages in male Osteocalcin-deficient mice. As early as at 6 weeks of age, male Osteocalcin−/− mice had significantly smaller testes than their WT littermates and this phenotype progressively worsened over time (FIG. 2A). Sperm count in the seminal fluid of Osteocalcin−/− and WT littermate male mice was also measured. It was found that sperm count was already decreased by 37% in 6 weeks old Osteocalcin−/− mice and that this decrease reached 60% of the sperm count in WT mice at 6 months of age (FIG. 2B).

Example 3

Figure 3:
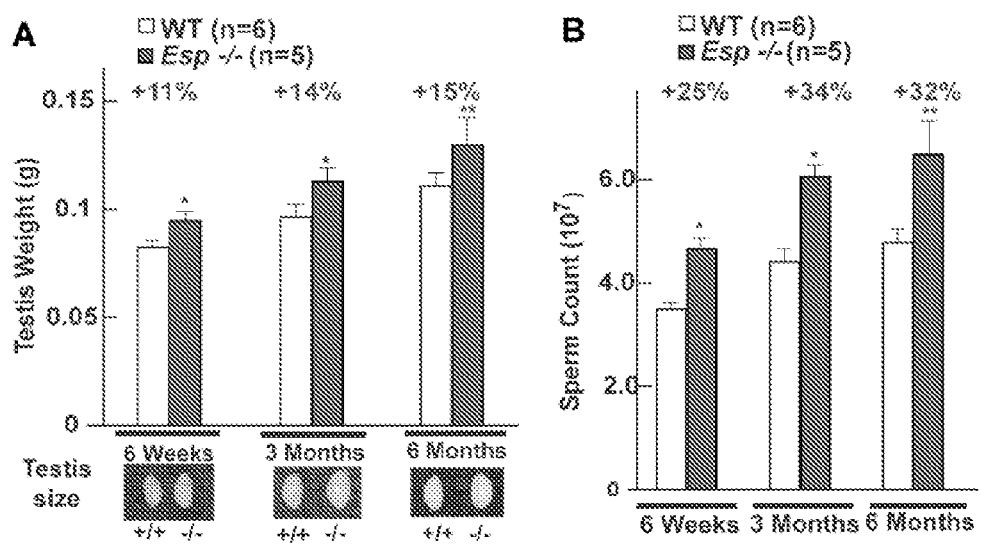
FIG. 3. Analysis of testicular weight (A), size (lower panel in A) and sperm count (B) of Esp−/− and wild-type (+/+) littermate mice at 6 weeks, 3 months and 6 months of age.

Esp-Deficient and Osteocalcin-Deficient Mice have Opposite Reproductive Phenotypes Esp encodes a phosphatase which decreases osteocalcin bioactivity to such an extent that Esp−/− and Osteocalcin−/− mice display metabolic abnormalities that are the mirror image of one another (Hinoi et al., 2008, J. Cell Biol. 183: 1235-1242; Ferron et al., 2008, Proc. Natl. Acad. Sci. USA 105:5266-5270; Lee et al., 2007, Cell 130:456-469). Esp−/− mice were tested for abnormalities of spermatogenesis. As shown in FIG. 3A, Esp−/− mice had significantly bigger testes than WT littermates at both 6 and 12 weeks of age. Moreover, their sperm count was significantly increased (FIG. 3B). These data strongly suggest, although they do not prove, that, as is the case for energy metabolism, Esp and Osteocalcin are in the same genetic pathway and that it is the uncarboxylated form of osteocalcin that regulates spermatogenesis.

Example 4

Osteocalcin Regulates Germ Cell Apoptosis

Figure 4:
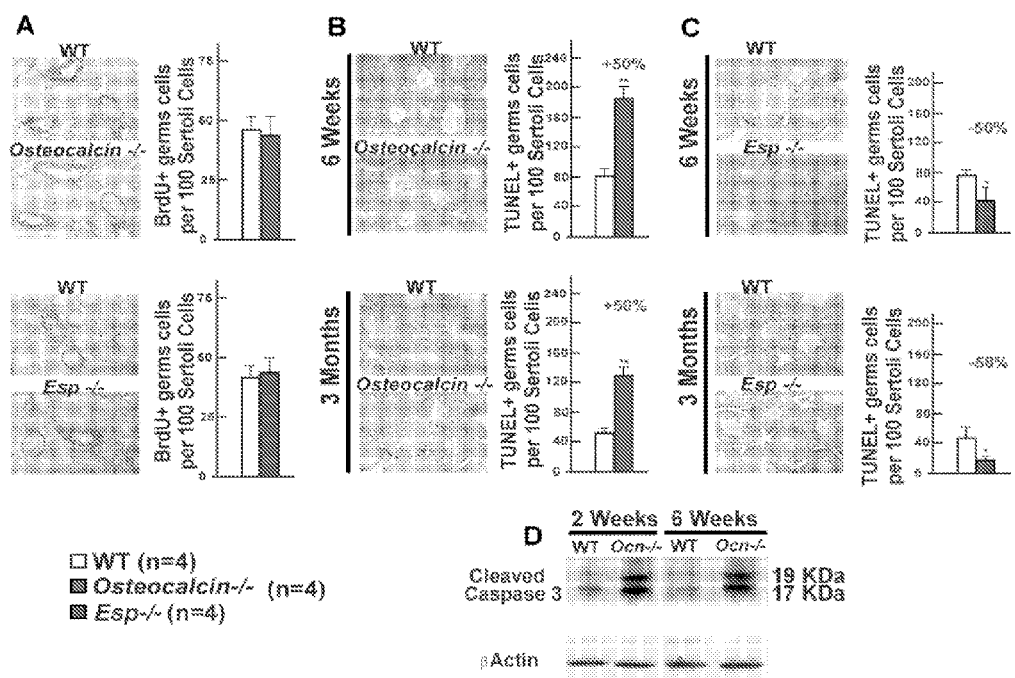
FIG. 4. Analysis of cell proliferation in 2-week-old testes from WT and Osteocalcin mutant mice 1 day after bromodeoxyuridine (BrdU) injection (A). TUNEL analysis of Osteocalcin−/−, Esp−/− testes at 6 weeks and 3 months of age (B-C). Western-blot analysis of extracts from 2-week and 6 week-old Osteocalcin−/− testes using an anti Cleaved Caspase-3 (Asp175) (5A1) Rabbit antibody (D). β-Actin was used as a loading control.

The proliferation and apoptosis of germ cells in Osteocalcin−/− or in Esp−/− mice were studied. When using BrdU labeling in vivo, no abnormalities in germ cell proliferation in Osteocalcin−/− or in the Esp−/− mice were detected at any time point (FIG. 4A). In contrast, study of apoptosis by TUNEL assay consistently showed a significant increase in the apoptosis of germ cells in Osteocalcin−/− mice as young as 2 weeks of age (FIG. 4B). In 12 week-old Osteocalcin−/− mutant mice, there was a 50% increase in germ cell apoptosis compared to WT mice (FIG. 4B). Conversely, a decrease was observed in the number of apoptotic germ cells in Esp−/− mice compared to WT littermates at all time points analyzed (FIG. 4C). Molecularly, it could be shown that Caspase 3, one of the main effectors of apoptosis, was significantly more abundant in Osteocalcin−/− than in WT testes (FIG. 4D).

Figure 14:
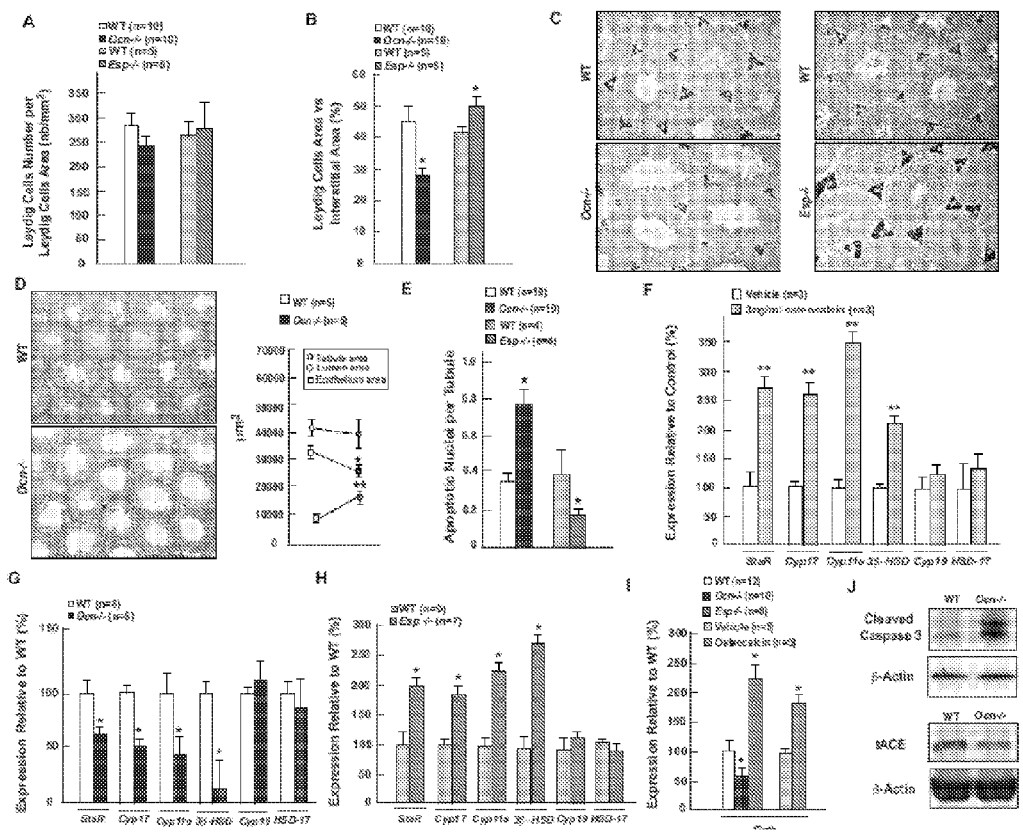
FIG. 14. Cellular and molecular events triggered by osteocalcin in Leydig cells. (A-C) Histological analyses of Leydig cells in Ocn–/– and Esp–/– mice: (A) Absolute number of Leydig cells per testis was quantified by the number of 3β-HSD positive cells. (B) Ratio between Leydig cells (immunopositive for 3β-HSD) versus testis interstitial areas in WT, Ocn–/–, and Esp–/– mice. (C) 3β-HSD immunohistochemistry staining of WT, Ocn–/–, and Esp–/– testes. (D) Quantification of tubule, lumen, and epithelium areas in WT and Ocn–/– mice. (E) Germ cell apoptosis analysis by TUNEL assay in WT, Ocn–/–, and Esp–/– testes. (F—H) qPCR analysis of the expression of steroidogenic acute regulatory protein (StAR), cholesterol side-chain cleavage enzyme (Cyp11a), cytochrome P-450 17 alpha (Cyp17), 3-β-hydroxysteroid dehydrogenase (3β-HSD), aromatase enzyme (Cyp19), and 17β-hydroxysteroid dehydrogenase (HSD-17) in testis after treatment with vehicle or 3 ng/ml of osteocalcin (F) in Ocn–/– compared to WT littermate testes (G) and in Esp–/– compared to WT littermate testes (H). (I) qPCR analysis of Grth/Ddx25 expression in WT, Ocn–/–, Esp–/–, and WT mice treated with vehicle or osteocalcin (3 ng/g of body weight). (J) Western blot analysis of cleaved caspase 3 and tACE in WT and Ocn–/– testes. Error bars represent SEM. Student's t test (*) P<0.05, (**) P<0.001.
Figure 15:
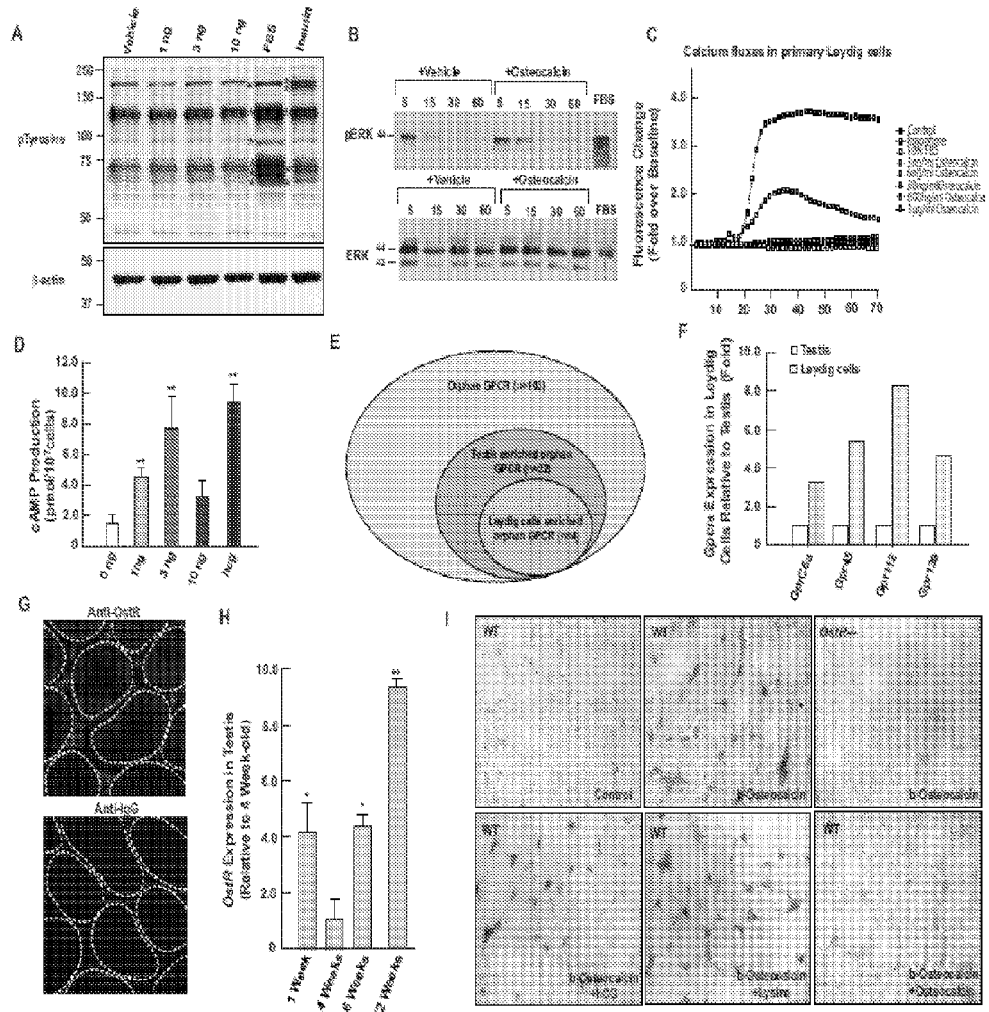
FIG. 15. G-protein coupled receptor OstR is a receptor for osteocalcin. (A) Anti-phospho-tyrosine antibody Western blot analysis of TM3 Leydig cells treated with increasing concentration of osteocalcin, or 10% FBS, or insulin as positive controls, for 1 minute (upper panel). Proteins phosphorylated on tyrosine residues appear in positive controls (asterisks) but not in osteocalcin treated cells. Equal loading was assessed using an anti-actin antibody (lower panel). (B) Western blot analysis of TM3 Leydig cells showing the absence of ERK1/2 phosphorylation upon stimulation with vehicle or osteocalcin. (C) Calcium fluxes in primary Leydig cells upon stimulation with increasing doses of osteocalcin, 10% FBS, and ionophore (A23187) were used as positive controls. (D) cAMP production upon osteocalcin stimulation is increased in TM3 Leydig cells. (E) Schematic representation of the results obtained by the differential expression search for OstR. Among the 103 orphan GPCRs expressed in testis and ovary, 22 were predominantly expressed in testis and only four were enriched in primary Leydig cells compared to the expression in whole testis. (F) Relative expression of Gprc6a, Gpr45, Gpr112, and Gpr139 in Leydig cells compared to whole testis. (G) Immunofluorescence analysis of OstR expression in WT testes coronal section. Anti-IgG was used as negative control. (H) qPCR analysis of OstR expression in 1, 4, 6, and 12 week-old WT testes. (I) Cross sections of testes from WT and OstR-deficient mice stained with biotinylated osteocalcin (b-osteocalcin). Upper left panel: WT testis stained with avidin-biotin complex only; upper middle panel: WT testis stained with 10 nM of b-osteocalcin; upper right panel: testis from OstR-deficient mice stained with 10 nM of b-osteocalcin; lower left panel: WT testis stained with 10 nM of b-osteocalcin in the presence of 1000 nM hCG; lower middle panel: WT testis stained with 10 nM of b-osteocalcin in the presence of 1000 nM lysine; lower right panel: WT testis stained with 10 nM of b-osteocalcin in the presence of 1000 nM of unlabeled osteocalcin. Error bars represent SEM. Student's t test (*) P<0.05, (**) P<0.001.
Figure 16:
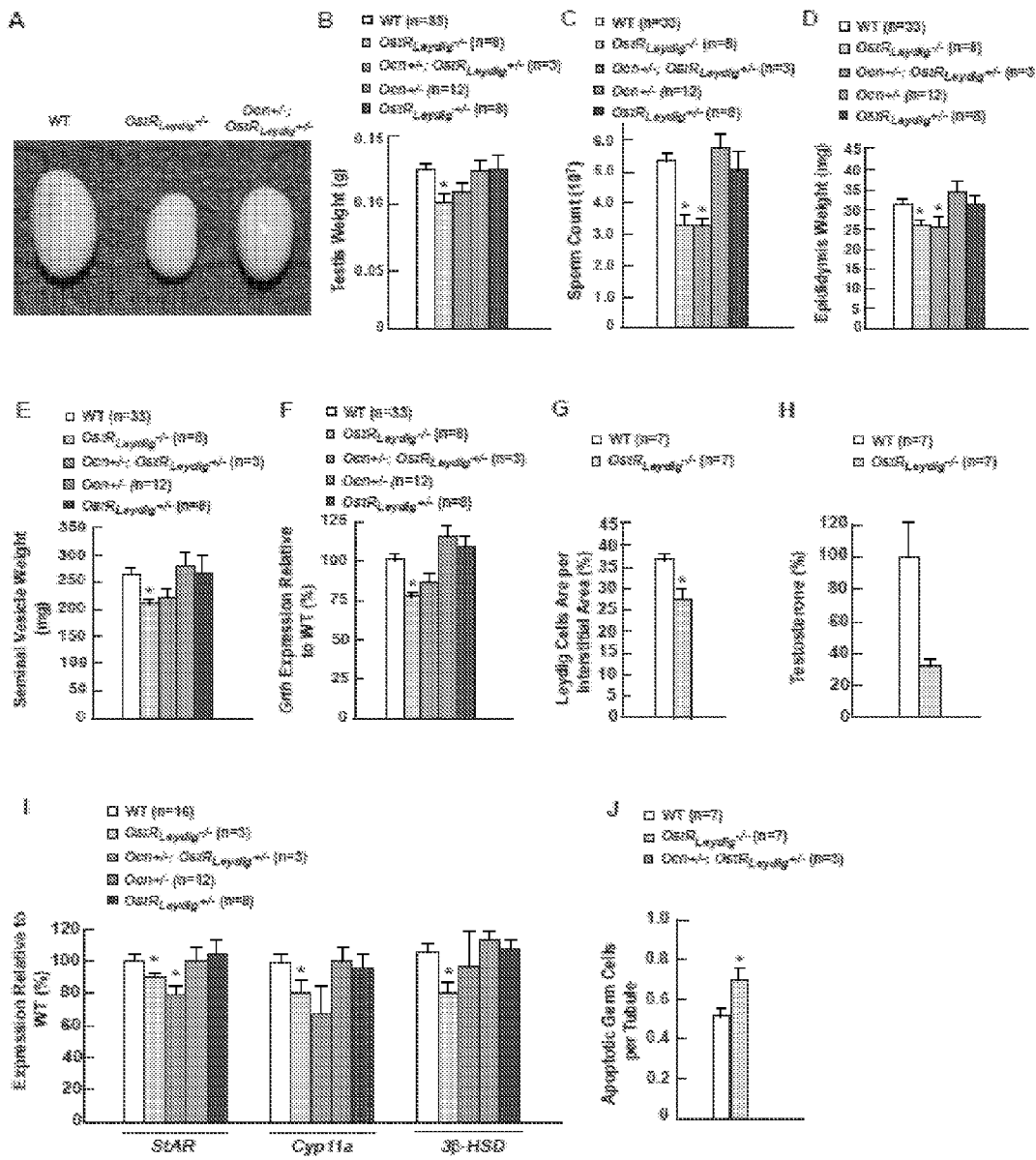
FIG. 16. Specific deletion of OstR in Leydig cells decreases male fertility. (A-E) Fertility in mice lacking OstR in Leydig cells only ($OstR_{Leydig}$–/–) or lacking one allele of Ocn or one allele of OstR in Leydig cells only (Ocn+/– or $OstR_{Leydig}$+/–), or in compound heterozygous mice (Ocn+/– and $OstR_{Leydig}$+/–) compared to control littermates. (A) Testis size, (B) testis weight, (C) sperm count, (D-E) epididymides and seminal vesicles weights. (F) qPCR analysis of Grth expression in mice of indicated genotypes. (G) Ratio between Leydig cells (stained by immunohistochemistry of 3β-HSD) versus testis interstitial areas. (H) Ratio of circulating testosterone levels measured in WT and $OstR_{Leydig}$–/–. (I) qPCR analysis of StAR, Cyp11a, and 3β-HSD in $OstR_{Leydig}$–/– and Ocn+/–; $OstR_{Leydig}$+/– compared to WT littermate testes. (J) Germ cell apoptosis analysis by TUNEL assay. Error bars represent SEM. Student's t test (*) P<0.05.
Figure 17:
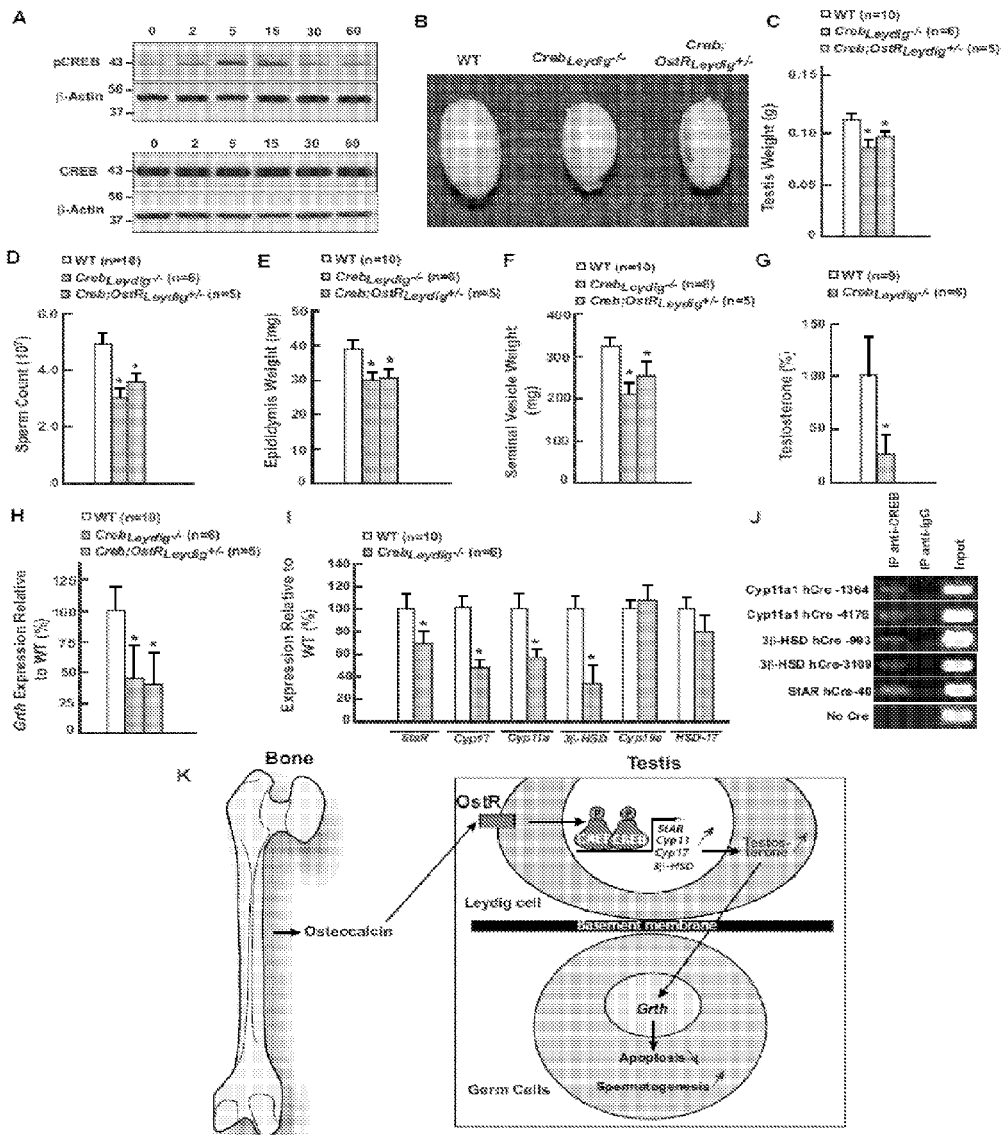
FIG. 17. CREB is a transcription factor mediating osteocalcin-evoked gene expression in Leydig cells. (A) Western blot analysis of CREB activation upon stimulation with osteocalcin. (B-F) Fertility in mice lacking Creb in Leydig cells ($Creb_{Leydig}$–/–) or lacking one allele of Creb or one allele of OstR in Leydig cells only ($Creb_{Leydig}$+/– or $OstR_{Leydig}$+/–), or of compound heterozygous mice ($Creb_{Leydig}$+/–; $OstR_{Leydig}$+/–) compared to control littermates. (B) Testis size, (C) testis weight, (D) sperm count, (E-F) epididymides and seminal vesicle weights. (G) Quantification of circulating testosterone levels represented as fold change compared to WT. (H) qPCR analysis of Grth expression in mice of indicated genotypes. (I) qPCR analysis of StAR, Cyp11a, Cyp17, 3β-HSD, Cyp19, and HSD-17 in $Creb_{Leydig}$–/– compared to control littermate testes. (J) Chromatin immunoprecipitation (ChIP) using anti-CREB antibody and unspecific isotype IgG antibody. (K) Model representing the current knowledge about the regulation of male fertility by the skeleton. Error bars represent SEM. Student's t test (*) P<0.05.

The morphology of Leydig cells was studied by immunostaining of 3-β-hydroxysteroid dehydrogenase/Δ-5-4 isomerase (3β-HSD). The number of Leydig cells was not significantly affected by the absence of osteocalcin or Esp, nor was expression of genes affecting cell proliferation (FIG. 14A and data not shown). Nevertheless, Leydig cells appeared hypotrophic in Ocn−/− testes as determined by the significant decrease of the ratio between the Leydig cells and interstitial areas observed in Ocn−/− compared to WT testes (FIG. 14B-C). Conversely, this ratio was increased in Esp−/− testes (FIG. 14B-C).

Figure 20:
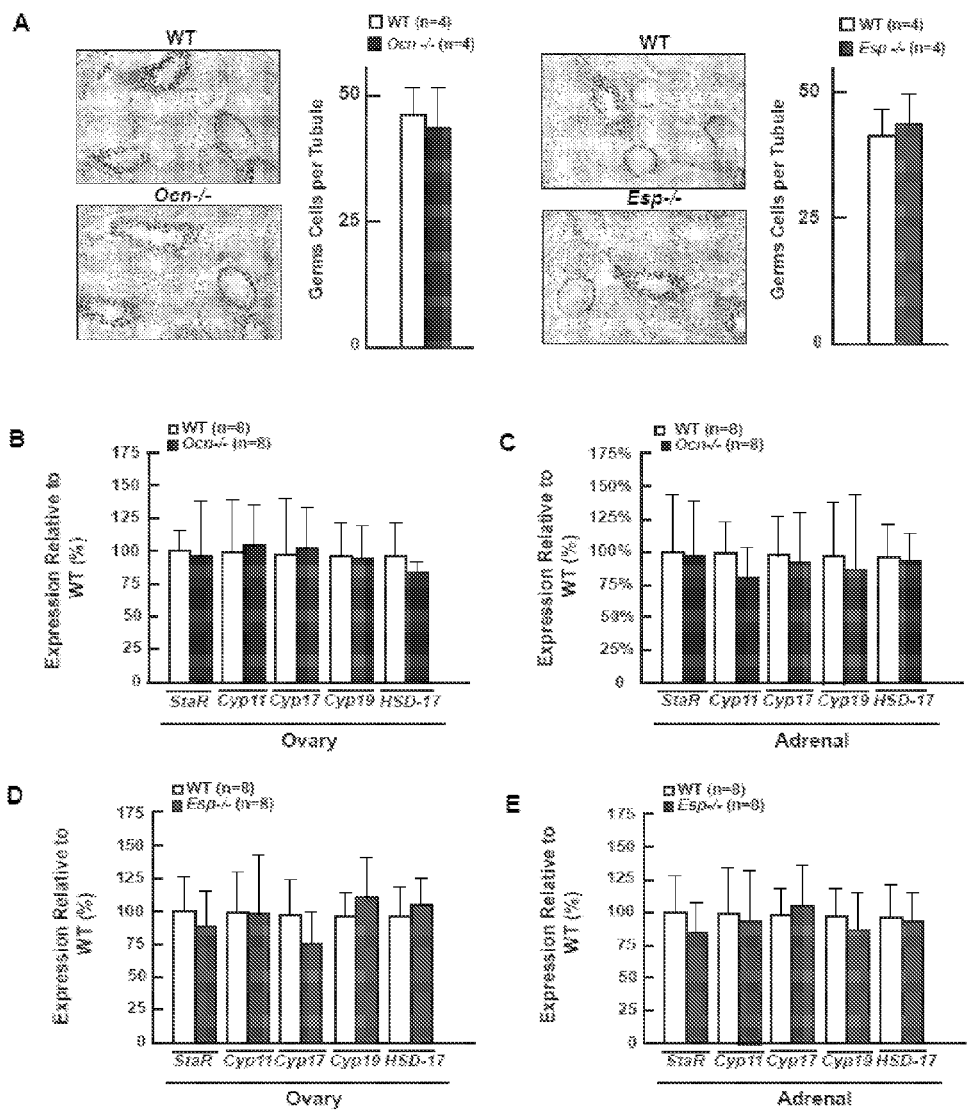
FIG. 20. (A) Germ cell proliferation analyzed by BrdU staining in 2-week-old WT, Ocn-/-, and Esp-/- male littermates. (B-E) qPCR analysis of StAR, Cyp11a, Cyp17, 3β-HSD, Cyp19, and HSD-17 in (B) Ocn-/- and WT ovaries, (C) Ocn-/- and WT adrenals, (D) Esp-/- and WT ovaries, and (E) Esp-/- and WT adrenals. Error bars represent SEM.
Figure 21:
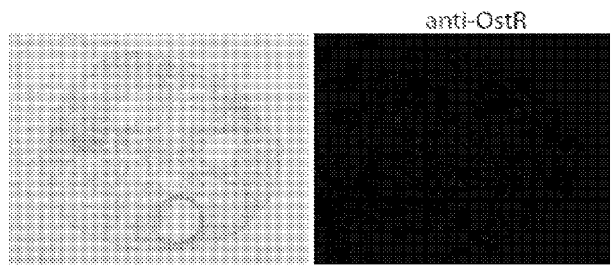
FIG. 21. (A) Schematic representation of the results obtained by the differential expression search for the osteocalcin receptor (OstR). Among the 103 orphan GPCRs expressed in testis and ovary, 22 were predominantly expressed in testis and only four (Gprc6a, Gpr139, Gpr112, and Gpr45) were enriched in primary Leydig cells compared to their expression in whole testis. (B) Immunofluorescence of OstR and IgG control in coronal sections of WT ovaries.

The size of the epithelium in testis tubules was significantly decreased in Ocn−/− mice, a feature suggesting that osteocalcin regulates, presumably through its effect on testosterone biosynthesis, germ cell numbers (FIG. 14D). In view of this result, and since testosterone inhibits germ cell apoptosis (Brinkworth et al., 1995, J. Reprod. Feral. 105:25-33; Henriksen et al., 1995, Endocrinology 136:3285-3291; Sinha Hikim and Swerdloff, 1999, Rev. Reprod. 4:38-47), TUNEL assays were performed. Those assays showed a 50% increase in germ cell apoptosis in Ocn−/− compared to WT mice and a 50% decrease in Esp−/− testes (FIG. 14F). In vivo BrdU labeling did not reveal any abnormalities in germ cell proliferation in either Ocn−/− or Esp−/− mice (FIG. 20A).

Since osteocalcin favors testosterone synthesis by Leydig cells, whether osteocalcin affects the expression of enzymes necessary for testosterone biosynthesis such as StAR, Cyp11a, Cyp17, and 3β-HSD was tested. Uncarboxylated osteocalcin increased expression of these genes in Leydig cell cultures (FIGS. 14G and 14H). Accordingly, their expression was significantly decreased in Ocn−/− and increased in Esp−/− testes (FIG. 14H), while it was unaffected in Ocn−/− and Esp−/− ovaries or adrenal glands (FIG. 21B-E). Of note, there was no change in expression of Cyp19, the gene encoding the testosterone aromatase, or of HSD-17, in Ocn−/− and Esp−/− testes (FIGS. 14G and 14H).

Further support for the notion that osteocalcin influences germ cell apoptosis through testosterone was provided by an examination of the expression of Gonadotropin Regulated Testicular Helicase (Grth). This gene has emerged as an essential regulator of spermatogenesis whose expression in germ cells is regulated by testosterone and inhibits germ cell apoptosis (Dufau and Tsai-Morris, 2007, Trends Endocrinol. Metab. 18:314-320; Sheng et al., 2006, J. Biol. Chem. 281: 35048-35056; Tsai-Morris et al., 2007, Mol. Hum. Reprod. 13:887-892). Grth expression was decreased in Ocn−/− and increased in Esp−/− testes (FIG. 14I). GRTH inhibits activation of Caspase 3, a determinant of apoptosis (Gutti et al., 2008, J. Biol. Chem. 283:17055-17064) and favors expression of tACE, a protein favoring germ cell maturation. Consistent with these notions, Western blot analyses showed an increase of cleaved caspase 3 protein accumulation and a decrease of tACE in Ocn−/− testes (FIG. 14J).

Example 5

Osteocalcin Regulates Testosterone Production

Figure 5:
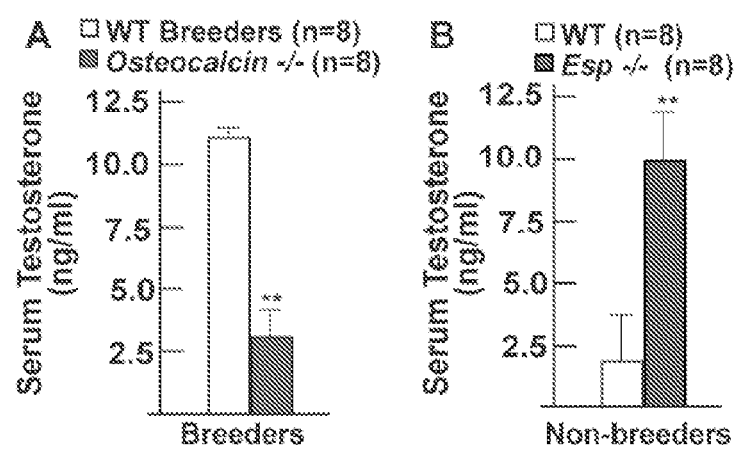
FIG. 5. Analysis of testosterone serum levels in Osteocalcin−/− and WT littermate breeder mice at 3 months of age (A). Analysis of testosterone serum level of Esp−/− and WT littermate non-breeder mice (B) at 3 months of age.

The low sperm count without any abnormality in proliferation and the increase in apoptosis of germ cells suggested that the reproduction phenotype of the Osteocalcin−/− males could be due to a decrease in testosterone secretion or action. To determine if that was the case, testosterone levels were measured in Osteocalcin−/−, Esp−/−, and WT mice. As shown in FIG. 5, there was a 70% decrease in the level of circulating testosterone in Osteocalcin−/− male mice while, in contrast, this level was increased in Esp−/− male mice.

Figure 6:
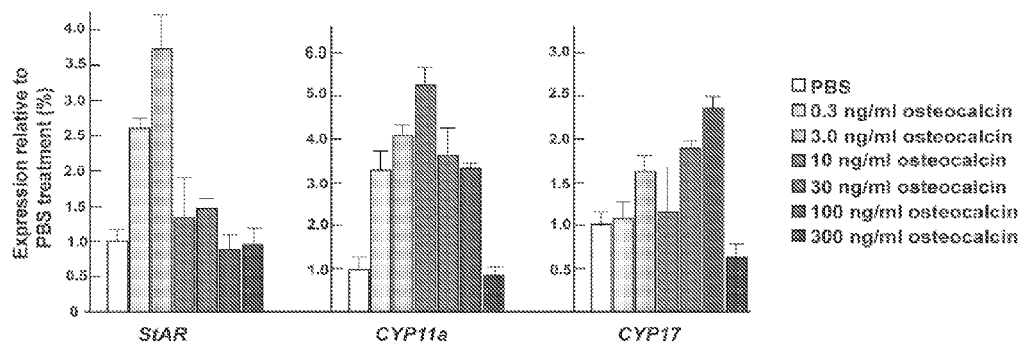
FIG. 6. Quantitative PCR (qPCR) analysis of StAR, Cyp17, and Cyp11a expression in TM3 Leydig cells cultured in the presence of different concentrations of osteocalcin (from 0.3 to 300 ng/ml) for 2 hours.

To further prove that osteocalcin is a regulator of testosterone synthesis, a well-characterized mouse Leydig cell line, the TM3 cell line (Mather, 1980, Biol. Reprod. 23:243-252), was used. These cells have been extensively used as a model of Leydig cells for in vitro studies and have been shown to express SF-1, an important transcriptional regulator of most genes involved in testosterone biosynthesis (Mather, 1980, Biol. Reprod. 23:243-252; Cammas, 1997, Mol. Endocrinol. 11:867-876; Dakhova et al., 2009, Endocrinology 150:404-412). TM3 cells were treated with increasing amounts of osteocalcin and assayed for the expression of genes encoding enzymes of the steroidogenic cascade. As shown in FIG. 6, osteocalcin specifically increased the expression of StAR, a cholesterol shuttle molecule, and of two cytochrome P450 steroid hydroxylases (Cyp11a and Cyp17). Thus, whether looked at by in vivo or cell-based assays, osteocalcin promotes testosterone biosynthesis.

Figure 11:
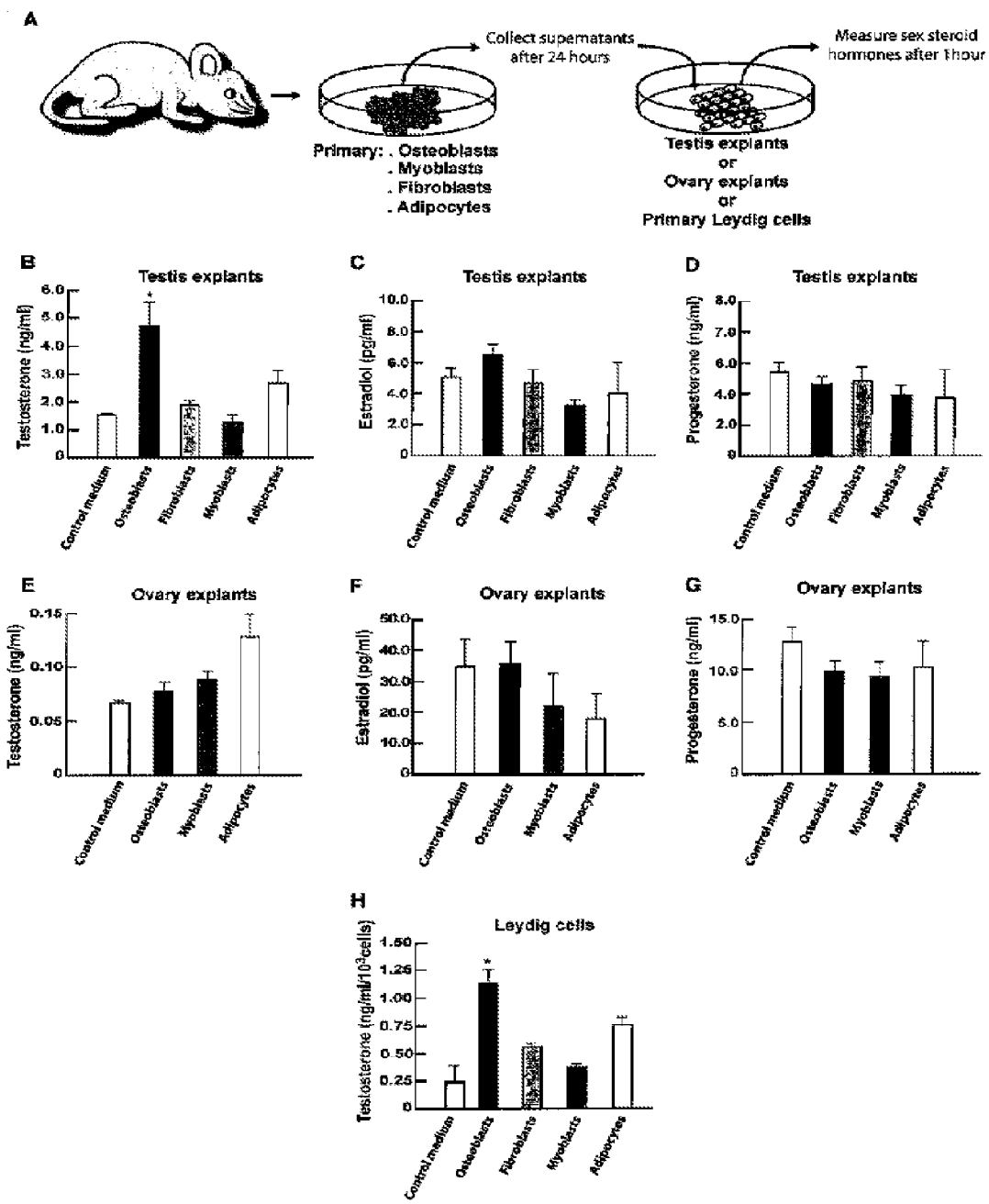
FIG. 11. Osteoblasts enhance testosterone biosynthesis by Leydig cells. (A) Schematic representation of the cell-based assay used to determine the role of various mesenchymal cells in steroid sex hormone production. Various primary mesenchymal cells from mice were cultured in Leydig cell medium and supernatants were collected after 24 hours. Then, testis or ovary explants or primary Leydig cells were cultured for 1 hour with these supernatants and radioimmunoassays (RIAs) were performed to measure levels of testosterone, estradiol, or progesterone. (B-D) Testis explants cultured in the presence of supernatants of different mesenchymal cell cultures: RIA measurement of (B) testosterone, (C) estradiol, and (D) progesterone levels. (E-G) Ovary explants cultured in the presence of supernatants of different mesenchymal cell cultures: RIA measurement of (E) testosterone, (F) estradiol, and (G) progesterone levels. (H) Testosterone production by primary Leydig cells cultured in the presence of osteocalcin (3 ng/ml of culture medium) or vehicle. Error bars represent SEM. Student's t test (*) $P<0.05$.

In a further series of experiments, supernatants of mesenchymal cell cultures were assayed for their ability to affect hormone production by testes and/or ovaries. In these cell-based assays (FIG. 11A), of all those tested, the supernatants of osteoblast cultures increased testosterone secretion by testis explants to the largest extent (over 3 fold), while not affecting estradiol and progesterone secretion by testes or ovaries (FIG. 11B-G). Since testosterone is produced by Leydig cells of the testes, whether osteoblast-derived molecule(s) act directly on Leydig cells was tested by culturing primary mouse Leydig cells in the presence or absence of supernatants of osteoblast cultures or cultures of other mesenchymal cell types. In the conditions of this assay, supernatants of osteoblast cultures were the only ones able to increase testosterone production by Leydig cells significantly (more than 4 fold) (FIG. 11H). These experiments indicate that osteoblasts are the cells of mesenchymal origin that affect testosterone biosynthesis to the largest extent, and that they do so through secreted molecule(s) acting on Leydig cells of the testis. This novel endocrine function of osteoblasts was restricted to androgen production. Adipocytes also enhanced sex steroid hormone secretion, albeit to a lesser extent.

Figure 12:
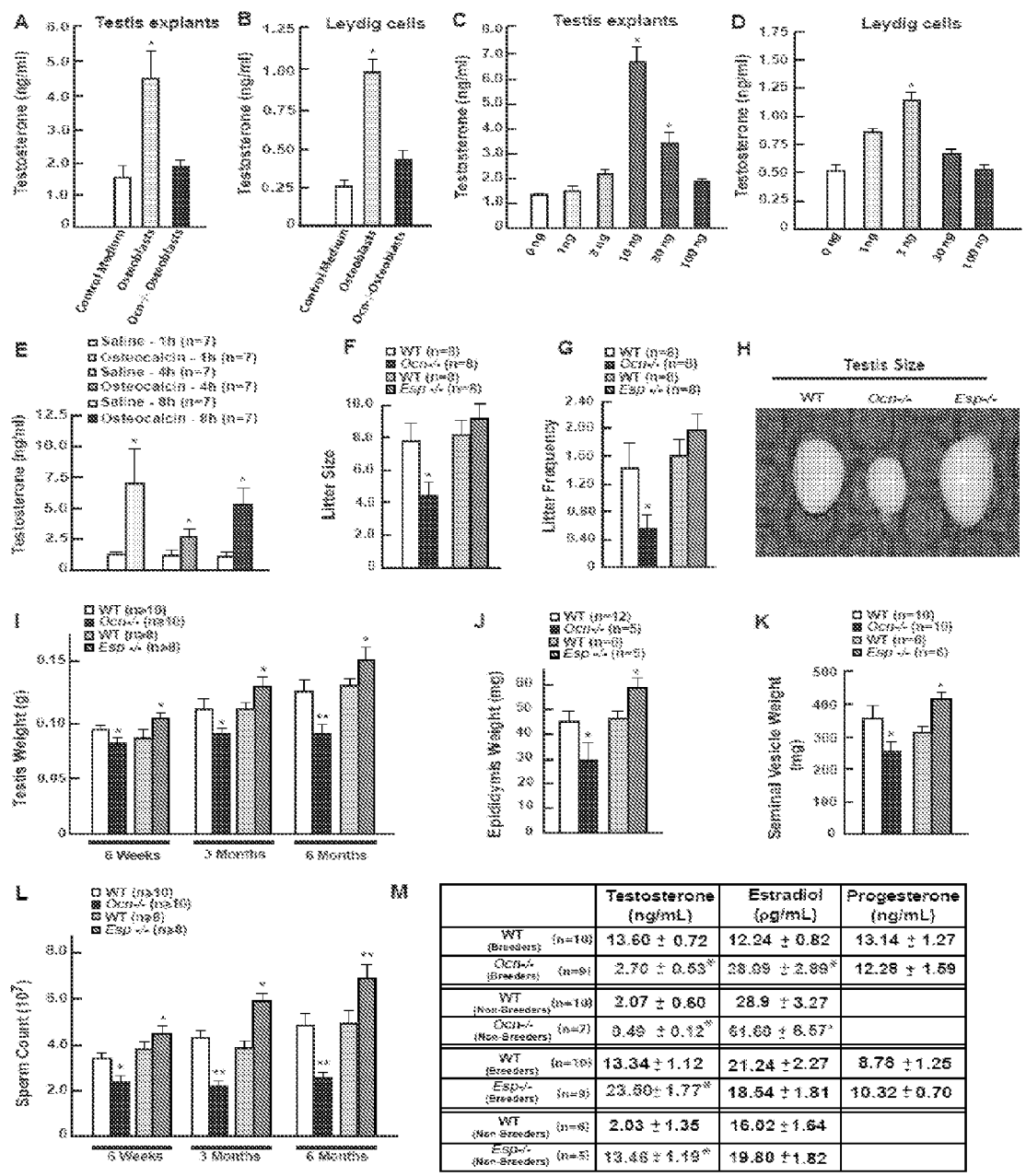
FIG. 12. Osteocalcin favors male fertility by increasing testosterone production by Leydig cells. (A-B) Testosterone production by testis explants (A) or primary Leydig cells (B) cultured in the presence of supernatants of wild type (WT) or Ocn−/− osteoblast cultures. (C-D) Testosterone production by testis explants (C) or primary Leydig cells (D) following stimulation with increasing doses of osteocalcin (0, 0.3, 1, 3, 10, 100 ng/ml of culture medium). (E) Circulating testosterone levels in WT mice 1 hour, 4 hours, and 8 hours after vehicle or osteocalcin (3 ng/g of body weight) injection. (F-G) Comparison between the average litter size (F) and frequency (G) generated by WT, Ocn−/−, or Esp−/− male littermate mice crossed with WT females (breeding was tested from 6 to 16 weeks of age). (H-L) Testis size (H), testis weight (I), epididymides weight (J), seminal vesicles weight (K), and sperm count (L) in Ocn−/− and Esp−/− compared to WT littermate mice. (M) Circulating steroid sex hormone levels in Ocn−/− and Esp−/− compared to WT littermate mice. The analyses were performed on breeder and non-breeder mice. Error bars represent SEM. Student's t test (*) $P<0.05$, (**) $P<0.001$.

Several lines of evidence indicated that osteocalcin is the osteoblast-derived hormone enhancing testosterone secretion by Leydig cells. First, supernatants of wild type (WT) but not of Osteocalcin (Ocn)−/− osteoblast cultures increased testosterone production by testis explants and mouse Leydig cells (FIG. 12A-B). Second, treating testis explants or Leydig cells with increasing amounts of uncarboxylated osteocalcin, the active form of the hormone, resulted in a dose-dependent increase in testosterone secretion (FIG. 12C-D). Third, injection of osteocalcin in WT mice increased circulating levels of testosterone (FIG. 12E). Fourth, to determine if osteocalcin regulates male fertility in vivo, loss-(Ocn−/− mice) and gain-of-function (Esp−/− mice) mouse models for osteocalcin (Lee et al., 2007, Cell 130:456-469) were used. When Ocn−/− males were crossed with WT female mice, the litter sizes were nearly two-fold smaller than when WT males were crossed with WT female mice (FIG. 12F). Conversely, the number of pups per litter was consistently increased when Esp−/− males were bred with WT female mice (FIG. 12F). The frequency of litters over a period of 8 weeks was also decreased in the case of the loss-of-function model and increased in the gain-of-function model (FIG. 12G). Testis size and weight were significantly decreased in Ocn−/− and increased in Esp−/− mice at 3 months of age (FIGS. 12H and 12I). The weights of epididymides and seminal vesicles as well as sperm count were also significantly decreased in Ocn−/− and increased in Esp−/− mice (FIG. 12J-L). These abnormalities worsened over time (FIGS. 12I and 12L).

Figure 18:
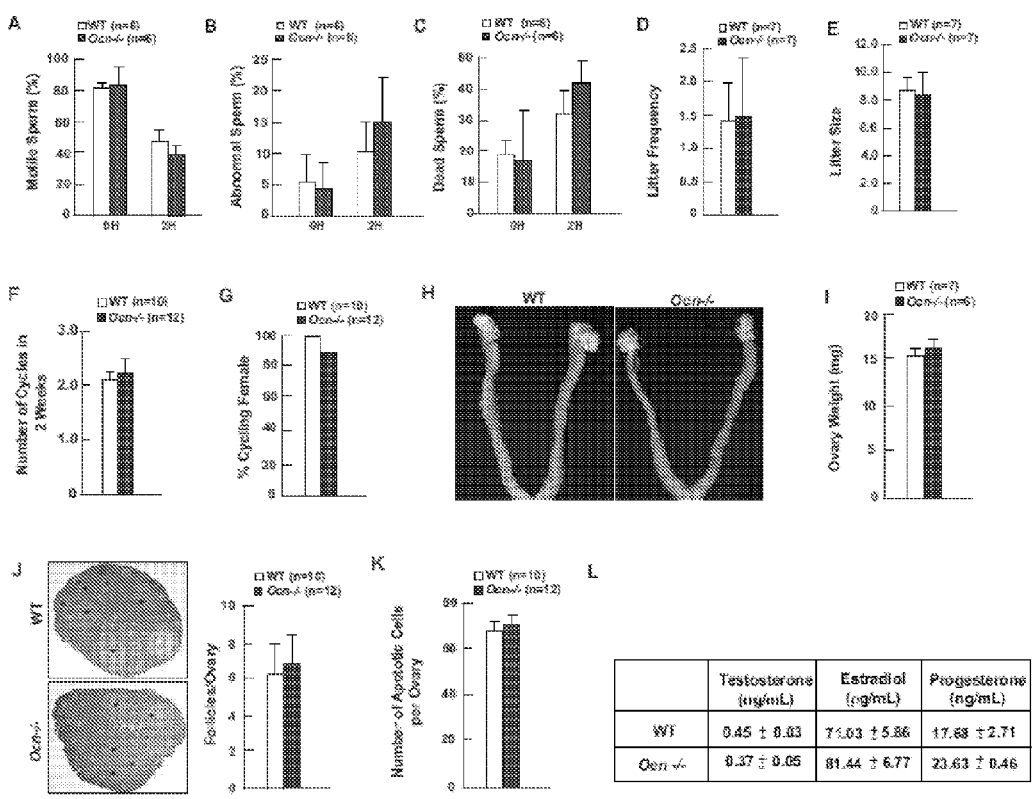
FIG. 18. (A-C) Sperm motility and morphology analyses. (A) Percentage (%) of motile sperm, (B) abnormal sperm, and (C) dead sperm in WT and Ocn–/– male littermate mice analyzed immediately and 2 hours after dissection. (D-E) Fertility analysis of Ocn–/– females. (D) Comparison between the average litter frequency and (E) size generated by wild type (WT) and Ocn–/– female littermates crossed with WT males (breeding was tested from 6 to 16 weeks of age). (F) Average number of cycles within 2 weeks in WT and Ocn–/– female littermate mice. (G) Percentage of WT and Ocn–/– female littermate mice to cycle. (H) Uteri and ovaries of WT and Ocn–/– female littermate mice. (I) Ovary weight of WT and Ocn–/– female littermate mice. (J) Histological analyses of ovary sections and number of follicles from WT and Ocn–/– female littermate mice. Follicles are indicated by asterisks (*). (K) Number of apoptotic cells per WT and Ocn–/– ovaries. (L) Circulating steroid sex hormone levels in WT and Ocn–/– female littermate mice. Error bars represent SEM.

Motility of sperm from both WT and Ocn−/− males was assessed by videomicroscopy immediately after dissemination from the caudal epididymis or after 2 hours of incubation under conditions known to prepare sperm for fertilization (Suarez and Osman, 1987, Biol. Reprod. 36:1191-1198). In both cases, the percentage of motile sperm did not differ between Ocn−/− and WT mice (FIG. 18A). Likewise, the percentage of abnormally shaped or dead sperm was similar in WT and Ocn−/− mice (FIG. 18B-C).

Consistent with the fact that osteocalcin favors testosterone synthesis in Leydig cells ex vivo, circulating levels of testosterone were markedly decreased in Ocn−/− and increased in Esp−/− mice. Circulating progesterone levels were similar in Ocn−/− and WT mice and, although circulating levels of estradiol were higher in Ocn−/− than in WT mice, they remained within the normal range (FIG. 12M). The most likely explanation for this mild increase in circulating estradiol levels in the Ocn−/− mice is that the increase in the number of adipocytes caused by Osteocalcin inactivation may result in an increase in the aromatization of testosterone into estrogen in fat (Nelson and Bulun, 2001, J. Am. Acad. Dermatol. 45:S116-124; Simpson et al., 2000, Trends Endocrinol. Metab. 11:184-188; Simpson, 2003, J. Steroid Biochem. Mol. Biol. 86:225-230). Estradiol levels were not affected in Esp−/− mice. As predicted by the co-culture assays, female fertility, ovary weight, morphology of the uterus, follicle numbers, and circulating levels of steroid sex hormones were normal in Ocn−/− female mice (FIG. 18D-L). Taken together, these cell biology and genetic experiments identify osteocalcin as a secreted molecule favoring male fertility by increasing testosterone production by Leydig cells.

Example 6

Daily Osteocalcin Injections Affect Sperm Counts and Germ Cell Apoptosis

Figure 7:
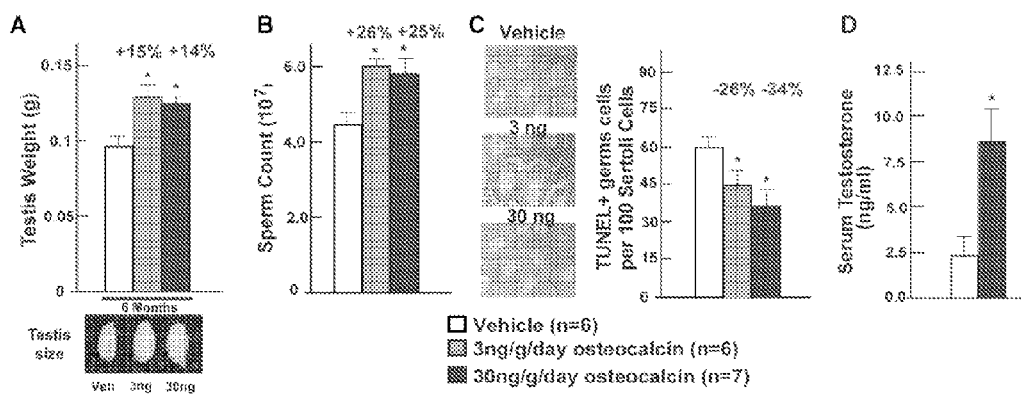
FIG. 7. Analysis of testis weight and size (lower panel) (A), sperm count (B), apoptosis (C) and testosterone serum levels (D) in WT mice injected once daily with vehicle (veh) or a dose of osteocalcin (0, 3 or 30 ng/g) from 2 to 4 months of age.

WT mice (n=6) were injected daily with either 3 ng/g or 30 ng/g of uncarboxylated osteocalcin for 12 weeks. Uncarboxylated osteocalcin, at both doses, significantly increased testis weight and sperm count and decreased sperm cell apoptosis (FIG. 7A-C). Likewise, serum testosterone levels were increased in osteocalcin-injected mice compared to vehicle-injected mice (FIG. 7D). Hence, whether looked at by genetic models of loss-of-function or gain-of-function of osteocalcin or by pharmacological means to increase osteocalcin serum levels, osteocalcin acts as a regulator of testosterone production and male germ cell production.

Example 7

Osteocalcin is not Expressed in Testis

Figure 8:
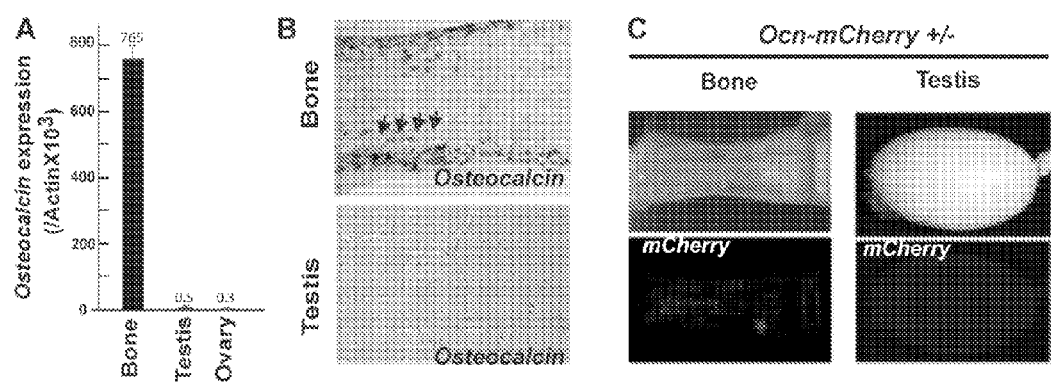
FIG. 8. qPCR analysis of Osteocalcin expression in bone, testis, and ovary of 3 month-old WT mice (A). In situ hybridization analysis of Osteocalcin expression in bone and testis of 3 month-old WT mice (B). Analysis of mCherry fluorescent protein in bone and testis of Osteocalcin-mCherry Knockin mice (C).

Given the nature and severity of the Osteocalcin−/− phenotype, a possible concern was that Osteocalcin could be in fact expressed at low, but nevertheless biologically important, levels in some cell types of the testis. This concern was even more legitimate since Esp is known to be expressed in Sertoli cells (Dacquin et al., 2004, Dev. Dyn. 229:826-834). To begin addressing this concern, several different experiments were performed. First, Osteocalcin expression in bone versus testes was compared by quantitative PCR. A 1,000 fold higher expression in bone than in testis was observed (FIG. 8A). Second, in situ hybridizations were performed for Osteocalcin expression but failed to detect any signal in the testis (FIG. 8B). Third, the Cherry gene, a fluorescent reporter gene, was knocked into the Osteocalcin locus to create Ocn-Cherry mice. Using this reporter, a strong signal could be detected in osteoblasts but staining could not be detected in testes (FIG. 8C). Taken together, these results, albeit negative, strongly suggest that osteocalcin is not expressed in any cell type of the testes.

Figure 13:
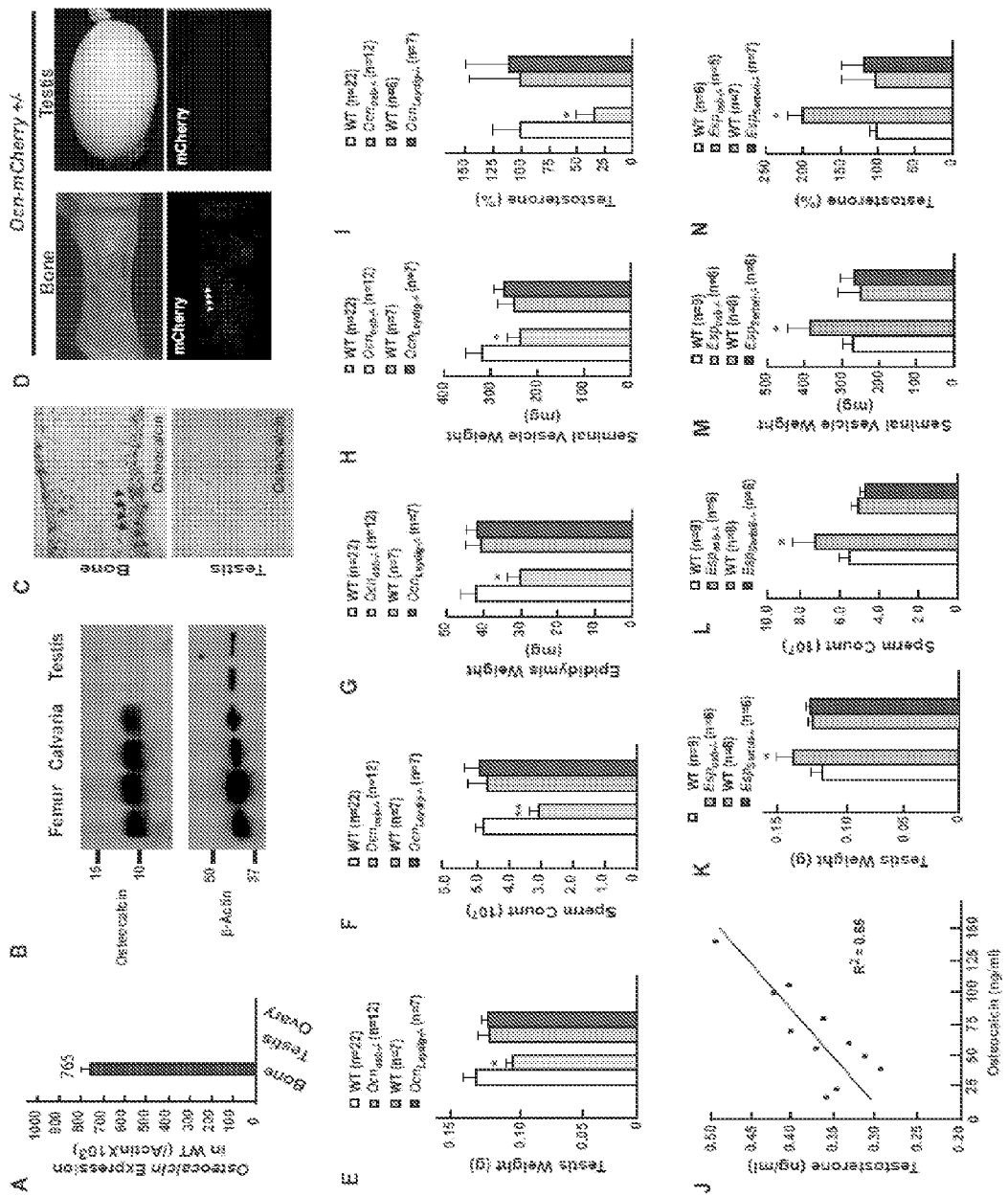
FIG. 13. Osteocalcin promotes male fertility through its expression in osteoblasts. (A) qPCR analysis of Osteocalcin expression in bone, testes, and ovaries of 3 month-old WT mice. (B) Western blot analysis of osteocalcin in femur, calvaria, and testis. (C) In situ hybridization analysis of Osteocalcin expression in bone and testis of 3 month-old WT mice. (D). Analysis of mCherry fluorescent protein in bone and testis of Osteocalcin-mCherry Knock-in mice. (E-I) Fertility in mice lacking Ocn specifically in osteoblasts ($Ocn_{osb}$−/−) or Leydig cells ($Ocn_{Leydig}$−/−) compared to WT littermates: (E) Testes weihts, (F) sperm count, (G) epididymides and seminal vesicle (H) weights, and (I) ratio of circulating testosterone levels measured in WT and $Ocn_{osb}$–/– or in WT and $Ocn_{Leydig}$–/– littermate mice. (J) Linear regression representation of circulating testosterone levels versus circulating osteocalcin levels in $Ocn_{osb}$–/– mice (n=11). Each dot represents one $Ocn_{osb}$–/– mouse. (K-M) Fertility in mice lacking Esp specifically in osteoblasts ($Esp_{osb}$–/–) or Leydig cells ($Esp_{Leydig}$–/–) compared to WT littermates: (K) Testes weight, (L) sperm count and (M) seminal vesicle weight. (N) Ratio of circulating testosterone levels measured in WT and $Esp_{osb}$–/– or in WT and $Esp_{Leydig}$–/– littermate mice. Error bars represent SEM. Student's t test (*) P<0.05, (**) P<0.001.

Gene expression and cell-specific gene deletion experiments were performed to further determine that osteocalcin regulates male fertility as an osteoblast-secreted molecule, not as a testis-secreted factor. When comparing Osteocalcin expression in bone, testes, and ovaries by quantitative PCR (qPCR), it was observed that Osteocalcin expression was more than 750 fold higher in bone than in gonads; furthermore, Osteocalcin transcript or protein was not detected in testes by in situ hybridization or Western blot analyses (FIG. 13A-C). To be able to trace Osteocalcin-expressing cells in vivo, the mCherry fluorescent reporter gene was knocked into the Ocn locus (Ocn-mCherry mice) (FIG. 19A-B). While the expected strong signal was observed in osteoblasts, there was no detectable mCherry fluorescence in testes (FIG. 13D). Thus, through multiple assays, Osteocalcin expression was not detected in testes.

Example 8

Generation of a Floxed Allele for Osteocalcin

Although the expression study described above did not identify Osteocalcin expression in Sertoli, germ cells or Leydig cells of the testes, there remained a concern that the sensitivity of the techniques used was not sufficient to detect a very low expression of Osteocalcin in these cells and that such expression could be the true cause of the reproduction phenotype observed in the Osteocalcin−/− mice. To more formally exclude this possibility, Osteocalcin cell-specific knockout lines may be generated and analyzed. The first step toward this goal is to generate a floxed allele of the Osteocalcin locus. Following the same deletion strategy previously used to create the complete knockout allele (Ducy et al., 1996, Nature 382:448-452), a targeting vector harboring LoxP sites flanking the Osteocalcin locus was generated (FIG. 9A). Upon recombination by the Cre recombinase specifically expressed in a particular cell type, both Osteocalcin genes should be deleted in those cells. As shown in FIG. 9B, mice harboring this floxed allele have already been obtained; such mice can be used to generate and analyze mice lacking osteocalcin in a cell-specific manner.

Cell-specific loss- and gain-of-function models of osteocalcin were generated by crossing mice harboring floxed alleles of Ocn (FIG. 19C-D) or Esp with either the al (I) Collagen-Cre transgenic mice or the Cyp17-iCre transgenic mice to delete genes in osteoblasts or in Leydig cells only, respectively (Bridges et al., 2008, Dev Dyn. 224:245-251). Testis size and weight, epididymides and seminal vesicle weights, sperm count, and circulating testosterone levels were all reduced in 12 week-old $Ocn_{osb}$−/− mice while none of these parameters were affected in mice lacking Osteocalcin in Leydig cells only (FIG. 13E-I). There was a tight correlation between osteocalcin and testosterone circulating levels in $Ocn_{osb}$−/− mice (FIG. 13J). Conversely, $Esp_{osb}$−/− mice displayed testis abnormalities identical to those of Esp−/− mice and that were the mirror image of Ocn−/− or $Ocn_{osb}$−/− mice. Inactivation of Esp in Sertoli cells, where this gene is expressed (Dacquin et al., 2004, Dev. Dyn. 229:826-834; Jamin et al., 2003, Mol. Cell. Endocrinol. 211:15-19), had no detectable deleterious consequence on testis biology (FIG. 13K-N). Hence, it is only through its expression in osteoblasts that osteocalcin promotes male fertility.

Example 9

Esp-Deficient Mice

Esp-deficient mice are mice in which one (+/−) or both alleles (−/−) for OST-PTP have been inactivated in all of the cells in the animal. The mice were made by homologous recombination of a targeted OST-PTP allele with a transgene having a sequence encoding a nuclear-localized LacZ cassette, which is homologously recombined into exon 6 of the OST-PTP allele, such that the transgene is in frame with the OST-PTP gene, and expression of the transgene is operably linked to the native gene expression regulatory sequences of the OST-PTP allele. The production of Esp-deficient mice is described in more detail in International Patent Publication No. WO 2008 033518; Ducy et al., 1996, Nature 382:448-452; and Lee et al., 2007, Cell 130:456-469.

Example 10

Osteocalcin-Deficient and Other Mice

"Osteocalcin-deficient mice" as used herein means a strain of mice in which both osteocalcin alleles were deleted. Generation of Osteocalcin−/− mice was previously reported (Ducy et al., 1996, Nature 382:448-452). Exon 4 of osteocalcin gene 1 (OG1), coding for the mature protein, and the entire osteocalcin gene 2 (OG2) sequence, were deleted, while osteocalcin-related gene (ORG) was left in place. Correct targeting resulted in the replacement of the entire mature osteocalcin protein-coding sequences by the pGKNeo selection cassette.

Figure 9:
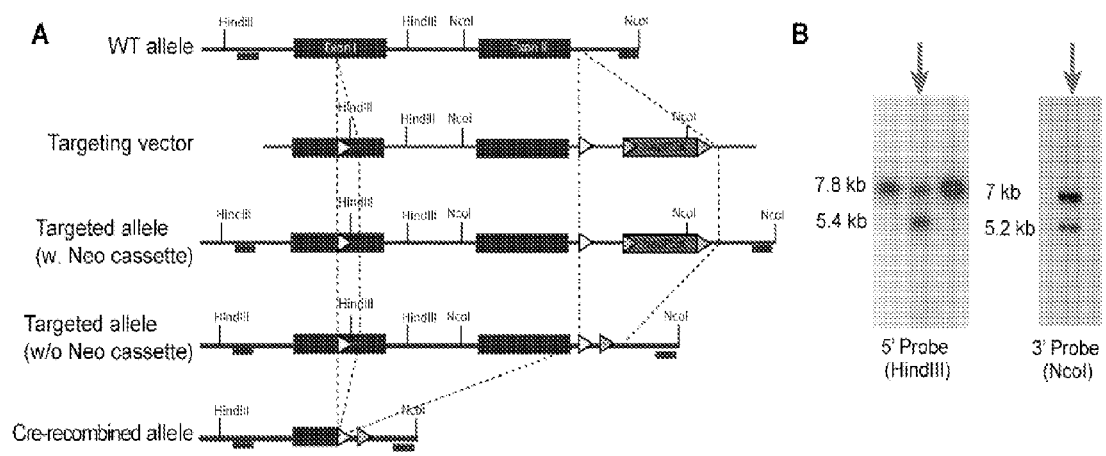
FIG. 9. Targeting strategy to generate conditional Osteocalcin−/− mice through homologous recombination in embryonic stem (ES) cells (A). Identification of an ES cell clone targeted for the Osteocalcin floxed allele (red arrows) by Southern blot analysis. A 400-bp fragment and a 540-bp fragment respectively located at the 5' end and 3' end of the genomic locus was used as a probe external to the targeting vector. Hybridization of these probes with Hind III or NcoI-digested genomic DNA yielded both a WT and a lower targeted band in the targeted ES cells (B).
Figure 19:
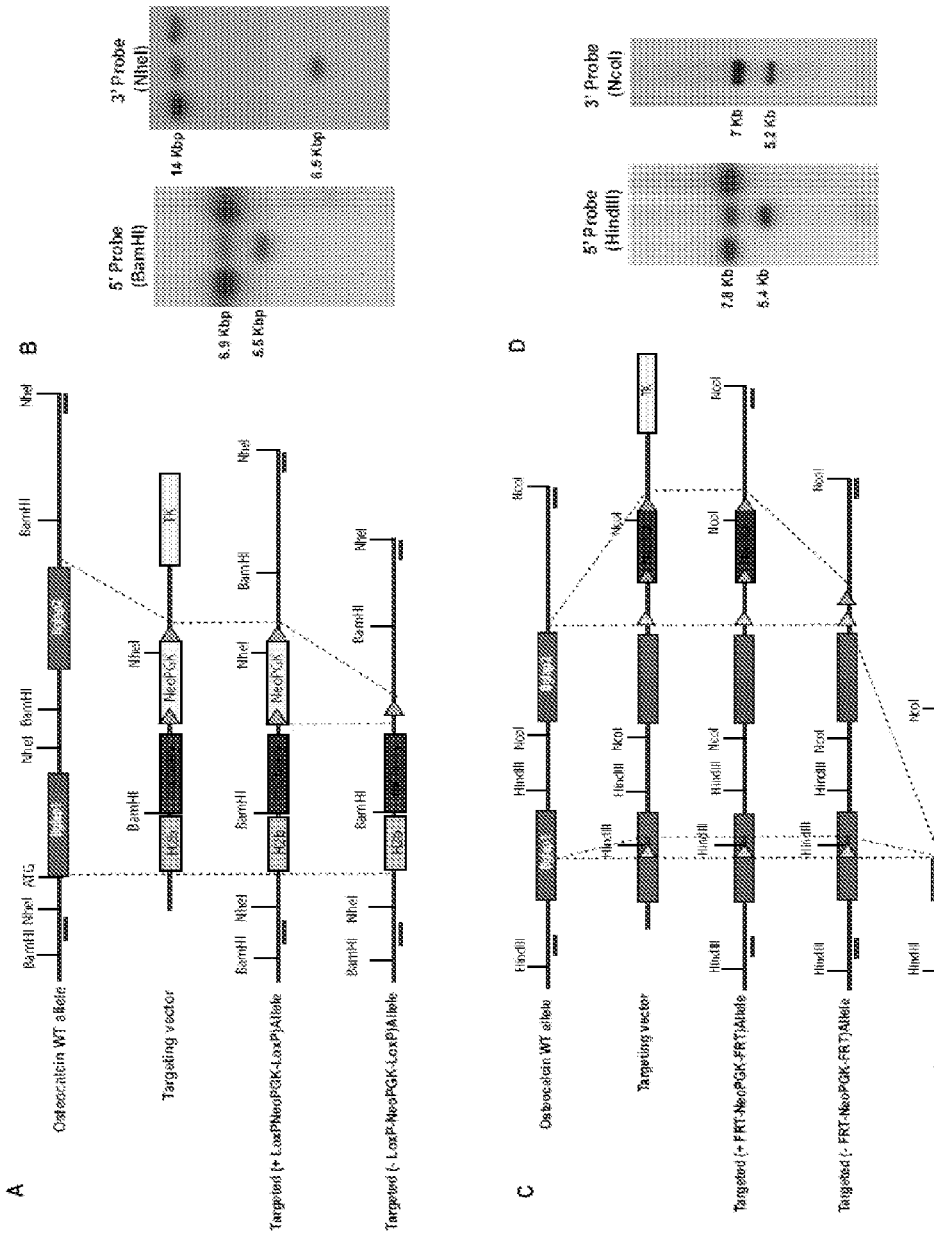
FIG. 19. (A-B) Generation of Ocn-mCherry knock-in allele. (A) Schematic representation of the targeting strategy. The open reading frames of Exons Bglap1 and Bglap2 are represented by dark rectangles with white lettering; thin lines represent untranslated regions of the Ocn locus. The neomycin resistance gene (for positive selection) flanked by two LoxP sites (triangles) (FRT-neoPGK-FRT) and the HSV-tk cassette (for negative selection) are indicated. (B) Southern blot performed with 5' and 3' probes; the position of each probe is shown in (A). (C-D) Generation of Ocn conditional allele. (C) Schematic representation of the targeting strategy. The open reading frames of Exons Bglap1 and Bglap2 are represented by dark rectangles with white lettering. Thin lines represent untranslated regions of the Ocn locus. The neomycin resistance gene (for positive selection) flanked by two FRT sites (FRT-neoPGK-FRT), the HSV-tk cassette (for negative selection), and LoxP are indicated. (D) Southern blot performed with 5' and 3' probes; the position of each probe is shown in (C).
Figure 22:
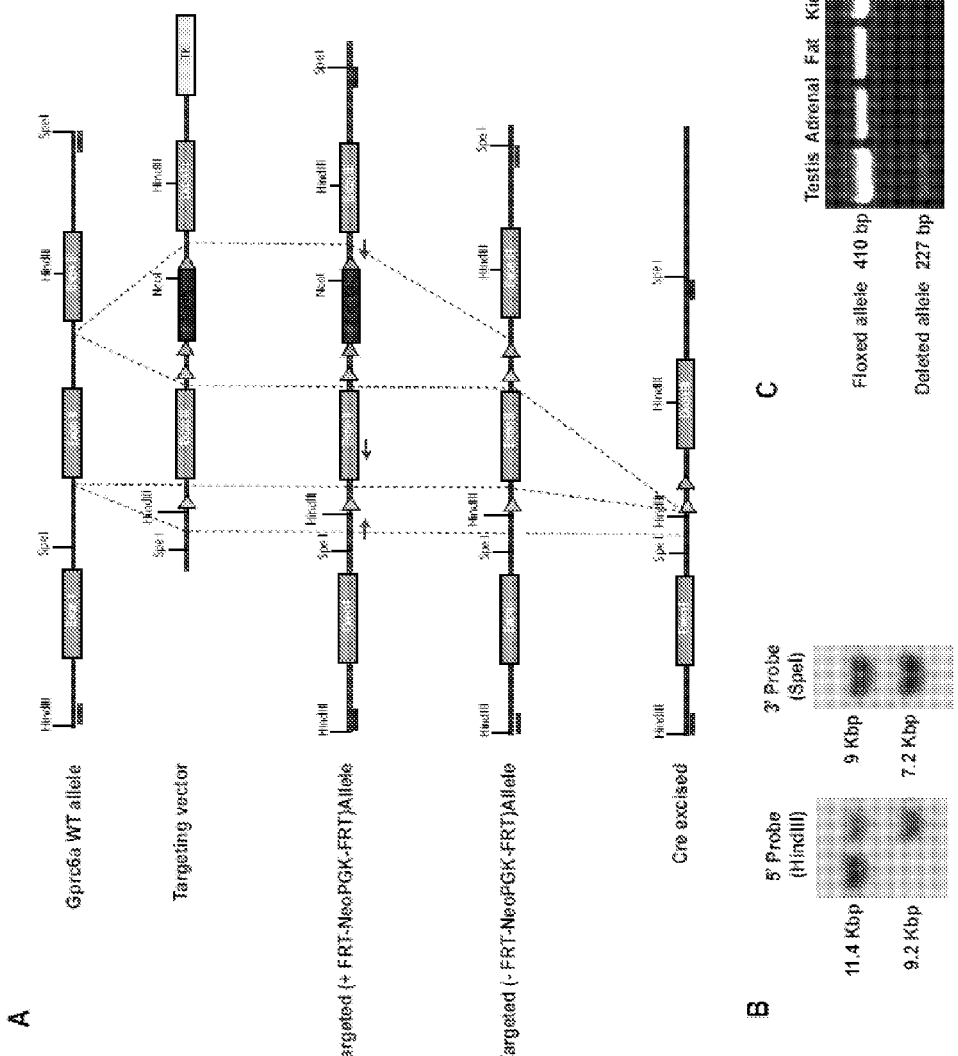
FIG. 22. (A-B) Generation of OstR conditional allele. (A) Schematic representation of the targeting strategy. The open reading frames of ExonI, ExonII, and ExonIII are represented by grey rectangles with white lettering and thin lines represent untranslated regions of the OstR locus. The neomycin resistance gene (for positive selection) flanked by two FRT sites (grey triangles) (FRT-neoPGK-FRT), the HSV-tk cassettes (for negative selection) and LoxP sites (light triangles) are indicated. (B) Southern blot performed with 5' and 3' probes; the position of each probe is shown in (A). (C) Specificity of OstR deletion was tested by PCR in the indicated tissues. Primer positions are shown in (A).

All experiments giving rise to the data shown in FIGS. 11-22 were performed on the 129-Sv (Taconic) genetic background. Control littermates were used in all these experiments. Mouse genotypes were determined by PCR. Strategies for generating transgenic mice are depicted in FIGS. 9, 19, and 22.

Example 11

Laboratory Measurements

Blood was collected by heart puncture of isoflurane anesthetized mice. Osteocalcin levels were quantified by IRMA (Immunotopics kit).

Example 12

Gene Expression Analyses

Gene expression analyses were performed using real time PCR. DNAse I-treated total RNA was converted to cDNA with the SuperScript III kit (Invitrogen). Real-time PCR were performed using the Taq SYBR Green Supermix with ROX (Biorad) on an MX3000 instrument (Stratagene); beta-actin amplification was used as an internal reference for each sample. All primers were from SuperArray.

Example 13

Recombinant Osteocalcin

Recombinant osteocalcin was bacterially produced and purified on glutathione beads according to standard procedures. Osteocalcin was then cleaved from the GST subunit using thrombin digestion. Thrombin contamination was removed using an affinity column. The purity of the product was qualitatively assessed by SDS-PAGE. Bacteria do not have a gamma-carboxylase gene. Therefore, recombinant osteocalcin produced in bacteria is always completely undercarboxylated at all three sites.

Example 14

ELISA to Measure Undercarboxylated Osteocalcin

Carboxylation levels of osteocalcin in the serum are usually assessed indirectly by hydroxyapatite (HA) pull down followed by measurement of the unbound fraction of osteocalcin using a commercially available radioimmunoassay (RIA). The HA assay is based on the principle that undercarboxylated osteocalcin has a decreased binding affinity for HA compared to carboxylated osteocalcin. HA-based measurements of undercarboxylated osteocalcin have some limitations, as this method requires a relatively large volume of serum. Moreover, the HA pull down assay of osteocalcin is a semi-quantitative method, as it does not precisely quantify the serum concentration of undercarboxylated osteocalcin, but only estimates the percentage of osteocalcin having a low HA affinity. In order to measure more precisely undercarboxylated osteocalcin, an enzyme-linked immunosorbent assay (ELISA) system was developed for the quantification of mouse undercarboxylated osteocalcin.

Figure 10:
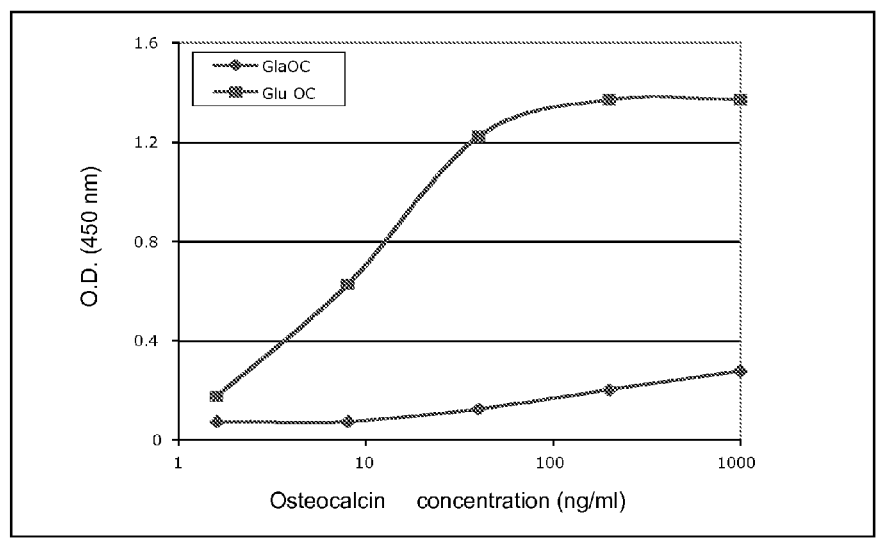
FIG. 10. Measurement of uncarboxylated (Glu OC) and carboxylated (Gla OC) osteocalcin using uncarboxylated osteocalcin ELISA.

Goats were immunized with full-length bacterially produced fully uncarboxylated osteocalcin. Using affinity columns, polyclonal antibodies were purified from these goat anti-sera that recognized either the osteocalcin C-terminal region between amino acids 25 and 46 (OC25-46) or the uncarboxylated central region between amino acids 11 and 26 (unOC11-26). Dot blot analysis verified that the OC25-46 antibodies recognized both uncarboxylated and carboxylated osteocalcin, while the unOC11-26 recognized specifically uncarboxylated osteocalcin. The OC25-46 antibodies were next conjugated to horseradish peroxidase (HRP), while the unOC11-26 antibodies were coated on ELISA plates using standard procedures. To test the specificity of the ELISA system, different concentrations of uncarboxylated or carboxylated osteocalcin were incubated on the plate for 18 h at 4° C., then the wells were washed 5 times and incubated in the presence of the OC25-46 HRP conjugated antibodies for 1 h at room temperature. Following 5 washes, the immunocomplex was incubated with an HRP substrate, TMB, which is converted to a blue compound by peroxidases. The reaction was stopped with 0.18 M $H_2SO_4$ and absorbance (O.D.) at 450 nm was measured using an ELISA plate reader. As shown in FIG. 10, this assay allows the specific quantification of uncarboxylated osteocalcin in a physiological concentration range (1 to 100 ng/ml).

Example 15

Preparation of Primary Leydig Cells and Testis Explants

Adult mouse Leydig cells were isolated by mechanical dissociation of the testes followed by purification on a 0-90% Percoll gradient (Hunter et al., 1982, Mol. Cell. Endocrinol. 25:35-47; Schumacher et al., 1978, FEBS Lett. 91:333-338). Primary Leydig cells were cultured in Minimal Essential Medium (MEM+GlutaMAX, Invitrogen) supplemented with 1× PenStrep, 25 mM HEPES, pH 7.4 and 0.07% BSA at 33° C. in 5% $CO_2$. After 3 hours of attaching and starvation, cells were washed once with culture medium and then used for experiments. The preparation of testis explants was adapted from Powlin et al., 1998, Toxicol. Sci. 46:61-74. Explants were washed 3 times with PBS 1× and placed in serum free RPMI medium for 2 hours before being used for experiments.

Example 16

Osteocalcin Stimulation of Leydig Cells or Testis Explants

Primary Leydig cells and testis explants were washed 3 times with PBS 1× and stimulated with different doses of recombinant osteocalcin prepared as previously described (Ferron et al., 2008, Proc. Natl. Acad. Sci. USA 105:5266-5270) or with human chorionic gonadotropin (hCG) as a positive control. After 1 hour, an aliquot of medium was collected for measurements of testosterone. Cells were then maintained for 3 additional hours and lysed in 1 ml TRIZOL® (Invitrogen) for RNA isolation.

Example 17

Sperm Counts and Hormone Measurements

Caudal epididymides were minced in 1 ml PBS and the number of cells released counted after 1 hour. The total sperm count was assessed in the final suspension by using a hemacytometer (Dakhova et al., 2009, Endocrinology 150:404-412). Circulating levels of testosterone, estradiol (E2), and progesterone were measured by radioimmunoassay (RIA) from Diagnostic Systems Laboratories (Testosterone RIA DSL-4000, Estradiol RIA DSL-43100, and Progesterone RIA-3900).

Example 18

Histology

One testis or ovary from each mouse was randomly selected for molecular analysis and the other one was used for histology. Specimens were collected, weighed, and fixed in Bouin's fixative for histological analyses before being dehydrated through graded ethanol, processed for paraffin embedding, and serially sectioned at 5 μm. For histological analysis, sections of testes and ovaries were stained with periodic acid-Schiff and counterstained with hematoxylin. TUNEL labeling was performed using the ApopTag Peroxydase In Situ Apoptosis detection kit (Millipore-57100). Apoptotic indices were determined by counting the total number of TUNEL-positive cells or the number of TUNEL positive spermatocytes for all stage tubules. Approximately 500 tubules were counted on at least 4 cross-sections located at midtestis for each animal.

Example 19

Gene Expression Studies

RNA was purified from tissues, primary Leydig cells, or cultured cells using TRIZOL® (Invitrogen). RNA isolation, cDNA preparation, and qPCR analysis was carried out following standard protocols. qPCR analyses were performed using specific quantitative PCR primers from SABiosciences.

Example 20 cAMP Quantification

For cAMP measurements, TM3 Leydig cells were plated in 6 cm dishes ($10^7$ cells per dish) a day before experiment. Cells were serum starved for 16 hours (in the presence of 0.1% BSA) then pre-incubated in the presence of 0.5 mM IBMX for 30 minutes and stimulated with the indicated concentration of osteocalcin (also in the presence of 0.5 mM IBMX) for 30 minutes. cAMP concentration was measured with the Parameter cAMP kit (R&D Systems, KGE002).

Example 21

Receptor Binding Assays

For binding studies, testes from 8-week old mice were snap frozen in liquid nitrogen and 20 μm thick sections were prepared and dessicated overnight at +4° C. under vacuum. On the following day, sections were rehydrated in ice-cold binding buffer (50 mM TrisHCl, pH 7.4, 10 mM $MgCl_2$, 0.1 mM EDTA and 0.1% BSA) for 15 minutes and incubated for 1 hour in the presence of biotinylated osteocalcin. For competition assays, a 100-fold molar excess of unlabeled osteocalcin, glycine, lysine, or hCG was added. After 3 washes in cold PBS, sections were incubated for 1 hour in the detection system containing 0.1% BSA (ABC Elite, Vector Laboratories), washed again, and incubated with DAB peroxidase substrate kit (Vector Laboratories) according to the manufacturer's protocol. After a final wash, sections were mounted in water-based mounting medium. As negative controls, sections incubated with the detection system only (ABC Elite and DAB) or OstR−/− testis sections (Basura et al., 2008, Hear. Res. 244:45-50) were used.

Example 22

Preparation, Purification, and Culture of Primary Mesenchymal Cells

Primary osteoblasts were isolated from 5 day-old Ocn−/− or WT littermate calvaria bones. Calvaria bones were dissected and placed in digestion medium (αMEM, 1 mg/ml collagenase P (BM), 2.5% trypsin/EDTA) for 60 minutes at 37° C. under vigorous shaking. The cell suspension was transferred, free of bone pieces, into a culture plate and cultured for 1 week in αMEM/10% FBS (pH 6.9) and in mineralization medium (αMEM/10% FBS, 5 mM β-glycerophosphate and 10 μg/ml ascorbic acid) thereafter. Upon complete differentiation, cells were cultured for 24 hours in a specific medium for primary Leydig cells or tissue explants (testis or ovary) in the presence of 0.1% BSA. Supernatants were collected, centrifuged to remove cell debris, and stored at −80° C.

Primary adipocytes were isolated from visceral fat pads (white adipocytes), dissected, and minced in PBS. Tissues were redigested for 1 hour at 37° C. in 1 mg/ml collagenase (in KRP buffer; 20 mM HEPES, 120 mM NaCl, 6 mM KCl, 1.2 mM $MgSO_4$, 1 mM $CaCl_2$, 0.6 mM $Na_2HPO_4$, 0.4 mM $NaH_2PO_4$, 2.5 mM d-glucose, 2% BSA, pH 7.4) as described (Ferron et al., 2008, Proc. Natl. Acad. Sci. USA 105:5266-5270; Lee et al., 2007, Cell 130:456-469). Isolated white fat adipocytes were then directly cultured for 2 hours in αMEM supplemented with 0.1% BSA. After 3 washes with PBS 1×, adipocytes were cultured for at least 8 hours in a specific medium for primary Leydig cells or tissue explants (testis or ovary) in the presence of 0.1% BSA. Supernatants were collected, centrifuged to remove cell debris, and stored at −80° C.

Primary fibroblasts were isolated from 5 day-old mice as described (Hakkinen et al., 2001, Methods Cell Sci. 23:189-196). Purified fibroblasts were cultured for at least 24 hours in a specific medium for primary Leydig cells or tissue explants (testis or ovary) in the presence of 0.1% BSA. Supernatants were collected, centrifuged to remove cell debris, and stored at −80° C.

Primary myoblasts were isolated from 5 day-old mice as described (Springer and Blau, 1997, Somat. Cell Mol. Genet. 23:203-209). Purified myoblasts were cultured for at least 24 hours in a specific medium for primary Leydig cells or tissue explants (testis or ovary) in the presence of 0.1% BSA. Supernatants were collected, centrifuged to remove cell debris, and stored at −80° C.

Example 23

Assays with Testis and Ovary Explants

Preparation of testis explants was adapted from Powlin et al., 1998, Toxicol. Sci. 46:61-74). Testes from WT animals were decapsulated and 30 mg of testicular parenchyma was placed into a 10 ml glass scintillation vial containing 5 ml of culture medium (RPMI-1640, 5% FCS, 50 mg/ml soybean trypsin inhibitor) and used for each different condition. The vial was capped, briefly vortexed, and incubated vertically for 2 hours at 34° C. under vigorous shaking (175 rpm). Testes explants were then washed 3 times with PBS 1×, placed in fresh serum free RPMI medium for 2 hours, washed again 3 times with PBS 1×, and incubated for 1 hour with supernatants collected from various mesenchymal cell cultures. At the end of the incubation period, 1.4 ml of cultured medium were collected and centrifuged at 14,000 g for 5 minutes (4° C.) to pellet all remaining testicular parenchyma. The resulting supernatant was frozen at −80° C. until radioimmuno assays (RIA) were performed to measure the circulating levels of testosterone, estradiol, or progesterone. As a positive control, testis explants were cultured with medium containing hCG (1 IU/ml). hCG binds to the LH receptor on Leydig cells to stimulate testosterone production. This stimulation confirmed the viability of the explants.

Preparation of ovary explants was adapted from (Powlin et al., 1998, Toxicol. Sci. 46:61-74). Ovaries from WT animals were removed, cleared of fat, weighed, thoroughly minced with scissors into approximately <1 $mm^3$, and placed into a 10 ml glass scintillation vial containing 1 ml of culture medium (RPMI-1640, 5% FCS, 50 mg/ml soybean trypsin inhibitor). Two ovaries were used for each different condition. The vial was capped, briefly vortexed, and incubated vertically for 2 hours at 34° C. under vigorous shaking (175 rpm). Ovary explants were then washed 3 times with PBS 1×, placed in fresh serum free RPMI medium for 2 hours, washed again 3 times with PBS 1×, and incubated for 1 hour with supernatants collected from various mesenchymal cell cultures. At the end of the incubation period, the culture medium was centrifuged at 14,000 g for 5 min (4° C.) to pellet all remaining tissues. The resulting supernatant was frozen at −80° C. until analyzed for testosterone, estradiol, or progesterone levels.

Example 24

Assessment of Estrus Cycle

Weanling WT or Ocn−/− female mice were inspected daily for vaginal opening and estrus cycling was determined in sexually mature WT or Ocn−/− female mice by light microscope analysis of vaginal epithelial cell smears (Walters et al., 2007, Endocrinology. 148:3674-3684). To define estrus cycle length, daily vaginal samples were collected for 14 consecutive days.

Example 25

In Situ mRNA Hybridization

Ten μm coronal sections of mouse testis or bone were cut in a cryostat and mounted on positively charged microscope slides. For hybridization, cryosections were incubated with DIG-labelled riboprobe at 69° C., followed by incubation with alkaline phosphatase-conjugated anti-DIG antibody. Color development was performed by incubation with NBT/BCIP.

Example 26

Immunohistochemistry and Immunofluorescence

Immunohistochemistry was performed according to Qin et al., 2008, PLoS One 3:e3285. Mouse testes were fixed overnight in Bouin's fixative, dehydrated through graded ethanol, processed for paraffin embedding, and sectioned at 5 μm. Goat polyclonal anti-3β-HSD (Santa Cruz Biotechnology) was used as primary antibody and a biotinylated rabbit anti-goat antibody (Jackson ImmunoResearch) was used as secondary antibody. The VECTASTAIN ABC KIT® (Vector laboratories) and 3,3'-diaminobenzidine (DAB) substrate kit (Vector laboratories) were used for reaction development.

For immunofluorescence studies, animals were anesthetized and perfused transcardially with ice-cold saline, followed by PFA 4%/PBS. Mouse testes and ovaries were dissected, postfixed overnight in PFA 4%/PBS, and then cryoprotected by overnight immersion in a 20% sucrose solution. Frozen testes or ovaries were sliced in 20 μm coronal sections using a cryotome, dried at room temperature for 20 minutes, washed with PBS, and blocked with appropriate serum for 1 hour. Sections were then incubated with rabbit anti-OstR for 24 hours at 4° C., rinsed, and incubated with a donkey anti-rabbit antibody (Cy3; Jackson immunoresearch).

Example 27

Germ Cell Proliferation

Proliferation analysis was performed by BrdU staining in 2 week-old WT and Ocn−/− mice (Wang et al., 2003, Endocrinology 144:5058-5064). Two hours before sacrifice, mice received an intraperitoneal injection of BrdU (40 μg/g body weight). BrdU staining was performed on sections prepared as above using a BrdU staining kit (Invitrogen, 93-3943) and hematoxylin counterstaing.

Example 28

Leydig Cell Analysis

Testes of WT, Ocn−/−, and Esp−/− mice were dissected and fixed in Bouin's fixative for histological analyses. Tissues were dehydrated through graded ethanol, processed for paraffin embedding, serially sectioned at 5 μm, and stained by immunohistochemistry with anti-3β-HSD as described above. The ratio between Leydig cell area (reflected by immunostaining) and interstitially area was measured by computer analysis using a 40× objective lens and an 8× ocular lens with test grid by counting 100 test points in 35-40 sites, as described (Dakhova et al., 2009, Endocrinology 150:404-412). The ratio percentage was obtained by counting points over Leydig cells area and dividing by the total number of points counted over interstitial area. The total number of Leydig cells per testis was calculated by dividing the total area of Leydig cells by the total number of Leydig cells in this area (number of Leydig cells/mm$^2$).

Example 29

Sperm Preparation and Hyperactivation

All routine chemicals and compounds were purchased from Sigma-Aldrich with exceptions noted below. A mouse sperm capacitating medium (Suarez and Osman, 1987, Biol. Reprod. 36:1191-1198; Suarez., 2008, Hum. Reprod. Update 14:647-657) was used for incubating and washing sperm. The medium consisted of 110 mM NaCl, 2.68 mM KCl, 0.36 mM NaH$_2$PO$_4$, 25 mM NaHCO$_3$, 25 mM 4-(2-hydroxyethyl)-1-piperazineethanesulfonic acid (HEPES) (EMD), 5.56 mM glucose, 1.0 mM pyruvic acid, 0.006% penicillin G (Na), 2.4 mM CaCl$_2$, 0.49 mM MgCl$_2$, and 20 mg/ml BSA (EMD). The medium was adjusted to pH 7.6 and 290-310 mOsm/kg).

Sperm were obtained from freshly dissected epididymides as follows. A 100 microliter droplet of medium was covered by mineral oil in a 35×10 mm Petri dish (Falcon), which was equilibrated in a 37° C., 5% CO$_2$ incubator prior to use. Caudal epididymides were cleaned of fat and then blood was gently pushed out of surface vessels. The epididymides were placed under the mineral oil in the Petri dish. Several cuts were made in the coiled tubules near the vas deferens and the thick fluid containing sperm was gently pulled out of each cut using forceps and transferred under the oil to the medium droplet. Sperm were allowed to disperse for 10 minutes in the incubator and then were diluted with medium to 5×106/ml. To promote capacitation and hyperactivation, sperm were incubated at 37° C. and 5% CO$_2$ for 2 hours.

Example 30

Analysis of Sperm Motility

Samples of sperm were placed on slides on a 37° C. stage of a Zeiss Axiovert 35 microscope and videotaped at 30 Hz using 200× bright field microscopy and stroboscopic illumination provided by a 75 W xenon flash tube (Chadwick-Helmuth Co., El Monte, Calif.). Videotaping was conducted using a black-and-white Dage CCD 72 video camera (Dage-MTI, Inc., Michigan City).

Example 31

Gpcr Expression Analysis in Testis and Ovary

Expression of the following 103 orphan GPCRs: Gpr1, Gpr101, Gpr107, Gpr108, Gpr110, Gpr111, Gpr112, Gpr113, Gpr114, Gpr115, Gpr116, Gpr119, Gpr12, Gpr120, Gpr123, Gpr124, Gpr125, Gpr126, Gpr128, Gpr132, Gpr133, Gpr135, Gpr137, Gpr137b, Gpr137c, Gpr139, Gpr141, Gpr142, Gpr143, Gpr144, Gpr146, Gpr149, Gpr15, Gpr150, Gpr151, Gpr152, Gpr153, Gpr155, Gpr156, Gpr158, Gpr160, Gpr161, Gpr162, Gpr165, Gpr17, Gpr171, Gpr172b, Gpr173, Gpr174, Gpr175, Gpr176, Gpr177, Gpr179, Gpr18, Gpr180, Gpr182, Gpr183, Gpr19, Gpr20, Gpr21, Gpr22, Gpr25, Gpr26, Gpr27, Gpr3, Gpr31, Gpr31c, Gpr33, Gpr34, Gpr35, Gpr37, Gpr3711, Gpr39, Gpr4, Gpr44, Gpr45, Gpr50, Gpr52, Gpr55, Gpr56, Gpr6, Gpr61, Gpr62, Gpr63, Gpr64, Gpr65, Gpr68, Gpr75, Gpr77, Gpr81, Gpr82, Gpr83, Gpr84, Gpr85, Gpr87, Gpr88, Gpr89, Gpr97, Gpr98, Gprc5a, Gprc5b, Gprc5c, Gprc5d, Gprc6a, Tmem181, Lgr5, Lgr4, Lanc11, Mrgprh, Mrgprg, pgr151 were tested by qPCR in testes and ovaries isolated from 8 week-old WT mice. The 22 most highly expressed genes in testes were tested for expression in primary Leydig cells and their expression in Leydig cells was compared with their expression in whole testes. The expression of four genes were specifically enriched in Leydig cells.

Example 32

Western Blotting

Western blotting was performed according to standard procedures. Frozen testes were homogenized and lysed with 1×RIPA buffer. Membranes were blocked and then incubated overnight with primary antibody in TBST-5% BSA, followed by incubation with appropriate HRP-conjugated secondary antibody. Signals were visualized with ECL. The following primary antibodies were used: anti-phospho-tyrosin (9416), anti-pERK1/2 (4370), anti-ERK1/2 (9102), anti-pCREB (9198), anti-CREB (4820), anti-Cleaved Caspase-3 (Asp175) (9661) (all from Cell Signaling), and anti-tACE (H-300): sc-13973 and anti-CHD5 (H-185): sc-68390 from Santa Cruz; the anti-osteocalcin was described in Ferron et al., 2010, Biochem. Biophys. Res. Comm. 397:691-696.

Example 33

Measurement of Intracellular Calcium

Isolated primary Leydig cells were resuspended in buffer containing 95 mM NaCl, 4.8 mM KCl, 1.2 mM $MgSO_4$, 1.2 mM $KH_2PO_4$, 5.6 mM glucose, 25 mM $NaHCO_3$, 1.7 mM $CaCl_2$, 0.25 mM sodium purivate, 1× PenStrep, 20 mM HEPES, 0.3% BSA, pH 7.4 at 37° C. (reagents from Sigma Aldrich, except for sodium pyruvate, PenStrep and HEPES from Invitrogen), plated at the density of 17-25000 cells/well on 96-well plate and placed in an incubator at 33° C., 5% $CO_2$ for 2 hours. Afterward, the FLIPR dye (Calcium Plus Assay Kit Dye, Molecular Devices) diluted in the same buffer supplemented with 2.5 mM probenecid, pH 7.4 was exchanged for the previous medium and incubated with the cells for an additional 30-45 minutes. Following the incubation with the dye, cells were placed in a BD Pathway 855 High-Content Bioimager, recorded for 10-20 seconds to get baseline fluorescence, and then stimulated with doses of osteocalcin ranging from 0.3 to 500 ng/ml as well as control substances: medium, calcium ionophore A23187, 10% FBS, 400 μM $Arginine^{2+}$, 100 μM ATP/UTP mix and recorded for an additional 2-5 minutes. The probing time was varied between 1 and 5 seconds. Obtained images were analyzed for the change in fluorescence using ImageJ 1.41.

Example 34

Chromatin Immunoprecipitation

Chromatin immunoprecipitation was performed on lysates from TM3 Leydig cells using the ChIP AssayKit (Millipore, #17-295) and an anti-CREB antibody (Cell Signaling, #4820). CREB binding sites in the promoters of indicated genes were obtained from previous bioinformatics analyzes (Zhang et al., 2005, Proc. Natl. Acad. Sci. USA. 102:4459-4464). Binding of CREB to the indicated regions of DNA was detected by PCR using the following primers: Cyp11a hCRE-1364 forward 5'-CTCAGGTCTTCATGA TTGTGG-3' (SEQ ID NO:18), reverse 5'-CGAAAGAGAGTGTATCCACC-3' (SEQ ID NO:19); Cyp11a hCRE-4176 forward 5'-CCTT-TACGTGGAATAACATTCA-3' (SEQ ID NO:20), reverse 5'-ATAGGGAATCACGG TGTAGC-3' (SEQ ID NO:21); 3β-HSD hCRE-993 forward 5'-GCAGCTTCAAGGAT-TACGTAA-3' (SEQ ID NO:22), reverse 5'-CATCTTGT-GAACTGGTGGCT-3' (SEQ ID NO:23); HSD3beta hCRE-3109 forward 5'-TCCATAGAACAGACTACCTAC-3' (SEQ ID NO:24), reverse 5'-GATCACAGCTGAGGAAGGC-3' (SEQ ID NO:25); StAR hCRE-40 forward 5'-TGATGCAC-CTCAGTTACTGG-3' (SEQ ID NO:26), reverse 5'-GCTGT-GCATCATCA CTTGAG-3' (SEQ ID NO:27) and the region which did not contain CREB binding sequence as a negative control forward 5'-CATACGTGCACTGTCTTAGC-3' (SEQ ID NO:28), reverse 5'-ACTCCTCCAGTAACTCCTTC-3' (SEQ ID NO:29).

Example 35

OstR, a G-Protein Coupled Receptor Transducing Osteocalcin Signals in Leydig Cells To better understand osteocalcin's molecular mode of action, a search for a receptor expressed in Leydig cells that could transduce osteocalcin's signal (OstR) was carried out. To that end, a two-steps experimental strategy was used.

First, the signal transduction pathway used by osteocalcin in Leydig cells was defined. For that purpose, Leydig cells were treated with uncarboxylated osteocalcin and assayed for tyrosine phosphorylation, ERK activation, intracellular calcium accumulation, and cAMP production using in each case an appropriate positive control. Osteocalcin consistently induced cAMP production in Leydig cells to a level comparable to that induced by human chorionic gonadotropin (hCG), the positive control, but did not induce tyrosine phosphorylation, ERK activation, or intracellular calcium accumulation in these cells (FIG. 15A-D). Since these data implied that the osteocalcin receptor may be a G-protein coupled receptor (GPCR), the second step of this experimental strategy took advantage of the dichotomy of function of osteocalcin between males and females. Specifically, a search was done for orphan GPCRs that were expressed in testis at a level at least 5-fold higher than in ovary. Twenty-two out of 103 orphan GPCRs tested were predominantly expressed in testes; out of these 22, only 4 were enriched in Leydig cells (FIG. 15E-F). Among them, GPRC6a stood out because its deletion in all cells results in a metabolic and fertility phenotype reminiscent of the one observed in Ocn−/− mice (Pi et al., 2008, PLoS One 3:e3858).

Immunohistochemistry verified that Gprc6a is expressed only in Leydig cells in testes and not in follicular cells of the ovary (FIG. 15G and FIG. 21A). Post-natally, Gprc6a expression peaked within the first week of life, when testosterone circulating levels are elevated. Gprc6a expression then decreased but increase again at 6 weeks of age, when circulating levels of testosterone also rebound (FIG. 15I). Binding assays were performed on mouse testes using biotinylated osteocalcin as a ligand. Under the conditions of this assay, osteocalcin bound to Leydig cells and the specificity of this binding was confirmed by several criteria (FIG. 15J). First, there was no signal when using avidin-biotin alone; second, there was no signal in other cellular compartments of the testicular tubules; third, no binding was detected when using GPRC6a-deficient testes; fourth, osteocalcin binding could be competed away by an excess (100 fold) of unlabeled osteocalcin but not by the same excess of hCG or of other molecules proposed as ligands of GPRC6a (Wellendorph and Brauner-Osborne, 2004, Gene 335:37-46) (FIG. 15J). These data identify GPRC6a as a receptor of osteocalcin in Leydig cells. Therefore, GPRC6a is also referred to herein as OstR.

To define OstR function in Leydig cells in vivo, OstR$_{Leydig}$−/− mice were generated. Prior to analyzing these OstR$_{Leydig}$−/− mice, it was verified that OstR had been deleted, although partially, in testis but not in other organs (FIG. 22A-C). In OstR$_{Leydig}$−/− male mice, testes size and weight, epididymides and seminal vesicle weight, sperm count, circulating testosterone levels, and Leydig cell area were all reduced, as was the expression of Grth and the 3 genes controlling testosterone biosynthesis that are regulated by osteocalcin (FIG. 16A-I). Accordingly, the number of apoptotic germ cells increased compared to WT testes (FIG. 16J). To establish genetically that OstR may be the signaling receptor for osteocalcin in Leydig cells, compound mutant mice lacking one allele of Ocn and one allele of OstR in Leydig cells only (Ocn+/−; OstR$_{Leydig}$+/− mice) were analyzed. Whether looking at testes, epididymides and seminal vesicle weight, or sperm count, Ocn+/−; OstR$_{Leydig}$+/− mice had a phenotype identical to the one observed in OstR$_{Leydig}$−/− and Ocn$_{osb}$−/− mice (FIG. 16A-I).

Example 36

CREB is a Transcriptional Effector of Osteocalcin Signaling in Leydig Cells

The observations that cAMP production increases in Leydig cells treated with osteocalcin and that OstR is a GPCR implied that CREB could be a transcriptional mediator of osteocalcin functions in Leydig cells. The fact that osteocalcin treatment of Leydig cells favors CREB phosphorylation supported this hypothesis (FIG. 17A). This contention was tested further through the generation of mice lacking CREB in Leydig cells only (Creb$_{Leydig}$−/− mice).

Twelve week-old Creb$_{Leydig}$−/− male mice displayed a reduction in testis size and weight, in epididymides and seminal vesicle weight, in sperm count, and in circulating testosterone levels similar to the one seen in Ocn−/− and OstR$_{Leydig}$−/− mice (FIG. 17B-G). Creb$_{Leydig}$−/− mice also demonstrated a strong decrease in the expression of Grth and of the 4 genes involved in testosterone biosynthesis whose expression is regulated by osteocalcin (FIG. 17H-I). In agreement with these data, binding sites for CREB were identified in the promoters of Cyp11a, 3β-HSD and StAR (Zhang et al., 2005, Proc. Natl. Acad. Sci. USA. 102:4459-4464) and CREB could bind to those promoter sites (FIG. 17J). To establish that CREB acts downstream of OstR in Leydig cells to regulate male fertility, compound heterozygous mice lacking one copy of Creb and one copy of OstR in Leydig cells were generated. The fertility phenotype of these Creb$_{Leydig}$+/−; OstR$_{Leydig}$+/− male mice was similar to that observed in Creb$_{Leydig}$−/− or OStR$_{Leydig}$−/− male mice (FIG. 17B-G). This decrease in male fertility was not observed in single heterozygous mutant mice. Thus, CREB is a transcriptional mediator of osteocalcin regulation of testosterone biosynthesis in Leydig cells.

What is claimed is:

1. A method of treatment for increasing low sperm count, increasing low testosterone, or decreasing excessive apoptosis in testes in male mammals comprising administering to a male mammal in need of such treatment a pharmaceutical composition comprising a therapeutically effective amount of undercarboxylated/uncarboxylated osteocalcin and a pharmaceutically acceptable carrier or excipient.

2. The method of claim 1 where the male mammal is a human and the osteocalcin is human osteocalcin.

3. The method of claim 2 where at least one of the glutamic acids in the undercarboxylated/uncarboxylated osteocalcin at positions 17, 21 and 24 is not carboxylated.

4. The method of claim 3 where all three of the glutamic acids in the undercarboxylated/uncarboxylated osteocalcin at positions 17, 21 and 24 are not carboxylated.

5. The method of claim 2 where the undercarboxylated/uncarboxylated osteocalcin is a preparation of undercarboxylated/uncarboxylated osteocalcin in which more than about 20% of the total Glu residues at positions 17, 21 and 24 are not carboxylated.

6. The method of claim 1 where the undercarboxylated/uncarboxylated osteocalcin shares at least 80% amino acid sequence identity with mature human osteocalcin when the undercarboxylated/uncarboxylated osteocalcin and mature human osteocalcin are aligned for maximum sequence homology.

7. The method of claim 1 where the undercarboxylated/uncarboxylated osteocalcin shares about 90% amino acid sequence identity with mature human osteocalcin when the undercarboxylated/uncarboxylated osteocalcin and mature human osteocalcin are aligned for maximum sequence homology.

8. The method of claim 1 where the undercarboxylated/uncarboxylated osteocalcin differs at 1, 2, 3, 4, 5, 6, 7, 8, 9, or 10 amino acid residues from mature human osteocalcin.

9. The method of claim 1 where the undercarboxylated/uncarboxylated osteocalcin is a polypeptide selected from the group consisting of:
(a) a fragment comprising mature human osteocalcin missing the last 10 amino acids from the C-terminal end;
(b) a fragment comprising mature human osteocalcin missing the first 10 amino acids from the N-terminal end;
(c) a fragment comprising amino acids 62-90 of SEQ ID NO:2;
(d) a fragment comprising amino acids 1-36 of mature human osteocalcin; and
(e) variants of the above.

10. The method of claim 1 where the undercarboxylated/uncarboxylated osteocalcin polypeptide comprises an amino acid sequence
YLYQWLGAPVPYPDPLX$_1$PRRX$_2$VCX$_3$LNPDCDEL-ADHIGFQEAYRRFYGPV (SEQ ID NO:13)
wherein
X$_1$, X$_2$ and X$_3$ are each independently selected from an amino acid or amino acid analog, with the proviso that if X$_1$, X$_2$ and X$_3$ are each glutamic acid, then X$_1$ is not carboxylated, or less than 50 percent of X$_2$ is carboxylated, and/or less than 50 percent of X$_3$ is carboxylated,
or said osteocalcin polypeptide comprises an amino acid sequence that is different from SEQ. ID. NO:13 at 1 to 7 positions other than X$_1$, X$_2$ and X$_3$; and/or
wherein said amino acid sequence of SEQ. ID. NO:13 includes one or more amide backbone substitutions.

* * * * *

SEQUENCE LISTING

```
<160> NUMBER OF SEQ ID NOS: 31

<210> SEQ ID NO 1
<211> LENGTH: 498
<212> TYPE: DNA
<213> ORGANISM: Homo sapiens
<220> FEATURE:
<221> NAME/KEY: CDS
<222> LOCATION: (19)..(318)

<400> SEQUENCE: 1
cgcagccacc gagacacc atg aga gcc ctc aca ctc ctc gcc cta ttg gcc      51
                    Met Arg Ala Leu Thr Leu Leu Ala Leu Leu Ala
                    1               5                   10 ctg gcc gca ctt tgc atc gct ggc cag gca ggt gcg aag ccc agc ggt      99
Leu Ala Ala Leu Cys Ile Ala Gly Gln Ala Gly Ala Lys Pro Ser Gly
            15                  20                  25 gca gag tcc agc aaa ggt gca gcc ttt gtg tcc aag cag gag ggc agc      147
Ala Glu Ser Ser Lys Gly Ala Ala Phe Val Ser Lys Gln Glu Gly Ser
        30                  35                  40 gag gta gtg aag aga ccc agg cgc tac ctg tat caa tgg ctg gga gcc      195
Glu Val Val Lys Arg Pro Arg Arg Tyr Leu Tyr Gln Trp Leu Gly Ala
    45                  50                  55 cca gtc ccc tac ccg gat ccc ctg gag ccc agg agg gag gtg tgt gag      243
Pro Val Pro Tyr Pro Asp Pro Leu Glu Pro Arg Arg Glu Val Cys Glu
60                  65                  70                  75 ctc aat ccg gac tgt gac gag ttg gct gac cac atc ggc ttt cag gag     291
```

```
Leu Asn Pro Asp Cys Asp Glu Leu Ala Asp His Ile Gly Phe Gln Glu
             80                  85                  90 gcc tat cgg cgc ttc tac ggc ccg gtc tagggtgtcg ctctgctggc         338
Ala Tyr Arg Arg Phe Tyr Gly Pro Val
         95                  100 ctggccggca accccagttc tgctcctctc caggcaccct tctttcctct tccccttgcc  398
cttgccctga cctcccagcc ctatggatgt ggggtcccca tcatcccagc tgctcccaaa  458
taaactccag aagaggaatc tgaaaaaaaa aaaaaaaaa                         498

<210> SEQ ID NO 2
<211> LENGTH: 100
<212> TYPE: PRT
<213> ORGANISM: Homo sapiens

<400> SEQUENCE: 2

Met Arg Ala Leu Thr Leu Leu Ala Leu Leu Ala Leu Ala Ala Leu Cys
1               5                   10                  15

Ile Ala Gly Gln Ala Gly Ala Lys Pro Ser Gly Ala Glu Ser Ser Lys
            20                  25                  30

Gly Ala Ala Phe Val Ser Lys Gln Glu Gly Ser Glu Val Val Lys Arg
        35                  40                  45

Pro Arg Arg Tyr Leu Tyr Gln Trp Leu Gly Ala Pro Val Pro Tyr Pro
    50                  55                  60

Asp Pro Leu Glu Pro Arg Arg Glu Val Cys Glu Leu Asn Pro Asp Cys
65                  70                  75                  80

Asp Glu Leu Ala Asp His Ile Gly Phe Gln Glu Ala Tyr Arg Arg Phe
                85                  90                  95

Tyr Gly Pro Val
            100

<210> SEQ ID NO 3
<211> LENGTH: 494
<212> TYPE: DNA
<213> ORGANISM: mus musculus

<400> SEQUENCE: 3
agaacagaca agtcccacac agcagcttgg cccagaccta gcagacacca tgaggaccat   60
ctttctgctc actctgctga ccctggctgc gctctgtctc tctgacctca cagatgccaa  120
gcccagcggc cctgagtctg acaaagcctt catgtccaag caggagggca ataaggtagt  180
gaacagactc cggcgctacc ttggagcctc agtccccagc ccagatcccc tggagcccac  240
ccgggagcag tgtgagctta accctgcttg tgacgagcta tcagaccagt atggcttgaa  300
gaccgcctac aaacgcatct atggtatcac tatttaggac ctgtgctgcc ctaaagccaa  360
actctggcag ctcggctttg gctgctctcc gggacttgat cctccctgtc ctctctctct  420
gccctgcaag tatggatgtc acagcagctc caaaataaag ttcagatgag gaagtgcaaa  480
aaaaaaaaaa aaaa                                                    494

<210> SEQ ID NO 4
<211> LENGTH: 470
<212> TYPE: DNA
<213> ORGANISM: mus musculus
<220> FEATURE:
<221> NAME/KEY: CDS
<222> LOCATION: (49)..(333)

<400> SEQUENCE: 4
```

```
gaacagacaa gtcccacaca gcagcttggt gcacacctag cagacacc atg agg acc      57
                                                      Met Arg Thr
                                                       1 ctc tct ctg ctc act ctg ctg gcc ctg gct gcg ctg tgt ctc tct gac     105
Leu Ser Leu Leu Thr Leu Leu Ala Leu Ala Ala Leu Cys Leu Ser Asp
  5              10                  15 ctc aca gat ccc aag ccc agc ggc cct gag tct gac aaa gcc ttc atg     153
Leu Thr Asp Pro Lys Pro Ser Gly Pro Glu Ser Asp Lys Ala Phe Met
 20              25                  30                  35 tcc aag cag gag ggc aat aag gta gtg aac aga ctc cgg cgc tac ctt     201
Ser Lys Gln Glu Gly Asn Lys Val Val Asn Arg Leu Arg Arg Tyr Leu
             40                  45                  50 gga gcc tca gtc ccc agc cca gat ccc ctg gag ccc acc cgg gag cag     249
Gly Ala Ser Val Pro Ser Pro Asp Pro Leu Glu Pro Thr Arg Glu Gln
         55                  60                  65 tgt gag ctt aac cct gct tgt gac gag cta tca gac cag tat ggc ttg     297
Cys Glu Leu Asn Pro Ala Cys Asp Glu Leu Ser Asp Gln Tyr Gly Leu
     70                  75                  80 aag acc gcc tac aaa cgc atc tac ggt atc act att taggacctgt          343
Lys Thr Ala Tyr Lys Arg Ile Tyr Gly Ile Thr Ile
 85                  90                  95 gctgccctaa agccaaactc tggcagctcg gctttggctg ctctccggga cttgatcctc   403
cctgtcctct ctctctgccc tgcaagtatg gatgtcacag cagctccaaa ataaagttca   463
gatgagg                                                              470

<210> SEQ ID NO 5
<211> LENGTH: 95
<212> TYPE: PRT
<213> ORGANISM: mus musculus

<400> SEQUENCE: 5

Met Arg Thr Leu Ser Leu Leu Thr Leu Leu Ala Leu Ala Ala Leu Cys
 1               5                  10                  15

Leu Ser Asp Leu Thr Asp Pro Lys Pro Ser Gly Pro Glu Ser Asp Lys
             20                  25                  30

Ala Phe Met Ser Lys Gln Glu Gly Asn Lys Val Val Asn Arg Leu Arg
         35                  40                  45

Arg Tyr Leu Gly Ala Ser Val Pro Ser Pro Asp Pro Leu Glu Pro Thr
     50                  55                  60

Arg Glu Gln Cys Glu Leu Asn Pro Ala Cys Asp Glu Leu Ser Asp Gln
 65                  70                  75                  80

Tyr Gly Leu Lys Thr Ala Tyr Lys Arg Ile Tyr Gly Ile Thr Ile
             85                  90                  95

<210> SEQ ID NO 6
<211> LENGTH: 3236
<212> TYPE: DNA
<213> ORGANISM: homo sapiens
<220> FEATURE:
<221> NAME/KEY: CDS
<222> LOCATION: (29)..(2302)

<400> SEQUENCE: 6
gtgacccacc tgcctcctcc gcagagca atg gcg gtg tct gcc ggg tcc gcg      52
                                Met Ala Val Ser Ala Gly Ser Ala
                                 1               5 cgg acc tcg ccc agc tca gat aaa gta cag aaa gac aag gct gaa ctg    100
Arg Thr Ser Pro Ser Ser Asp Lys Val Gln Lys Asp Lys Ala Glu Leu
         10                  15                  20
```

-continued

| | |
|---|---|
| atc tca ggg ccc agg cag gac agc cga ata ggg aaa ctc ttg ggt ttt<br>Ile Ser Gly Pro Arg Gln Asp Ser Arg Ile Gly Lys Leu Leu Gly Phe<br>25                      30                        35                        40 | 148 |
| gag tgg aca gat ttg tcc agt tgg cgg agg ctg gtg acc ctg ctg aat<br>Glu Trp Thr Asp Leu Ser Ser Trp Arg Arg Leu Val Thr Leu Leu Asn<br>                      45                        50                        55 | 196 |
| cga cca acg gac cct gca agc tta gct gtc ttt cgt ttt ctt ttt ggg<br>Arg Pro Thr Asp Pro Ala Ser Leu Ala Val Phe Arg Phe Leu Phe Gly<br>              60                        65                        70 | 244 |
| ttc ttg atg gtg cta gac att ccc cag gag cgg ggg ctc agc tct ctg<br>Phe Leu Met Val Leu Asp Ile Pro Gln Glu Arg Gly Leu Ser Ser Leu<br>        75                        80                        85 | 292 |
| gac cgg aaa tac ctt gat ggg ctg gat gtg tgc cgc ttc ccc ttg ctg<br>Asp Arg Lys Tyr Leu Asp Gly Leu Asp Val Cys Arg Phe Pro Leu Leu<br>    90                        95                        100 | 340 |
| gat gcc cta cgc cca ctg cca ctt gac tgg atg tat ctt gtc tac acc<br>Asp Ala Leu Arg Pro Leu Pro Leu Asp Trp Met Tyr Leu Val Tyr Thr<br>105                      110                     115                    120 | 388 |
| atc atg ttt ctg ggg gca ctg ggc atg atg ctg ggc ctg tgc tac cgg<br>Ile Met Phe Leu Gly Ala Leu Gly Met Met Leu Gly Leu Cys Tyr Arg<br>                      125                        130                     135 | 436 |
| ata agc tgt gtg tta ttc ctg ctg cca tac tgg tat gtg ttt ctc ctg<br>Ile Ser Cys Val Leu Phe Leu Leu Pro Tyr Trp Tyr Val Phe Leu Leu<br>        140                        145                     150 | 484 |
| gac aag aca tca tgg aac aac cac tcc tat ctg tat ggg ttg ttg gcc<br>Asp Lys Thr Ser Trp Asn Asn His Ser Tyr Leu Tyr Gly Leu Leu Ala<br>155                      160                     165 | 532 |
| ttt cag cta aca ttc atg gat gca aac cac tac tgg tct gtg gac ggt<br>Phe Gln Leu Thr Phe Met Asp Ala Asn His Tyr Trp Ser Val Asp Gly<br>            170                     175                     180 | 580 |
| ctg ctg aat gcc cat agg agg aat gcc cac gtg ccc ctt tgg aac tat<br>Leu Leu Asn Ala His Arg Arg Asn Ala His Val Pro Leu Trp Asn Tyr<br>185                      190                     195                    200 | 628 |
| gca gtg ctc cgt ggc cag atc ttc att gtg tac ttc att gcg ggt gtg<br>Ala Val Leu Arg Gly Gln Ile Phe Ile Val Tyr Phe Ile Ala Gly Val<br>                      205                     210                    215 | 676 |
| aaa aag ctg gat gca gac tgg gtt gaa ggc tat tcc atg gaa tat ttg<br>Lys Lys Leu Asp Ala Asp Trp Val Glu Gly Tyr Ser Met Glu Tyr Leu<br>        220                        225                     230 | 724 |
| tcc cgg cac tgg ctc ttc agt ccc ttc aaa ctg ctg ttg tct gag gag<br>Ser Arg His Trp Leu Phe Ser Pro Phe Lys Leu Leu Leu Ser Glu Glu<br>            235                     240                     245 | 772 |
| ctg act agc ctg ctg gtc gtg cac tgg ggt ggg ctg ctg ctt gac ctc<br>Leu Thr Ser Leu Leu Val Val His Trp Gly Gly Leu Leu Leu Asp Leu<br>250                      255                     260 | 820 |
| tca gct ggt ttc ctg ctc ttt ttt gat gtc tca aga tcc att ggc ctg<br>Ser Ala Gly Phe Leu Leu Phe Phe Asp Val Ser Arg Ser Ile Gly Leu<br>265                      270                     275                    280 | 868 |
| ttc ttt gtg tcc tac ttc cac tgc atg aat tcc cag ctt ttc agc att<br>Phe Phe Val Ser Tyr Phe His Cys Met Asn Ser Gln Leu Phe Ser Ile<br>                      285                     290                    295 | 916 |
| ggt atg ttc tcc tac gtc atg ctg gcc agc agc cct ctc ttc tgc tcc<br>Gly Met Phe Ser Tyr Val Met Leu Ala Ser Ser Pro Leu Phe Cys Ser<br>        300                        305                     310 | 964 |
| cct gag tgg cct cgg aag ctg gtg tcc tac tgc ccc cga agg ttg caa<br>Pro Glu Trp Pro Arg Lys Leu Val Ser Tyr Cys Pro Arg Arg Leu Gln<br>315                      320                     325 | 1012 |
| caa ctg ttg ccc ctc aag gca gcc cct cag ccc agt gtt tcc tgt gtg<br>Gln Leu Leu Pro Leu Lys Ala Ala Pro Gln Pro Ser Val Ser Cys Val<br>        330                        335                     340 | 1060 |

```
tat aag agg agc cgg ggc aaa agt ggc cag aag cca ggg ctg cgc cat    1108
Tyr Lys Arg Ser Arg Gly Lys Ser Gly Gln Lys Pro Gly Leu Arg His
345                 350                 355                 360 cag ctg gga gct gcc ttc acc ctg ctc tac ctc ctg gag cag cta ttc    1156
Gln Leu Gly Ala Ala Phe Thr Leu Leu Tyr Leu Leu Glu Gln Leu Phe
                365                 370                 375 ctg ccc tat tct cat ttt ctc acc cag ggc tat aac aac tgg aca aat    1204
Leu Pro Tyr Ser His Phe Leu Thr Gln Gly Tyr Asn Asn Trp Thr Asn
            380                 385                 390 ggg ctg tat ggc tat tcc tgg gac atg atg gtg cac tcc cgc tcc cac    1252
Gly Leu Tyr Gly Tyr Ser Trp Asp Met Met Val His Ser Arg Ser His
        395                 400                 405 cag cac gtg aag atc acc tac cgt gat ggc cgc act ggc gaa ctg ggc    1300
Gln His Val Lys Ile Thr Tyr Arg Asp Gly Arg Thr Gly Glu Leu Gly
    410                 415                 420 tac ctt aac cct ggg gta ttt aca cag agt cgg cga tgg aag gat cat    1348
Tyr Leu Asn Pro Gly Val Phe Thr Gln Ser Arg Arg Trp Lys Asp His
425                 430                 435                 440 gca gac atg ctg aag caa tat gcc act tgc ctg agc cgc ctg ctt ccc    1396
Ala Asp Met Leu Lys Gln Tyr Ala Thr Cys Leu Ser Arg Leu Leu Pro
                445                 450                 455 aag tat aat gtc act gag ccc cag atc tac ttt gat att tgg gtc tcc    1444
Lys Tyr Asn Val Thr Glu Pro Gln Ile Tyr Phe Asp Ile Trp Val Ser
            460                 465                 470 atc aat gac cgc ttc cag cag agg att ttt gac cct cgt gtg gac atc    1492
Ile Asn Asp Arg Phe Gln Gln Arg Ile Phe Asp Pro Arg Val Asp Ile
        475                 480                 485 gtg cag gcc gct tgg tca ccc ttt cag cgc aca tcc tgg gtg caa cca    1540
Val Gln Ala Ala Trp Ser Pro Phe Gln Arg Thr Ser Trp Val Gln Pro
    490                 495                 500 ctc ttg atg gac ctg tct ccc tgg agg gcc aag tta cag gaa atc aag    1588
Leu Leu Met Asp Leu Ser Pro Trp Arg Ala Lys Leu Gln Glu Ile Lys
505                 510                 515                 520 agc agc cta gac aac cac act gag gtg gtc ttc att gca gat ttc cct    1636
Ser Ser Leu Asp Asn His Thr Glu Val Val Phe Ile Ala Asp Phe Pro
                525                 530                 535 gga ctg cac ttg gag aat ttt gtg agt gaa gac ctg ggc aac act agc    1684
Gly Leu His Leu Glu Asn Phe Val Ser Glu Asp Leu Gly Asn Thr Ser
            540                 545                 550 atc cag ctg ctg cag ggg gaa gtg act gtg gag ctt gtg gca gaa cag    1732
Ile Gln Leu Leu Gln Gly Glu Val Thr Val Glu Leu Val Ala Glu Gln
        555                 560                 565 aag aac cag act ctt cga gag gga gaa aaa atg cag ttg cct gct ggt    1780
Lys Asn Gln Thr Leu Arg Glu Gly Glu Lys Met Gln Leu Pro Ala Gly
    570                 575                 580 gag tac cat aag gtg tat acg aca tca cct agc cct tct tgc tac atg    1828
Glu Tyr His Lys Val Tyr Thr Thr Ser Pro Ser Pro Ser Cys Tyr Met
585                 590                 595                 600 tac gtc tat gtc aac act aca gag ctt gca ctg gag caa gac ctg gca    1876
Tyr Val Tyr Val Asn Thr Thr Glu Leu Ala Leu Glu Gln Asp Leu Ala
                605                 610                 615 tat ctg caa gaa tta aag gaa aag gtg gag aat gga agt gaa aca ggg    1924
Tyr Leu Gln Glu Leu Lys Glu Lys Val Glu Asn Gly Ser Glu Thr Gly
            620                 625                 630 cct cta ccc cca gag ctg cag cct ctg ttg gaa ggg gaa gta aaa ggg    1972
Pro Leu Pro Pro Glu Leu Gln Pro Leu Leu Glu Gly Glu Val Lys Gly
        635                 640                 645 ggc cct gag cca aca cct ctg gtt cag acc ttt ctt aga cgc caa caa    2020
Gly Pro Glu Pro Thr Pro Leu Val Gln Thr Phe Leu Arg Arg Gln Gln
```

```
                650             655             660
agg ctc cag gag att gaa cgc cgg cga aat act cct ttc cat gag cga    2068
Arg Leu Gln Glu Ile Glu Arg Arg Arg Asn Thr Pro Phe His Glu Arg
665                 670                 675                 680 ttc ttc cgc ttc ttg ttg cga aag ctc tat gtc ttt cgc cgc agc ttc    2116
Phe Phe Arg Phe Leu Leu Arg Lys Leu Tyr Val Phe Arg Arg Ser Phe
                685                 690                 695 ctg atg act tgt atc tca ctt cga aat ctg ata tta ggc cgt cct tcc    2164
Leu Met Thr Cys Ile Ser Leu Arg Asn Leu Ile Leu Gly Arg Pro Ser
        700                 705                 710 ctg gag cag ctg gcc cag gag gtg act tat gca aac ttg aga ccc ttt    2212
Leu Glu Gln Leu Ala Gln Glu Val Thr Tyr Ala Asn Leu Arg Pro Phe
    715                 720                 725 gag gca gtt gga gaa ctg aat ccc tca aac acg gat tct tca cat tct    2260
Glu Ala Val Gly Glu Leu Asn Pro Ser Asn Thr Asp Ser Ser His Ser
730                 735                 740 aat cct cct gag tca aat cct gat cct gtc cac tca gag ttc            2302
Asn Pro Pro Glu Ser Asn Pro Asp Pro Val His Ser Glu Phe
745                 750                 755 tgaagggggc cagatgttgg gtgcagatgt agaagcagcc agtcacagac ccattctatg    2362
caatggacat ttatttgaaa aaaattctca aaagttttt ttttttttt ggggggcgg      2422
ggttctaaag ctgtttttaa ctccgagatt acaacttaga ggaaccaagg aaataaagca   2482
aataagattt aacaacccaa gattaagagg ccaggaagag gttagacgca atgtgaaact   2542
gtcctcctag gataaggttt aaagtggctt tttgggggct gggtgccgtg gctcacgcct   2602
gtaatcccag cattttggga ggctgaggtg ggcagatcac ttgaggccag gagttcgaga   2662
ccagcctggc caacatggca aaaccccttc tctactaaaa atacaaaaat tagccagacg   2722
tggtggtggg tgcctgtaat ccaactaccc aggaggctga ggcatgagaa tcgcttgggc   2782
ccaggaggtg gaggttgcag tgagccgaga tcgagccact gcactcctgg caacagagc    2842
aagacttcgt ctcaaaataa ataaataaag tggctcttgg ggaaaagcaa tttaatgtac   2902
cacgatgaat agctaactgt tcccaagtgt ttgctatgtg caacacaccg cgtgagcagt   2962
gttacctgca ttattacatt aggctgagag gtaaaataat ttgcccgaag acatacagct   3022
agtgacgaat ggactgatgg tttgaactta acgtctattt gacttaaggt cctgcaccct   3082
gccacttgta atttcagaa tcactgataa tctgaaataa tgcagcttaa acatgttt      3142
cttaattaaa agtataaaaa aaaaaaaaaa aaaaaaaaaa aaaaaaaaaa aaaaaaaaaa   3202
aaaaaaaaaa aaaaaaaaaa aaaaaaaaaa aaaa                                3236
```

<210> SEQ ID NO 7
<211> LENGTH: 758
<212> TYPE: PRT
<213> ORGANISM: homo sapiens

<400> SEQUENCE: 7

Met Ala Val Ser Ala Gly Ser Ala Arg Thr Ser Pro Ser Ser Asp Lys
1               5                   10                  15

Val Gln Lys Asp Lys Ala Glu Leu Ile Ser Gly Pro Arg Gln Asp Ser
            20                  25                  30

Arg Ile Gly Lys Leu Leu Gly Phe Glu Trp Thr Asp Leu Ser Ser Trp
        35                  40                  45

Arg Arg Leu Val Thr Leu Leu Asn Arg Pro Thr Asp Pro Ala Ser Leu
    50                  55                  60

Ala Val Phe Arg Phe Leu Phe Gly Phe Leu Met Val Leu Asp Ile Pro

```
              65                  70                  75                  80
Gln Glu Arg Gly Leu Ser Ser Leu Asp Arg Lys Tyr Leu Asp Gly Leu
                    85                  90                  95
Asp Val Cys Arg Phe Pro Leu Leu Asp Ala Leu Arg Pro Leu Pro Leu
                100                 105                 110
Asp Trp Met Tyr Leu Val Tyr Thr Ile Met Phe Leu Gly Ala Leu Gly
                115                 120                 125
Met Met Leu Gly Leu Cys Tyr Arg Ile Ser Cys Val Leu Phe Leu Leu
                130                 135                 140
Pro Tyr Trp Tyr Val Phe Leu Leu Asp Lys Thr Ser Trp Asn Asn His
145                 150                 155                 160
Ser Tyr Leu Tyr Gly Leu Leu Ala Phe Gln Leu Thr Phe Met Asp Ala
                165                 170                 175
Asn His Tyr Trp Ser Val Asp Gly Leu Leu Asn Ala His Arg Arg Asn
                180                 185                 190
Ala His Val Pro Leu Trp Asn Tyr Ala Val Leu Arg Gly Gln Ile Phe
                195                 200                 205
Ile Val Tyr Phe Ile Ala Gly Val Lys Lys Leu Asp Ala Asp Trp Val
                210                 215                 220
Glu Gly Tyr Ser Met Glu Tyr Leu Ser Arg His Trp Leu Phe Ser Pro
225                 230                 235                 240
Phe Lys Leu Leu Leu Ser Glu Glu Leu Thr Ser Leu Leu Val Val His
                245                 250                 255
Trp Gly Gly Leu Leu Leu Asp Leu Ser Ala Gly Phe Leu Leu Phe Phe
                260                 265                 270
Asp Val Ser Arg Ser Ile Gly Leu Phe Phe Val Ser Tyr Phe His Cys
                275                 280                 285
Met Asn Ser Gln Leu Phe Ser Ile Gly Met Phe Ser Tyr Val Met Leu
                290                 295                 300
Ala Ser Ser Pro Leu Phe Cys Ser Pro Glu Trp Pro Arg Lys Leu Val
305                 310                 315                 320
Ser Tyr Cys Pro Arg Arg Leu Gln Gln Leu Leu Pro Leu Lys Ala Ala
                325                 330                 335
Pro Gln Pro Ser Val Ser Cys Val Tyr Lys Arg Ser Arg Gly Lys Ser
                340                 345                 350
Gly Gln Lys Pro Gly Leu Arg His Gln Leu Gly Ala Ala Phe Thr Leu
                355                 360                 365
Leu Tyr Leu Leu Glu Gln Leu Phe Leu Pro Tyr Ser His Phe Leu Thr
                370                 375                 380
Gln Gly Tyr Asn Asn Trp Thr Asn Gly Leu Tyr Gly Tyr Ser Trp Asp
385                 390                 395                 400
Met Met Val His Ser Arg Ser His Gln His Val Lys Ile Thr Tyr Arg
                405                 410                 415
Asp Gly Arg Thr Gly Glu Leu Gly Tyr Leu Asn Pro Gly Val Phe Thr
                420                 425                 430
Gln Ser Arg Arg Trp Lys Asp His Ala Asp Met Leu Lys Gln Tyr Ala
                435                 440                 445
Thr Cys Leu Ser Arg Leu Leu Pro Lys Tyr Asn Val Thr Glu Pro Gln
                450                 455                 460
Ile Tyr Phe Asp Ile Trp Val Ser Ile Asn Asp Arg Phe Gln Gln Arg
465                 470                 475                 480
Ile Phe Asp Pro Arg Val Asp Ile Val Gln Ala Ala Trp Ser Pro Phe
                485                 490                 495
```

```
Gln Arg Thr Ser Trp Val Gln Pro Leu Leu Met Asp Leu Ser Pro Trp
                500                 505                 510
Arg Ala Lys Leu Gln Glu Ile Lys Ser Ser Leu Asp Asn His Thr Glu
            515                 520                 525
Val Val Phe Ile Ala Asp Phe Pro Gly Leu His Leu Glu Asn Phe Val
        530                 535                 540
Ser Glu Asp Leu Gly Asn Thr Ser Ile Gln Leu Leu Gln Gly Glu Val
545                 550                 555                 560
Thr Val Glu Leu Val Ala Glu Lys Asn Gln Thr Leu Arg Glu Gly
                565                 570                 575
Glu Lys Met Gln Leu Pro Ala Gly Glu Tyr His Lys Val Tyr Thr Thr
                580                 585                 590
Ser Pro Ser Pro Ser Cys Tyr Met Tyr Val Tyr Val Asn Thr Thr Glu
            595                 600                 605
Leu Ala Leu Glu Gln Asp Leu Ala Tyr Leu Gln Glu Leu Lys Glu Lys
        610                 615                 620
Val Glu Asn Gly Ser Glu Thr Gly Pro Leu Pro Glu Leu Gln Pro
625                 630                 635                 640
Leu Leu Glu Gly Glu Val Lys Gly Gly Pro Glu Pro Thr Pro Leu Val
                645                 650                 655
Gln Thr Phe Leu Arg Arg Gln Gln Arg Leu Gln Glu Ile Glu Arg Arg
            660                 665                 670
Arg Asn Thr Pro Phe His Glu Arg Phe Phe Arg Phe Leu Leu Arg Lys
        675                 680                 685
Leu Tyr Val Phe Arg Arg Ser Phe Leu Met Thr Cys Ile Ser Leu Arg
        690                 695                 700
Asn Leu Ile Leu Gly Arg Pro Ser Leu Glu Gln Leu Ala Gln Glu Val
705                 710                 715                 720
Thr Tyr Ala Asn Leu Arg Pro Phe Glu Ala Val Gly Glu Leu Asn Pro
                725                 730                 735
Ser Asn Thr Asp Ser Ser His Ser Asn Pro Pro Glu Ser Asn Pro Asp
            740                 745                 750
Pro Val His Ser Glu Phe
        755

<210> SEQ ID NO 8
<211> LENGTH: 2905
<212> TYPE: DNA
<213> ORGANISM: mus musculus
<220> FEATURE:
<221> NAME/KEY: CDS
<222> LOCATION: (75)..(2345)

<400> SEQUENCE: 8
agacagcaag tctaagtctg gaggttccac tgggtccgac ctggctgcag agaggctcac      60
ctgtccctgc agtc atg gct gtg cac cgc ggc tcc gca ctg gtt gct ccc     110
                Met Ala Val His Arg Gly Ser Ala Leu Val Ala Pro
                  1               5                  10 gcc tca gat aaa gta cag aaa aac aag tct gca cag aca tca gga ctg     158
Ala Ser Asp Lys Val Gln Lys Asn Lys Ser Ala Gln Thr Ser Gly Leu
        15                  20                  25 aaa cag ggc agc cga atg gag aaa att tta ggg ttt gaa tgg aca gat     206
Lys Gln Gly Ser Arg Met Glu Lys Ile Leu Gly Phe Glu Trp Thr Asp
    30                  35                  40 tta tct agc tgg cag agt gtc gtg acc ctg ctt aac aaa cca acg gac     254
Leu Ser Ser Trp Gln Ser Val Val Thr Leu Leu Asn Lys Pro Thr Asp
```

```
               45                  50                  55                  60 cct gca aac ctg gct gtc ttt cgt ttt ctc ttt gct ttc ttg atg ctg       302
Pro Ala Asn Leu Ala Val Phe Arg Phe Leu Phe Ala Phe Leu Met Leu
                 65                  70                  75 ctg gac att ccc cag gaa cgc ggc ctt agc tcc ctg gac cga aaa tac       350
Leu Asp Ile Pro Gln Glu Arg Gly Leu Ser Ser Leu Asp Arg Lys Tyr
                 80                  85                  90 ttg gat ggg ctg gat gtg tgc cgt ttc ccc ttg ctg gat gcc ttg cgc       398
Leu Asp Gly Leu Asp Val Cys Arg Phe Pro Leu Leu Asp Ala Leu Arg
                 95                 100                 105 cca ctg cca ctg gac tgg atg tat ctt gtc tac acc atc atg ttt ctg       446
Pro Leu Pro Leu Asp Trp Met Tyr Leu Val Tyr Thr Ile Met Phe Leu
        110                 115                 120 ggg gca ctg ggc atg atg ctg ggg cta tgc tac cgg cta agc tgt gtg       494
Gly Ala Leu Gly Met Met Leu Gly Leu Cys Tyr Arg Leu Ser Cys Val
125                 130                 135                 140 tta ttc ctg cta ccg tac tgg tac gtg ttt ctc ctg gac aag act tcg       542
Leu Phe Leu Leu Pro Tyr Trp Tyr Val Phe Leu Leu Asp Lys Thr Ser
                145                 150                 155 tgg aac aat cac tcc tat ctg tat ggt ttg ttg gcc ttt cag ttg aca       590
Trp Asn Asn His Ser Tyr Leu Tyr Gly Leu Leu Ala Phe Gln Leu Thr
        160                 165                 170 ttc atg gat gca aac cac tac tgg tct gtg gat ggc ttg ctg aat gcc       638
Phe Met Asp Ala Asn His Tyr Trp Ser Val Asp Gly Leu Leu Asn Ala
        175                 180                 185 cga aag aag aat gct cac gtg ccc ctt tgg aac tac aca gtt ctg cgt       686
Arg Lys Lys Asn Ala His Val Pro Leu Trp Asn Tyr Thr Val Leu Arg
        190                 195                 200 ggc cag atc ttc atc gtg tac ttc atc gcg ggt gtg aag aag ctc gat       734
Gly Gln Ile Phe Ile Val Tyr Phe Ile Ala Gly Val Lys Lys Leu Asp
205                 210                 215                 220 gct gac tgg gtt ggg ggc tac tcc atg gag cac ctg tcc cgg cac tgg       782
Ala Asp Trp Val Gly Gly Tyr Ser Met Glu His Leu Ser Arg His Trp
                225                 230                 235 ctc ttc agt ccc ttc aag ctg gtg ttg tcg gag gag ctg aca agc ctg       830
Leu Phe Ser Pro Phe Lys Leu Val Leu Ser Glu Glu Leu Thr Ser Leu
        240                 245                 250 ctg gta gta cac tgg tgt ggg ctt ctc ctt gac ctc tcg gct ggc ttc       878
Leu Val Val His Trp Cys Gly Leu Leu Leu Asp Leu Ser Ala Gly Phe
        255                 260                 265 ctg ctc ttc ttt gat gcc tcc aga ccc gtc ggc ctg ttc ttc gtg tcc       926
Leu Leu Phe Phe Asp Ala Ser Arg Pro Val Gly Leu Phe Phe Val Ser
        270                 275                 280 tac ttt cac tgc atg aac tcg cag ctc ttc agc atc ggg atg ttt ccc       974
Tyr Phe His Cys Met Asn Ser Gln Leu Phe Ser Ile Gly Met Phe Pro
285                 290                 295                 300 tat gtc atg ctg gcc agc agc cct ctc ttc tgc tca gct gaa tgg cct      1022
Tyr Val Met Leu Ala Ser Ser Pro Leu Phe Cys Ser Ala Glu Trp Pro
                305                 310                 315 cgg aag ttg gta gcc cga tgc ccg aaa agg ctg caa gag ctg ctg ccc      1070
Arg Lys Leu Val Ala Arg Cys Pro Lys Arg Leu Gln Glu Leu Leu Pro
        320                 325                 330 acc aaa gcc gct cct cgg cct agt gct tcc tgt gtg tat aag agg tcc      1118
Thr Lys Ala Ala Pro Arg Pro Ser Ala Ser Cys Val Tyr Lys Arg Ser
        335                 340                 345 cgg ggc aaa gct ggc ccg aag ccc ggg ctg cgc cac cag ctg gga gcc      1166
Arg Gly Lys Ala Gly Pro Lys Pro Gly Leu Arg His Gln Leu Gly Ala
350                 355                 360 atc ttc acc ctg ctc tac ctc cta gag cag ctc ttc ctg ccc tat tcc      1214
```

```
              Ile Phe Thr Leu Leu Tyr Leu Leu Glu Gln Leu Phe Leu Pro Tyr Ser
              365                 370                 375                 380 cac ttc ctg acc cag ggt tac aat aac tgg aca aat ggg ctg tat ggc            1262
His Phe Leu Thr Gln Gly Tyr Asn Asn Trp Thr Asn Gly Leu Tyr Gly
                            385                 390                 395 tat tcc tgg gac atg atg gtg cac tcc cgc tcc cac cag cac gta aag            1310
Tyr Ser Trp Asp Met Met Val His Ser Arg Ser His Gln His Val Lys
            400                 405                 410 atc acc tac cgc gac ggc ctc acg ggc gag cta ggc tac ctt aac cct            1358
Ile Thr Tyr Arg Asp Gly Leu Thr Gly Glu Leu Gly Tyr Leu Asn Pro
        415                 420                 425 ggg gta ttc aca cag agc cgg cga tgg aag gat cat gca gac atg ctg            1406
Gly Val Phe Thr Gln Ser Arg Arg Trp Lys Asp His Ala Asp Met Leu
    430                 435                 440 aag caa tat gcc act tgc ctg agc ctc ctt ccc aag tac aat gtc                1454
Lys Gln Tyr Ala Thr Cys Leu Ser Leu Leu Pro Lys Tyr Asn Val
445                 450                 455                 460 act gag ccc cag atc tac ttt gat att tgg gtc tcc atc aat gac cgc            1502
Thr Glu Pro Gln Ile Tyr Phe Asp Ile Trp Val Ser Ile Asn Asp Arg
                            465                 470                 475 ttc cag cag agg ctt ttt gac cct cgt gtg gac atc gtg cag gct gtc            1550
Phe Gln Gln Arg Leu Phe Asp Pro Arg Val Asp Ile Val Gln Ala Val
            480                 485                 490 tgg tcc ccc ttc cag cgc aca cct tgg gtg cag cca ctc ttg atg gat            1598
Trp Ser Pro Phe Gln Arg Thr Pro Trp Val Gln Pro Leu Leu Met Asp
        495                 500                 505 tta tct ccc tgg agg acc aag tta cag gat att aag agc agt ctg gac            1646
Leu Ser Pro Trp Arg Thr Lys Leu Gln Asp Ile Lys Ser Ser Leu Asp
    510                 515                 520 aac cac acc gag gtg gtc ttc att gca gat ttc cct ggg ctt cac ttg            1694
Asn His Thr Glu Val Val Phe Ile Ala Asp Phe Pro Gly Leu His Leu
525                 530                 535                 540 gag aat ttt gtg agt gaa gac ctg ggc aac act agc atc cag ctg ctg            1742
Glu Asn Phe Val Ser Glu Asp Leu Gly Asn Thr Ser Ile Gln Leu Leu
                545                 550                 555 cag gga gaa gtc acc gtg gaa ttg gtg gca gaa cag aaa aat cag act            1790
Gln Gly Glu Val Thr Val Glu Leu Val Ala Glu Gln Lys Asn Gln Thr
            560                 565                 570 ctt caa gaa gga gag aaa atg cag ttg cct gct gga gag tac cat aaa            1838
Leu Gln Glu Gly Glu Lys Met Gln Leu Pro Ala Gly Glu Tyr His Lys
        575                 580                 585 gtc tat act gta tca tct agt cct tcc tgc tac atg tac gtc tat gtc            1886
Val Tyr Thr Val Ser Ser Ser Pro Ser Cys Tyr Met Tyr Val Tyr Val
    590                 595                 600 aac act aca gag gtc gca ctg gag caa gac ctg gca tat ctg caa gaa            1934
Asn Thr Thr Glu Val Ala Leu Glu Gln Asp Leu Ala Tyr Leu Gln Glu
605                 610                 615                 620 tta aag gag aag gtg gag aac gga agt gaa aca ggg ccc ctg cct cca            1982
Leu Lys Glu Lys Val Glu Asn Gly Ser Glu Thr Gly Pro Leu Pro Pro
                625                 630                 635 gaa ctt cag cct ctt ttg gaa ggg gaa gta aaa ggg ggc cct gag cca            2030
Glu Leu Gln Pro Leu Leu Glu Gly Glu Val Lys Gly Gly Pro Glu Pro
            640                 645                 650 aca cct ctg gtc caa act ttt ctc aga cga cag agg aag ctc caa gaa            2078
Thr Pro Leu Val Gln Thr Phe Leu Arg Arg Gln Arg Lys Leu Gln Glu
        655                 660                 665 att gaa cgc agg cga aat agc cct ttc cat gag cga ttt ctc cgc ttc            2126
Ile Glu Arg Arg Arg Asn Ser Pro Phe His Glu Arg Phe Leu Arg Phe
    670                 675                 680
```

```
gtg ctg cga aag ctc tac gtc ttt cga cgc agc ttc ctg atg act cga    2174
Val Leu Arg Lys Leu Tyr Val Phe Arg Arg Ser Phe Leu Met Thr Arg
685                 690                 695                 700 att tca ctc cga aac ctg cta tta ggc cgc cct tcc cta gag caa cta    2222
Ile Ser Leu Arg Asn Leu Leu Leu Gly Arg Pro Ser Leu Glu Gln Leu
            705                 710                 715 gcc caa gag gtg aca tat gca aac ttg cga cca ttt gaa cca gtt gat    2270
Ala Gln Glu Val Thr Tyr Ala Asn Leu Arg Pro Phe Glu Pro Val Asp
        720                 725                 730 gag tca agt gct tca aac aca gat tct tca aat cac ccg tca gag cca    2318
Glu Ser Ser Ala Ser Asn Thr Asp Ser Ser Asn His Pro Ser Glu Pro
    735                 740                 745 gat tct gag cat gtt cac tct gag ttc tgagggatgt acagatgctc          2365
Asp Ser Glu His Val His Ser Glu Phe
750                 755 tgtgcagatg tggggggcagc ctgttatagg cttattgtct acgcaaagaa catattttg    2425 gagaaaaatg atatgggaca ggctttcaca gtacagccca ggctggcctc aaactcatgg    2485
ttggtccctc tgcttcagcc tgttttgtaa ttacatagta tcaccaaacc tagttgcttt    2545 tcccttaca ttttttcccc ttataagttc tttaaaatta tagcttacat ttttctttt    2605 ttcttttttt tttttttgta ttttttcttt gtcaagacag gtctctctct gtgtagcact    2665
ggctgtcctg gaactcactc tgtagtccag gctggcctcc aactcagaaa ttctcctgcc    2725
tctgcctccc aagtgctggg attaaaggtg tgtgccacca cgccccactg ggcttttagt    2785
ttttatagac aagatttctc catgtagacc agaccagctc tcctgagtgc tgaaattaaa    2845
ggcacgggac atcactacct ggctttctta ttaaacttgt tttagtggtc tcaacaaaaa    2905

<210> SEQ ID NO 9
<211> LENGTH: 757
<212> TYPE: PRT
<213> ORGANISM: mus musculus

<400> SEQUENCE: 9

Met Ala Val His Arg Gly Ser Ala Leu Val Ala Pro Ala Ser Asp Lys
1               5                   10                  15

Val Gln Lys Asn Lys Ser Ala Gln Thr Ser Gly Leu Lys Gln Gly Ser
            20                  25                  30

Arg Met Glu Lys Ile Leu Gly Phe Glu Trp Thr Asp Leu Ser Ser Trp
        35                  40                  45

Gln Ser Val Val Thr Leu Leu Asn Lys Pro Thr Asp Pro Ala Asn Leu
    50                  55                  60

Ala Val Phe Arg Phe Leu Phe Ala Phe Leu Met Leu Leu Asp Ile Pro
65                  70                  75                  80

Gln Glu Arg Gly Leu Ser Ser Leu Asp Arg Lys Tyr Leu Asp Gly Leu
                85                  90                  95

Asp Val Cys Arg Phe Pro Leu Leu Asp Ala Leu Arg Pro Leu Pro Leu
            100                 105                 110

Asp Trp Met Tyr Leu Val Tyr Thr Ile Met Phe Leu Gly Ala Leu Gly
        115                 120                 125

Met Met Leu Gly Leu Cys Tyr Arg Leu Ser Cys Val Leu Phe Leu Leu
130                 135                 140

Pro Tyr Trp Tyr Val Phe Leu Leu Asp Lys Thr Ser Trp Asn Asn His
145                 150                 155                 160

Ser Tyr Leu Tyr Gly Leu Leu Ala Phe Gln Leu Thr Phe Met Asp Ala
                165                 170                 175
```

-continued

```
Asn His Tyr Trp Ser Val Asp Gly Leu Leu Asn Ala Arg Lys Lys Asn
            180                 185                 190

Ala His Val Pro Leu Trp Asn Tyr Thr Val Leu Arg Gly Gln Ile Phe
            195                 200                 205

Ile Val Tyr Phe Ile Ala Gly Val Lys Lys Leu Asp Ala Asp Trp Val
            210                 215                 220

Gly Gly Tyr Ser Met Glu His Leu Ser Arg His Trp Leu Phe Ser Pro
225                 230                 235                 240

Phe Lys Leu Val Leu Ser Glu Glu Leu Thr Ser Leu Leu Val Val His
            245                 250                 255

Trp Cys Gly Leu Leu Leu Asp Leu Ser Ala Gly Phe Leu Leu Phe Phe
            260                 265                 270

Asp Ala Ser Arg Pro Val Gly Leu Phe Phe Val Ser Tyr Phe His Cys
            275                 280                 285

Met Asn Ser Gln Leu Phe Ser Ile Gly Met Phe Pro Tyr Val Met Leu
            290                 295                 300

Ala Ser Ser Pro Leu Phe Cys Ser Ala Glu Trp Pro Arg Lys Leu Val
305                 310                 315                 320

Ala Arg Cys Pro Lys Arg Leu Gln Glu Leu Leu Pro Thr Lys Ala Ala
            325                 330                 335

Pro Arg Pro Ser Ala Ser Cys Val Tyr Lys Arg Ser Arg Gly Lys Ala
            340                 345                 350

Gly Pro Lys Pro Gly Leu Arg His Gln Leu Gly Ala Ile Phe Thr Leu
            355                 360                 365

Leu Tyr Leu Leu Glu Gln Leu Phe Leu Pro Tyr Ser His Phe Leu Thr
            370                 375                 380

Gln Gly Tyr Asn Asn Trp Thr Asn Gly Leu Tyr Gly Tyr Ser Trp Asp
385                 390                 395                 400

Met Met Val His Ser Arg Ser His Gln His Val Lys Ile Thr Tyr Arg
            405                 410                 415

Asp Gly Leu Thr Gly Glu Leu Gly Tyr Leu Asn Pro Gly Val Phe Thr
            420                 425                 430

Gln Ser Arg Arg Trp Lys Asp His Ala Asp Met Leu Lys Gln Tyr Ala
            435                 440                 445

Thr Cys Leu Ser Leu Leu Pro Lys Tyr Asn Val Thr Glu Pro Gln
450                 455                 460

Ile Tyr Phe Asp Ile Trp Val Ser Ile Asn Asp Arg Phe Gln Gln Arg
465                 470                 475                 480

Leu Phe Asp Pro Arg Val Asp Ile Val Gln Ala Val Trp Ser Pro Phe
            485                 490                 495

Gln Arg Thr Pro Trp Val Gln Pro Leu Leu Met Asp Leu Ser Pro Trp
            500                 505                 510

Arg Thr Lys Leu Gln Asp Ile Lys Ser Ser Leu Asp Asn His Thr Glu
            515                 520                 525

Val Val Phe Ile Ala Asp Phe Pro Gly Leu His Leu Glu Asn Phe Val
530                 535                 540

Ser Glu Asp Leu Gly Asn Thr Ser Ile Gln Leu Leu Gln Gly Glu Val
545                 550                 555                 560

Thr Val Glu Leu Val Ala Glu Gln Lys Asn Gln Thr Leu Gln Glu Gly
            565                 570                 575

Glu Lys Met Gln Leu Pro Ala Gly Glu Tyr His Lys Val Tyr Thr Val
            580                 585                 590

Ser Ser Ser Pro Ser Cys Tyr Met Tyr Val Tyr Val Asn Thr Thr Glu
```

```
                595                 600                 605
Val Ala Leu Glu Gln Asp Leu Ala Tyr Leu Gln Glu Leu Lys Glu Lys
610                 615                 620

Val Glu Asn Gly Ser Glu Thr Gly Pro Leu Pro Glu Leu Gln Pro
625                 630                 635                 640

Leu Leu Glu Gly Glu Val Lys Gly Gly Pro Glu Pro Thr Pro Leu Val
                645                 650                 655

Gln Thr Phe Leu Arg Arg Gln Arg Lys Leu Gln Glu Ile Glu Arg Arg
                660                 665                 670

Arg Asn Ser Pro Phe His Glu Arg Phe Leu Arg Phe Val Leu Arg Lys
                675                 680                 685

Leu Tyr Val Phe Arg Arg Ser Phe Leu Met Thr Arg Ile Ser Leu Arg
                690                 695                 700

Asn Leu Leu Leu Gly Arg Pro Ser Leu Glu Gln Leu Ala Gln Glu Val
705                 710                 715                 720

Thr Tyr Ala Asn Leu Arg Pro Phe Glu Pro Val Asp Glu Ser Ser Ala
                725                 730                 735

Ser Asn Thr Asp Ser Ser Asn His Pro Ser Glu Pro Asp Ser Glu His
                740                 745                 750

Val His Ser Glu Phe
                755

<210> SEQ ID NO 10
<211> LENGTH: 5555
<212> TYPE: DNA
<213> ORGANISM: mus musculus
<220> FEATURE:
<221> NAME/KEY: CDS
<222> LOCATION: (316)..(5430)

<400> SEQUENCE: 10
ggctgtggga gagcagaaga ggagctggaa gagcagccta caacagctgt cgggagggac    60
cagggctagt tcacacttgg aagctgggat gccaggaccg gccctcctgc ctctctcggt   120
ctccatcggc ctcctggtca gctcactcca cactgagacg attctgaagt aagatgctcc   180
tggctcctca cagactctgc tacaagagac agagtgaagt gtccccaggg ctcagagcct   240
ttgactctgc tccttccctt cccacggctg agttggcaca ggagcacctg ggtgagctgc   300
accagactta agaag atg agg ccc ctg att ctg tta gct gcc ctc ctc tgg   351
              Met Arg Pro Leu Ile Leu Leu Ala Ala Leu Leu Trp
                1               5                  10 ctc cag gac tct ttg gcc cag gaa gat gta tgc tca tcc ttg gat ggg   399
Leu Gln Asp Ser Leu Ala Gln Glu Asp Val Cys Ser Ser Leu Asp Gly
           15                  20                  25 agc cca gac agg cag ggt gga ggt cca cct ctg agt gtg aac gtc agc   447
Ser Pro Asp Arg Gln Gly Gly Gly Pro Pro Leu Ser Val Asn Val Ser
         30                  35                  40 agc cgc gga aag cct acc agc ctg ttt ctg agc tgg gta gct gca gag   495
Ser Arg Gly Lys Pro Thr Ser Leu Phe Leu Ser Trp Val Ala Ala Glu
45                  50                  55                  60 cca gtt gga ttt gac tat gcc ctc tgc ctc agg gct atg aac ttg tcg   543
Pro Gly Gly Phe Asp Tyr Ala Leu Cys Leu Arg Ala Met Asn Leu Ser
                 65                  70                  75 ggt ttt cca gaa ggg caa cag ctc caa gct cat acc aac gag tcc agc   591
Gly Phe Pro Glu Gly Gln Gln Leu Gln Ala His Thr Asn Glu Ser Ser
             80                  85                  90 ttt gag ttc cat ggc ctg gtg cca ggg agt cgc tac cag ctg gaa ctg   639
Phe Glu Phe His Gly Leu Val Pro Gly Ser Arg Tyr Gln Leu Glu Leu
```

-continued

```
              95                  100                 105
act gtc cta aga ccc tgt tgg cag aat gtc aca att acc ctc act gct      687
Thr Val Leu Arg Pro Cys Trp Gln Asn Val Thr Ile Thr Leu Thr Ala
    110                 115                 120 cga act gcc cct aca gtg gtc cgt gga ctg caa ctg cat agc act ggg      735
Arg Thr Ala Pro Thr Val Val Arg Gly Leu Gln Leu His Ser Thr Gly
125                 130                 135                 140 agc cca gcc agc ctg gaa gcc tca tgg agc gat gcc tct ggg gat caa      783
Ser Pro Ala Ser Leu Glu Ala Ser Trp Ser Asp Ala Ser Gly Asp Gln
                145                 150                 155 gac agc tat caa ctt ctc ctc tac cac ccg gaa tcc cac act ctg gca      831
Asp Ser Tyr Gln Leu Leu Leu Tyr His Pro Glu Ser His Thr Leu Ala
    160                 165                 170 tgt aat gtc tct gtg tcc cct gac acc ctg tct tac aat ttt ggt gac      879
Cys Asn Val Ser Val Ser Pro Asp Thr Leu Ser Tyr Asn Phe Gly Asp
    175                 180                 185 ctc ttg cca ggt agt cag tat gtc ttg gag gtt atc acc tgg gct ggc      927
Leu Leu Pro Gly Ser Gln Tyr Val Leu Glu Val Ile Thr Trp Ala Gly
    190                 195                 200 agt ctc cat gcg aag act agc atc ctc caa tgg aca gag cct gtc cct      975
Ser Leu His Ala Lys Thr Ser Ile Leu Gln Trp Thr Glu Pro Val Pro
205                 210                 215                 220 cct gat cac cta aca ctg cgt gcc ttg ggt acc agt agc ctg caa gcc     1023
Pro Asp His Leu Thr Leu Arg Ala Leu Gly Thr Ser Ser Leu Gln Ala
                225                 230                 235 ttc tgg aac agc tct gaa ggg gcc acc tgg ttt cac ctg ata ctt aca     1071
Phe Trp Asn Ser Ser Glu Gly Ala Thr Trp Phe His Leu Ile Leu Thr
    240                 245                 250 gac ctc cta gag ggt acc aac ctg acc aaa gtg gtc aga caa ggc atc     1119
Asp Leu Leu Glu Gly Thr Asn Leu Thr Lys Val Val Arg Gln Gly Ile
    255                 260                 265 tca acc cac acc ttc ctt cgc ctg tct ccg ggt aca cct tac cag ctg     1167
Ser Thr His Thr Phe Leu Arg Leu Ser Pro Gly Thr Pro Tyr Gln Leu
    270                 275                 280 aag atc tgt gct gct gct ggg ccc cac cag att tgg gga ccc aat gcc     1215
Lys Ile Cys Ala Ala Ala Gly Pro His Gln Ile Trp Gly Pro Asn Ala
285                 290                 295                 300 act gag tgg acc tat ccc tct tac cca tct gac ctg gtg ctg acc ccc     1263
Thr Glu Trp Thr Tyr Pro Ser Tyr Pro Ser Asp Leu Val Leu Thr Pro
                305                 310                 315 tta tgg aat gag ctc tgg gca agc tgg aag gca ggg cag gga gcc cgg     1311
Leu Trp Asn Glu Leu Trp Ala Ser Trp Lys Ala Gly Gln Gly Ala Arg
    320                 325                 330 gat ggc tat gta ctg aag tta agt ggg cca gtg gag aat aca act act     1359
Asp Gly Tyr Val Leu Lys Leu Ser Gly Pro Val Glu Asn Thr Thr Thr
    335                 340                 345 ctg ggt cct gag gag tgc aac gct gtc ttc cca ggg ccc ctg cct cca     1407
Leu Gly Pro Glu Glu Cys Asn Ala Val Phe Pro Gly Pro Leu Pro Pro
350                 355                 360 gga cac tac act ttg ggg ctg agg gtt cta gct gga cct tat gat gcc     1455
Gly His Tyr Thr Leu Gly Leu Arg Val Leu Ala Gly Pro Tyr Asp Ala
365                 370                 375                 380 tgg gta gag ggc agt atc tgg ctg gct gaa tct gct gct cgt ccc atg     1503
Trp Val Glu Gly Ser Ile Trp Leu Ala Glu Ser Ala Ala Arg Pro Met
                385                 390                 395 gag gtc cct ggt gcc aga ctg tgg cta gaa gga ctg gaa gct act aag     1551
Glu Val Pro Gly Ala Arg Leu Trp Leu Glu Gly Leu Glu Ala Thr Lys
    400                 405                 410 caa cct ggg aga cgg gcg ctg ctc tat tct gtt gat gcc cca ggc ctc     1599
```

```
Gln Pro Gly Arg Arg Ala Leu Leu Tyr Ser Val Asp Ala Pro Gly Leu
            415                 420                 425 cta ggg aac atc tct gtg tct tct ggt gcc act cat gtc acc ttc tgt         1647
Leu Gly Asn Ile Ser Val Ser Ser Gly Ala Thr His Val Thr Phe Cys
        430                 435                 440 ggc ttg gta ccc gga gcg cac tac agg gtg gac att gcc tca tcc atg         1695
Gly Leu Val Pro Gly Ala His Tyr Arg Val Asp Ile Ala Ser Ser Met
445                 450                 455                 460 gga gac atc act cag agc ctc aca ggc tac aca agt ccc ctg cca cca         1743
Gly Asp Ile Thr Gln Ser Leu Thr Gly Tyr Thr Ser Pro Leu Pro Pro
                465                 470                 475 cag tct ctg gag atc atc agc cgg aac agc cca tct gac ctg act atc         1791
Gln Ser Leu Glu Ile Ile Ser Arg Asn Ser Pro Ser Asp Leu Thr Ile
            480                 485                 490 ggt tgg gct cca gca cca ggg cag atg gaa ggt tat aag gtc acc tgg         1839
Gly Trp Ala Pro Ala Pro Gly Gln Met Glu Gly Tyr Lys Val Thr Trp
        495                 500                 505 cat cag gat ggc agc cag agg tca cct ggc gac ctt gtt gac ttg ggc         1887
His Gln Asp Gly Ser Gln Arg Ser Pro Gly Asp Leu Val Asp Leu Gly
510                 515                 520 cct gac att tcg agc ctg act ctg aaa tct ctg gta cct ggt tcc tgc         1935
Pro Asp Ile Ser Ser Leu Thr Leu Lys Ser Leu Val Pro Gly Ser Cys
525                 530                 535                 540 tac acc gtg tca gca tgg gcc tgg tct ggg aac ctc agc tct gac tct         1983
Tyr Thr Val Ser Ala Trp Ala Trp Ser Gly Asn Leu Ser Ser Asp Ser
                545                 550                 555 cag aag att cac agt tgc acc cgt ccc gct cct ccc acc aac ctg agc         2031
Gln Lys Ile His Ser Cys Thr Arg Pro Ala Pro Pro Thr Asn Leu Ser
            560                 565                 570 ctg ggc ttt gcc cac cag cct gca aca ctg agg gct tcc tgg tgt cac         2079
Leu Gly Phe Ala His Gln Pro Ala Thr Leu Arg Ala Ser Trp Cys His
        575                 580                 585 cca ccg ggt ggc agg gat gcc ttt cag tta cgg ctt tac agg ctg agg         2127
Pro Pro Gly Gly Arg Asp Ala Phe Gln Leu Arg Leu Tyr Arg Leu Arg
590                 595                 600 ccc ctg aca ctg gaa agt gag aag atc cta tcc cag gag gcc cag aac         2175
Pro Leu Thr Leu Glu Ser Glu Lys Ile Leu Ser Gln Glu Ala Gln Asn
605                 610                 615                 620 ttc tcc tgg gcc cag ctg cct gca ggc tat gaa ttc cag gta cag ctg         2223
Phe Ser Trp Ala Gln Leu Pro Ala Gly Tyr Glu Phe Gln Val Gln Leu
                625                 630                 635 tct acc ttg tgg ggg tcg gag gag agc ggc agt gcc aac acc aca ggc         2271
Ser Thr Leu Trp Gly Ser Glu Glu Ser Gly Ser Ala Asn Thr Thr Gly
            640                 645                 650 tgg aca ccc ccc tca gct cct aca ttg gta aat gtg acc agt gaa gcc         2319
Trp Thr Pro Pro Ser Ala Pro Thr Leu Val Asn Val Thr Ser Glu Ala
        655                 660                 665 ccc acc cag ctc cac gta tcc tgg gtc cac gct gct ggg gac cgg agc         2367
Pro Thr Gln Leu His Val Ser Trp Val His Ala Ala Gly Asp Arg Ser
670                 675                 680 agc tac caa gtg acc cta tac cag gag agc act cgg aca gcc acc agc         2415
Ser Tyr Gln Val Thr Leu Tyr Gln Glu Ser Thr Arg Thr Ala Thr Ser
685                 690                 695                 700 att gtg ggg ccc aag gca gac agc aca agc ttt tgg ggt ttg act cct         2463
Ile Val Gly Pro Lys Ala Asp Ser Thr Ser Phe Trp Gly Leu Thr Pro
                705                 710                 715 ggc act aag tac aag gtg gaa gcc atc tcc tgg gct ggg ccc ctt tac         2511
Gly Thr Lys Tyr Lys Val Glu Ala Ile Ser Trp Ala Gly Pro Leu Tyr
            720                 725                 730
```

| | | |
|---|---|---|
| act gca gca gcc aac gtt tct gct tgg acc tac cca ctc aca ccc aat<br>Thr Ala Ala Ala Asn Val Ser Ala Trp Thr Tyr Pro Leu Thr Pro Asn<br>735                        740                     745 | 2559 |
| gag ctg ctc gcc tct atg cag gca ggc agt gct gtg gtt aac ctg gcc<br>Glu Leu Leu Ala Ser Met Gln Ala Gly Ser Ala Val Val Asn Leu Ala<br>750                        755                     760 | 2607 |
| tgg ccc agt ggt ccc ttg ggg caa ggg aca tgc cat gcc caa ctc tca<br>Trp Pro Ser Gly Pro Leu Gly Gln Gly Thr Cys His Ala Gln Leu Ser<br>765                        770                  775                 780 | 2655 |
| gat gct gga cac ctt tca tgg gag caa ccg ctg tcg cta ggc caa gac<br>Asp Ala Gly His Leu Ser Trp Glu Gln Pro Leu Ser Leu Gly Gln Asp<br>                  785                     790                     795 | 2703 |
| ctc ctc atg cta agg aat ctt ata cca gga cat acg gtt tca ttg tct<br>Leu Leu Met Leu Arg Asn Leu Ile Pro Gly His Thr Val Ser Leu Ser<br>                  800                     805                     810 | 2751 |
| gtg aag tgt cgg gca gga cca ctc cag gcc tcc act cac ccc ctg gtg<br>Val Lys Cys Arg Ala Gly Pro Leu Gln Ala Ser Thr His Pro Leu Val<br>                  815                     820                     825 | 2799 |
| ctg tct gta gag cct ggc cct gtg gaa gat gtg ttc tgt caa cct gag<br>Leu Ser Val Glu Pro Gly Pro Val Glu Asp Val Phe Cys Gln Pro Glu<br>830                        835                     840 | 2847 |
| gcc acc tac ctg tcc ctg aac tgg acg atg cct act gga gat gtg gct<br>Ala Thr Tyr Leu Ser Leu Asn Trp Thr Met Pro Thr Gly Asp Val Ala<br>845                        850                     855                     860 | 2895 |
| gtc tgt ctg gtg gag gta gag cag ctg gtg cca gga ggg agc gct cat<br>Val Cys Leu Val Glu Val Glu Gln Leu Val Pro Gly Gly Ser Ala His<br>                  865                     870                     875 | 2943 |
| ttt gtc ttc cag gtc aac acc tcg gag gat gca ctt ctg ctc ccc aac<br>Phe Val Phe Gln Val Asn Thr Ser Glu Asp Ala Leu Leu Leu Pro Asn<br>                  880                     885                     890 | 2991 |
| ttg acg ccc acc act tct tac cgc ctt agc ctc act gtg ctg ggt ggg<br>Leu Thr Pro Thr Thr Ser Tyr Arg Leu Ser Leu Thr Val Leu Gly Gly<br>895                        900                     905 | 3039 |
| aat cgc cag tgg agc cgg gcg gtt acc ctg gtg tgc act act tct gct<br>Asn Arg Gln Trp Ser Arg Ala Val Thr Leu Val Cys Thr Thr Ser Ala<br>                  910                     915                     920 | 3087 |
| gag gtt tgg cac ccc cca gag cta gct gag gcc ccc cag gtg gag ctg<br>Glu Val Trp His Pro Pro Glu Leu Ala Glu Ala Pro Gln Val Glu Leu<br>925                        930                     935                     940 | 3135 |
| ggg aca ggg atg ggt gtg aca gtc aca cgt ggc atg ttt ggt aaa gat<br>Gly Thr Gly Met Gly Val Thr Val Thr Arg Gly Met Phe Gly Lys Asp<br>                  945                     950                     955 | 3183 |
| gac ggg cag atc cag tgg tat ggc ata att gcc acc atc aac atg aca<br>Asp Gly Gln Ile Gln Trp Tyr Gly Ile Ile Ala Thr Ile Asn Met Thr<br>                  960                     965                     970 | 3231 |
| ctg gcc cag cct tcc cag gaa gcc atc aac cac aca tgg tat gac cac<br>Leu Ala Gln Pro Ser Gln Glu Ala Ile Asn His Thr Trp Tyr Asp His<br>                  975                     980                     985 | 3279 |
| tac tat aga gga cat gac tcc tac ctg gct ctc ctg   ttc cca aac ccc<br>Tyr Tyr Arg Gly His Asp Ser Tyr Leu Ala Leu Leu   Phe Pro Asn Pro<br>         990                     995                     1000 | 3327 |
| ttc   tac cca gag cct tgg   gct gtg cca aga tcc   tgg aca gta cct<br>Phe   Tyr Pro Glu Pro Trp   Ala Val Pro Arg Ser   Trp Thr Val Pro<br>1005                     1010                     1015 | 3372 |
| gtg   ggt aca gag gac tgt   gac aac acc cag gag   ata tgc aat ggg<br>Val   Gly Thr Glu Asp Cys   Asp Asn Thr Gln Glu   Ile Cys Asn Gly<br>1020                     1025                     1030 | 3417 |
| cat   ctc aag cca ggc ttc   cag tat agg ttc agc   att gca gcc ttt<br>His   Leu Lys Pro Gly Phe   Gln Tyr Arg Phe Ser   Ile Ala Ala Phe<br>1035                     1040                     1045 | 3462 |

| | | |
|---|---|---|
| agt agg ctc agc tct cca gag acc atc ctg gcc ttc tcc gcc ttc<br>Ser Arg Leu Ser Ser Pro Glu Thr Ile Leu Ala Phe Ser Ala Phe<br>1050                         1055                       1060 | | 3507 |
| tca gag cct cag gct agc atc tct ctg gtg gcc atg ccc ctg aca<br>Ser Glu Pro Gln Ala Ser Ile Ser Leu Val Ala Met Pro Leu Thr<br>1065                         1070                       1075 | | 3552 |
| gtt atg atg ggg act gtg gtg ggc tgc atc atc att gtg tgt gca<br>Val Met Met Gly Thr Val Val Gly Cys Ile Ile Ile Val Cys Ala<br>1080                         1085                       1090 | | 3597 |
| gtg cta tgc ttg ttg tgc cgg cgg cgc ctg aag gga cca agg tca<br>Val Leu Cys Leu Leu Cys Arg Arg Arg Leu Lys Gly Pro Arg Ser<br>1095                         1100                       1105 | | 3642 |
| gag aag aat ggc ttt tcc cag gag ttg atg cct tac aac ctg tgg<br>Glu Lys Asn Gly Phe Ser Gln Glu Leu Met Pro Tyr Asn Leu Trp<br>1110                         1115                       1120 | | 3687 |
| cgg acc cat cgg ccc atc ccc agc cat agc ttc cgg cag agc tat<br>Arg Thr His Arg Pro Ile Pro Ser His Ser Phe Arg Gln Ser Tyr<br>1125                         1130                       1135 | | 3732 |
| gag gcc aag agt gca cgt gca cac cag gcc ttc ttc cag gaa ttt<br>Glu Ala Lys Ser Ala Arg Ala His Gln Ala Phe Phe Gln Glu Phe<br>1140                         1145                       1150 | | 3777 |
| gag gag ctg aag gag gtg ggc aag gac cag ccc aga cta gag gct<br>Glu Glu Leu Lys Glu Val Gly Lys Asp Gln Pro Arg Leu Glu Ala<br>1155                         1160                       1165 | | 3822 |
| gag cat cct gcc aac atc acc aag aac cgg tac cca cac gtg cta<br>Glu His Pro Ala Asn Ile Thr Lys Asn Arg Tyr Pro His Val Leu<br>1170                         1175                       1180 | | 3867 |
| cct tat gac cac tcc agg gtc agg ctg acc cag cta tca gga gag<br>Pro Tyr Asp His Ser Arg Val Arg Leu Thr Gln Leu Ser Gly Glu<br>1185                         1190                       1195 | | 3912 |
| cct cat tct gac tac atc aat gcc aac ttc atc cca ggc tat agc<br>Pro His Ser Asp Tyr Ile Asn Ala Asn Phe Ile Pro Gly Tyr Ser<br>1200                         1205                       1210 | | 3957 |
| cac cca cag gag atc att gcc acc cag ggg cct ctc aaa aag acg<br>His Pro Gln Glu Ile Ile Ala Thr Gln Gly Pro Leu Lys Lys Thr<br>1215                         1220                       1225 | | 4002 |
| gtc gag gac ttc tgg cgg ttg gtg tgg gag cag caa gtc cac gtg<br>Val Glu Asp Phe Trp Arg Leu Val Trp Glu Gln Gln Val His Val<br>1230                         1235                       1240 | | 4047 |
| atc atc atg cta act gtg ggc atg gag aat ggg cgg gta ctg tgt<br>Ile Ile Met Leu Thr Val Gly Met Glu Asn Gly Arg Val Leu Cys<br>1245                         1250                       1255 | | 4092 |
| gag cac tac tgg cca gtc aac tcc acg cct gtc acc cac ggt cac<br>Glu His Tyr Trp Pro Val Asn Ser Thr Pro Val Thr His Gly His<br>1260                         1265                       1270 | | 4137 |
| atc acc acc cac ctc ctg gca gag gaa tct gag gac gag tgg acc<br>Ile Thr Thr His Leu Leu Ala Glu Glu Ser Glu Asp Glu Trp Thr<br>1275                         1280                       1285 | | 4182 |
| agg agg gaa ttc cag ctg cag cac ggt gca gag caa aaa cag agg<br>Arg Arg Glu Phe Gln Leu Gln His Gly Ala Glu Gln Lys Gln Arg<br>1290                         1295                       1300 | | 4227 |
| cgc gtg aag cag ctg cag ttc acg acc tgg cca gac cac agt gtc<br>Arg Val Lys Gln Leu Gln Phe Thr Thr Trp Pro Asp His Ser Val<br>1305                         1310                       1315 | | 4272 |
| ccc gag gct ccc agc tct ctg ctc gct ttt gtg gaa ctg gtg cag<br>Pro Glu Ala Pro Ser Ser Leu Leu Ala Phe Val Glu Leu Val Gln<br>1320                         1325                       1330 | | 4317 |
| gag gag gtg aag gca act cag ggc aag ggg ccc atc ctg gtg cat<br>Glu Glu Val Lys Ala Thr Gln Gly Lys Gly Pro Ile Leu Val His | | 4362 |

```
                                  1335                    1340                    1345
tgc    agt    gcg    ggt    gtg    ggc    agg    aca    ggc    acc    ttt    gtg    gct    ctc    tta       4407
Cys    Ser    Ala    Gly    Val    Gly    Arg    Thr    Gly    Thr    Phe    Val    Ala    Leu    Leu
1350                         1355                                  1360 ccg    gct    gtt    cga    caa    cta    gag    gaa    gaa    cag    gtg    gtc    gat    gtg    ttc       4452
Pro    Ala    Val    Arg    Gln    Leu    Glu    Glu    Glu    Gln    Val    Val    Asp    Val    Phe
1365                         1370                                  1375 aac    act    gtg    tac    ata    ctc    cgg    ctg    cac    cgg    ccc    ctc    atg    atc    cag       4497
Asn    Thr    Val    Tyr    Ile    Leu    Arg    Leu    His    Arg    Pro    Leu    Met    Ile    Gln
1380                         1385                                  1390 acc    ttg    agt    caa    tac    atc    ttc    ctg    cac    agc    tgc    ctg    ctg    aac    aag       4542
Thr    Leu    Ser    Gln    Tyr    Ile    Phe    Leu    His    Ser    Cys    Leu    Leu    Asn    Lys
1395                         1400                                  1405 att    ctg    gaa    ggg    ccc    tct    gac    gcc    tca    gac    tcc    ggc    ccc    atc    cct       4587
Ile    Leu    Glu    Gly    Pro    Ser    Asp    Ala    Ser    Asp    Ser    Gly    Pro    Ile    Pro
1410                         1415                                  1420 gtg    atg    aat    ttt    gca    caa    gct    tgt    gcc    aag    agg    gca    gcc    aat    gcc       4632
Val    Met    Asn    Phe    Ala    Gln    Ala    Cys    Ala    Lys    Arg    Ala    Ala    Asn    Ala
1425                         1430                                  1435 aat    gcc    ggt    ttc    ttg    aag    gag    tac    agg    ctc    ctg    aag    cag    gcc    atc       4677
Asn    Ala    Gly    Phe    Leu    Lys    Glu    Tyr    Arg    Leu    Leu    Lys    Gln    Ala    Ile
1440                         1445                                  1450 aag    gat    gag    act    ggc    tct    ctg    ctg    ccc    tct    cct    gac    tat    aat    cag       4722
Lys    Asp    Glu    Thr    Gly    Ser    Leu    Leu    Pro    Ser    Pro    Asp    Tyr    Asn    Gln
1455                         1460                                  1465 aac    agc    atc    gcc    tcc    tgt    cat    cat    tct    cag    gag    cag    ttg    gcc    ctg       4767
Asn    Ser    Ile    Ala    Ser    Cys    His    His    Ser    Gln    Glu    Gln    Leu    Ala    Leu
1470                         1475                                  1480 gtg    gag    gag    agc    cct    gct    gat    aac    atg    ctg    gca    gcc    tcg    ctc    ttc       4812
Val    Glu    Glu    Ser    Pro    Ala    Asp    Asn    Met    Leu    Ala    Ala    Ser    Leu    Phe
1485                         1490                                  1495 cct    ggt    ggg    ccg    tct    ggt    cgc    gac    cat    gtg    gtg    ctg    act    ggc    tcg       4857
Pro    Gly    Gly    Pro    Ser    Gly    Arg    Asp    His    Val    Val    Leu    Thr    Gly    Ser
1500                         1505                                  1510 gcc    gga    cca    aag    gaa    ctc    tgg    gaa    atg    gtg    tgg    gaa    cat    ggc    gcc       4902
Ala    Gly    Pro    Lys    Glu    Leu    Trp    Glu    Met    Val    Trp    Glu    His    Gly    Ala
1515                         1520                                  1525 tat    gtg    ctt    gtc    tcc    ctg    ggt    ctg    cct    gat    acc    aag    gag    aag    cca       4947
Tyr    Val    Leu    Val    Ser    Leu    Gly    Leu    Pro    Asp    Thr    Lys    Glu    Lys    Pro
1530                         1535                                  1540 caa    gac    atc    tgg    cca    atg    gag    atg    cag    cct    att    gtc    aca    gac    atg       4992
Gln    Asp    Ile    Trp    Pro    Met    Glu    Met    Gln    Pro    Ile    Val    Thr    Asp    Met
1545                         1550                                  1555 gtg    aca    gtg    cac    aga    gtg    gct    gag    agc    aac    aca    gct    ggc    tgg    ccc       5037
Val    Thr    Val    His    Arg    Val    Ala    Glu    Ser    Asn    Thr    Ala    Gly    Trp    Pro
1560                         1565                                  1570 agt    acc    ctc    atc    aga    gtt    ata    cat    ggg    gac    agt    ggg    acg    gaa    agg       5082
Ser    Thr    Leu    Ile    Arg    Val    Ile    His    Gly    Asp    Ser    Gly    Thr    Glu    Arg
1575                         1580                                  1585 cag    gtt    caa    tgc    ctg    cag    ttt    cca    cac    tgc    gag    act    ggg    agt    gag       5127
Gln    Val    Gln    Cys    Leu    Gln    Phe    Pro    His    Cys    Glu    Thr    Gly    Ser    Glu
1590                         1595                                  1600 ctc    cca    gct    aac    acc    cta    ctg    acc    ttc    ctt    gat    gct    gtg    ggc    cag       5172
Leu    Pro    Ala    Asn    Thr    Leu    Leu    Thr    Phe    Leu    Asp    Ala    Val    Gly    Gln
1605                         1610                                  1615 tgc    tgc    tcc    cgg    ggc    aat    agc    aag    aag    cca    ggg    acc    ctg    ctc    agt       5217
Cys    Cys    Ser    Arg    Gly    Asn    Ser    Lys    Lys    Pro    Gly    Thr    Leu    Leu    Ser
1620                         1625                                  1630 cac    tcc    agc    aag    gtc    aca    aac    cag    ctg    agc    acc    ttc    ttg    gct    atg       5262
```

```
                      His Ser Ser Lys Val Thr Asn Gln Leu Ser Thr Phe Leu Ala Met
                      1635                1640                1645 gaa cag ctg cta cag caa gca ggg acc gag cgc aca gtg gat gtc                5307
Glu Gln Leu Leu Gln Gln Ala Gly Thr Glu Arg Thr Val Asp Val
1650                1655                1660 ttc agt gtg gcc ctg aag cag aca cag gcc tgt ggc ctt aag acc                5352
Phe Ser Val Ala Leu Lys Gln Thr Gln Ala Cys Gly Leu Lys Thr
1665                1670                1675 cca acg ctg gag cag tat atc tac ctc tac aac tgt ctg aac agc                5397
Pro Thr Leu Glu Gln Tyr Ile Tyr Leu Tyr Asn Cys Leu Asn Ser
1680                1685                1690 gca ttg agg aac agg ctg ccc cga gct agg aag tgaccttgcc                     5440
Ala Leu Arg Asn Arg Leu Pro Arg Ala Arg Lys
1695                1700                1705 ctgctaggca tcacgttcca gcaatccacc caggcctggc ttccccagga gaacagatct          5500
attcggcctc acgctgtcaa agggcagagt ctgggaataa agggtaaatc tcgag               5555

<210> SEQ ID NO 11
<211> LENGTH: 1705
<212> TYPE: PRT
<213> ORGANISM: mus musculus

<400> SEQUENCE: 11

Met Arg Pro Leu Ile Leu Leu Ala Ala Leu Leu Trp Leu Gln Asp Ser
1               5                   10                  15

Leu Ala Gln Glu Asp Val Cys Ser Ser Leu Asp Gly Ser Pro Asp Arg
                20                  25                  30

Gln Gly Gly Gly Pro Pro Leu Ser Val Asn Val Ser Ser Arg Gly Lys
            35                  40                  45

Pro Thr Ser Leu Phe Leu Ser Trp Val Ala Ala Glu Pro Gly Gly Phe
        50                  55                  60

Asp Tyr Ala Leu Cys Leu Arg Ala Met Asn Leu Ser Gly Phe Pro Glu
65                  70                  75                  80

Gly Gln Gln Leu Gln Ala His Thr Asn Glu Ser Ser Phe Glu Phe His
                85                  90                  95

Gly Leu Val Pro Gly Ser Arg Tyr Gln Leu Glu Leu Thr Val Leu Arg
            100                 105                 110

Pro Cys Trp Gln Asn Val Thr Ile Thr Leu Thr Ala Arg Thr Ala Pro
        115                 120                 125

Thr Val Val Arg Gly Leu Gln Leu His Ser Thr Gly Ser Pro Ala Ser
    130                 135                 140

Leu Glu Ala Ser Trp Ser Asp Ala Ser Gly Asp Gln Asp Ser Tyr Gln
145                 150                 155                 160

Leu Leu Leu Tyr His Pro Glu Ser His Thr Leu Ala Cys Asn Val Ser
                165                 170                 175

Val Ser Pro Asp Thr Leu Ser Tyr Asn Phe Gly Asp Leu Leu Pro Gly
            180                 185                 190

Ser Gln Tyr Val Leu Glu Val Ile Thr Trp Ala Gly Ser Leu His Ala
        195                 200                 205

Lys Thr Ser Ile Leu Gln Trp Thr Glu Pro Val Pro Pro Asp His Leu
    210                 215                 220

Thr Leu Arg Ala Leu Gly Thr Ser Ser Leu Gln Ala Phe Trp Asn Ser
225                 230                 235                 240

Ser Glu Gly Ala Thr Trp Phe His Leu Ile Leu Thr Asp Leu Leu Glu
                245                 250                 255
```

```
Gly Thr Asn Leu Thr Lys Val Val Arg Gln Gly Ile Ser Thr His Thr
            260                 265                 270

Phe Leu Arg Leu Ser Pro Gly Thr Pro Tyr Gln Leu Lys Ile Cys Ala
            275                 280                 285

Ala Ala Gly Pro His Gln Ile Trp Gly Pro Asn Ala Thr Glu Trp Thr
290                 295                 300

Tyr Pro Ser Tyr Pro Ser Asp Leu Val Leu Thr Pro Leu Trp Asn Glu
305                 310                 315                 320

Leu Trp Ala Ser Trp Lys Ala Gly Gln Gly Ala Arg Asp Gly Tyr Val
            325                 330                 335

Leu Lys Leu Ser Gly Pro Val Glu Asn Thr Thr Thr Leu Gly Pro Glu
            340                 345                 350

Glu Cys Asn Ala Val Phe Pro Gly Pro Leu Pro Pro Gly His Tyr Thr
            355                 360                 365

Leu Gly Leu Arg Val Leu Ala Gly Pro Tyr Asp Ala Trp Val Glu Gly
            370                 375                 380

Ser Ile Trp Leu Ala Glu Ser Ala Ala Arg Pro Met Glu Val Pro Gly
385                 390                 395                 400

Ala Arg Leu Trp Leu Glu Gly Leu Glu Ala Thr Lys Gln Pro Gly Arg
            405                 410                 415

Arg Ala Leu Leu Tyr Ser Val Asp Ala Pro Gly Leu Leu Gly Asn Ile
            420                 425                 430

Ser Val Ser Ser Gly Ala Thr His Val Thr Phe Cys Gly Leu Val Pro
            435                 440                 445

Gly Ala His Tyr Arg Val Asp Ile Ala Ser Ser Met Gly Asp Ile Thr
            450                 455                 460

Gln Ser Leu Thr Gly Tyr Thr Ser Pro Leu Pro Pro Gln Ser Leu Glu
465                 470                 475                 480

Ile Ile Ser Arg Asn Ser Pro Ser Asp Leu Thr Ile Gly Trp Ala Pro
            485                 490                 495

Ala Pro Gly Gln Met Glu Gly Tyr Lys Val Thr Trp His Gln Asp Gly
            500                 505                 510

Ser Gln Arg Ser Pro Gly Asp Leu Val Asp Leu Gly Pro Asp Ile Ser
            515                 520                 525

Ser Leu Thr Leu Lys Ser Leu Val Pro Gly Ser Cys Tyr Thr Val Ser
530                 535                 540

Ala Trp Ala Trp Ser Gly Asn Leu Ser Ser Asp Ser Gln Lys Ile His
545                 550                 555                 560

Ser Cys Thr Arg Pro Ala Pro Pro Thr Asn Leu Ser Leu Gly Phe Ala
            565                 570                 575

His Gln Pro Ala Thr Leu Arg Ala Ser Trp Cys His Pro Pro Gly Gly
            580                 585                 590

Arg Asp Ala Phe Gln Leu Arg Leu Tyr Arg Leu Arg Pro Leu Thr Leu
            595                 600                 605

Glu Ser Glu Lys Ile Leu Ser Gln Glu Ala Gln Asn Phe Ser Trp Ala
            610                 615                 620

Gln Leu Pro Ala Gly Tyr Glu Phe Gln Val Gln Leu Ser Thr Leu Trp
625                 630                 635                 640

Gly Ser Glu Glu Ser Gly Ser Ala Asn Thr Thr Gly Trp Thr Pro Pro
                645                 650                 655

Ser Ala Pro Thr Leu Val Asn Val Thr Ser Glu Ala Pro Thr Gln Leu
            660                 665                 670

His Val Ser Trp Val His Ala Ala Gly Asp Arg Ser Ser Tyr Gln Val
```

```
            675                 680                 685
Thr Leu Tyr Gln Glu Ser Thr Arg Thr Ala Thr Ser Ile Val Gly Pro
690                 695                 700
Lys Ala Asp Ser Thr Ser Phe Trp Gly Leu Thr Pro Gly Thr Lys Tyr
705                 710                 715                 720
Lys Val Glu Ala Ile Ser Trp Ala Gly Pro Leu Tyr Thr Ala Ala
                    725                 730                 735
Asn Val Ser Ala Trp Thr Tyr Pro Leu Thr Pro Asn Glu Leu Leu Ala
                740                 745                 750
Ser Met Gln Ala Gly Ser Ala Val Val Asn Leu Ala Trp Pro Ser Gly
            755                 760                 765
Pro Leu Gly Gln Gly Thr Cys His Ala Gln Leu Ser Asp Ala Gly His
770                 775                 780
Leu Ser Trp Glu Gln Pro Leu Ser Leu Gly Gln Asp Leu Leu Met Leu
785                 790                 795                 800
Arg Asn Leu Ile Pro Gly His Thr Val Ser Leu Ser Val Lys Cys Arg
                    805                 810                 815
Ala Gly Pro Leu Gln Ala Ser Thr His Pro Leu Val Leu Ser Val Glu
                820                 825                 830
Pro Gly Pro Val Glu Asp Val Phe Cys Gln Pro Glu Ala Thr Tyr Leu
                835                 840                 845
Ser Leu Asn Trp Thr Met Pro Thr Gly Asp Val Ala Val Cys Leu Val
850                 855                 860
Glu Val Glu Gln Leu Val Pro Gly Gly Ser Ala His Phe Val Phe Gln
865                 870                 875                 880
Val Asn Thr Ser Glu Asp Ala Leu Leu Leu Pro Asn Leu Thr Pro Thr
                    885                 890                 895
Thr Ser Tyr Arg Leu Ser Leu Thr Val Leu Gly Gly Asn Arg Gln Trp
                900                 905                 910
Ser Arg Ala Val Thr Leu Val Cys Thr Thr Ser Ala Glu Val Trp His
            915                 920                 925
Pro Pro Glu Leu Ala Glu Ala Pro Gln Val Glu Leu Gly Thr Gly Met
930                 935                 940
Gly Val Thr Val Thr Arg Gly Met Phe Gly Lys Asp Asp Gly Gln Ile
945                 950                 955                 960
Gln Trp Tyr Gly Ile Ile Ala Thr Ile Asn Met Thr Leu Ala Gln Pro
                    965                 970                 975
Ser Gln Glu Ala Ile Asn His Thr Trp Tyr Asp His Tyr Tyr Arg Gly
                980                 985                 990
His Asp Ser Tyr Leu Ala Leu Leu Phe Pro Asn Pro Phe Tyr Pro Glu
            995                 1000                1005
Pro Trp Ala Val Pro Arg Ser Trp Thr Pro Val Gly Thr Glu
        1010                1015                1020
Asp Cys Asp Asn Thr Gln Glu Ile Cys Asn Gly His Leu Lys Pro
        1025                1030                1035
Gly Phe Gln Tyr Arg Phe Ser Ile Ala Ala Phe Ser Arg Leu Ser
        1040                1045                1050
Ser Pro Glu Thr Ile Leu Ala Phe Ser Ala Phe Ser Glu Pro Gln
        1055                1060                1065
Ala Ser Ile Ser Leu Val Ala Met Pro Leu Thr Val Met Met Gly
        1070                1075                1080
Thr Val Val Gly Cys Ile Ile Ile Val Cys Ala Val Leu Cys Leu
        1085                1090                1095
```

```
Leu Cys Arg Arg Arg Leu Lys Gly Pro Arg Ser Glu Lys Asn Gly
    1100                1105                1110

Phe Ser Gln Glu Leu Met Pro Tyr Asn Leu Trp Arg Thr His Arg
    1115                1120                1125

Pro Ile Pro Ser His Ser Phe Arg Gln Ser Tyr Glu Ala Lys Ser
    1130                1135                1140

Ala Arg Ala His Gln Ala Phe Phe Gln Glu Phe Glu Glu Leu Lys
    1145                1150                1155

Glu Val Gly Lys Asp Gln Pro Arg Leu Glu Ala Glu His Pro Ala
    1160                1165                1170

Asn Ile Thr Lys Asn Arg Tyr Pro His Val Leu Pro Tyr Asp His
    1175                1180                1185

Ser Arg Val Arg Leu Thr Gln Leu Ser Gly Glu Pro His Ser Asp
    1190                1195                1200

Tyr Ile Asn Ala Asn Phe Ile Pro Gly Tyr Ser His Pro Gln Glu
    1205                1210                1215

Ile Ile Ala Thr Gln Gly Pro Leu Lys Lys Thr Val Glu Asp Phe
    1220                1225                1230

Trp Arg Leu Val Trp Glu Gln Gln Val His Val Ile Ile Met Leu
    1235                1240                1245

Thr Val Gly Met Glu Asn Gly Arg Val Leu Cys Glu His Tyr Trp
    1250                1255                1260

Pro Val Asn Ser Thr Pro Val Thr His Gly His Ile Thr Thr His
    1265                1270                1275

Leu Leu Ala Glu Glu Ser Glu Asp Glu Trp Thr Arg Arg Glu Phe
    1280                1285                1290

Gln Leu Gln His Gly Ala Glu Gln Lys Gln Arg Arg Val Lys Gln
    1295                1300                1305

Leu Gln Phe Thr Thr Trp Pro Asp His Ser Val Pro Glu Ala Pro
    1310                1315                1320

Ser Ser Leu Leu Ala Phe Val Glu Leu Val Gln Glu Glu Val Lys
    1325                1330                1335

Ala Thr Gln Gly Lys Gly Pro Ile Leu Val His Cys Ser Ala Gly
    1340                1345                1350

Val Gly Arg Thr Gly Thr Phe Val Ala Leu Leu Pro Ala Val Arg
    1355                1360                1365

Gln Leu Glu Glu Glu Gln Val Val Asp Val Phe Asn Thr Val Tyr
    1370                1375                1380

Ile Leu Arg Leu His Arg Pro Leu Met Ile Gln Thr Leu Ser Gln
    1385                1390                1395

Tyr Ile Phe Leu His Ser Cys Leu Leu Asn Lys Ile Leu Glu Gly
    1400                1405                1410

Pro Ser Asp Ala Ser Asp Ser Gly Pro Ile Pro Val Met Asn Phe
    1415                1420                1425

Ala Gln Ala Cys Ala Lys Arg Ala Ala Asn Ala Asn Ala Gly Phe
    1430                1435                1440

Leu Lys Glu Tyr Arg Leu Leu Lys Gln Ala Ile Lys Asp Glu Thr
    1445                1450                1455

Gly Ser Leu Leu Pro Ser Pro Asp Tyr Asn Gln Asn Ser Ile Ala
    1460                1465                1470

Ser Cys His His Ser Gln Glu Gln Leu Ala Leu Val Glu Glu Ser
    1475                1480                1485
```

```
Pro Ala Asp Asn Met Leu Ala Ala Ser Leu Phe Pro Gly Gly Pro
    1490                1495                1500

Ser Gly Arg Asp His Val Val Leu Thr Gly Ser Ala Gly Pro Lys
    1505                1510                1515

Glu Leu Trp Glu Met Val Trp Glu His Gly Ala Tyr Val Leu Val
    1520                1525                1530

Ser Leu Gly Leu Pro Asp Thr Lys Glu Lys Pro Gln Asp Ile Trp
    1535                1540                1545

Pro Met Glu Met Gln Pro Ile Val Thr Asp Met Val Thr Val His
    1550                1555                1560

Arg Val Ala Glu Ser Asn Thr Ala Gly Trp Pro Ser Thr Leu Ile
    1565                1570                1575

Arg Val Ile His Gly Asp Ser Gly Thr Glu Arg Gln Val Gln Cys
    1580                1585                1590

Leu Gln Phe Pro His Cys Glu Thr Gly Ser Glu Leu Pro Ala Asn
    1595                1600                1605

Thr Leu Leu Thr Phe Leu Asp Ala Val Gly Gln Cys Cys Ser Arg
    1610                1615                1620

Gly Asn Ser Lys Lys Pro Gly Thr Leu Leu Ser His Ser Ser Lys
    1625                1630                1635

Val Thr Asn Gln Leu Ser Thr Phe Leu Ala Met Glu Gln Leu Leu
    1640                1645                1650

Gln Gln Ala Gly Thr Glu Arg Thr Val Asp Val Phe Ser Val Ala
    1655                1660                1665

Leu Lys Gln Thr Gln Ala Cys Gly Leu Lys Thr Pro Thr Leu Glu
    1670                1675                1680

Gln Tyr Ile Tyr Leu Tyr Asn Cys Leu Asn Ser Ala Leu Arg Asn
    1685                1690                1695

Arg Leu Pro Arg Ala Arg Lys
    1700                1705

<210> SEQ ID NO 12
<211> LENGTH: 49
<212> TYPE: PRT
<213> ORGANISM: homo sapiens

<400> SEQUENCE: 12

Tyr Leu Tyr Gln Trp Leu Gly Ala Pro Val Pro Tyr Pro Asp Pro Leu
1               5                   10                  15

Glu Pro Arg Arg Glu Val Cys Glu Leu Asn Pro Asp Cys Asp Glu Leu
            20                  25                  30

Ala Asp His Ile Gly Phe Gln Glu Ala Tyr Arg Arg Phe Tyr Gly Pro
        35                  40                  45
Val

<210> SEQ ID NO 13
<211> LENGTH: 49
<212> TYPE: PRT
<213> ORGANISM: homo sapiens
<220> FEATURE:
<221> NAME/KEY: VARIANT
<222> LOCATION: (17)..(17)
<223> OTHER INFORMATION: Xaa can be any amino acid.
<220> FEATURE:
<221> NAME/KEY: VARIANT
<222> LOCATION: (17)..(17)
<223> OTHER INFORMATION: If Xaa at positions 17, 21, and 24 are all Glu,
      then Glu17 is not carboxylated, or less than 50% of Glu21 is
      carboxylated, and/or less than 50% of Glu24 is carboxylated, or 1
```

```
        to 7 positions other than 17, 21, and 24 are any aa other than the
        specified aa.
<220> FEATURE:
<221> NAME/KEY: VARIANT
<222> LOCATION: (21)..(21)
<223> OTHER INFORMATION: Xaa can be any amino acid.
<220> FEATURE:
<221> NAME/KEY: VARIANT
<222> LOCATION: (21)..(21)
<223> OTHER INFORMATION: If Xaa at positions 17, 21, and 24 are all Glu,
        then Glu17 is not carboxylated, or less than 50% of Glu21 is
        carboxylated, and/or less than 50% of Glu24 is carboxylated, or 1
        to 7 positions other than 17, 21, and 24 are any aa other than the
        specified aa.
<220> FEATURE:
<221> NAME/KEY: VARIANT
<222> LOCATION: (24)..(24)
<223> OTHER INFORMATION: Xaa can be any amino acid.
<220> FEATURE:
<221> NAME/KEY: VARIANT
<222> LOCATION: (24)..(24)
<223> OTHER INFORMATION: If Xaa at positions 17, 21, and 24 are all Glu,
        then Glu17 is not carboxylated, or less than 50% of Glu21 is
        carboxylated, and/or less than 50% of Glu24 is carboxylated, or 1
        to 7 positions other than 17, 21, and 24 are any aa other than the
        specified aa.

<400> SEQUENCE: 13

Tyr Leu Tyr Gln Trp Leu Gly Ala Pro Val Pro Tyr Pro Asp Pro Leu
1               5                   10                  15

Xaa Pro Arg Arg Xaa Val Cys Xaa Leu Asn Pro Asp Cys Asp Glu Leu
            20                  25                  30

Ala Asp His Ile Gly Phe Gln Glu Ala Tyr Arg Arg Phe Tyr Gly Pro
        35                  40                  45

Val

<210> SEQ ID NO 14
<211> LENGTH: 5136
<212> TYPE: DNA
<213> ORGANISM: Rattus norvegicus
<220> FEATURE:
<221> NAME/KEY: CDS
<222> LOCATION: (1)..(5136)

<400> SEQUENCE: 14 atg agg ccc ctg att ctg tta gct gcc ctc ctc tgg ctc cag ggc ttt      48
Met Arg Pro Leu Ile Leu Leu Ala Ala Leu Leu Trp Leu Gln Gly Phe
1               5                   10                  15 ttg gcc gag gac gac gca tgc tca tcc ttg gaa ggg agc cca gac agg      96
Leu Ala Glu Asp Asp Ala Cys Ser Ser Leu Glu Gly Ser Pro Asp Arg
            20                  25                  30 cag ggt gga ggt cca ctt ctg agt gtg aac gtc agt agc cat gga aag     144
Gln Gly Gly Gly Pro Leu Leu Ser Val Asn Val Ser Ser His Gly Lys
        35                  40                  45 tct acc agc ctg ttt ctg agc tgg gta gct gca gag ctg ggc gga ttt     192
Ser Thr Ser Leu Phe Leu Ser Trp Val Ala Ala Glu Leu Gly Gly Phe
    50                  55                  60 gac tat gcc ctc agc ctc agg agt gtg aac tcc tca ggt tct cca gaa     240
Asp Tyr Ala Leu Ser Leu Arg Ser Val Asn Ser Ser Gly Ser Pro Glu
65              70                  75                  80 ggg caa cag ctc cag gct cac aca aat gag tcc ggc ttt gag ttc cat     288
Gly Gln Gln Leu Gln Ala His Thr Asn Glu Ser Gly Phe Glu Phe His
                85                  90                  95 ggc ctg gtg cca ggg agt cgc tac cag cta aaa ctg act gtc cta aga     336
Gly Leu Val Pro Gly Ser Arg Tyr Gln Leu Lys Leu Thr Val Leu Arg
            100                 105                 110
```

| | | |
|---|---|---|
| ccc tgt tgg cag aat gtc aca att acc ctc act gcc cga act gcc ccg<br>Pro Cys Trp Gln Asn Val Thr Ile Thr Leu Thr Ala Arg Thr Ala Pro<br>115                    120                    125 | | 384 |
| aca gtg gtc cgt gga ctg cag ctg cat agc gct ggg agc cca gcc agg<br>Thr Val Val Arg Gly Leu Gln Leu His Ser Ala Gly Ser Pro Ala Arg<br>130                    135                    140 | | 432 |
| ctg gaa gcc tcg tgg agt gat gcc cct gga gat caa gac agc tac caa<br>Leu Glu Ala Ser Trp Ser Asp Ala Pro Gly Asp Gln Asp Ser Tyr Gln<br>145                    150                    155                    160 | | 480 |
| ctt ctc ctc tac cac ctg gaa tcc caa act ctg gca tgc aat gtc tct<br>Leu Leu Leu Tyr His Leu Glu Ser Gln Thr Leu Ala Cys Asn Val Ser<br>                    165                    170                    175 | | 528 |
| gtg tcc cct gac acc ctg tct tac agt ttt ggc gac ctt tgc cca ggt<br>Val Ser Pro Asp Thr Leu Ser Tyr Ser Phe Gly Asp Leu Leu Pro Gly<br>                        180                    185                    190 | | 576 |
| act cag tat gtc ttg gag gtt atc acc tgg gct ggc agt ctc cat gcg<br>Thr Gln Tyr Val Leu Glu Val Ile Thr Trp Ala Gly Ser Leu His Ala<br>                    195                    200                    205 | | 624 |
| aag act agt atc ctc cag tgg aca gag cct gtc cct cct gat cac cta<br>Lys Thr Ser Ile Leu Gln Trp Thr Glu Pro Val Pro Pro Asp His Leu<br>210                    215                    220 | | 672 |
| gca cta cgt gcc ttg ggt acc agt agc ctg caa gcc ttc tgg aac agc<br>Ala Leu Arg Ala Leu Gly Thr Ser Ser Leu Gln Ala Phe Trp Asn Ser<br>225                    230                    235                    240 | | 720 |
| tct gaa ggg gcc acc tcg ttt cac ctg atg ctc aca gac ctc ctc ggg<br>Ser Glu Gly Ala Thr Ser Phe His Leu Met Leu Thr Asp Leu Leu Gly<br>                        245                    250                    255 | | 768 |
| ggc acc aac acg act gcg gtg atc aga caa ggg gtc tcg acc cac acc<br>Gly Thr Asn Thr Thr Ala Val Ile Arg Gln Gly Val Ser Thr His Thr<br>                    260                    265                    270 | | 816 |
| ttt ctt cac cta tct ccg ggt aca cct cat gag ctg aag att tgt gct<br>Phe Leu His Leu Ser Pro Gly Thr Pro His Glu Leu Lys Ile Cys Ala<br>                    275                    280                    285 | | 864 |
| tct gct ggg ccc cac cag atc tgg gga ccc agt gcc acc gag tgg acc<br>Ser Ala Gly Pro His Gln Ile Trp Gly Pro Ser Ala Thr Glu Trp Thr<br>290                    295                    300 | | 912 |
| tat ccc tct tac cca tct gac ctg gtg ctg act ccc tta cgg aat gag<br>Tyr Pro Ser Tyr Pro Ser Asp Leu Val Leu Thr Pro Leu Arg Asn Glu<br>305                    310                    315                    320 | | 960 |
| ctc tgg gcc agc tgg aag gca ggg ctg gga gcc cgg gac ggc tat gta<br>Leu Trp Ala Ser Trp Lys Ala Gly Leu Gly Ala Arg Asp Gly Tyr Val<br>                    325                    330                    335 | | 1008 |
| ctg aag tta agt ggg cca atg gag agt acg tct acc ctg ggc ccg gaa<br>Leu Lys Leu Ser Gly Pro Met Glu Ser Thr Ser Thr Leu Gly Pro Glu<br>                    340                    345                    350 | | 1056 |
| gag tgc aat gca gtc ttc cca ggg ccc ctg cct ccg gga cac tac act<br>Glu Cys Asn Ala Val Phe Pro Gly Pro Leu Pro Pro Gly His Tyr Thr<br>                    355                    360                    365 | | 1104 |
| ttg cag ctg aag gtt cta gct gga cct tat gat gcc tgg gtg gag ggc<br>Leu Gln Leu Lys Val Leu Ala Gly Pro Tyr Asp Ala Trp Val Glu Gly<br>370                    375                    380 | | 1152 |
| agt acc tgg ctg gct gaa tct gct gcc ctt ccc agg gag gtc cct ggt<br>Ser Thr Trp Leu Ala Glu Ser Ala Ala Leu Pro Arg Glu Val Pro Gly<br>385                    390                    395                    400 | | 1200 |
| gcc aga ctg tgg cta gat gga ctg gaa gct tcc aag cag cct ggg aga<br>Ala Arg Leu Trp Leu Asp Gly Leu Glu Ala Ser Lys Gln Pro Gly Arg<br>                    405                    410                    415 | | 1248 |
| cgg gcg cta ctc tat tct gac gat gcc cca ggc tcc cta ggg aac atc<br>Arg Ala Leu Leu Tyr Ser Asp Asp Ala Pro Gly Ser Leu Gly Asn Ile<br>                    420                    425                    430 | | 1296 |

| | | |
|---|---|---|
| tct gtg ccc tct ggt gcc act cac gtc att ttc tgt ggc ctg gta cct<br>Ser Val Pro Ser Gly Ala Thr His Val Ile Phe Cys Gly Leu Val Pro<br>435 440 445 | 1344 | |
| gga gcc cac tat agg gtg gac att gcc tca tcc acg ggg gac atc tct<br>Gly Ala His Tyr Arg Val Asp Ile Ala Ser Ser Thr Gly Asp Ile Ser<br>450 455 460 | 1392 | |
| cag agc atc tca ggc tat aca agt ccc ctg cca ccg cag tca ctg gag<br>Gln Ser Ile Ser Gly Tyr Thr Ser Pro Leu Pro Pro Gln Ser Leu Glu<br>465 470 475 480 | 1440 | |
| gtc atc agc agg agc agc cca tct gac ctg act att gct tgg ggt cca<br>Val Ile Ser Arg Ser Ser Pro Ser Asp Leu Thr Ile Ala Trp Gly Pro<br>485 490 495 | 1488 | |
| gca cca ggg cag ctg gaa ggt tat aag gtt acc tgg cat cag gat ggc<br>Ala Pro Gly Gln Leu Glu Gly Tyr Lys Val Thr Trp His Gln Asp Gly<br>500 505 510 | 1536 | |
| agc cag agg tct cct ggc gac ctt gtt gac ttg ggc cct gac act ttg<br>Ser Gln Arg Ser Pro Gly Asp Leu Val Asp Leu Gly Pro Asp Thr Leu<br>515 520 525 | 1584 | |
| agc ctg act ctg aaa tct ctg gta ccc ggc tcc tgc tac acc gtg tca<br>Ser Leu Thr Leu Lys Ser Leu Val Pro Gly Ser Cys Tyr Thr Val Ser<br>530 535 540 | 1632 | |
| gca tgg gcc tgg gcc ggg aac ctc gac tct gac tct cag aag att cac<br>Ala Trp Ala Trp Ala Gly Asn Leu Asp Ser Asp Ser Gln Lys Ile His<br>545 550 555 560 | 1680 | |
| agc tgc acc cgc ccc gct cct ccc acc aac ctg agt ctg ggc ttt gcc<br>Ser Cys Thr Arg Pro Ala Pro Pro Thr Asn Leu Ser Leu Gly Phe Ala<br>565 570 575 | 1728 | |
| cac cag cct gcg gca ctg aag gct tcc tgg tat cac cca ccg ggt ggc<br>His Gln Pro Ala Ala Leu Lys Ala Ser Trp Tyr His Pro Pro Gly Gly<br>580 585 590 | 1776 | |
| agg gat gcc ttt cac tta cgg ctt tac agg ctg agg cct ctg aca ctg<br>Arg Asp Ala Phe His Leu Arg Leu Tyr Arg Leu Arg Pro Leu Thr Leu<br>595 600 605 | 1824 | |
| gaa agt gag aag gtc cta cct cgg gag gcc cag aac ttc tcc tgg gcc<br>Glu Ser Glu Lys Val Leu Pro Arg Glu Ala Gln Asn Phe Ser Trp Ala<br>610 615 620 | 1872 | |
| cag ctg act gca ggc tgt gag ttc cag gta cag ctg tct acc ttg tgg<br>Gln Leu Thr Ala Gly Cys Glu Phe Gln Val Gln Leu Ser Thr Leu Trp<br>625 630 635 640 | 1920 | |
| ggg tct gag aga agc agc agt gcc aac gcc aca ggc tgg aca ccc cct<br>Gly Ser Glu Arg Ser Ser Ser Ala Asn Ala Thr Gly Trp Thr Pro Pro<br>645 650 655 | 1968 | |
| tca gct cct aca ctg gta aac gtg acc agc gat gct cct acc cag ctc<br>Ser Ala Pro Thr Leu Val Asn Val Thr Ser Asp Ala Pro Thr Gln Leu<br>660 665 670 | 2016 | |
| caa gta tcc tgg gcc cac gtt cct ggg ggc cgg agc cgc tac caa gtg<br>Gln Val Ser Trp Ala His Val Pro Gly Gly Arg Ser Arg Tyr Gln Val<br>675 680 685 | 2064 | |
| acc cta tac cag gag agt acc cgg aca gcc acc agc atc atg ggg ccc<br>Thr Leu Tyr Gln Glu Ser Thr Arg Thr Ala Thr Ser Ile Met Gly Pro<br>690 695 700 | 2112 | |
| aag gaa gat ggc acg agc ttt ttg ggt ttg act cct ggc act aag tac<br>Lys Glu Asp Gly Thr Ser Phe Leu Gly Leu Thr Pro Gly Thr Lys Tyr<br>705 710 715 720 | 2160 | |
| aag gtg gaa gtc atc tcc tgg gct ggg ccc ctc tac act gca gca gcc<br>Lys Val Glu Val Ile Ser Trp Ala Gly Pro Leu Tyr Thr Ala Ala Ala<br>725 730 735 | 2208 | |
| aac gtt tct gcc tgg acc tac cca ctc ata ccc aat gag ctg ctc gtg<br>Asn Val Ser Ala Trp Thr Tyr Pro Leu Ile Pro Asn Glu Leu Leu Val | 2256 | |

-continued

```
                     740                 745                 750
tca atg cag gca ggc agt gct gtg gtt aac ctg gcc tgg ccc agt ggt      2304
Ser Met Gln Ala Gly Ser Ala Val Val Asn Leu Ala Trp Pro Ser Gly
            755                 760                 765 ccc ctg ggg caa ggg gca tgc cac gcc caa ctc tca gat gct gga cac      2352
Pro Leu Gly Gln Gly Ala Cys His Ala Gln Leu Ser Asp Ala Gly His
770                 775                 780 ctc tca tgg gag caa ccc ctg aaa cta ggc caa gag ctc ttc atg cta      2400
Leu Ser Trp Glu Gln Pro Leu Lys Leu Gly Gln Glu Leu Phe Met Leu
785                 790                 795                 800 agg gat ctc aca cca gga cat acc atc tcg atg tca gtg agg tgt cgg      2448
Arg Asp Leu Thr Pro Gly His Thr Ile Ser Met Ser Val Arg Cys Arg
            805                 810                 815 gca ggg ccg ctc cag gcc tct acg cac ctt gtg gtg ctg tct gtg gag      2496
Ala Gly Pro Leu Gln Ala Ser Thr His Leu Val Val Leu Ser Val Glu
                820                 825                 830 cct ggc cct gtg gaa gat gtg ctc tgt cat cca gag gcc acc tac ctg      2544
Pro Gly Pro Val Glu Asp Val Leu Cys His Pro Glu Ala Thr Tyr Leu
            835                 840                 845 gcc ctg aac tgg acg atg cct gct gga gac gtg gat gtc tgt ctg gtg      2592
Ala Leu Asn Trp Thr Met Pro Ala Gly Asp Val Asp Val Cys Leu Val
850                 855                 860 gtg gta gag cgg ctg gtg ccg gga ggg ggc act cat ttt gtc ttc cag      2640
Val Val Glu Arg Leu Val Pro Gly Gly Gly Thr His Phe Val Phe Gln
865                 870                 875                 880 gtc aac acc tca ggg gat gct ctt ctg ttg ccc aac ttg atg ccc acc      2688
Val Asn Thr Ser Gly Asp Ala Leu Leu Leu Pro Asn Leu Met Pro Thr
            885                 890                 895 act tct tac cgc ctt agc ctc acc gtt ctg ggc agg aat agt cgg tgg      2736
Thr Ser Tyr Arg Leu Ser Leu Thr Val Leu Gly Arg Asn Ser Arg Trp
                900                 905                 910 agc cgg gcg gtt tcc ctg gtg tgc agt act tct gct gag gct tgg cac      2784
Ser Arg Ala Val Ser Leu Val Cys Ser Thr Ser Ala Glu Ala Trp His
            915                 920                 925 ccc cca gag cta gct gag ccc ccc cag gtg gag ctg ggg aca ggg atg      2832
Pro Pro Glu Leu Ala Glu Pro Pro Gln Val Glu Leu Gly Thr Gly Met
930                 935                 940 ggt gtg aca gtc atg cgt ggc atg ttt ggt aaa gat gac ggg cag atc      2880
Gly Val Thr Val Met Arg Gly Met Phe Gly Lys Asp Asp Gly Gln Ile
945                 950                 955                 960 cag tgg tat ggc ata att gcc acc atc aac atg acg ctg gcc cag cct      2928
Gln Trp Tyr Gly Ile Ile Ala Thr Ile Asn Met Thr Leu Ala Gln Pro
                965                 970                 975 tcc cgg gaa gcc atc aat tac aca tgg tat gac cac tac tat aga gga      2976
Ser Arg Glu Ala Ile Asn Tyr Thr Trp Tyr Asp His Tyr Tyr Arg Gly
            980                 985                 990 tgt gag tcc ttc ctg gct ctc ctg  ttc cca aac ccc ttc  tac cca gag    3024
Cys Glu Ser Phe Leu Ala Leu Leu  Phe Pro Asn Pro Phe  Tyr Pro Glu
                995                 1000                1005 cct tgg gct ggg cca aga tcc tgg aca gta cct gtg  ggt act gag         3069
Pro Trp Ala Gly Pro Arg Ser Trp Thr Val Pro Val  Gly Thr Glu
            1010                1015                1020 gac tgt gac aac acc caa gag  ata tgc aat ggg cgt  ctc aag tca        3114
Asp Cys Asp Asn Thr Gln Glu  Ile Cys Asn Gly Arg  Leu Lys Ser
        1025                1030                1035 ggc ttc cag tat agg ttc agc  gtt gtg gcc ttt agt  agg ctc aac        3159
Gly Phe Gln Tyr Arg Phe Ser  Val Val Ala Phe Ser  Arg Leu Asn
        1040                1045                1050 act cca gag acc atc ctc gcc  ttc tcg gcc ttc tca  gag ccc cgg        3204
```

```
Thr Pro Glu Thr Ile Leu Ala Phe Ser Ala Phe Ser Glu Pro Arg
    1055                1060                1065 gcc agc atc tct ctg gcg atc att ccc ctg aca gtt atg ctg ggg        3249
Ala Ser Ile Ser Leu Ala Ile Ile Pro Leu Thr Val Met Leu Gly
    1070                1075                1080 gct gtg gtg ggc agc att gtc att gtg tgt gca gtg cta tgc ttg        3294
Ala Val Val Gly Ser Ile Val Ile Val Cys Ala Val Leu Cys Leu
    1085                1090                1095 ctc cgc tgg cgg tgc ctg aag gga cca aga tca gag aag gat ggc        3339
Leu Arg Trp Arg Cys Leu Lys Gly Pro Arg Ser Glu Lys Asp Gly
    1100                1105                1110 ttt tcc aag gag ctg atg cct tac aac ctg tgg cgg acc cat cgg        3384
Phe Ser Lys Glu Leu Met Pro Tyr Asn Leu Trp Arg Thr His Arg
    1115                1120                1125 cct atc ccc atc cat agc ttc cgg cag agc tat gag gcc aag agc        3429
Pro Ile Pro Ile His Ser Phe Arg Gln Ser Tyr Glu Ala Lys Ser
    1130                1135                1140 gca cat gca cac cag acc ttc ttc cag gaa ttt gag gag ttg aag        3474
Ala His Ala His Gln Thr Phe Phe Gln Glu Phe Glu Glu Leu Lys
    1145                1150                1155 gag gta ggc aag gac cag ccc cga cta gag gct gag cat ccg gac        3519
Glu Val Gly Lys Asp Gln Pro Arg Leu Glu Ala Glu His Pro Asp
    1160                1165                1170 aac atc atc aag aac cgg tac cca cac gtg ctg ccc tat gac cac        3564
Asn Ile Ile Lys Asn Arg Tyr Pro His Val Leu Pro Tyr Asp His
    1175                1180                1185 tcc agg gtc agg ctg acc cag cta cca gga gag cct cat tct gac        3609
Ser Arg Val Arg Leu Thr Gln Leu Pro Gly Glu Pro His Ser Asp
    1190                1195                1200 tac atc aat gcc aac ttc atc cca ggc tat agc cac aca cag gag        3654
Tyr Ile Asn Ala Asn Phe Ile Pro Gly Tyr Ser His Thr Gln Glu
    1205                1210                1215 atc att gcc acc cag ggg cct ctc aaa aag acg cta gag gac ttc        3699
Ile Ile Ala Thr Gln Gly Pro Leu Lys Lys Thr Leu Glu Asp Phe
    1220                1225                1230 tgg cgg ttg gta tgg gag cag caa gtc cac gtg atc atc atg ctg        3744
Trp Arg Leu Val Trp Glu Gln Gln Val His Val Ile Ile Met Leu
    1235                1240                1245 act gtg ggc atg gag aac ggg cgg gta ctg tgt gag cac tac tgg        3789
Thr Val Gly Met Glu Asn Gly Arg Val Leu Cys Glu His Tyr Trp
    1250                1255                1260 cca gcc aac tcc acg cct gtt act cac ggt cac atc acc atc cac        3834
Pro Ala Asn Ser Thr Pro Val Thr His Gly His Ile Thr Ile His
    1265                1270                1275 ctc ctg gca gag gag cct gag gat gag tgg acc agg agg gaa ttc        3879
Leu Leu Ala Glu Glu Pro Glu Asp Glu Trp Thr Arg Arg Glu Phe
    1280                1285                1290 cag ctg cag cac ggt acc gag caa aaa cag agg cga gtg aag cag        3924
Gln Leu Gln His Gly Thr Glu Gln Lys Gln Arg Arg Val Lys Gln
    1295                1300                1305 ctg cag ttc act acc tgg cca gac cac agt gtc ccg gag gct ccc        3969
Leu Gln Phe Thr Thr Trp Pro Asp His Ser Val Pro Glu Ala Pro
    1310                1315                1320 agc tct ctg ctc gct ttt gta gaa ctg gta cag gag cag gtg cag        4014
Ser Ser Leu Leu Ala Phe Val Glu Leu Val Gln Glu Gln Val Gln
    1325                1330                1335 gcc act cag ggc aag gga ccc atc ctg gtg cat tgc agt gct ggc        4059
Ala Thr Gln Gly Lys Gly Pro Ile Leu Val His Cys Ser Ala Gly
    1340                1345                1350
```

```
gtg ggg agg aca ggc acc ttt gtg gct ctc ttg cgg cta ctg cga       4104
Val Gly Arg Thr Gly Thr Phe Val Ala Leu Leu Arg Leu Leu Arg
1355                1360                1365 caa cta gag gaa gag aag gtg gcc gat gtg ttc aac act gtg tac       4149
Gln Leu Glu Glu Glu Lys Val Ala Asp Val Phe Asn Thr Val Tyr
    1370                1375                1380 ata ctc cgg ttg cac cgg ccc ctc atg atc cag acc ctg agt caa       4194
Ile Leu Arg Leu His Arg Pro Leu Met Ile Gln Thr Leu Ser Gln
1385                1390                1395 tac atc ttc ctg cac agt tgc ctg ctg aac aag att ctg gaa ggg       4239
Tyr Ile Phe Leu His Ser Cys Leu Leu Asn Lys Ile Leu Glu Gly
    1400                1405                1410 ccc cct gac agc tcc gac tcc ggc ccc atc tct gtg atg gat ttt       4284
Pro Pro Asp Ser Ser Asp Ser Gly Pro Ile Ser Val Met Asp Phe
1415                1420                1425 gca cag gct tgt gcc aag agg gca gcc aac gcc aat gct ggt ttc       4329
Ala Gln Ala Cys Ala Lys Arg Ala Ala Asn Ala Asn Ala Gly Phe
    1430                1435                1440 ttg aag gag tac aag ctc ctg aag cag gcc atc aag gat ggg act       4374
Leu Lys Glu Tyr Lys Leu Leu Lys Gln Ala Ile Lys Asp Gly Thr
1445                1450                1455 ggc tct ctg ctg ccc cct cct gac tac aat cag aac agc att gtc       4419
Gly Ser Leu Leu Pro Pro Pro Asp Tyr Asn Gln Asn Ser Ile Val
    1460                1465                1470 tcc cgt cgt cat tct cag gag cag ttc gcc ctg gtg gag gag tgc       4464
Ser Arg Arg His Ser Gln Glu Gln Phe Ala Leu Val Glu Glu Cys
1475                1480                1485 cct gag gat agc atg ctg gaa gcc tca ctc ttc cct ggt ggt ccg       4509
Pro Glu Asp Ser Met Leu Glu Ala Ser Leu Phe Pro Gly Gly Pro
    1490                1495                1500 tct ggt tgt gat cat gtg gtg ctg act ggc tca gcc gga cca aag       4554
Ser Gly Cys Asp His Val Val Leu Thr Gly Ser Ala Gly Pro Lys
1505                1510                1515 gaa ctc tgg gaa atg gtg tgg gag cat gat gcc cat gtg ctc gtc       4599
Glu Leu Trp Glu Met Val Trp Glu His Asp Ala His Val Leu Val
    1520                1525                1530 tcc ctg ggc ctg cct gat acc aag gag aag cca cca gac atc tgg       4644
Ser Leu Gly Leu Pro Asp Thr Lys Glu Lys Pro Pro Asp Ile Trp
1535                1540                1545 cca gtg gag atg cag cct att gtc aca gac atg gtg aca gtg cac       4689
Pro Val Glu Met Gln Pro Ile Val Thr Asp Met Val Thr Val His
    1550                1555                1560 aga gtg tct gag agc aac aca aca act ggc tgg ccc agc acc ctc       4734
Arg Val Ser Glu Ser Asn Thr Thr Thr Gly Trp Pro Ser Thr Leu
1565                1570                1575 ttc aga gtc ata cac ggg gag agt gga aag gaa agg cag gtt caa       4779
Phe Arg Val Ile His Gly Glu Ser Gly Lys Glu Arg Gln Val Gln
    1580                1585                1590 tgc ctg caa ttt cca tgc tct gag tct ggg tgt gag ctc cca gct       4824
Cys Leu Gln Phe Pro Cys Ser Glu Ser Gly Cys Glu Leu Pro Ala
1595                1600                1605 aac acc cta ctg acc ttc ctt gat gct gtg ggc cag tgc tgc ttc       4869
Asn Thr Leu Leu Thr Phe Leu Asp Ala Val Gly Gln Cys Cys Phe
    1610                1615                1620 cgg ggc aag agc aag aag cca ggg acc ctg ctc agc cac tcc agc       4914
Arg Gly Lys Ser Lys Lys Pro Gly Thr Leu Leu Ser His Ser Ser
1625                1630                1635 aaa aac aca aac cag ctg ggc acc ttc ttg gct atg gaa cag ctg       4959
Lys Asn Thr Asn Gln Leu Gly Thr Phe Leu Ala Met Glu Gln Leu
    1640                1645                1650
```

```
tta cag caa gca ggg aca gag cgc aca gtg gac gtc ttc aat gtg      5004
Leu Gln Gln Ala Gly Thr Glu Arg Thr Val Asp Val Phe Asn Val
    1655                1660                1665 gcc ctg aag cag tca cag gcc tgc ggc ctt atg acc cca aca ctg      5049
Ala Leu Lys Gln Ser Gln Ala Cys Gly Leu Met Thr Pro Thr Leu
    1670                1675                1680 gag cag tat atc tac ctc tac aac tgt ctg aac agc gca ctg ctg      5094
Glu Gln Tyr Ile Tyr Leu Tyr Asn Cys Leu Asn Ser Ala Leu Leu
    1685                1690                1695 aac ggg ctg ccc aga gct ggg aag tgg cct gcg ccc tgc tag          5136
Asn Gly Leu Pro Arg Ala Gly Lys Trp Pro Ala Pro Cys
    1700                1705                1710

<210> SEQ ID NO 15
<211> LENGTH: 1711
<212> TYPE: PRT
<213> ORGANISM: Rattus norvegicus

<400> SEQUENCE: 15

Met Arg Pro Leu Ile Leu Leu Ala Ala Leu Leu Trp Leu Gln Gly Phe
1               5                   10                  15

Leu Ala Glu Asp Asp Ala Cys Ser Ser Leu Glu Gly Ser Pro Asp Arg
            20                  25                  30

Gln Gly Gly Gly Pro Leu Leu Ser Val Asn Val Ser Ser His Gly Lys
        35                  40                  45

Ser Thr Ser Leu Phe Leu Ser Trp Val Ala Glu Leu Gly Gly Phe
    50                  55                  60

Asp Tyr Ala Leu Ser Leu Arg Ser Val Asn Ser Ser Gly Ser Pro Glu
65                  70                  75                  80

Gly Gln Gln Leu Gln Ala His Thr Asn Glu Ser Gly Phe Glu Phe His
                85                  90                  95

Gly Leu Val Pro Gly Ser Arg Tyr Gln Leu Lys Leu Thr Val Leu Arg
            100                 105                 110

Pro Cys Trp Gln Asn Val Thr Ile Thr Leu Thr Ala Arg Thr Ala Pro
        115                 120                 125

Thr Val Val Arg Gly Leu Gln Leu His Ser Ala Gly Ser Pro Ala Arg
    130                 135                 140

Leu Glu Ala Ser Trp Ser Asp Ala Pro Gly Asp Gln Asp Ser Tyr Gln
145                 150                 155                 160

Leu Leu Leu Tyr His Leu Glu Ser Gln Thr Leu Ala Cys Asn Val Ser
                165                 170                 175

Val Ser Pro Asp Thr Leu Ser Tyr Ser Phe Gly Asp Leu Leu Pro Gly
            180                 185                 190

Thr Gln Tyr Val Leu Glu Val Ile Thr Trp Ala Gly Ser Leu His Ala
        195                 200                 205

Lys Thr Ser Ile Leu Gln Trp Thr Glu Pro Val Pro Pro Asp His Leu
    210                 215                 220

Ala Leu Arg Ala Leu Gly Thr Ser Ser Leu Gln Ala Phe Trp Asn Ser
225                 230                 235                 240

Ser Glu Gly Ala Thr Ser Phe His Leu Met Leu Thr Asp Leu Leu Gly
                245                 250                 255

Gly Thr Asn Thr Thr Ala Val Ile Arg Gln Gly Val Ser Thr His Thr
            260                 265                 270

Phe Leu His Leu Ser Pro Gly Thr Pro His Glu Leu Lys Ile Cys Ala
        275                 280                 285
```

```
Ser Ala Gly Pro His Gln Ile Trp Gly Pro Ser Ala Thr Glu Trp Thr
290                 295                 300
Tyr Pro Ser Tyr Pro Ser Asp Leu Val Leu Thr Pro Leu Arg Asn Glu
305                 310                 315                 320
Leu Trp Ala Ser Trp Lys Ala Gly Leu Gly Ala Arg Asp Gly Tyr Val
                325                 330                 335
Leu Lys Leu Ser Gly Pro Met Glu Ser Thr Ser Thr Leu Gly Pro Glu
                340                 345                 350
Glu Cys Asn Ala Val Phe Pro Gly Pro Leu Pro Pro Gly His Tyr Thr
            355                 360                 365
Leu Gln Leu Lys Val Leu Ala Gly Pro Tyr Asp Ala Trp Val Glu Gly
370                 375                 380
Ser Thr Trp Leu Ala Glu Ser Ala Ala Leu Pro Arg Glu Val Pro Gly
385                 390                 395                 400
Ala Arg Leu Trp Leu Asp Gly Leu Glu Ala Ser Lys Gln Pro Gly Arg
                405                 410                 415
Arg Ala Leu Leu Tyr Ser Asp Asp Ala Pro Gly Ser Leu Gly Asn Ile
                420                 425                 430
Ser Val Pro Ser Gly Ala Thr His Val Ile Phe Cys Gly Leu Val Pro
            435                 440                 445
Gly Ala His Tyr Arg Val Asp Ile Ala Ser Ser Thr Gly Asp Ile Ser
450                 455                 460
Gln Ser Ile Ser Gly Tyr Thr Ser Pro Leu Pro Gln Ser Leu Glu
465                 470                 475                 480
Val Ile Ser Arg Ser Ser Pro Ser Asp Leu Thr Ile Ala Trp Gly Pro
                485                 490                 495
Ala Pro Gly Gln Leu Glu Gly Tyr Lys Val Thr Trp His Gln Asp Gly
            500                 505                 510
Ser Gln Arg Ser Pro Gly Asp Leu Val Asp Leu Gly Pro Asp Thr Leu
            515                 520                 525
Ser Leu Thr Leu Lys Ser Leu Val Pro Gly Ser Cys Tyr Thr Val Ser
530                 535                 540
Ala Trp Ala Trp Ala Gly Asn Leu Asp Ser Asp Ser Gln Lys Ile His
545                 550                 555                 560
Ser Cys Thr Arg Pro Ala Pro Pro Thr Asn Leu Ser Leu Gly Phe Ala
                565                 570                 575
His Gln Pro Ala Ala Leu Lys Ala Ser Trp Tyr His Pro Pro Gly Gly
            580                 585                 590
Arg Asp Ala Phe His Leu Arg Leu Tyr Arg Leu Arg Pro Leu Thr Leu
            595                 600                 605
Glu Ser Glu Lys Val Leu Pro Arg Glu Ala Gln Asn Phe Ser Trp Ala
610                 615                 620
Gln Leu Thr Ala Gly Cys Glu Phe Gln Val Gln Leu Ser Thr Leu Trp
625                 630                 635                 640
Gly Ser Glu Arg Ser Ser Ala Asn Ala Thr Gly Trp Thr Pro Pro
                645                 650                 655
Ser Ala Pro Thr Leu Val Asn Val Thr Ser Asp Ala Pro Thr Gln Leu
                660                 665                 670
Gln Val Ser Trp Ala His Val Pro Gly Gly Arg Ser Arg Tyr Gln Val
            675                 680                 685
Thr Leu Tyr Gln Glu Ser Thr Arg Thr Ala Ser Ile Met Gly Pro
690                 695                 700
Lys Glu Asp Gly Thr Ser Phe Leu Gly Leu Thr Pro Gly Thr Lys Tyr
```

-continued

```
            705                 710                 715                 720
Lys Val Glu Val Ile Ser Trp Ala Gly Pro Leu Tyr Thr Ala Ala
                    725                 730                 735

Asn Val Ser Ala Trp Thr Tyr Pro Leu Ile Pro Asn Glu Leu Leu Val
                740                 745                 750

Ser Met Gln Ala Gly Ser Ala Val Val Asn Leu Ala Trp Pro Ser Gly
                755                 760                 765

Pro Leu Gly Gln Gly Ala Cys His Ala Gln Leu Ser Asp Ala Gly His
                770                 775                 780

Leu Ser Trp Glu Gln Pro Leu Lys Leu Gly Gln Glu Leu Phe Met Leu
785                 790                 795                 800

Arg Asp Leu Thr Pro Gly His Thr Ile Ser Met Ser Val Arg Cys Arg
                805                 810                 815

Ala Gly Pro Leu Gln Ala Ser Thr His Leu Val Val Leu Ser Val Glu
                820                 825                 830

Pro Gly Pro Val Glu Asp Val Leu Cys His Pro Glu Ala Thr Tyr Leu
                835                 840                 845

Ala Leu Asn Trp Thr Met Pro Ala Gly Asp Val Asp Val Cys Leu Val
850                 855                 860

Val Val Glu Arg Leu Val Pro Gly Gly Gly Thr His Phe Val Phe Gln
865                 870                 875                 880

Val Asn Thr Ser Gly Asp Ala Leu Leu Leu Pro Asn Leu Met Pro Thr
                885                 890                 895

Thr Ser Tyr Arg Leu Ser Leu Thr Val Leu Gly Arg Asn Ser Arg Trp
                900                 905                 910

Ser Arg Ala Val Ser Leu Val Cys Ser Thr Ser Ala Glu Ala Trp His
                915                 920                 925

Pro Pro Glu Leu Ala Glu Pro Pro Gln Val Glu Leu Gly Thr Gly Met
                930                 935                 940

Gly Val Thr Val Met Arg Gly Met Phe Gly Lys Asp Asp Gly Gln Ile
945                 950                 955                 960

Gln Trp Tyr Gly Ile Ile Ala Thr Ile Asn Met Thr Leu Ala Gln Pro
                965                 970                 975

Ser Arg Glu Ala Ile Asn Tyr Thr Trp Tyr Asp His Tyr Tyr Arg Gly
                980                 985                 990

Cys Glu Ser Phe Leu Ala Leu Leu Phe Pro Asn Pro Phe Tyr Pro Glu
                995                 1000                1005

Pro Trp Ala Gly Pro Arg Ser Trp Thr Val Pro Val Gly Thr Glu
                1010                1015                1020

Asp Cys Asp Asn Thr Gln Glu Ile Cys Asn Gly Arg Leu Lys Ser
                1025                1030                1035

Gly Phe Gln Tyr Arg Phe Ser Val Val Ala Phe Ser Arg Leu Asn
                1040                1045                1050

Thr Pro Glu Thr Ile Leu Ala Phe Ser Ala Phe Ser Glu Pro Arg
                1055                1060                1065

Ala Ser Ile Ser Leu Ala Ile Ile Pro Leu Thr Val Met Leu Gly
                1070                1075                1080

Ala Val Val Gly Ser Ile Val Ile Val Cys Ala Val Leu Cys Leu
                1085                1090                1095

Leu Arg Trp Arg Cys Leu Lys Gly Pro Arg Ser Glu Lys Asp Gly
                1100                1105                1110

Phe Ser Lys Glu Leu Met Pro Tyr Asn Leu Trp Arg Thr His Arg
                1115                1120                1125
```

```
Pro Ile Pro Ile His Ser Phe Arg Gln Ser Tyr Glu Ala Lys Ser
    1130            1135                1140

Ala His Ala His Gln Thr Phe Phe Gln Glu Phe Glu Glu Leu Lys
    1145            1150                1155

Glu Val Gly Lys Asp Gln Pro Arg Leu Glu Ala Glu His Pro Asp
    1160            1165                1170

Asn Ile Ile Lys Asn Arg Tyr Pro His Val Leu Pro Tyr Asp His
    1175            1180                1185

Ser Arg Val Arg Leu Thr Gln Leu Pro Gly Glu Pro His Ser Asp
    1190            1195                1200

Tyr Ile Asn Ala Asn Phe Ile Pro Gly Tyr Ser His Thr Gln Glu
    1205            1210                1215

Ile Ile Ala Thr Gln Gly Pro Leu Lys Lys Thr Leu Glu Asp Phe
    1220            1225                1230

Trp Arg Leu Val Trp Glu Gln Val His Val Ile Ile Met Leu
    1235            1240                1245

Thr Val Gly Met Glu Asn Gly Arg Val Leu Cys Glu His Tyr Trp
    1250            1255                1260

Pro Ala Asn Ser Thr Pro Val Thr His Gly His Ile Thr Ile His
    1265            1270                1275

Leu Leu Ala Glu Pro Glu Asp Glu Trp Thr Arg Arg Glu Phe
    1280            1285                1290

Gln Leu Gln His Gly Thr Glu Gln Lys Gln Arg Arg Val Lys Gln
    1295            1300                1305

Leu Gln Phe Thr Thr Trp Pro Asp His Ser Val Pro Glu Ala Pro
    1310            1315                1320

Ser Ser Leu Leu Ala Phe Val Glu Leu Val Gln Glu Gln Val Gln
    1325            1330                1335

Ala Thr Gln Gly Lys Gly Pro Ile Leu Val His Cys Ser Ala Gly
    1340            1345                1350

Val Gly Arg Thr Gly Thr Phe Val Ala Leu Leu Arg Leu Leu Arg
    1355            1360                1365

Gln Leu Glu Glu Glu Lys Val Ala Asp Val Phe Asn Thr Val Tyr
    1370            1375                1380

Ile Leu Arg Leu His Arg Pro Leu Met Ile Gln Thr Leu Ser Gln
    1385            1390                1395

Tyr Ile Phe Leu His Ser Cys Leu Leu Asn Lys Ile Leu Glu Gly
    1400            1405                1410

Pro Pro Asp Ser Ser Asp Ser Gly Pro Ile Ser Val Met Asp Phe
    1415            1420                1425

Ala Gln Ala Cys Ala Lys Arg Ala Ala Asn Ala Asn Ala Gly Phe
    1430            1435                1440

Leu Lys Glu Tyr Lys Leu Leu Lys Gln Ala Ile Lys Asp Gly Thr
    1445            1450                1455

Gly Ser Leu Leu Pro Pro Pro Asp Tyr Asn Gln Asn Ser Ile Val
    1460            1465                1470

Ser Arg Arg His Ser Gln Glu Gln Phe Ala Leu Val Glu Glu Cys
    1475            1480                1485

Pro Glu Asp Ser Met Leu Glu Ala Ser Leu Phe Pro Gly Gly Pro
    1490            1495                1500

Ser Gly Cys Asp His Val Val Leu Thr Gly Ser Ala Gly Pro Lys
    1505            1510                1515
```

| | | | | | | | | | | |
|---|---|---|---|---|---|---|---|---|---|---|
| Glu | Leu | Trp | Glu | Met | Val | Trp | Glu | His | Asp | Ala | His | Val | Leu | Val |
| | 1520 | | | | 1525 | | | | 1530 | |

Ser Leu Gly Leu Pro Asp Thr Lys Glu Lys Pro Pro Asp Ile Trp
    1535                1540                1545

Pro Val Glu Met Gln Pro Ile Val Thr Asp Met Val Thr Val His
    1550                1555                1560

Arg Val Ser Glu Ser Asn Thr Thr Thr Gly Trp Pro Ser Thr Leu
    1565                1570                1575

Phe Arg Val Ile His Gly Glu Ser Gly Lys Glu Arg Gln Val Gln
    1580                1585                1590

Cys Leu Gln Phe Pro Cys Ser Glu Ser Gly Cys Glu Leu Pro Ala
    1595                1600                1605

Asn Thr Leu Leu Thr Phe Leu Asp Ala Val Gly Gln Cys Cys Phe
    1610                1615                1620

Arg Gly Lys Ser Lys Lys Pro Gly Thr Leu Leu Ser His Ser Ser
    1625                1630                1635

Lys Asn Thr Asn Gln Leu Gly Thr Phe Leu Ala Met Glu Gln Leu
    1640                1645                1650

Leu Gln Gln Ala Gly Thr Glu Arg Thr Val Asp Val Phe Asn Val
    1655                1660                1665

Ala Leu Lys Gln Ser Gln Ala Cys Gly Leu Met Thr Pro Thr Leu
    1670                1675                1680

Glu Gln Tyr Ile Tyr Leu Tyr Asn Cys Leu Asn Ser Ala Leu Leu
    1685                1690                1695

Asn Gly Leu Pro Arg Ala Gly Lys Trp Pro Ala Pro Cys
    1700                1705                1710

<210> SEQ ID NO 16
<211> LENGTH: 3247
<212> TYPE: DNA
<213> ORGANISM: Homo sapiens
<220> FEATURE:
<221> NAME/KEY: CDS
<222> LOCATION: (91)..(1395)

<400> SEQUENCE: 16
gggcgggcct cggggctaag agcgcgacgc ctagagcggc agacggcgca gtgggccgag      60
aaggaggcgc agcagccgcc ctggcccgtc atg gag atg gaa aag gag ttc gag     114
                                    Met Glu Met Glu Lys Glu Phe Glu
                                    1               5 cag atc gac aag tcc ggg agc tgg gcg gcc att tac cag gat atc cga     162
Gln Ile Asp Lys Ser Gly Ser Trp Ala Ala Ile Tyr Gln Asp Ile Arg
    10              15                  20 cat gaa gcc agt gac ttc cca tgt aga gtg gcc aag ctt cct aag aac     210
His Glu Ala Ser Asp Phe Pro Cys Arg Val Ala Lys Leu Pro Lys Asn
25              30                  35                  40 aaa aac cga aat agg tac aga gac gtc agt ccc ttt gac cat agt cgg     258
Lys Asn Arg Asn Arg Tyr Arg Asp Val Ser Pro Phe Asp His Ser Arg
                45                  50                  55 att aaa cta cat caa gaa gat aat gac tat atc aac gct agt ttg ata     306
Ile Lys Leu His Gln Glu Asp Asn Asp Tyr Ile Asn Ala Ser Leu Ile
            60                  65                  70 aaa atg gaa gaa gcc caa agg agt tac att ctt acc cag ggc cct ttg     354
Lys Met Glu Glu Ala Gln Arg Ser Tyr Ile Leu Thr Gln Gly Pro Leu
        75                  80                  85 cct aac aca tgc ggt cac ttt tgg gag atg gtg tgg gag cag aaa agc     402
Pro Asn Thr Cys Gly His Phe Trp Glu Met Val Trp Glu Gln Lys Ser
    90                  95                  100

```
agg ggt gtc gtc atg ctc aac aga gtg atg gag aaa ggt tcg tta aaa    450
Arg Gly Val Val Met Leu Asn Arg Val Met Glu Lys Gly Ser Leu Lys
105             110                 115                 120 tgc gca caa tac tgg cca caa aaa gaa gaa aaa gag atg atc ttt gaa    498
Cys Ala Gln Tyr Trp Pro Gln Lys Glu Glu Lys Glu Met Ile Phe Glu
                125                 130                 135 gac aca aat ttg aaa tta aca ttg atc tct gaa gat atc aag tca tat    546
Asp Thr Asn Leu Lys Leu Thr Leu Ile Ser Glu Asp Ile Lys Ser Tyr
            140                 145                 150 tat aca gtg cga cag cta gaa ttg gaa aac ctt aca acc caa gaa act    594
Tyr Thr Val Arg Gln Leu Glu Leu Glu Asn Leu Thr Thr Gln Glu Thr
            155                 160                 165 cga gag atc tta cat ttc cac tat acc aca tgg cct gac ttt gga gtc    642
Arg Glu Ile Leu His Phe His Tyr Thr Thr Trp Pro Asp Phe Gly Val
170                 175                 180 cct gaa tca cca gcc tca ttc ttg aac ttt ctt ttc aaa gtc cga gag    690
Pro Glu Ser Pro Ala Ser Phe Leu Asn Phe Leu Phe Lys Val Arg Glu
185                 190                 195                 200 tca ggg tca ctc agc ccg gag cac ggg ccc gtt gtg gtg cac tgc agt    738
Ser Gly Ser Leu Ser Pro Glu His Gly Pro Val Val Val His Cys Ser
                205                 210                 215 gca ggc atc ggc agg tct gga acc ttc tgt ctg gct gat acc tgc ctc    786
Ala Gly Ile Gly Arg Ser Gly Thr Phe Cys Leu Ala Asp Thr Cys Leu
                220                 225                 230 ctg ctg atg gac aag agg aaa gac cct tct tcc gtt gat atc aag aaa    834
Leu Leu Met Asp Lys Arg Lys Asp Pro Ser Ser Val Asp Ile Lys Lys
                235                 240                 245 gtg ctg tta gaa atg agg aag ttt cgg atg ggg ttg atc cag aca gcc    882
Val Leu Leu Glu Met Arg Lys Phe Arg Met Gly Leu Ile Gln Thr Ala
250                 255                 260 gac cag ctg cgc ttc tcc tac ctg gct gtg atc gaa ggt gcc aaa ttc    930
Asp Gln Leu Arg Phe Ser Tyr Leu Ala Val Ile Glu Gly Ala Lys Phe
265                 270                 275                 280 atc atg ggg gac tct tcc gtg cag gat cag tgg aag gag ctt tcc cac    978
Ile Met Gly Asp Ser Ser Val Gln Asp Gln Trp Lys Glu Leu Ser His
                285                 290                 295 gag gac ctg gag ccc cca ccc gag cat atc ccc cca cct ccc cgg cca   1026
Glu Asp Leu Glu Pro Pro Pro Glu His Ile Pro Pro Pro Pro Arg Pro
                300                 305                 310 ccc aaa cga atc ctg gag cca cac aat ggg aaa tgc agg gag ttc ttc   1074
Pro Lys Arg Ile Leu Glu Pro His Asn Gly Lys Cys Arg Glu Phe Phe
            315                 320                 325 cca aat cac cag tgg gtg aag gaa gag acc cag gag gat aaa gac tgc   1122
Pro Asn His Gln Trp Val Lys Glu Glu Thr Gln Glu Asp Lys Asp Cys
            330                 335                 340 ccc atc aag gaa gaa aaa gga agc ccc tta aat gcc gca ccc tac ggc   1170
Pro Ile Lys Glu Glu Lys Gly Ser Pro Leu Asn Ala Ala Pro Tyr Gly
345                 350                 355                 360 atc gaa agc atg agt caa gac act gaa gtt aga agt cgg gtc gtg ggg   1218
Ile Glu Ser Met Ser Gln Asp Thr Glu Val Arg Ser Arg Val Val Gly
                365                 370                 375 gga agt ctt cga ggt gcc cag gct gcc tcc cca gcc aaa ggg gag ccg   1266
Gly Ser Leu Arg Gly Ala Gln Ala Ala Ser Pro Ala Lys Gly Glu Pro
            380                 385                 390 tca ctg ccc gag aag gac gag gac cat gca ctg agt tac tgg aag ccc   1314
Ser Leu Pro Glu Lys Asp Glu Asp His Ala Leu Ser Tyr Trp Lys Pro
            395                 400                 405 ttc ctg gtc aac atg tgc gtg gct acg gtc ctc acg gcc ggc gct tac   1362
Phe Leu Val Asn Met Cys Val Ala Thr Val Leu Thr Ala Gly Ala Tyr
```

```
                410              415              420
ctc tgc tac agg ttc ctg ttc aac agc aac aca tagcctgacc ctcctccact    1415
Leu Cys Tyr Arg Phe Leu Phe Asn Ser Asn Thr
425                 430              435 ccacctccac ccactgtccg cctctgcccg cagagcccac gcccgactag caggcatgcc    1475
gcggtaggta agggccgccg gaccgcgtag agagccgggc cccggacgga cgttggttct    1535
gcactaaaac ccatcttccc cggatgtgtg tctcacccct catccttta  cttttgccc     1595
cttccacttt gagtaccaaa tccacaagcc attttttgag gagagtgaaa gagagtacca    1655
tgctggcggc gcagagggaa ggggcctaca cccgtcttgg ggctcgcccc acccagggct    1715
ccctcctgga gcatcccagg cggcgcacgc caacagcccc ccccttgaat ctgcagggag    1775
caactctcca ctccatattt atttaaacaa ttttttcccc aaaggcatcc atagtgcact    1835
agcatttct  tgaaccaata atgtattaaa attttttgat gtcagccttg catcaagggc    1895
tttatcaaaa agtacaataa taaatcctca ggtagtactg ggaatggaag gctttgccat    1955
gggcctgctg cgtcagacca gtactgggaa ggaggacggt tgtaagcagt tgttatttag    2015
tgatattgtg ggtaacgtga gaagatagaa caatgctata atatataatg aacacgtggg    2075
tatttaataa gaaacatgat gtgagattac tttgtcccgc ttattctcct ccctgttatc    2135
tgctagatct agttctcaat cactgctccc ccgtgtgtat tagaatgcat gtaaggtctt    2195
cttgtgtcct gatgaaaaat atgtgcttga aatgagaaac tttgatctct gcttactaat    2255
gtgccccatg tccaagtcca acctgcctgt gcatgacctg atcattacat ggctgtggtt    2315
cctaagcctg ttgctgaagt cattgtcgct cagcaatagg gtgcagtttt ccaggaatag    2375
gcatttgcta attcctggca tgacactcta gtgacttcct ggtgaggccc agcctgtcct    2435
ggtacagcag ggtcttgctg taactcagac attccaaggg tatgggaagc catattcaca    2495
cctcacgctc tggacatgat ttagggaagc agggacaccc cccgccccc  acctttggga    2555
tcagcctccg ccattccaag tcaacactct tcttgagcag accgtgattt ggaagagagg    2615
cacctgctgg aaaccacact tcttgaaaca gcctgggtga cggtccttta ggcagcctgc    2675
cgccgtctct gtcccggttc accttgccga gagaggcgcg tctgccccac cctcaaaccc    2735
tgtggggcct gatggtgctc acgactcttc ctgcaaaggg aactgaagac ctccacatta    2795
agtggctttt taacatgaaa aacacggcag ctgtagctcc cgagctactc tcttgccagc    2855
attttcacat tttgcctttc tcgtggtaga agccagtaca gagaaattct gtggtgggaa    2915
cattcgaggt gtcaccctgc agagctatgg tgaggtgtgg ataaggctta ggtgccaggc    2975
tgtaagcatt ctgagctggc ttgttgtttt taagtcctgt atatgtatgt agtagtttgg    3035
gtgtgtatat atagtagcat ttcaaaatgg acgtactggt ttaacctcct atccttggag    3095
agcagctggc tctccacctt gttacacatt atgttagaga ggtagcgagc tgctctgcta    3155
tatgccttaa gccaatattt actcatcagg tcattatttt ttacaatggc catggaataa    3215
accattttta caaaataaa  aacaaaaaaa gc                                  3247
```

<210> SEQ ID NO 17
<211> LENGTH: 435
<212> TYPE: PRT
<213> ORGANISM: Homo sapiens

<400> SEQUENCE: 17

```
Met Glu Met Glu Lys Glu Phe Glu Gln Ile Asp Lys Ser Gly Ser Trp
1               5                   10                  15
```

```
Ala Ala Ile Tyr Gln Asp Ile Arg His Glu Ala Ser Asp Phe Pro Cys
            20                  25                  30

Arg Val Ala Lys Leu Pro Lys Asn Lys Asn Arg Asn Arg Tyr Arg Asp
        35                  40                  45

Val Ser Pro Phe Asp His Ser Arg Ile Lys Leu His Gln Glu Asp Asn
    50                  55                  60

Asp Tyr Ile Asn Ala Ser Leu Ile Lys Met Glu Glu Ala Gln Arg Ser
65                  70                  75                  80

Tyr Ile Leu Thr Gln Gly Pro Leu Pro Asn Thr Cys Gly His Phe Trp
                85                  90                  95

Glu Met Val Trp Glu Gln Lys Ser Arg Gly Val Val Met Leu Asn Arg
                100                 105                 110

Val Met Glu Lys Gly Ser Leu Lys Cys Ala Gln Tyr Trp Pro Gln Lys
            115                 120                 125

Glu Glu Lys Glu Met Ile Phe Glu Asp Thr Asn Leu Lys Leu Thr Leu
        130                 135                 140

Ile Ser Glu Asp Ile Lys Ser Tyr Tyr Thr Val Arg Gln Leu Glu Leu
145                 150                 155                 160

Glu Asn Leu Thr Thr Gln Glu Thr Arg Glu Ile Leu His Phe His Tyr
                165                 170                 175

Thr Thr Trp Pro Asp Phe Gly Val Pro Glu Ser Pro Ala Ser Phe Leu
                180                 185                 190

Asn Phe Leu Phe Lys Val Arg Glu Ser Gly Ser Leu Ser Pro Glu His
            195                 200                 205

Gly Pro Val Val His Cys Ser Ala Gly Ile Gly Arg Ser Gly Thr
210                 215                 220

Phe Cys Leu Ala Asp Thr Cys Leu Leu Leu Met Asp Lys Arg Lys Asp
225                 230                 235                 240

Pro Ser Ser Val Asp Ile Lys Lys Val Leu Leu Glu Met Arg Lys Phe
                245                 250                 255

Arg Met Gly Leu Ile Gln Thr Ala Asp Gln Leu Arg Phe Ser Tyr Leu
            260                 265                 270

Ala Val Ile Glu Gly Ala Lys Phe Ile Met Gly Asp Ser Ser Val Gln
        275                 280                 285

Asp Gln Trp Lys Glu Leu Ser His Glu Asp Leu Glu Pro Pro Glu
    290                 295                 300

His Ile Pro Pro Pro Arg Pro Pro Lys Arg Ile Leu Glu Pro His
305                 310                 315                 320

Asn Gly Lys Cys Arg Glu Phe Phe Pro Asn His Gln Trp Val Lys Glu
                325                 330                 335

Glu Thr Gln Glu Asp Lys Asp Cys Pro Ile Lys Glu Glu Lys Gly Ser
            340                 345                 350

Pro Leu Asn Ala Ala Pro Tyr Gly Ile Glu Ser Met Ser Gln Asp Thr
        355                 360                 365

Glu Val Arg Ser Arg Val Val Gly Gly Ser Leu Arg Gly Ala Gln Ala
    370                 375                 380

Ala Ser Pro Ala Lys Gly Glu Pro Ser Leu Pro Glu Lys Asp Glu Asp
385                 390                 395                 400

His Ala Leu Ser Tyr Trp Lys Pro Phe Leu Val Asn Met Cys Val Ala
                405                 410                 415

Thr Val Leu Thr Ala Gly Ala Tyr Leu Cys Tyr Arg Phe Leu Phe Asn
                420                 425                 430

Ser Asn Thr
```

-continued

435

<210> SEQ ID NO 18
<211> LENGTH: 21
<212> TYPE: DNA
<213> ORGANISM: unknown
<220> FEATURE:
<223> OTHER INFORMATION: synthetic primer

<400> SEQUENCE: 18
ctcaggtctt catgattgtg g                                          21

<210> SEQ ID NO 19
<211> LENGTH: 20
<212> TYPE: DNA
<213> ORGANISM: unknown
<220> FEATURE:
<223> OTHER INFORMATION: synthetic primer

<400> SEQUENCE: 19
cgaaagagag tgtatccacc                                            20

<210> SEQ ID NO 20
<211> LENGTH: 22
<212> TYPE: DNA
<213> ORGANISM: unknown
<220> FEATURE:
<223> OTHER INFORMATION: synthetic primer

<400> SEQUENCE: 20
cctttacgtg gaataacatt ca                                         22

<210> SEQ ID NO 21
<211> LENGTH: 20
<212> TYPE: DNA
<213> ORGANISM: unknown
<220> FEATURE:
<223> OTHER INFORMATION: synthetic primer

<400> SEQUENCE: 21
atagggaatc acggtgtagc                                            20

<210> SEQ ID NO 22
<211> LENGTH: 21
<212> TYPE: DNA
<213> ORGANISM: unknown
<220> FEATURE:
<223> OTHER INFORMATION: synthetic primer

<400> SEQUENCE: 22
gcagcttcaa ggattacgta a                                          21

<210> SEQ ID NO 23
<211> LENGTH: 20
<212> TYPE: DNA
<213> ORGANISM: unknown
<220> FEATURE:
<223> OTHER INFORMATION: synthetic primer

<400> SEQUENCE: 23
catcttgtga actggtggct                                            20

<210> SEQ ID NO 24
<211> LENGTH: 21
<212> TYPE: DNA
<213> ORGANISM: unknown

<220> FEATURE:
<223> OTHER INFORMATION: synthetic primer

<400> SEQUENCE: 24
tccatagaac agactaccta c                                                     21

<210> SEQ ID NO 25
<211> LENGTH: 19
<212> TYPE: DNA
<213> ORGANISM: unknown
<220> FEATURE:
<223> OTHER INFORMATION: synthetic primer

<400> SEQUENCE: 25
gatcacagct gaggaaggc                                                        19

<210> SEQ ID NO 26
<211> LENGTH: 20
<212> TYPE: DNA
<213> ORGANISM: unknown
<220> FEATURE:
<223> OTHER INFORMATION: synthetic primer

<400> SEQUENCE: 26
tgatgcacct cagttactgg                                                       20

<210> SEQ ID NO 27
<211> LENGTH: 20
<212> TYPE: DNA
<213> ORGANISM: unknown
<220> FEATURE:
<223> OTHER INFORMATION: synthetic primer

<400> SEQUENCE: 27
gctgtgcatc atcacttgag                                                       20

<210> SEQ ID NO 28
<211> LENGTH: 20
<212> TYPE: DNA
<213> ORGANISM: unknown
<220> FEATURE:
<223> OTHER INFORMATION: synthetic primer

<400> SEQUENCE: 28
catacgtgca ctgtcttagc                                                       20

<210> SEQ ID NO 29
<211> LENGTH: 20
<212> TYPE: DNA
<213> ORGANISM: unknown
<220> FEATURE:
<223> OTHER INFORMATION: synthetic primer

<400> SEQUENCE: 29
actcctccag taactccttc                                                       20

<210> SEQ ID NO 30
<211> LENGTH: 2860
<212> TYPE: DNA
<213> ORGANISM: Homo sapiens
<220> FEATURE:
<221> NAME/KEY: CDS
<222> LOCATION: (23)..(2803)

<400> SEQUENCE: 30
actgagcaaa tgagatagaa ac atg gca ttc tta att ata cta att acc tgc            52

```
                Met Ala Phe Leu Ile Ile Leu Ile Thr Cys
                  1               5                  10 ttt gtg att att ctt gct act tca cag cct tgc cag acc cct gat gac    100
Phe Val Ile Ile Leu Ala Thr Ser Gln Pro Cys Gln Thr Pro Asp Asp
             15                  20                  25 ttt gtg gct gcc act tct ccg gga cat atc ata att gga ggt ttg ttt    148
Phe Val Ala Ala Thr Ser Pro Gly His Ile Ile Ile Gly Gly Leu Phe
             30                  35                  40 gct att cat gaa aaa atg ttg tcc tca gaa gac tct ccc aga cga cca    196
Ala Ile His Glu Lys Met Leu Ser Ser Glu Asp Ser Pro Arg Arg Pro
             45                  50                  55 caa atc cag gag tgt gtt ggc ttt gaa ata tca gtt ttt ctt caa act    244
Gln Ile Gln Glu Cys Val Gly Phe Glu Ile Ser Val Phe Leu Gln Thr
             60                  65                  70 ctt gcc atg ata cac agc att gag atg atc aac aat tca aca ctc tta    292
Leu Ala Met Ile His Ser Ile Glu Met Ile Asn Asn Ser Thr Leu Leu
 75                  80                  85                  90 tct gga gtc aaa ctg ggg tat gaa atc tat gac act tgt aca gaa gtc    340
Ser Gly Val Lys Leu Gly Tyr Glu Ile Tyr Asp Thr Cys Thr Glu Val
             95                  100                 105 aca gtg gca atg gca gcc act ctg agg ttt ctt tct aaa ttc aac tgc    388
Thr Val Ala Met Ala Ala Thr Leu Arg Phe Leu Ser Lys Phe Asn Cys
             110                 115                 120 tcc aga gaa act gtg gag ttt aag tgt gac tat tcc agc tac atg cca    436
Ser Arg Glu Thr Val Glu Phe Lys Cys Asp Tyr Ser Ser Tyr Met Pro
             125                 130                 135 aga gtt aag gct gtc ata ggt tct ggg tac tca gaa ata act atg gct    484
Arg Val Lys Ala Val Ile Gly Ser Gly Tyr Ser Glu Ile Thr Met Ala
             140                 145                 150 gtc tcc agg atg ttg aat tta cag ctc atg cca cag gtg ggt tat gaa    532
Val Ser Arg Met Leu Asn Leu Gln Leu Met Pro Gln Val Gly Tyr Glu
155                  160                 165                 170 tca act gca gaa atc ctg agt gac aaa att cgc ttt cct tca ttt tta    580
Ser Thr Ala Glu Ile Leu Ser Asp Lys Ile Arg Phe Pro Ser Phe Leu
             175                 180                 185 cgg act gtg ccc agt gac ttc cat caa att aaa gca atg gct cac ctg    628
Arg Thr Val Pro Ser Asp Phe His Gln Ile Lys Ala Met Ala His Leu
             190                 195                 200 att cag aaa tct ggt tgg aac tgg att ggc atc ata acc aca gat gat    676
Ile Gln Lys Ser Gly Trp Asn Trp Ile Gly Ile Ile Thr Thr Asp Asp
             205                 210                 215 gac tat gga cga ttg gct ctt aac act ttt ata att cag gct gaa gca    724
Asp Tyr Gly Arg Leu Ala Leu Asn Thr Phe Ile Ile Gln Ala Glu Ala
             220                 225                 230 aat aac gtg tgc ata gcc ttc aaa gag gtt ctt cca gcc ttt ctt tca    772
Asn Asn Val Cys Ile Ala Phe Lys Glu Val Leu Pro Ala Phe Leu Ser
235                  240                 245                 250 gat aat acc att gaa gtc aga atc aat cgg aca ctg aag aaa atc att    820
Asp Asn Thr Ile Glu Val Arg Ile Asn Arg Thr Leu Lys Lys Ile Ile
             255                 260                 265 tta gaa gcc cag gtt aat gtc att gtg gta ttt ctg agg caa ttc cat    868
Leu Glu Ala Gln Val Asn Val Ile Val Val Phe Leu Arg Gln Phe His
             270                 275                 280 gtt ttt gat ctc ttc aat aaa gcc att gaa atg aat ata aat aag atg    916
Val Phe Asp Leu Phe Asn Lys Ala Ile Glu Met Asn Ile Asn Lys Met
             285                 290                 295 tgg att gct agt gat aat tgg tca act gcc acc aag att acc acc att    964
Trp Ile Ala Ser Asp Asn Trp Ser Thr Ala Thr Lys Ile Thr Thr Ile
             300                 305                 310
```

| | | |
|---|---|---|
| cct aat gtt aaa aag att ggc aaa gtt gta ggg ttt gcc ttt aga aga<br>Pro Asn Val Lys Lys Ile Gly Lys Val Val Gly Phe Ala Phe Arg Arg<br>315                    320                    325                    330 | 1012 |
| ggg aat ata tcc tct ttc cat tcc ttt ctt caa aat ctg cac ttg ctt<br>Gly Asn Ile Ser Ser Phe His Ser Phe Leu Gln Asn Leu His Leu Leu<br>                335                    340                    345 | 1060 |
| ccc agt gac agt cac aaa ctc tta cat gaa tat gcc atg cat tta tct<br>Pro Ser Asp Ser His Lys Leu Leu His Glu Tyr Ala Met His Leu Ser<br>                350                    355                    360 | 1108 |
| gcc tgc gca tat gtc aag gac act gat ttg agt caa tgc ata ttc aat<br>Ala Cys Ala Tyr Val Lys Asp Thr Asp Leu Ser Gln Cys Ile Phe Asn<br>            365                    370                    375 | 1156 |
| cat tct caa agg act ttg gcc tac aag gct aac aag gct ata gaa agg<br>His Ser Gln Arg Thr Leu Ala Tyr Lys Ala Asn Lys Ala Ile Glu Arg<br>380                    385                    390 | 1204 |
| aac ttc gtc atg aga aat gac ttc ctc tgg gac tat gct gag cca gga<br>Asn Phe Val Met Arg Asn Asp Phe Leu Trp Asp Tyr Ala Glu Pro Gly<br>395                    400                    405                    410 | 1252 |
| ctc att cat agt att cag ctt gca gtg ttt gcc ctt ggt tat gcc att<br>Leu Ile His Ser Ile Gln Leu Ala Val Phe Ala Leu Gly Tyr Ala Ile<br>                415                    420                    425 | 1300 |
| cgg gat ctg tgt caa gct cgt gac tgt cag aac ccc aac gcc ttt caa<br>Arg Asp Leu Cys Gln Ala Arg Asp Cys Gln Asn Pro Asn Ala Phe Gln<br>            430                    435                    440 | 1348 |
| cca tgg gag tta ctt ggt gtg cta aaa aat gtg aca ttc act gat gga<br>Pro Trp Glu Leu Leu Gly Val Leu Lys Asn Val Thr Phe Thr Asp Gly<br>445                    450                    455 | 1396 |
| tgg aat tca ttt cat ttt gat gct cac ggg gat tta aat act gga tat<br>Trp Asn Ser Phe His Phe Asp Ala His Gly Asp Leu Asn Thr Gly Tyr<br>460                    465                    470 | 1444 |
| gat gtt gtg ctc tgg aag gag atc aat gga cac atg act gtc act aag<br>Asp Val Val Leu Trp Lys Glu Ile Asn Gly His Met Thr Val Thr Lys<br>475                    480                    485                    490 | 1492 |
| atg gca gaa tat gac cta cag aat gat gtc ttc atc atc cca gat cag<br>Met Ala Glu Tyr Asp Leu Gln Asn Asp Val Phe Ile Ile Pro Asp Gln<br>                495                    500                    505 | 1540 |
| gaa aca aaa aat gag ttc agg aat ctt aag caa att caa tct aaa tgc<br>Glu Thr Lys Asn Glu Phe Arg Asn Leu Lys Gln Ile Gln Ser Lys Cys<br>            510                    515                    520 | 1588 |
| tcc aag gaa tgc agt cct ggg caa atg aag aaa act aca aga agt caa<br>Ser Lys Glu Cys Ser Pro Gly Gln Met Lys Lys Thr Thr Arg Ser Gln<br>            525                    530                    535 | 1636 |
| cac atc tgt tgc tat gaa tgt cag aac tgt cct gaa aat cat tac act<br>His Ile Cys Cys Tyr Glu Cys Gln Asn Cys Pro Glu Asn His Tyr Thr<br>540                      545                    550 | 1684 |
| aat cag aca gat atg cct cac tgc ctt tta tgc aac aac aaa act cac<br>Asn Gln Thr Asp Met Pro His Cys Leu Leu Cys Asn Asn Lys Thr His<br>555                    560                    565                    570 | 1732 |
| tgg gcc cct gtt agg agc act atg tgc ttt gaa aag gaa gtg gaa tat<br>Trp Ala Pro Val Arg Ser Thr Met Cys Phe Glu Lys Glu Val Glu Tyr<br>                575                    580                    585 | 1780 |
| ctc aac tgg aat gac tcc ttg gcc atc cta ctc ctg att ctc tcc cta<br>Leu Asn Trp Asn Asp Ser Leu Ala Ile Leu Leu Leu Ile Leu Ser Leu<br>            590                    595                    600 | 1828 |
| ctg gga atc ata ttt gtt ctg gtt gtt ggc ata ata ttt aca aga aac<br>Leu Gly Ile Ile Phe Val Leu Val Val Gly Ile Ile Phe Thr Arg Asn<br>            605                    610                    615 | 1876 |
| ctg aac aca cct gtt gtg aaa tca tcc ggg gga tta aga gtc tgc tat<br>Leu Asn Thr Pro Val Val Lys Ser Ser Gly Gly Leu Arg Val Cys Tyr<br>620                    625                    630 | 1924 |

```
gtg atc ctt ctc tgt cat ttc ctc aat ttt gcc agc acg agc ttt ttc    1972
Val Ile Leu Leu Cys His Phe Leu Asn Phe Ala Ser Thr Ser Phe Phe
635                 640                 645                 650 att gga gaa cca caa gac ttc aca tgt aaa acc agg cag aca atg ttt    2020
Ile Gly Glu Pro Gln Asp Phe Thr Cys Lys Thr Arg Gln Thr Met Phe
                    655                 660                 665 gga gtg agc ttt act ctt tgc atc tcc tgc att ttg acg aag tct ctg    2068
Gly Val Ser Phe Thr Leu Cys Ile Ser Cys Ile Leu Thr Lys Ser Leu
                670                 675                 680 aaa att ttg cta gcc ttc agc ttt gat ccc aaa tta cag aaa ttt ctg    2116
Lys Ile Leu Leu Ala Phe Ser Phe Asp Pro Lys Leu Gln Lys Phe Leu
            685                 690                 695 aag tgc ctc tat aga ccg atc ctt att atc ttc act tgc acg ggc atc    2164
Lys Cys Leu Tyr Arg Pro Ile Leu Ile Ile Phe Thr Cys Thr Gly Ile
700                 705                 710 cag gtt gtc att tgc aca ctc tgg cta atc ttt gca gca cct act gta    2212
Gln Val Val Ile Cys Thr Leu Trp Leu Ile Phe Ala Ala Pro Thr Val
715                 720                 725                 730 gag gtg aat gtc tcc ttg ccc aga gtc atc atc ctg gag tgt gag gag    2260
Glu Val Asn Val Ser Leu Pro Arg Val Ile Ile Leu Glu Cys Glu Glu
                    735                 740                 745 gga tcc ata ctt gca ttt ggc acc atg ctg ggc tac att gcc atc ctg    2308
Gly Ser Ile Leu Ala Phe Gly Thr Met Leu Gly Tyr Ile Ala Ile Leu
                750                 755                 760 gcc ttc att tgc ttc ata ttt gct ttc aaa ggc aaa tat gag aat tac    2356
Ala Phe Ile Cys Phe Ile Phe Ala Phe Lys Gly Lys Tyr Glu Asn Tyr
            765                 770                 775 aat gaa gcc aaa ttc att aca ttt ggc atg ctc att tac ttc ata gct    2404
Asn Glu Ala Lys Phe Ile Thr Phe Gly Met Leu Ile Tyr Phe Ile Ala
780                 785                 790 tgg atc aca ttc atc cct atc tat gct acc aca ttt ggc aaa tat gta    2452
Trp Ile Thr Phe Ile Pro Ile Tyr Ala Thr Thr Phe Gly Lys Tyr Val
795                 800                 805                 810 cca gct gtg gag att att gtc ata tta ata tct aac tat gga atc ctg    2500
Pro Ala Val Glu Ile Ile Val Ile Leu Ile Ser Asn Tyr Gly Ile Leu
                    815                 820                 825 tat tgc aca ttc atc ccc aaa tgc tat gtt att att tgt aag caa gag    2548
Tyr Cys Thr Phe Ile Pro Lys Cys Tyr Val Ile Ile Cys Lys Gln Glu
                830                 835                 840 att aac aca aag tct gcc ttt ctc aag atg atc tac agt tat tct tcc    2596
Ile Asn Thr Lys Ser Ala Phe Leu Lys Met Ile Tyr Ser Tyr Ser Ser
            845                 850                 855 cat agt gtg agc agc att gcc ctg agt cct gct tca ctg gac tcc atg    2644
His Ser Val Ser Ser Ile Ala Leu Ser Pro Ala Ser Leu Asp Ser Met
860                 865                 870 agc ggc aat gtc aca atg acc aat ccc agc tct agt ggc aag tct gca    2692
Ser Gly Asn Val Thr Met Thr Asn Pro Ser Ser Ser Gly Lys Ser Ala
875                 880                 885                 890 acc tgg cag aaa agc aaa gat ctt cag gca caa gca ttt gca cac ata    2740
Thr Trp Gln Lys Ser Lys Asp Leu Gln Ala Gln Ala Phe Ala His Ile
                    895                 900                 905 tgc agg gaa aat gcc aca agt gta tct aaa act ttg cct cga aaa aga    2788
Cys Arg Glu Asn Ala Thr Ser Val Ser Lys Thr Leu Pro Arg Lys Arg
                910                 915                 920 atg tca agt ata tga ataagcctta ggagatgcca cattccagaa taaaatgttt    2843
Met Ser Ser Ile
            925 ccagggtctt tgcatct                                                 2860
```

<210> SEQ ID NO 31
<211> LENGTH: 926
<212> TYPE: PRT
<213> ORGANISM: Homo sapiens

<400> SEQUENCE: 31

Met Ala Phe Leu Ile Ile Leu Ile Thr Cys Phe Val Ile Ile Leu Ala
1               5                   10                  15

Thr Ser Gln Pro Cys Gln Thr Pro Asp Asp Phe Val Ala Ala Thr Ser
            20                  25                  30

Pro Gly His Ile Ile Ile Gly Gly Leu Phe Ala Ile His Glu Lys Met
        35                  40                  45

Leu Ser Glu Asp Ser Pro Arg Arg Pro Gln Ile Gln Glu Cys Val
    50                  55                  60

Gly Phe Glu Ile Ser Val Phe Leu Gln Thr Leu Ala Met Ile His Ser
65                  70                  75                  80

Ile Glu Met Ile Asn Asn Ser Thr Leu Leu Ser Gly Val Lys Leu Gly
                85                  90                  95

Tyr Glu Ile Tyr Asp Thr Cys Thr Glu Val Thr Val Ala Met Ala Ala
            100                 105                 110

Thr Leu Arg Phe Leu Ser Lys Phe Asn Cys Ser Arg Glu Thr Val Glu
        115                 120                 125

Phe Lys Cys Asp Tyr Ser Ser Tyr Met Pro Arg Val Lys Ala Val Ile
    130                 135                 140

Gly Ser Gly Tyr Ser Glu Ile Thr Met Ala Val Ser Arg Met Leu Asn
145                 150                 155                 160

Leu Gln Leu Met Pro Gln Val Gly Tyr Glu Ser Thr Ala Glu Ile Leu
                165                 170                 175

Ser Asp Lys Ile Arg Phe Pro Ser Phe Leu Arg Thr Val Pro Ser Asp
            180                 185                 190

Phe His Gln Ile Lys Ala Met Ala His Leu Ile Gln Lys Ser Gly Trp
        195                 200                 205

Asn Trp Ile Gly Ile Ile Thr Thr Asp Asp Asp Tyr Gly Arg Leu Ala
    210                 215                 220

Leu Asn Thr Phe Ile Ile Gln Ala Glu Ala Asn Asn Val Cys Ile Ala
225                 230                 235                 240

Phe Lys Glu Val Leu Pro Ala Phe Leu Ser Asp Asn Thr Ile Glu Val
                245                 250                 255

Arg Ile Asn Arg Thr Leu Lys Lys Ile Ile Leu Glu Ala Gln Val Asn
            260                 265                 270

Val Ile Val Val Phe Leu Arg Gln Phe His Val Phe Asp Leu Phe Asn
        275                 280                 285

Lys Ala Ile Glu Met Asn Ile Asn Lys Met Trp Ile Ala Ser Asp Asn
    290                 295                 300

Trp Ser Thr Ala Thr Lys Ile Thr Thr Ile Pro Asn Val Lys Lys Ile
305                 310                 315                 320

Gly Lys Val Val Gly Phe Ala Phe Arg Arg Gly Asn Ile Ser Ser Phe
                325                 330                 335

His Ser Phe Leu Gln Asn Leu His Leu Leu Pro Ser Ser His Lys
            340                 345                 350

Leu Leu His Glu Tyr Ala Met His Leu Ser Ala Cys Ala Tyr Val Lys
        355                 360                 365

Asp Thr Asp Leu Ser Gln Cys Ile Phe Asn His Ser Gln Arg Thr Leu
    370                 375                 380

```
Ala Tyr Lys Ala Asn Lys Ala Ile Glu Arg Asn Phe Val Met Arg Asn
385                 390                 395                 400

Asp Phe Leu Trp Asp Tyr Ala Glu Pro Gly Leu Ile His Ser Ile Gln
            405                 410                 415

Leu Ala Val Phe Ala Leu Gly Tyr Ala Ile Arg Asp Leu Cys Gln Ala
            420                 425                 430

Arg Asp Cys Gln Asn Pro Asn Ala Phe Gln Pro Trp Glu Leu Leu Gly
            435                 440                 445

Val Leu Lys Asn Val Thr Phe Thr Asp Gly Trp Asn Ser Phe His Phe
450                 455                 460

Asp Ala His Gly Asp Leu Asn Thr Gly Tyr Asp Val Val Leu Trp Lys
465                 470                 475                 480

Glu Ile Asn Gly His Met Thr Val Thr Lys Met Ala Glu Tyr Asp Leu
            485                 490                 495

Gln Asn Asp Val Phe Ile Ile Pro Asp Gln Glu Thr Lys Asn Glu Phe
            500                 505                 510

Arg Asn Leu Lys Gln Ile Gln Ser Lys Cys Ser Lys Glu Cys Ser Pro
            515                 520                 525

Gly Gln Met Lys Lys Thr Thr Arg Ser Gln His Ile Cys Cys Tyr Glu
530                 535                 540

Cys Gln Asn Cys Pro Glu Asn His Tyr Thr Asn Gln Thr Asp Met Pro
545                 550                 555                 560

His Cys Leu Leu Cys Asn Asn Lys Thr His Trp Ala Pro Val Arg Ser
            565                 570                 575

Thr Met Cys Phe Glu Lys Glu Val Glu Tyr Leu Asn Trp Asn Asp Ser
            580                 585                 590

Leu Ala Ile Leu Leu Leu Ile Leu Ser Leu Leu Gly Ile Ile Phe Val
            595                 600                 605

Leu Val Val Gly Ile Ile Phe Thr Arg Asn Leu Asn Thr Pro Val Val
            610                 615                 620

Lys Ser Ser Gly Gly Leu Arg Val Cys Tyr Val Ile Leu Leu Cys His
625                 630                 635                 640

Phe Leu Asn Phe Ala Ser Thr Ser Phe Phe Ile Gly Glu Pro Gln Asp
            645                 650                 655

Phe Thr Cys Lys Thr Arg Gln Thr Met Phe Gly Val Ser Phe Thr Leu
            660                 665                 670

Cys Ile Ser Cys Ile Leu Thr Lys Ser Leu Lys Ile Leu Leu Ala Phe
            675                 680                 685

Ser Phe Asp Pro Lys Leu Gln Lys Phe Leu Lys Cys Leu Tyr Arg Pro
            690                 695                 700

Ile Leu Ile Ile Phe Thr Cys Thr Gly Ile Gln Val Val Ile Cys Thr
705                 710                 715                 720

Leu Trp Leu Ile Phe Ala Ala Pro Thr Val Glu Val Asn Val Ser Leu
            725                 730                 735

Pro Arg Val Ile Ile Leu Glu Cys Glu Gly Ser Ile Leu Ala Phe
            740                 745                 750

Gly Thr Met Leu Gly Tyr Ile Ala Ile Leu Ala Phe Ile Cys Phe Ile
            755                 760                 765

Phe Ala Phe Lys Gly Lys Tyr Glu Asn Tyr Asn Glu Ala Lys Phe Ile
            770                 775                 780

Thr Phe Gly Met Leu Ile Tyr Phe Ile Ala Trp Ile Thr Phe Ile Pro
785                 790                 795                 800
```

```
Ile Tyr Ala Thr Thr Phe Gly Lys Tyr Val Pro Ala Val Glu Ile Ile
                    805             810                 815

Val Ile Leu Ile Ser Asn Tyr Gly Ile Leu Tyr Cys Thr Phe Ile Pro
            820             825                 830

Lys Cys Tyr Val Ile Ile Cys Lys Gln Glu Ile Asn Thr Lys Ser Ala
        835             840                 845

Phe Leu Lys Met Ile Tyr Ser Tyr Ser Ser His Ser Val Ser Ser Ile
    850             855             860

Ala Leu Ser Pro Ala Ser Leu Asp Ser Met Ser Gly Asn Val Thr Met
865             870             875                         880

Thr Asn Pro Ser Ser Ser Gly Lys Ser Ala Thr Trp Gln Lys Ser Lys
            885             890                     895

Asp Leu Gln Ala Gln Ala Phe Ala His Ile Cys Arg Glu Asn Ala Thr
            900             905                 910

Ser Val Ser Lys Thr Leu Pro Arg Lys Arg Met Ser Ser Ile
        915             920                 925
```